US012644154B2

(12) United States Patent
Milla et al.

(10) Patent No.: US 12,644,154 B2
(45) Date of Patent: Jun. 2, 2026

(54) DETERMINING WT-1-SPECIFIC T CELLS AND WT-1 SPECIFIC T CELL RECEPTORS (TCRS)

(71) Applicant: Adaptive Biotechnologies Corporation, Seattle, WA (US)

(72) Inventors: Marcos E. Milla, Seattle, WA (US); Mark Klinger, Seattle, WA (US); Peter J.R. Ebert, Seattle, WA (US); Timothy L. Hayes, Seattle, WA (US); Edward J. Osborne, Seattle, WA (US); Joyce K. Hu, Seattle, WA (US)

(73) Assignee: Adaptive Biotechnologies Corporation, Seattle, WA (US)

( * ) Notice: Subject to any disclaimer, the term of this patent is extended or adjusted under 35 U.S.C. 154(b) by 993 days.

(21) Appl. No.: 17/812,678

(22) Filed: Jul. 14, 2022

(65) Prior Publication Data

US 2023/0042101 A1 Feb. 9, 2023

Related U.S. Application Data

(60) Division of application No. 16/007,467, filed on Jun. 13, 2018, now Pat. No. 11,390,921, which is a continuation-in-part of application No. 15/827,639, filed on Nov. 30, 2017, now Pat. No. 10,435,745, which is a continuation of application No. 14/242,520, filed on Apr. 1, 2014, now Pat. No. 10,066,265.

(60) Provisional application No. 62/629,496, filed on Feb. 12, 2018, provisional application No. 62/519,088, filed on Jun. 13, 2017.

(51) Int. Cl.
| | |
|---|---|
| *C12Q 1/6881* | (2018.01) |
| *A61K 40/11* | (2025.01) |
| *A61K 40/32* | (2025.01) |
| *A61K 40/42* | (2025.01) |
| *C07K 14/47* | (2006.01) |
| *C07K 14/705* | (2006.01) |
| *C07K 14/725* | (2006.01) |
| *C07K 16/30* | (2006.01) |
| *A61K 39/00* | (2006.01) |

(52) U.S. Cl.
CPC ............ *C12Q 1/6881* (2013.01); *A61K 40/11* (2025.01); *A61K 40/32* (2025.01); *A61K 40/4243* (2025.01); *C07K 14/4748* (2013.01); *C07K 14/7051* (2013.01); *C07K 16/30* (2013.01); *A61K 2039/804* (2018.08); *C07K 2317/73* (2013.01); *C12Q 2600/106* (2013.01); *C12Q 2600/158* (2013.01); *C12Q 2600/16* (2013.01)

(58) Field of Classification Search
CPC ............ C12Q 1/6881; C12Q 2600/106; C12Q 2600/158; C12Q 2600/16; A61K 40/11;

A61K 40/32; A61K 40/4243; A61K 2039/804; C07K 14/4748; C07K 14/7051; C07K 16/30; C07K 2317/73
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 5,126,022 | A | 6/1992 | Soane et al. |
| 5,168,038 | A | 12/1992 | Tecott et al. |
| 5,189,147 | A | 2/1993 | Saito et al. |
| 5,210,015 | A | 5/1993 | Gelfand et al. |
| 5,296,351 | A | 3/1994 | Morley |
| 5,399,491 | A | 3/1995 | Kacian et al. |
| 5,449,752 | A | 9/1995 | Fujii et al. |
| 5,498,392 | A | 3/1996 | Wilding et al. |
| 5,506,126 | A | 4/1996 | Seed et al. |
| 5,587,128 | A | 12/1996 | Wilding et al. |
| 5,627,052 | A | 5/1997 | Schrader |
| 5,635,400 | A | 6/1997 | Brenner |
| 5,837,447 | A | 11/1998 | Gorski |
| 5,854,033 | A | 12/1998 | Lizardi |
| 5,858,195 | A | 1/1999 | Ramsey |
| 5,925,517 | A | 7/1999 | Tyagi et al. |
| 5,981,179 | A | 11/1999 | Lorinez et al. |
| 6,001,229 | A | 12/1999 | Ramsey |
| 6,010,607 | A | 1/2000 | Ramsey |
| 6,033,546 | A | 3/2000 | Ramsey |
| 6,054,034 | A | 4/2000 | Soane et al. |
| 6,087,096 | A | 7/2000 | Dau et al. |
| 6,090,592 | A | 7/2000 | Adams et al. |

(Continued)

FOREIGN PATENT DOCUMENTS

| | | |
|---|---|---|
| EP | 0303459 A2 | 2/1989 |
| EP | 0799897 A1 | 10/1997 |

(Continued)

OTHER PUBLICATIONS

US 6,331,391 B1, 12/2001, Wittrup et al. (withdrawn)

(Continued)

*Primary Examiner* — Kimberly Ballard
*Assistant Examiner* — Stacey N MacFarlane
(74) *Attorney, Agent, or Firm* — Brian E. Davy; Bozicevic, Field & Francis LLP

(57) ABSTRACT

The invention is directed to methods for determining antigen-specific T cells generally and to T cell receptors which bind an epitope of the Wilms' tumor antigen-1 (WT1) protein specifically. The disclosure also provides polynucleotides encoding the TCRs, engineered cells exogenously expressing the TCRs, and methods of making and using the TCRs and/or cells expressing the TCRs.

8 Claims, 34 Drawing Sheets

Specification includes a Sequence Listing.

(56) References Cited

U.S. PATENT DOCUMENTS

| | | | |
|---|---|---|---|
| 6,091,000 | A | 7/2000 | Haynes |
| 6,136,566 | A | 10/2000 | Sands et al. |
| 6,172,214 | B1 | 1/2001 | Brenner |
| 6,174,670 | B1 | 1/2001 | Wittwer et al. |
| 6,207,371 | B1 | 3/2001 | Zambrowicz et al. |
| 6,214,613 | B1 | 4/2001 | Higuchi et al. |
| 6,228,589 | B1 | 5/2001 | Brenner |
| 6,255,071 | B1 | 7/2001 | Beach et al. |
| 6,300,065 | B1 | 10/2001 | Kieke et al. |
| 6,300,070 | B1 | 10/2001 | Boles et al. |
| 6,312,690 | B1 | 11/2001 | Edelman et al. |
| 6,399,952 | B1 | 6/2002 | Maher et al. |
| 6,416,948 | B1 | 7/2002 | Pilarski et al. |
| 6,423,538 | B1 | 7/2002 | Wittrup et al. |
| 6,489,103 | B1 | 12/2002 | Griffiths et al. |
| 6,569,627 | B2 | 5/2003 | Wittwer et al. |
| 6,613,525 | B2 | 9/2003 | Nelson et al. |
| 6,919,434 | B1 | 7/2005 | Goto et al. |
| 6,969,597 | B2 | 11/2005 | Lukyanov et al. |
| 7,115,400 | B1 | 10/2006 | Adessi et al. |
| 7,148,040 | B2 | 12/2006 | Meagher et al. |
| 7,232,653 | B1 | 6/2007 | Austrup et al. |
| 7,329,731 | B2 | 2/2008 | Jakobsen et al. |
| 7,375,211 | B2 | 5/2008 | Kou |
| 7,537,897 | B2 | 5/2009 | Brenner et al. |
| 7,666,604 | B2 | 2/2010 | Jakobsen et al. |
| 7,741,463 | B2 | 6/2010 | Gormley et al. |
| 7,842,457 | B2 | 11/2010 | Berka et al. |
| 8,012,690 | B2 | 9/2011 | Berka et al. |
| 8,048,627 | B2 | 11/2011 | Dressman et al. |
| 8,236,503 | B2 | 8/2012 | Faham et al. |
| 8,394,590 | B2 | 3/2013 | Kwong et al. |
| 8,507,205 | B2 | 8/2013 | Faham |
| 8,628,927 | B2 | 1/2014 | Faham |
| 8,685,898 | B2 | 4/2014 | Wiley |
| 8,748,103 | B2 | 6/2014 | Faham |
| 8,795,970 | B2 | 8/2014 | Faham |
| 9,043,160 | B1 | 5/2015 | Moorhead et al. |
| 9,181,590 | B2 | 11/2015 | Robins et al. |
| 9,217,176 | B2 | 12/2015 | Faham et al. |
| 9,228,232 | B2 | 1/2016 | Faham et al. |
| 9,279,159 | B2 | 3/2016 | Robins et al. |
| 9,416,420 | B2 | 8/2016 | Faham et al. |
| 9,512,487 | B2 | 12/2016 | Faham et al. |
| 9,809,813 | B2 | 11/2017 | Robins et al. |
| 10,066,265 | B2 | 9/2018 | Klinger et al. |
| 10,155,992 | B2 | 12/2018 | Faham et al. |
| 10,246,752 | B2 | 4/2019 | Faham et al. |
| 10,266,901 | B2 | 4/2019 | Faham et al. |
| 10,323,276 | B2 | 6/2019 | Wiley |
| 2002/0076725 | A1 | 6/2002 | Toyosaki-Maeda et al. |
| 2003/0120061 | A1 | 6/2003 | Zhang |
| 2004/0146901 | A1 | 7/2004 | Morris et al. |
| 2005/0260570 | A1 | 11/2005 | Mao et al. |
| 2006/0046258 | A1 | 3/2006 | Lapidus et al. |
| 2006/0233812 | A1 | 10/2006 | Burnie et al. |
| 2006/0234234 | A1 | 10/2006 | Van Dongen et al. |
| 2006/0275752 | A1 | 12/2006 | Sindhi |
| 2007/0117134 | A1 | 5/2007 | Kou |
| 2007/0243564 | A1 | 10/2007 | Lawson et al. |
| 2008/0050780 | A1 | 2/2008 | Lee et al. |
| 2008/0069770 | A1 | 3/2008 | Hercend et al. |
| 2008/0166704 | A1 | 7/2008 | Marche et al. |
| 2008/0274904 | A1 | 11/2008 | Gormley et al. |
| 2009/0181859 | A1 | 7/2009 | Muraguchi |
| 2009/0197257 | A1 | 8/2009 | Harris |
| 2009/0253581 | A1 | 10/2009 | Van Eijk et al. |
| 2010/0021896 | A1 | 1/2010 | Han |
| 2010/0021984 | A1 | 1/2010 | Edd |
| 2010/0027896 | A1 | 2/2010 | Geva et al. |
| 2010/0034834 | A1 | 2/2010 | Robbins et al. |
| 2010/0092436 | A1 | 4/2010 | Bonyhadi et al. |
| 2010/0137143 | A1 | 6/2010 | Rothberg et al. |
| 2010/0151471 | A1 | 6/2010 | Faham et al. |
| 2010/0167353 | A1 | 7/2010 | Walder et al. |
| 2010/0173394 | A1 | 7/2010 | Colston, Jr. |
| 2010/0255471 | A1 | 10/2010 | Clarke |
| 2010/0285975 | A1 | 11/2010 | Mathies |
| 2010/0304982 | A1 | 12/2010 | Hinz et al. |
| 2010/0330571 | A1 | 12/2010 | Robins et al. |
| 2011/0003291 | A1 | 1/2011 | Pasqual et al. |
| 2011/0158957 | A1 | 6/2011 | Bonini et al. |
| 2011/0166034 | A1 | 7/2011 | Kwong et al. |
| 2011/0183863 | A1 | 7/2011 | Wagner et al. |
| 2011/0207134 | A1 | 8/2011 | Faham et al. |
| 2011/0207135 | A1 | 8/2011 | Faham et al. |
| 2012/0010096 | A1 | 1/2012 | Wohlgemuth et al. |
| 2012/0058902 | A1 | 3/2012 | Livingston et al. |
| 2012/0135409 | A1 | 5/2012 | Faham |
| 2012/0220494 | A1 | 8/2012 | Samuels et al. |
| 2013/0005584 | A1 | 1/2013 | Faham |
| 2013/0045221 | A1 | 2/2013 | Stauss et al. |
| 2013/0136799 | A1 | 5/2013 | Faham et al. |
| 2013/0150252 | A1 | 6/2013 | Faham |
| 2013/0196328 | A1 | 8/2013 | Pepin |
| 2013/0202718 | A1 | 8/2013 | Pepin |
| 2013/0236895 | A1 | 9/2013 | Faham |
| 2013/0273647 | A1 | 10/2013 | Sahin et al. |
| 2013/0302801 | A1 | 11/2013 | Asbury |
| 2014/0155277 | A1 | 6/2014 | Wiley |
| 2014/0194295 | A1 | 7/2014 | Robins et al. |
| 2014/0206548 | A1 | 7/2014 | Robins et al. |
| 2014/0206549 | A1 | 7/2014 | Robins et al. |
| 2014/0213463 | A1 | 7/2014 | Robins et al. |
| 2014/0221220 | A1 | 8/2014 | Robins et al. |
| 2014/0234835 | A1 | 8/2014 | Pepin |
| 2014/0235454 | A1 | 8/2014 | Faham |
| 2014/0255944 | A1 | 9/2014 | Carlton |
| 2014/0256567 | A1 | 9/2014 | Robins et al. |
| 2014/0315758 | A1 | 10/2014 | Sugiyama |
| 2014/0336059 | A1 | 11/2014 | Faham et al. |
| 2014/0342360 | A1 | 11/2014 | Faham et al. |
| 2014/0342367 | A1 | 11/2014 | Faham et al. |
| 2014/0356339 | A1 | 12/2014 | Faham et al. |
| 2015/0017630 | A1 | 1/2015 | Oved et al. |
| 2015/0031043 | A1 | 1/2015 | Faham et al. |
| 2015/0031553 | A1 | 1/2015 | Faham et al. |
| 2015/0038346 | A1 | 2/2015 | Faham et al. |
| 2015/0065352 | A1 | 3/2015 | Faham et al. |
| 2015/0167080 | A1 | 6/2015 | Moorhead et al. |
| 2015/0247182 | A1 | 9/2015 | Faham et al. |
| 2015/0247198 | A1 | 9/2015 | Klinger et al. |
| 2015/0247201 | A1 | 9/2015 | Faham et al. |
| 2015/0252419 | A1 | 9/2015 | Moorhead et al. |
| 2015/0259734 | A1 | 9/2015 | Asbury et al. |
| 2015/0275296 | A1 | 10/2015 | Klinger et al. |
| 2015/0275308 | A1 | 10/2015 | Carlton et al. |
| 2015/0299785 | A1 | 10/2015 | Livingston et al. |
| 2015/0299800 | A1 | 10/2015 | Faham et al. |
| 2016/0009781 | A1 | 1/2016 | Sugiyama et al. |
| 2016/0045551 | A1 | 2/2016 | Brentjens et al. |
| 2016/0186260 | A1 | 6/2016 | Klinger et al. |
| 2016/0201133 | A1 | 7/2016 | Faham et al. |
| 2016/0251721 | A1 | 9/2016 | Robins et al. |
| 2016/0251728 | A1 | 9/2016 | Faham et al. |
| 2016/0258025 | A1 | 9/2016 | Klinger et al. |
| 2016/0289760 | A1 | 10/2016 | Suzuki et al. |
| 2017/0088630 | A1 | 3/2017 | Scheinberg et al. |
| 2017/0335386 | A1 | 11/2017 | Livingston et al. |
| 2017/0349954 | A1 | 12/2017 | Faham et al. |
| 2018/0023143 | A9 | 1/2018 | Faham et al. |
| 2018/0037953 | A1 | 2/2018 | Emerson et al. |
| 2018/0073015 | A1 | 3/2018 | Robins et al. |
| 2018/0080078 | A1 | 3/2018 | Robins et al. |
| 2018/0080090 | A1 | 3/2018 | Faham et al. |
| 2018/0087109 | A1 | 3/2018 | Klinger et al. |
| 2018/0112278 | A1 | 4/2018 | Faham et al. |
| 2018/0312832 | A1 | 11/2018 | Robins et al. |
| 2018/0355429 | A1 | 12/2018 | Klinger et al. |

(56) References Cited

U.S. PATENT DOCUMENTS

| | | | |
|---|---|---|---|
| 2019/0062848 | A1 | 2/2019 | Faham et al. |
| 2019/0100810 | A1 | 4/2019 | Faham et al. |

FOREIGN PATENT DOCUMENTS

| | | | |
|---|---|---|---|
| EP | | 0972081 B1 | 6/2007 |
| EP | | 1544308 B1 | 1/2009 |
| EP | | 2062982 A1 | 5/2009 |
| EP | | 2088205 A1 | 8/2009 |
| EP | | 2088432 A1 | 8/2009 |
| JP | | 4262799 A | 9/1992 |
| JP | | 2006-501842 A | 1/2006 |
| JP | | 2007-515955 A | 6/2007 |
| JP | | 2007-536939 A | 12/2007 |
| WO | WO | 1997/013877 A1 | 4/1997 |
| WO | WO | 1997/046706 A1 | 12/1997 |
| WO | WO | 1999/019717 A1 | 4/1999 |
| WO | WO | 2001/014424 A2 | 3/2001 |
| WO | WO | 2002/024322 A2 | 3/2002 |
| WO | WO | 2005/111242 A2 | 11/2005 |
| WO | WO | 2006/110855 A2 | 10/2006 |
| WO | WO | 2009/095567 A2 | 8/2009 |
| WO | WO | 2009/145925 A1 | 12/2009 |
| WO | WO | 2010/053587 A2 | 5/2010 |
| WO | WO | 2010/083456 A1 | 7/2010 |
| WO | WO | 2010/151416 A1 | 12/2010 |
| WO | WO | 2011/017151 A2 | 2/2011 |
| WO | WO | 2011/106738 A2 | 9/2011 |
| WO | WO | 2011/107595 A1 | 9/2011 |
| WO | WO | 2012/027503 A2 | 3/2012 |
| WO | WO | 2012/048340 A2 | 4/2012 |
| WO | WO | 2013/036459 A2 | 3/2013 |
| WO | WO | 2014/145992 A1 | 9/2014 |
| WO | WO | 2015/153788 A1 | 10/2015 |
| WO | WO | 2016/069283 A1 | 5/2016 |
| WO | WO | 2016/138122 A1 | 9/2016 |
| WO | WO | 2016/161273 A1 | 10/2016 |
| WO | WO | 2017/089773 A1 | 6/2017 |

OTHER PUBLICATIONS

Aird, et al., "Analyzing and minimizing PCR amplification bias in Illumina sequencing libraries." Genome Biology (2011); 12: R18, pp. 1-14.

Akamatsu, Y. et al., "Essential Residues in V(D)J Recombination Signals." The Journal of Immunology (1994); 153 (10): 4520-4529.

Akatsuka, Y. et al., "Rapid screening of T-cell receptor (TCR) variable gene usage by multiplex PCR: Application for assessment of clonal composition", *Tissue Antigens*, 53(2):122-134 (1999).

Alexandre, D. et al. "*H. sapiens* rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.

Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.

Altman, et al., "Phenotypic analysis of antigen-specific T lymphocytes." Science (Jun. 20, 1996); 280 (5371): 1821.

Andreasson, et al. "The human IgE-encoding transcriptome to assess antibody repertoires and repertoire evolution", *J Mol Biol.*, 362(2):212-227 (2006). Epub Aug. 14, 2006.

Arstila, T.P., et al., "A direct estimate of the human αβ T cell receptor diversity," *Science*, 286(5441): 958-961 (1999).

Attaf, et al., "αß T cell receptors as predictors of health and disease." Cellular & Molecular Immunology (Jul. 2015); 12 (4): 391-399. Epub Jan. 26, 2015.

Barbas III, et al., "Assembly of combinatorial antibody libraries on phage surfaces: the gene III site." Proc Natl Acad Sci U S A. (Sep. 1991); 88(18): 7978-7982.

Barnard, et al., "PCR Bias Toward the Wild-Type k-rasand p53 Sequences: Implications for PCR Detection of Mutations and Cancer Diagnosis." BioTechniques (Oct. 1998); 25: 684-691.

Batzoglou, S. "The many faces of sequence alignment", *Briefings in Bioinformatics*, 6:6-22 (2005).

Becker-Andre and Hahlbrock. "Absolute mRNA quantification using the polymerase chain reaction (PCR). A novel approach by a PCR aided transcript titration assay (PATTY)", *Nucleic Acids Res.*, 17(22): 9437-9446 (1989).

Béné and Kaeda, "How and why minimal residual disease studies are necessary in leukemia: a review from WP10 and WP12 of the European LeukemiaNet", *Haematologica*, 94(8):1135-1150 (2009).

Benichou, J. et al., "Rep-Seq: uncovering the immunological repertoire through next-generation sequencing", *Immunology*, 135(3): 183-191 (2011).

Bentley, et al. "Accurate whole human genome sequencing using reversible terminator chemistry", *Nature*, 456(7218):53-59 (2008). doi: 10.1038/nature07517.

Bernard et al. "Color multiplexing hybridization probes using the apolipoprotein E locus as a model system for genotyping", Anal Biochem., 273(2):221-228 (1999).

Bernardin, F. et al., "Estimate of the total number of CD8+ clonal expansions In healthy adults using a new DNA heteroduplex-tracking assay for CDR3 repertoire analysis", *Journal of Immunological Methods*, 274(1-2):159-175 (2003).

Berzofsky, et al. "Progress on new vaccine strategies for the immunotherapy and prevention of cancer", *J Clin Invest.*, 113(11): 1515-1525 (2004).

Bessette, et al., "Rapid isolation of high-affinity protein binding peptides using bacterial display." Protein Engineering, Design and Selection (Oct. 2004); 17(10): 731-739.

Bhatia, et al., "Rolling Adhesion Kinematics of Yeast Engineered to Express Selectins." Biotechnology Progress (2003); 19(3): 1033-1037.

Bidwell, "Advances in DNA-based HLA-typing methods." Immunol Today (Jul. 1994); 15 (7): 303-307.

Boder and Wittrup, "Yeast surface display for screening combinatorial polypeptide libraries." Nat Biotechnol. (Jun. 1997); 15(6): 553-557.

Bonarius, H.P.J. et al. "Monitoring the T-Cell Receptor Repertoire at Single-Clone Resolution", *PLOS One*, 1(e55):1-10 (2006).

Boulware and Daugherty, "Protease specificity determination by using cellular libraries of peptide substrates (CLiPS)." PNAS (May 2006); 103 (20): 7583-7588.

BOUSSO. "Generation of MHC-peptide tetramers: a new opportunity for dissecting T-cell immune responses", Microbes Infect., 2(4):425-429, Abstract Only (2000).

Boyd, S.D. et al., "Measurement and Clinical Monitoring of Human Lymphocyte Clonality by Massively Parallel V-D-J Pyrosequencing." *Science Translational Medicine*, 1:12ra23, 40 pages, including Supplementary Materials (2009).

Bradbury, et al., "Use of Living Columns to Select Specific Phage Antibodies." BioTechnology (1993); 11: 1565-1568.

Brennan et al. "Predictable αβ T-cell receptor selection toward an HLA-B*3501—restricted human cytomegalovirus epitope", J. Virol., 81(13): 7269-7273 (2007).

Brenner, et al. "In vitro cloning of complex mixtures of DNA on microbeads: physical separation of differentially expressed cDNAs", *PNAS*, 97(4): 1665-1670 (2000).

Brown, et al. "Current techniques for single-cell lysis", *J. R. Soc. Interface*, 5:S131-S138 (2008).

Brüggemann, et al. "Clinical significance of minimal residual disease quantification in adult patients with standard-risk acute lymphoblastic leukemia", *Blood*, 107(3):1116-1123 (2006). Epub Sep. 29, 2005.

Bupp and Roth, "Altering retroviral tropism using a random-display envelope library." Mol Ther. (Mar. 2002); 5(3): 329-335.

Campana, et al. "Role of minimal residual disease monitoring in adult and pediatric acute lymphoblastic leukemia", *Hematol Oncol Clin North Am.*, 23(5): 1083-1098 (2009). doi: 10.1016/j.hoc.2009.07.010.

Campana. "Minimal residual disease in acute lymphoblastic leukemia", *Semin Hematol.*, 46(1):100-106 (2009).

(56) References Cited

OTHER PUBLICATIONS

Campbell et al. "Subclonal phylogenetic structures in cancer revealed by ultra-deep sequencing," *PNAS*, 105(35):13081-13086 (2008).

Casbon et al. "A method for counting PCR template molecules with application to next-generation sequencing", *Nucleic Acids Research*, 39(12): e81, 8 pages (2011).

Cha et al., "Improved Survival with T Cell Clonotype Stability After Anti-CTLA-4 Treatment in Cancer Patients." Sci Transl Med (2014); 6(238): 238ra70.

Charbit, et al., "Versatility of a vector for expressing foreign polypeptides at the surface of Gram-negative bacteria." Gene (1988); 70(1): 181-189.

Chattopadhyay, et al. "A live-cell assay to detect antigen-specific CD4+ T cells with diverse cytokine profiles", *Nat Med.*, 11(10): 1113-1117 (2005). Epub Sep. 25, 2005.

Chen, et al. "Microfluidic cell sorter with integrated piezoelectric actuator", *Biomed Microdevices*, 11(6): 1223-1231 (2009). doi: 10.1007/s10544-009-9341-5.

Chen, et al. "Total Gene Synthesis: Novel Single-Step and Convergent Strategies Applied to the Construction of a 779 Base Pair Bacteriorhodopsis", *Gene. J. Am. Chem Soc.*, 116: 8799-8800, Abstract Only (1994).

Chestnut, et al., "Selective isolation of transiently transfected cells from a mammalian cell population with vectors expressing a membrane anchored single-chain antibody." J Immunol Methods. (Jun. 1996); 193(1): 17-27.

Choi, et al. "Relapse in children with acute lymphoblastic leukemia involving selection of a preexisting drug-resistant subclone", *Blood*, 110(2):632-639 (2007).

Chou, et al., "Expression of Chimeric Monomer and Dimer Proteins on the Plasma Membrane of Mammalian Cells." Biotechnol Bioeng (Oct. 1999); 65(2): 160-169.

Cleary, et al. "Production of complex nucleic acid libraries using highly parallel in situ oligonucleotide synthesis", *Nat Methods*, 1(3): 241-248 (2004). Epub Nov. 18, 2004.

Cronin, et al. "Comprehensive next-generation cancer genome sequencing in the era of targeted therapy and personalized oncology", *Biomark Med.*, 5(3):293-305 (2011). (Abstract only). doi: 10.2217/bmm.11.37.

Dane, et al., "Isolation of cell specific peptide ligands using fluorescent bacterial display libraries." J Immunol Methods. (Feb. 2006); 309(1-2): 120-129. Epub Jan. 11, 2006.

Daugherty, et al., "Quantitative analysis of the effect of the mutation frequency on the affinity maturation of single chain Fv antibodies." PNAS (Feb. 2000); 97 (5): 2029-2034.

Day, et al., "Identification of non-amplifying CYP21 genes when using PCR-based diagnosis of 21-hydroxylase deficiency in congenital adrenal hyperplasia (CAH) affected pedigrees." Hum Mol Genet. (Dec. 1996); 5(12): 2039-2048.

De Cárcer, et al., "Strategy for Modular Tagged High-Throughput Amplicon Sequencing." Applied and Environmental Microbiology (Sep. 2011); 77(17): 6310-6312.

DeWitt, et al., "Dynamics of the Cytotoxic T Cell Response to a Model of Acute Viral Infection." J. Virol. (Apr. 2015); 89 (8): 4517-4526. Epub Feb. 4, 2015.

Diehl, et al. "BEAMing: single-molecule PCR on microparticles in water-in-oil emulsions", *Nat Methods*, 3(7):551-559, Abstract Only (2006).

Diviacco, et al. "A novel procedure for quantitative polymerase chain reaction by coamplification of competitive templates", *Gene*, 122(2):313-320 (1992).

Dressman, et al. "Transforming single DNA molecules into fluorescent magnetic particles for detection and enumeration of genetic variations", PNAS, 100(15):8817-8822 (2003). Epub Jul. 11, 2003.

Drmanac, et al. "Human genome sequencing using unchained base reads on self-assembling DNA nanoarrays", *Science*, 327(5961):78-81 (2010). Epub Nov. 5, 2009.

Droese, J., et al. "Validation of BIOMED-2 multiplex PCR tubes for detection of TCRB gene rearrangements in T-cell malignancies," *Leukemia*, 18:1531-1538 (2004).

Du and Egholm, "The Next-Generation Genome Sequencing: 454/ Roche GC FLX." Next-Generation Genome Sequencing: Towards Personalized Medicine, Wiley-VCH Verlag GmbH & Co., KGaA (2008); (ed. Michal Janitz), Chapter 4: pp. 43-56, 34 pages.

Du et al. "TCR spectratyping revealed T lymphocytes associated with graft-versus-host disease after allogeneic hematopoietic stem cell transplantation", *Leukemia & Lymphoma*, 48(8):1618-1627 (2007).

Dueñas and Borrebaeck, "Clonal Selection and Amplification of Phage Displayed Antibodies by Linking Antigen Recognition and Phage Replication." Bio/Technology (1994);12 (10): 999-1002.

Dueñas, M., et al. "In vitro immunization of naive human B cells yields high affinity immunoglobulin G antibodies as illustrated by phage display." Immunology (1996); 89.1: 1-7.

Dziubianau, M., et al., "TCR repertoire analysis by next generation sequencing allows complex differential diagnosis of T cell-related pathology." Am J Transplant (Nov. 2013); 13(11): 2842-2854. doi: 10.1111/ajt.12431. Epub Sep. 10, 2013.

Eid et al. "Real-time DNA sequencing from single polymerase molecules", *Science*, 323(5910):133-138 (2009). Epub Nov. 20, 2008.

Emerson, et al., "De novo detection and HLA-association of public T cell responses to Cytomegalovirus using high-throughput immune repertoire sequencing (VIR1P.1134)." The Journal of Immunology (May 2015); 194 (1 Supplement): 74.1, Abstract.

Emerson, et al., "Immunosequencing identifies signatures of cytomegalovirus exposure history and HLA-mediated effects on the T cell repertoire." Nature Genetics (May 2017); 49 (3): 659-665. Epub Apr. 3, 2017.

European Application No. 09764927.1, European Opposition dated Oct. 15, 2014 (in French only).

European Application No. 09764927.1, Notice of Opposition dated Oct. 14, 2014, Reference# 547-7.

European Application No. 09764927.1, Notice of Opposition dated Oct. 14, 2014, Reference# BR0-0001EP.

European Application No. 10732172.1, Extended European Search Report dated May 29, 2012, 5 pages.

European Application No. 16162568.6, Extended European Search Report dated Jul. 20, 2016, 6 pages.

European Application No. 09764927.1, EPO's Communication of Notices of Opposition, dated Nov. 21, 2014.

European Application No. 09764927.1, Opponent's Response to Submission of the Patentee dated Nov. 23, 2015.

European Application No. 09764927.1, Patentee's Observations/ Response dated May 27, 2015.

European Application No. 10732172.1 (EP Patent No. 2387627), EPO's Communication with Notice of Opposition, dated Jan. 4, 2017, filed by Ablynx, 26 pages.

European Application No. 11777704.5, European Search Report dated Jul. 26, 2013, 6 pages.

European Application No. 13195379.6, Extended European Search Report and Opinion dated Mar. 13, 2014, 6 pages.

European Application No. 15772627.4, Extended European Search Report dated Jul. 19, 2017, 8 pages.

European Application No. 16756268.5, Extended European Search Report dated Oct. 22, 2018, 20 pages.

European Application No. 16756268.5, Partial Supplementary European Search Report dated Jun. 19, 2018, 21 pages.

European Patent Application No. 16774304.6, Extended European Search Report dated Oct. 15, 2018, 9 pages.

European Patent No. EP 2387627 (Application No. 10732172.1), EPO Communication dated Oct. 29, 2018 with Grounds of Appeal filed by Ablynx NV, dated Oct. 24, 2018, 62 pages.

European Patent No. EP 2387627 (Application No. 10732172.1), Interlocutory Decision issued by the European Patent Office, dated Jun. 15, 2018, (Opposition Proceedings filed by Ablynx NV), 17 pages.

European Patent No. EP 2387627 (Application No. 10732172.1), Notice of Opposition filed by Ablynx NV, dated Dec. 22, 2016, 34 pages.

Faham, M. et al. "Deep-sequencing approach for minimal residual disease detection in acute lymphoblastic leukemia", *Blood*, 120(26): 5173-5180 (2012).

(56)          References Cited

OTHER PUBLICATIONS

Fanning, et al., "Development of the immunoglobulin repertoire." Clin Immunol Immunopathol. (Apr. 1996); 79(1): 1-14.

Feldhaus, et al., "Flow-cytometric isolation of human antibodies from a nonimmune *Saccharomyces cerevisiae* surface display library." Nat Biotechnol. (Feb. 2003); 21(2):163-70. Epub Jan. 21, 2003.

Födinger et al., "Multiplex PCR for rapid detection of T-cell receptor-gamma chain gene rearrangements in patients with lymphoproliferative diseases." British Journal of Haematology (1996); 94(1): 136-139.

Freeman, et al. "Quantitative RT-PCR: Pitfalls and Potential", *Biotechniques*, 6(1): 112-125 (1999).

Freeman, J.D., et al. "Profiling the T-Cell Receptor Beta-Chain Repertoire by Massively Parallel Sequencing", *Genome Research*, 19(10):1817-1824 (2009). Epub Jun. 18, 2009.

Fu et al. "Counting individual DNA molecules by the stochastic attachment of diverse labels", *PNAS*, 108(22): 9026-9031 and Supporting Materials, 8 pages (2011).

Fuller, et al. "The challenges of sequencing by synthesis", *Nat Biotechnol.*, 7(11): 1013-1023 (2009) (Abstract only). Epub Nov. 6, 2009.

Gratama, et al. "Measuring antigen-specific immune responses", 2008 update. *Cytometry A.*, 73(11): 971-974 (2008).

Greenberg, et al. "Profile of immunoglobulin heavy chain variable gene repertoires and highly selective detection of malignant clonotypes in acute lymphoblastic leukemia" J Leukoc Biol., 57(6):856-864 (1995).

Hadrup, et al. "Parallel detection of antigen-specific T-cell responses by multidimensional encoding of MHC multimers", *Nat Methods*, 6(7): 520-526 (2009) (Abstract Only). doi: 10.1038/nmeth.1345. Epub Jun. 21, 2009.

Han et al. "Immunorepertoire analysis by multiplex PCR amplification and high throughput sequencing", *The Journal of Immunology*, 182:42.6, 1 page (2009).

Hanes and Plückthun, "In vitro selection and evolution of functional proteins by using ribosome display." Proc Natl Acad Sci U S A. (May 1997); 94(10): 4937-4942.

He, et al. "IgH gene rearrangements as plasma biomarkers in Non-Hodgkin's lymphoma patients", *Oncotarget*, 2(3): 178-185 (2011).

Hedegaard and Klemm, "Type 1 fimbriae of *Escherichia coli* as carriers of heterologous antigenic sequences." Gene (Dec. 1989); 85(1): 115-124.

Hesse, et al., "V(D)J recombination: a functional definition of the joining signals." Genes Dev. (Jul. 1989); 3(7): 1053-1061.

Hofnung, M., "Chapter 4 Expression of Foreign Polypeptides at the *Escherichia coli* Cell Surface." Methods in Cell Biology (1991); 34: 77-105.

Holmes and Al-Rubeai, "Improved cell line development by a high throughput affinity capture surface display technique to select for high secretors." J Immunol Methods. (Nov. 1999); 230(1-2): 141-147.

Hoover and Lubkowski. "DNAWorks: an automated method for designing oligonucleotides for PCR-based gene synthesis", *Nucleic Acids Res.*, 30(10): e43, 7 pages (2002).

Howe, et al. "T cell receptor clonotype analysis of T cell responses: Diagnostic application of a clonotypic database", Blood (2003); 102 (11): Abstract 3918, p. 54b, 1 page.

Ilakovac, V., "Statistical hypothesis testing and some pitfalls." Biochemia Medica (2009); 19(1): 10-16, 4 pages. [online]. [Retrieved on Apr. 12, 2016]. Retrieved from the Internet: <URL:http://www.biochemia-medica.com/content/statistical-hypothesis-testing-and-some-pitfalls>PDF.

Illumina. TruSeq Sample Preparation Kit and Data Sheet. Illumina, Inc., San Diego, CA, 4 pages (2011).

Jurkat, Clone 6-1 (ATCC TIB-152) Webpage retrievable from the ATCC under http://www.lgcstandards-atcc.org/Products/ All MB-152. aspx#characteristics. Accessed Oct. 14, 2014.

Kanagawa, T., "Bias and artifacts in multitemplate polymerase chain reactions (PCR)." J Biosci Bioeng. (2003); 96(4): 317-323.

Kato et al. "Analysis of accumulated T cell clonotypes in patients with systemic lupus erythematosus," *Arthritis & Rheumatism*, 43(12):2712-2721 (2000).

Kedzierska, et al. "Tracking phenotypically and functionally distinct T cell subsets via T cell repertoire diversity", *Mol Immunol.*, 45(3): 607-618 (2008). Epub Aug. 24, 2007.

Kiianitsa, et al., "Development of Tools for T-Cell Repertoire Analysis (TCRB Spectratyping) for the Canine Model of Hematopoietic Cell Transplantation", *Blood*, ASH—Annual Meeting Abstracts, 110 (11): Abstract 4873, 2 pages (2007).

Kim, et al. "Polony multiplex analysis of gene expression (PMAGE) in mouse hypertrophic cardiomyopathy", *Science*, 316(5830):1481-1484 (2007).

Klarenbeek, P.L. et al. "Deep sequencing of antiviral T-cell responses to HCMV and EBV in humans reveals a stable repertoire that is maintained for many years." PLoS Pathogens (2012); 8.9: e1002889.

Klauser, et al., "Extracellular transport of cholera toxin B subunit using Neisseria IgA protease beta-domain: conformation-dependent outer membrane translocation." The EMBO Journal (Jun. 1990); 9(6): 1991-1999.

Klenerman, et al. "Tracking T cells with tetramers: new tales from new tools", *Nat Rev Immunol.*, 2(4):263-272 (2002).

Klinger et al. "Combining next-generation sequencing and immune assays: a novel method for identification of antigen-specific T cells", PLoS One, 8(9): e74231, 1-9 (2013).

Koumi, et al., "Evaluation and validation of the ABI 3700, ABI 3100, and the MegaBACE 1000 capillary array electrophoresis instruments for use with short tandem repeat microsatellite typing in a forensic environment." Electrophoresis (Jul. 2004); 25 (14): 2227-2241.

Langerak, et al. "Polymerase chain reaction-based clonality testing in tissue samples with reactive lymphoproliferations: usefulness and pitfalls. A report of the BIOMED-2 Concerted Action BMH4-CT98-3936", *Leukemia*, 21(2):222-229 (2007).

Larijani, et al., "The role of components of recombination signal sequences in immunoglobulin gene segment usage: a V81x model." Nucleic Acids Research (Jan. 1999); 27(11): 2304-2309.

Lee, et al., "A Functional Analysis of the Spacer of V(D)J Recombination Signal Sequences." PLoS Biology (2003); 1(1); e1, pp. 056-059.

Leone, et al. "Molecular beacon probes combined with amplification by NASBA enable homogeneous, real-time detection of RNA", *Nucleic Acids Research*, 26(9): 2150-2155 (1998).

Leproust, et al. "Synthesis of high-quality libraries of long (150mer) oligonucleotides by a novel depurination controlled process", *Nucleic Acids Res.*, 38(8): 2522-2540 (2010). Epub Mar. 22, 2010.

Li, et al. "Utilization of Ig heavy chain variable, diversity, and joining gene segments in children with B-lineage acute lymphoblastic leukemia: implications for the mechanisms of VDJ recombination and for pathogenesis", *Blood*, 103(12):4602-4609 (2004).

Linnemann, et al., "High-throughput identification of antigen-specific TCRs by TCR gene capture." Nature Medicine (Nov. 2013); 19 (11): 1534-1541. Epub Oct. 13, 2013.

Linnemann, et al., "TCR repertoires of intratumoral T-cell subsets." Immunological Reviews (2014); 257 (1): 72-82.

Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.

López-Pérez, R., et al. "Gene scanning of VDJH-amplified segments is a clinically relevant technique to detect contaminating tumor cells in the apheresis products of multiple myeloma patients undergoing autologous peripheral blood stem cell transplantation." Bone Marrow Transplantation (2001); 28(7): 665-672.

Lorimer, I. A., and Pastan, Ira. "Random recombination of antibody single chain Fv sequences after fragmentation with DNaseI in the presence of Mn2+." Nucleic Acids Research (1995); 23.15: 3067-3068.

Lossius, et al., "High-throughput sequencing of TCR repertoires in multiple sclerosis reveals intrathecal enrichment of EBV-reactive CD8+ T cells." European Journal of Immunology (Nov. 2014); 44 (11): 3439-3452. Epub Sep. 16, 2014.

(56)          References Cited

OTHER PUBLICATIONS

Lovisa, et al. "IGH and IGK gene rearrangements as PCR targets for pediatric Burkitt's lymphoma and mature B-ALL MRD analysis", *Lab Invest.*, 89(10):1182-1186 (2009).

Lu, et al., "Expression of thioredoxin random peptide libraries on the *Escherichia coli* cell surface as functional fusions to flagellin: a system designed for exploring protein-protein interactions." Biotechnology (N Y). (Apr. 1995); 13(4): 366-372.

Mackay, et al. "Real-time PCR in virology", *Nucleic Acids Res.*, 30(6): 1292-1305 (2002).

Mardis, E.R., "The impact of next-generation sequencing technology on genetics." Cell Press (2008); 24 (3): 133-141.

Mardis. "Next-generation DNA sequencing methods", *Annu. Rev. Genomics Hum. Genet.*, 9:387-402 (2008). doi: 10.11446/annurev.genom.9.081307.164359.

Margulies, et al. "Genome sequencing in microfabricated high-density picolitre reactors", *Nature*, 437(7057):376-380 (2005). Epub Jul. 31, 2005.

Mariani, S. et al., "Comprehensive assessment of the TCRBV repertoire in small T-cell samples by means of an improved and convenient multiplex PCR method," *Experimental Hematology*, 37(6):728-738 (2009).

Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).

Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).

McCafferty, et al., "Phage antibodies: filamentous phage displaying antibody variable domains." Nature (Dec. 1990); 348(6301): 552-554.

McLean et al. "Recognition of human cytomegalovirus by human primary immunoglobulins identifies an innate foundation to an adaptive immune response", J. Immunol., 174(8): 4768-4778 (2005).

Meier, et al. "The influence of different stimulation conditions on the assessment of antigen-induced CD154 expression on CD4+T cells", *Cytometry A.*, (11):1035-1042 (2008). doi: 10.1002/cyto.a.20640.

Meleshko, et al. "Rearrangements of IgH, TCRD and TCRG genes as clonality marker of childhood acute lymphoblastic leukemia", *Experimental Oncology*, 27(4):319-324 (2005).

Metzker, "Sequencing Technologies—The Next Generation", *Nature Reviews, Genetics*, 11:31-46 (2010).

Michálek, et al. "Detection and long-term in vivo monitoring of individual tumor-specific T cell clones in patients with metastatic melanoma", *J Immunol.*, 178(11):6789-6795 (2007).

Miqueu, P. et al. "Statistical analysis of CDR3 length distributions for the assessment of T and B cell repertoire biases", *Molecular Immunology*, 44:1057-1064 (2007).

Miqueu, P., et al., "Analysis of the peripheral T-cell repertoire in kidney transplant patients." Eur J Immunol. (Nov. 2010); 40(11): 3280-3290. Epub Oct. 27, 2010.

Molloy, et al. "Soluble T cell receptors: novel immunotherapies", *Curr Opin Pharmacol.*, 5(4): 438-443 (2005) (Abstract Only).

Morgan, et al. "Cancer regression in patients after transfer of genetically engineered lymphocytes", *Science*, 314(5796): 126-129 (2006). Epub Aug. 31, 2006.

Müller, et al., "Random peptide libraries displayed on adeno-associated virus to select for targeted gene therapy vectors." Nat Biotechnol. (Sep. 2003); 21(9): 1040-1046. Epub Aug. 3, 2003.

Nadel, et al., "Decreased Frequency of Rearrangement due to the Synergistic Effect of Nucleotide Changes in the Heptamer and Nonamer of the Recombination Signal Sequence of the Vκ Gene A2b, Which Is Associated with Increased Susceptibility of Navajos to Haemophilus influenzae Type b Disease." The Journal of Immunology (1998); 161(11): 6068-6073.

Nadel, et al., "Sequence of the Spacer in the Recombination Signal Sequence Affects V(D)J Rearrangement Frequency and Correlates with Nonrandom Vκ Usage In Vivo." Jornal of Experimental Medicine (1998); 187 (9): 1495-1503.

Nakajima, et al., "Expression of random peptide fused to invasin on bacterial cell surface for selection of cell-targeting peptides." Gene (Dec. 2000); 260 (1-2): 121-131.

Nakano, et al. "Single-molecule PCR using water-in-oil emulsion", *J Biotechnol.*, 102(2): 117-124, Abstract Only (2003).

Nardi, et al. "Quantitative monitoring by polymerase colony assay of known mutations resistant to ABL kinase inhibitors", *Oncogene*, 27(6):775-782 (2008). Epub Aug. 6, 2007, 1-8.

Neale, et al. "Comparative analysis of flow cytometry and polymerase chain reaction for the detection of minimal residual disease in childhood acute lymphoblastic leukemia", *Leukemia*, 18(5):934-938 (2004).

Needleman and Wunsch. "A general method applicable to the search for similarities in the amino acid sequence of two proteins", *J Mol Biol.*, 48(3): 443-453 (1970).

Newton, et al., "Immune response to cholera toxin epitope inserted in *Salmonella flagellin*." Science (Apr. 1989); 244(4900): 70-72.

Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).

Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.

Ogino and Wilson., "Quantification of PCR Bias Caused by a Single Nucleotide Polymorphism in SMN Gene Dosage Analysis." The Journal of Molecular Diagnostics (Nov. 2002); 4(4): 185-190.

Ohlin, Mats, et al. "Light chain shuffling of a high affinity antibody results in a drift in epitope recognition." Molecular Immunology (1996); 33.1: 47-56.

Palmowski, et al. "The use of HLA class I tetramers to design a vaccination strategy for melanoma patients", *Immunol Rev.*, 188: 155-163 (2002) (Abstract Only).

Palomaki, et al. "DNA sequencing of maternal plasma reliably identifies trisomy 18 and trisomy 13 as well as Down syndrome: an international collaborative study", *Genet Med.*, 14(3): 296-305 (2012). doi: 10.1038/gim.2011.73. Epub Feb. 2, 2012.

Panzara, et al., "Analysis of the T cell repertoire using the PCR and specific oligonucleotide primers." Biotechniques (1992); 12(5): 728-735.

Panzer-Grümayer et al. "Immunogenotype changes prevail in relapses of young children with *TEL-AML1*-positive acute lymphoblastic leukemia and derive mainly from clonal selection", *Clin Cancer Research*, 11(21):7720-7727 (2005).

PCT/US2009/006053, International Preliminary Report on Patentability dated May 10, 2011, 5 pages.

PCT/US2009/006053, International Search Report dated Jun. 15, 2010, 6 pages.

PCT/US2009/006053, Written Opinion dated Jun. 15, 2010, 4 pages.

PCT/US2010/021264, International Preliminary Report on Patentability mailed Jul. 19, 2011, 5 pages.

PCT/US2010/021264, International Search Report and Written Opinion mailed Apr. 14, 2010, 7 pages.

PCT/US2010/037477, International Preliminary Report on Patentability dated Jan. 4, 2012, 7 pages.

PCT/US2010/037477, International Search Report and Written Opinion mailed Sep. 24, 2010, 10 pages.

PCT/US2011/000791, International Preliminary Report on Patentability dated Nov. 6, 2012, 10 pages.

PCT/US2011/000791, International Search Report and Written Opinion dated Sep. 22, 2011, 13 pages.

PCT/US2011/049012, International Preliminary Report on Patentability dated Feb. 26, 2013, 5 pages.

PCT/US2011/049012, International Search Report and Written Opinion mailed Apr. 10, 2012, 9 pages.

PCT/US2015/023915, International Preliminary Report on Patentability dated Oct. 4, 2016, 7 pages.

(56) References Cited

OTHER PUBLICATIONS

PCT/US2015/023915, International Search Report and Written Opinion dated Aug. 26, 2015, 11 pages.

PCT/US2016/019343, International Preliminary Report on Patentability dated Aug. 29, 2017, 14 pages.

PCT/US2016/019343, International Search Report and Written Opinion mailed Jul. 22, 2016, 23 pages.

PCT/US2016/025535, International Preliminary Report on Patentability dated Oct. 3, 2017, 7 pages.

PCT/US2016/025535, International Search Report and Written Opinion mailed Jul. 11, 2016, 9 pages.

PCT/US2018/037299, International Search Report and Written Opinion mailed Oct. 2, 2018, 22 pages.

Qu, et al., "Efficient frequency-based de novo short-read clustering for error trimming in next-generation sequencing." Genome Research (2009), 19(7): 1309-1315.

Ramsden, et al., "Conservation of sequence in recombination signal sequence spacers." Nucleic Acids Res. (May 1994); 22(10): 1785-1796.

Reddy, et al. "Monoclonal antibodies isolated without screening by analyzing the variable-gene repertoire of plasma cells", Nature Biotechnology, 28(9): 965-969 (2010). doi: 10.1038/nbt.1673. Epub Aug. 29, 2010.

Reinartz et al. "Massively parallel signature sequencing (MPSS) as a tool for in-depth quantitative gene expression profiling in all organisms", Brief Funct Genomic Proteomic., 1(1): 95-104 (2002).

Robins, et al. "Immunosequencing: applications of immune repertoire deep sequencing", Curr Opin Immunol., 25(5): 646-652 (2013). Epub Oct. 16, 2013.

Robins, H. et al. "Overlap and Effective Size of the Human CD8+ T Cell Receptor Repertoire", Science Transitional Medicine, 2(47, 47ra64): and Supplemental Materials, 17 pages (2010).

Roh, et al., "Comparing microarrays and next-generation sequencing technologies for microbial ecology research." Trends Biotechnol. (Jun. 2010); 28(6): 291-299. Epub Apr. 8, 2010.

Schwartzman, Armin. "Empirical null and false discovery rate inference for exponential families." The Annals of Applied Statistics (2008); 2(4): 1332-1359.

Seder and Ahmed, "Similarities and differences in CD4+ and CD8+ effector and memory T cell generation." Nat Immunol. (2003); 4 (9): 835-842.

Shendure and Ji. "Next-generation DNA sequencing", Nature Biotechnology, 26(10):1135-1145 (2008).

Shendure, et al. "Advanced sequencing technologies: methods and goals", Nat Rev Genet., 5(5): 335-344 (2004).

Shoemaker et al. "Quantitative phenotypic analysis of yeast deletion mutants using a highly parallel molecular bar-coding strategy," Nature Genetics, 14(4): 450-456 (1996).

Sia, et al. "Microfluidic devices fabricated in poly(dimethylsiloxane) for biological studies", Electrophoresis, 24(21): 3563-3576, Abstract Only (2003).

Skulina et al. "Multiple Sclerosis: Brain-infiltrating CD8+ T cells persist as clonal expansions in the cerebrospinal fluid and blood", PNAS, 101(8):2428-2433 (2004).

Smith, et al. "Comparison of biosequences", Advances in Applied Mathematics, 2: 482-489 (1981).

Smith, G.P., "Filamentous fusion phage: novel expression vectors that display cloned antigens on the virion surface." Science (Jun. 1985); 228(4705): 1315-1317.

Sotomayor, et al., "Conversion of tumor-specific CD4+ T-cell tolerance to T-cell priming through in vivo ligation of CD40." Nature Medicine (Jul. 1999); 5(7): 780-787.

Spellman, et al., "Advances in the selection of HLA-compatible donors: refinements in HLA typing and matching over the first 20 years of the National Marrow Donor Program Registry." Biol Blood Marrow Transplant (2008); (9 Suppl):37-44. Epub Jun. 20, 2008.

Sramkova, et al. "Detectable minimal residual disease before allogeneic hematopoietic stem cell transplantation predicts extremely poor prognosis in children with acute lymphoblastic leukemia", Pediatr. Blood Cancer, 48(1):93-100 (2007).

Stemmer, et al. "Single-step assembly of a gene and entire plasmid from large Nos. of oligodeoxyribonucleotides", Gene, 164(1): 49-53 (1995).

Stickler, et al. "An in vitro human cell-based assay to rank the relative immunogenicity of proteins", Toxicol Sci., 77(2): 280-289 (2004). Epub Dec. 22, 2003.

Straten, Per thor, et al. "T-cell clonotypes in cancer", Journal of Translational Medicine, 2(1): 11, 10 pages (2004).

Struyk et al. "T cell receptors in rheumatoid arthritis", Arthritis & Rheumatism, 38(5):577-589 (1995).

Szczepek, et al., "A high frequency of circulating B cells share clonotypic Ig heavy-chain VDJ rearrangements with autologous bone marrow plasma cells in multiple myeloma, as measured by single-cell and in situ reverse transcriptase-polymerase chain reaction." Blood (1998); 92(8): 2844-2855.

Tam, James P. "Synthetic peptide vaccine design: synthesis and properties of a high-density multiple antigenic peptide system." Proceedings of the National Academy of Sciences (1988); 85.15: 5409-5413.

Tawfik, et al. "Man-made cell-like compartments for molecular evolution", Nat Biotechnol., 16(7): 652-656, Abstract Only (1998).

Theberge, et al., " Microdroplets in Microfluidics: An Evolving Platform for Discoveries in Chemistry and Biology." Angew Chem Int Ed Engl. (Aug. 9, 2010); 49(34): 5846-5868.

Turcotte and Rosenberg. "Immunotherapy for metastatic solid cancers", Adv Surg., 45: 341-360 (2011).

U.S. Appl. No. 61/145,039, filed Jan. 15, 2009, entitled "Adaptive Immunity Profiling and Methods for Generation of Monoclonal Antibodies", Inventor—Steven R. Wiley, 40 pages.

UK combined search and examination report dated Mar. 20, 2013 for GB 1300533.5.

UK Combined Search Report and Office action dated May 27, 2011 for UK application No. GB1105068.9.

UK Combined Search Report and Office action dated Jun. 29, 2012 for UK application No. GB1209668.1.

UK Search Report and office action dated Jan. 13, 2012 for UK application No. GB1120209.0.

UK Search Report and office action dated Jul. 7, 2010 for UK application No. GB1009641.0.

Van Der Velden, V.H.J., et al. "Detection of minimal residual disease in hematologic malignancies by realtime quantitative PCR: principles, approaches, and laboratory aspects," Leukemia, 17:1013-1034 (2003).

Van Dongen, J.J.M. et al. "Design and standardization of PCR primers and protocols for detection of clonal immunoglobulin and I-cell receptor gene recombinations in suspect lymphoproliferations: Report of the BIOMED-2 Concerted Action BMH4-CT98-3936", Leukemia, 17:2257-2317 (2003).

Van Dongen, J.J.M. et al. "Prognostic value of minimal residual disease in acute lymphoblastic leukaemia in childhood", The Lancet, 352:1731-1738 (1998).

Van Heijst, J.W.J., et al., "Quantitative assessment of T-cell repertoire recovery after hematopoietic stem cell transplantation." Nat Med. (2013); 19(3): 372-377.

Wälchli, et al. "A practical approach to T-cell receptor cloning and expression", PLoS One, 6(11): e27930, 11 pages (2011). doi: 10.1371/journal.pone.0027930. Epub Nov. 21, 2011.

Wang, et al. "High throughput sequencing reveals a complex pattern of dynamic interrelationships among human T cell subsets", PNAS, 107(4): 1518-1528 (2010).

Wang, X. et al. "Quantitative Measurement of Pathogen Specific Human Memory T Cell Repertoire Diversity using a CDR3 B-Specific Microarray", BMC Genomics, 8(329): 1-13 (2007).

Warren et al. "Exhaustive T-cell repertoire sequencing of human peripheral blood samples reveals signatures of antigen selection and a directly measured repertoire size of at least 1 million clonotypes", Genome Res., 21(5): 790-797 (2011). Epub Feb. 24, 2011.

Welch and Link. "Genomics of AML: clinical applications of next-generation sequencing", American Society of Hematology, 2011: 30-35 (2011). doi: 10.1182/asheducation-2011.1.30.

Willenbrock, et al., "Analysis of T-Cell Subpopulations in T-Cell Non-Hodgkin's Lymphoma of Angioimmunoblastic Lymphadenopa-

(56)  References Cited

OTHER PUBLICATIONS thy with Dysproteinemia Type by Single Target Gene Amplification of T Cell Receptorβ Gene Rearrangements." Am J Pathol. (May 2001); 158(5): 1851-1857.

Williams, et al. "Amplification of complex gene libraries by emulsion PCR", *Nat Methods*, 3(7): 545-550 (2006).

Wilson, et al., "The use of mRNA display to select high-affinity protein-binding peptides." PNAS (Mar. 2001); 98 (7): 3750-3755.

Wilson-Lingardo et al., "Deconvolution of Combinatorial Libraries for Drug Discovery: Experimental Comparison of Pooling Strategies." J. Med. Chem., (1996); 39 (14): 2720-2726.

Wittrup, "Protein engineering by cell-surface display." Current Opinion in Biotechnology (Aug. 2001); 12(4): 395-399.

Wolda. "Similarity Indices, Sample Size and Diversity", *Oecologia* (Berl), 50:296-302 (1981).

Wolfl, et al. "Activation-induced expression of CD137 permits detection, isolation, and expansion of the full repertoire of CD8+ T cells responding to antigen without requiring knowledge of epitope specificities", *Blood*, 110(1): 201-210 (2007). Epub Mar. 19, 2007.

Wolfl, et al. "Use of CD137 to study the full repertoire of CD8+ T cells without the need to know epitope specificities", *Cytometry A.*, 73(11): 1043-1049 (2008). doi: 10.1002/cyto.a.20594.

Woodsworth, Daniel J., et al., "Sequence analysis of T-cell repertoires in health and disease." Genome Medicine (2013); 5: 98, 13 pages.

Xie, Yang, et al., "A note on using permutation-based false discovery rate estimates to compare different analysis methods for microarray data." Bioinformatics (2005); 21.23: 4280-4288.

Xiong, et al. "Chemical gene synthesis: strategies, softwares, error corrections, and applications", *FEMS Microbiol Rev.*, 32(3): 522-540 (2008). doi: 10.1111/j.1574-6976.2008.00109.x. Epub Apr. 2, 2008.

Xiong, et al. "Non-polymerase-cycling-assembly-based chemical gene synthesis: strategies, methods, and progress", *Biotechnol Adv.*, 26(2): 121-134, Abstract Only (2008). Epub Nov. 7, 2007.

Xu, et al. "Simultaneous isolation of DNA and RNA from the same cell population obtained by laser capture microdissection for genome and transcriptome profiling", *J Mol Diagn.*, 10(2):129-134 (2008). doi: 10.2353/jmoldx.2008.070131. Epub Feb. 7, 2008.

Xu, et al., "Viral immunology. Comprehensive serological profiling of human populations using a synthetic human virome." Science (Jun. 2015); 348(6239):aaa0698.

Yao, et al. "Analysis of the CDR3 length repertoire and the diversity of TCRα chain in human peripheral blood T Lymphocytes", Cell Mol Immunol., 4(3): 215-220 (2007).

Yassai, M.B. et al. "A clonotype nomenclature for T cell receptors", *Immunogenetics*, 61:493-502 (2009).

Yon and Fried. "Precise gene fusion by PCR", *Nucleic Acids Research*, 17(12): 4895, 1 page (1989).

Yonezawa, et al., "DNA display for in vitro selection of diverse peptide libraries." Nucleic Acids Res. (Oct. 2003); 31(19): e118.

York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.

Zeng, et al., "Electrical Control of Individual Droplet Breaking and Droplet Contents Extraction." Anal. Chem. (2011); 83 (6): 2083-2089.

Zeng et al. "High-performance single cell genetic analysis using microfluidic emulsion generator arrays", *Anal. Chem.*, 82(8):3183-3190 (2010).

Zimmerman and Mannhalter. "Technical aspects of quantitative competitive PCR", *Biotechniques*, 21: 268-279 (1996).

Zwick, et al., "Identification and Characterization of a Peptide That Specifically Binds the Human, Broadly Neutralizing Anti-Human Immunodeficiency Virus Type 1 Antibody b12." Journal of Virology (Jul. 2001); 75(14): 6692-6699.

FIG. 1A
eJH30_WT1C_5
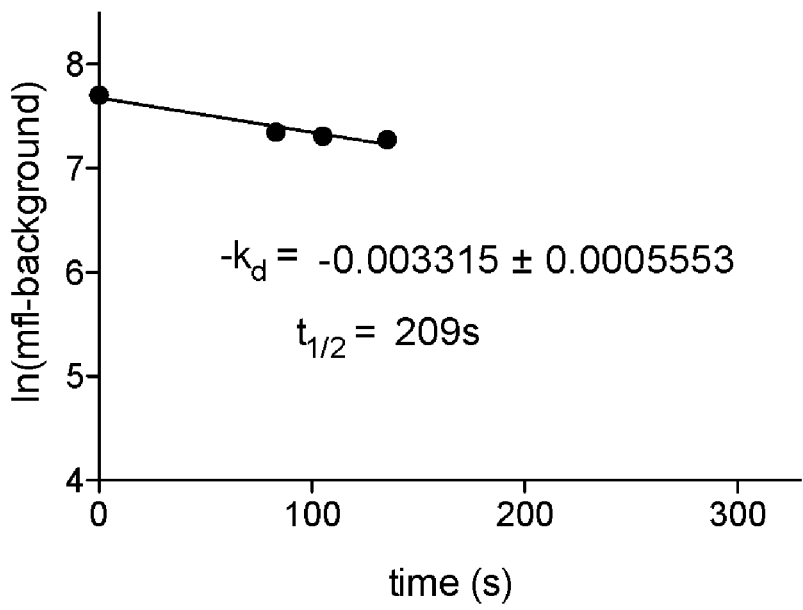
$-k_d = -0.003315 \pm 0.0005553$
$t_{1/2} = 209s$
FIG. 1B    eJH30_WT1C_8
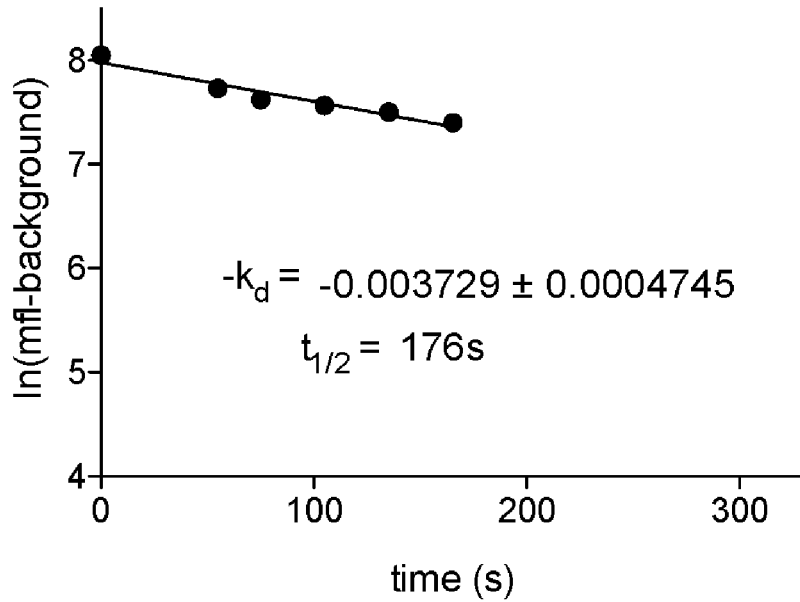
$-k_d = -0.003729 \pm 0.0004745$
$t_{1/2} = 176s$

FIG. 9
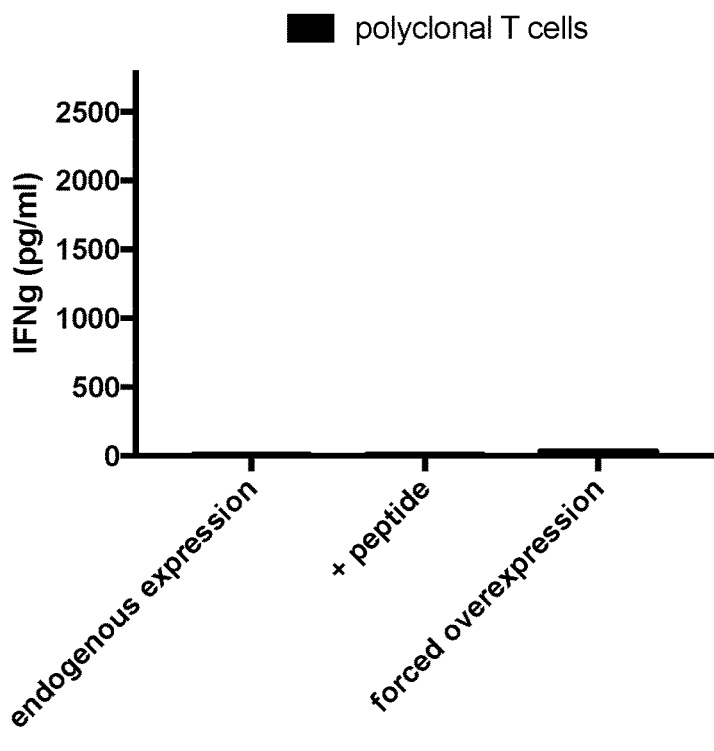
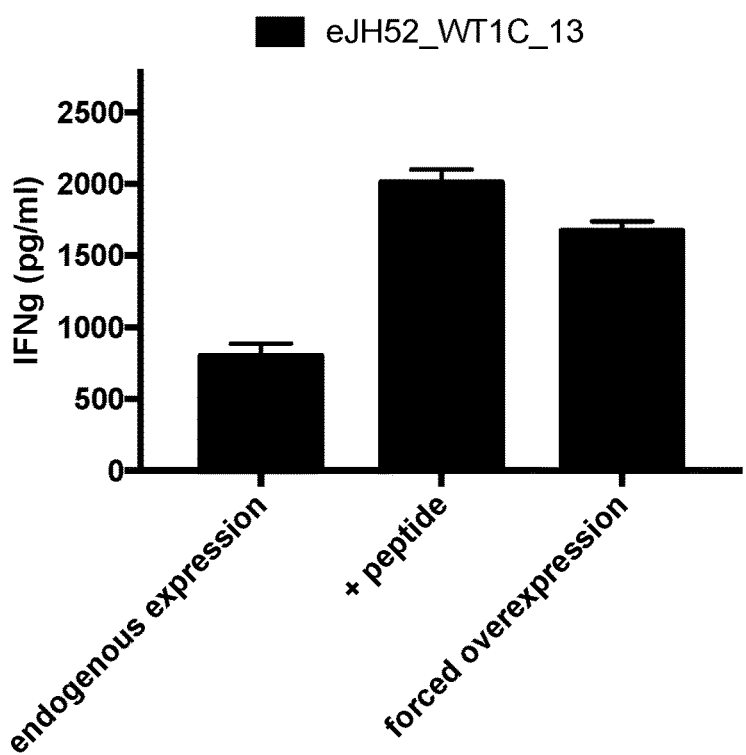

eJH30_7 eJH52_13 eJH64_6 eJH64_9

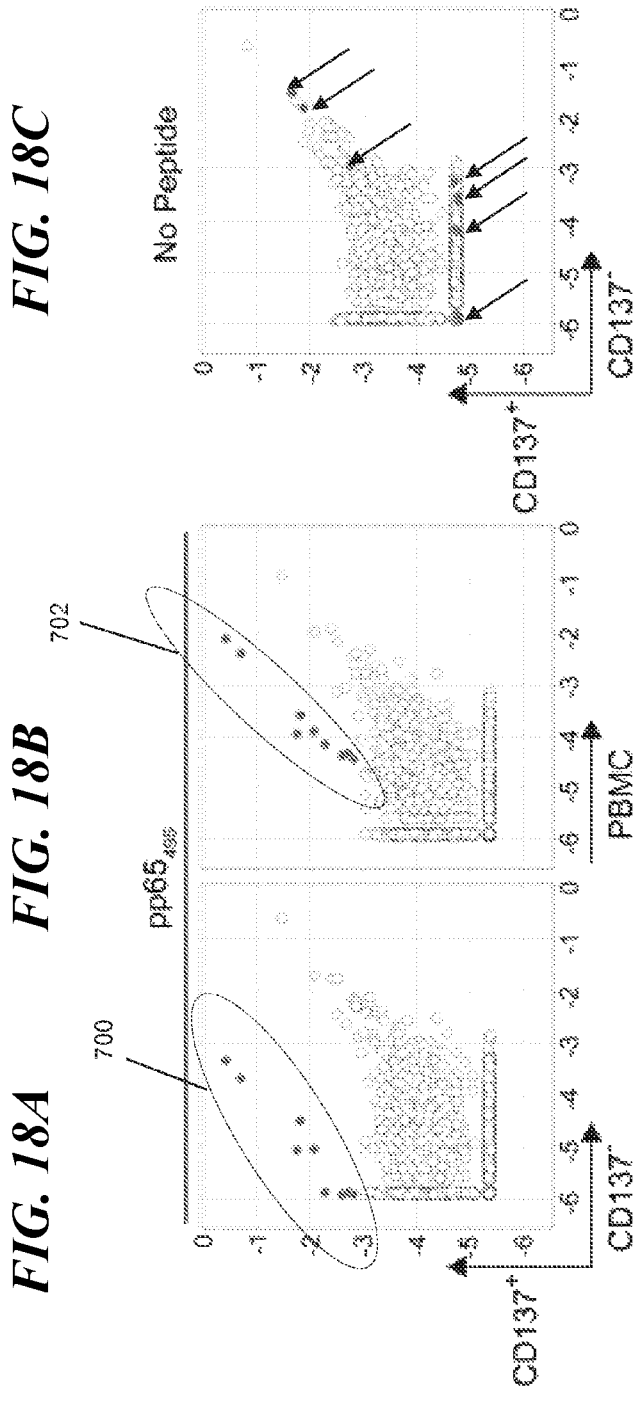

Exemplary Function For Determining Whether to Coalesce
Candidate Clonotypes Depending on Read Counts,
Base Differences and Q Scores

1

DETERMINING WT-1-SPECIFIC T CELLS AND WT-1 SPECIFIC T CELL RECEPTORS (TCRS)

CROSS-REFERENCE TO RELATED APPLICATIONS

This application is a continuation-in-part of and claims priority to U.S. patent application Ser. No. 15/827,639, filed Nov. 30, 2017, which is in turn a continuation of U.S. patent application Ser. No. 14/242,520, filed Apr. 1, 2014. This application also claims priority to U.S. Provisional Patent Application No. 62/519,088, filed Jun. 13, 2017, and U.S. Provisional Patent Application No. 62/629,496, filed Feb. 12, 2018. The disclosures of each of these referenced applications are hereby incorporated by reference in their entireties.

REFERENCE TO THE ELECTRONIC TEXT FILE SUBMITTED HEREWITH

The contents of the text file submitted electronically herewith are incorporated herein by reference in their entirety: A computer readable format copy of the Sequence Listing (filename: ADBS_079_02US_SeqList_ST25.txt; date recorded: Jun. 11, 2018; file size: 55.2 kilobytes).

BACKGROUND OF THE INVENTION

Many crucial immune functions are mediated by T cell receptors (TCRs), which comprise $\alpha$ and $\beta$ subunits that together bind to a complex consisting of an antigenic peptide and major histocompatibility complex (MHC) molecules. It is believed that several important diseases arise from aberrant T cell function: For example, cancers are thought to arise from a failure of immune surveillance, that is, the T cell function of detecting and destroying clones of transformed cells before they grow into tumors; and autoimmune diseases are thought to arise from an over active or aberrant response of T cells to self-antigens (Abbas et al, Cellular and Molecular Immunology, Fourth Edition (W. B. Saunders Company, 2000)). Consequently, there has been interest both in identifying and tracking antigen-specific T cells and in harnessing T cell functions in several therapeutic approaches for the treatment both cancer and autoimmune diseases, e.g. Molloy et al, Current Opinion in Pharmacology, 5: 438-443 (2005); Morgan et al, Science, 314: 126-129 (2006); Turcotte and Rosenberg, Adv. Surg., 45: 341-360 (2011). Several challenges are posed by these interests: Current techniques for identifying and tracking antigen-specific T cells, especially on a large scale, are difficult and expensive, and likewise, current techniques for identifying and isolating paired TCRα and TCRβ subunits that form a functional receptor are difficult and expensive. In regard to detecting antigen-specific T cells, the use of direct multimer staining requires laborious development of specific HLA-restricted reagents, and other assays, such as ELISPOT, intracellular cytokine staining, and proliferation assays, enumerate antigen-specific T cells based on detection of activation following stimulation of the T cells in vitro with antigen, e.g. Gratama et al, Cytometry A, 73A: 971-974 (2008). In regard to isolating functional pairs of TCR chains, typically a T cell of interest is identified and clonally expanded to enable isolation and analysis of nucleic acids encoding each subunit. Even for a common disease antigen, such as MART-1 in melanoma, the process of single cell analysis, cloning and receptor isolation must be repeated for each patient.

Recently, diagnostic and prognostic applications have been proposed that use large-scale DNA sequencing as the per-base cost of DNA sequencing has dropped and sequencing techniques have become more convenient, e.g. Welch et al, Hematology Am. Soc. Hematol. Educ. Program, 2011: 30-35; Cronin et al, Biomark Med., 5: 293-305 (2011); Palomaki et al, Genetics in Medicine (online publication 2 Feb. 2012). In particular, profiles of nucleic acids encoding immune molecules, such as T cell or B cell receptors, or their components, contain a wealth of information on the state of health or disease of an organism, so that diagnostic and prognostic indicators based on the use of such profiles are being developed for a wide variety of conditions, Faham and Willis, U.S. Patent Application Publication No. 2010/0151471; Freeman et al, Genome Research, 19: 1817-1824 (2009); Boyd et al, Sci. Transl. Med., 1(12): 12ra23 (2009); He et al, Oncotarget (Mar. 8, 2011). Current sequence-based profiles of immune repertoires consist of nucleic acids encoding only single receptor chains; thus, potentially useful information from correctly paired TCRα and TCRβ chains is not available.

Wilms' tumor oncogene protein (WT1) is a zinc finger transcription factor involved in the development of the urogenital system and is expressed in a variety of cancers. After birth, WT1 expression is limited to low expression in only a few cell types in normal tissues; however, in certain cancers, WT1 is overexpressed and associated with cancer cell survival and proliferation. Aberrant and/or overexpression of WT1 has been observed in Wilms' tumors, leukemias, and other cancers. Therefore, WT1 is an attractive target for immunotherapy.

SUMMARY OF THE INVENTION

In view of the above, it would be highly useful for cancer, infectious disease, and autoimmune disease treatment if there were available convenient methods for determining functional, antigen-specific, immune receptors from nucleic acids encoding subunits of the immune receptors that have been separately extracted and sequenced. As such, the present disclosure provides methods for determining functional, antigen-specific, immune receptors, in particular T cell receptors (TCRs), from nucleic acids encoding subunits of the immune receptors (e.g., TCR alpha and TCR beta chains) that have been separately extracted and sequenced. The present disclosure further provides TCRs specific for the WT1 oncoprotein and nucleic acid encoding the same, cells comprising such TCRs, methods of use, and methods of identifying and producing such TCRs. In some embodiments, the present disclosure provides one or both of the alpha (α) chain and the beta (β) chain of antigen-specific TCRs (e.g., WT1-specific TCR alpha and/or beta chains), and nucleic acids encoding these alpha and beta chains. In some embodiments, the present disclosure provides TCRs and T cells exogenously expressing TCRs specific for WT1 oncoprotein that are useful in therapeutic and/or diagnostic methods for WT1-expressing cancers. These and other aspects of the invention are exemplified in a number of implementations and applications described throughout the specification and summarized below.

In some embodiments, the present disclosure provides methods for determining antigen-specific T cells in a tissue sample comprising the following steps: (a) reacting a tissue sample comprising T cells with an antigen under activation conditions in a reaction mixture; (b) sorting T cells from the reaction mixture into a subset of antigen-specific T cells and/or activated T cells and a subset of non-antigen-specific T cells and/or un-activated T cells; (c) sequencing recombined nucleic acids encoding a T-cell receptor (TCR) chain or a portion thereof from the antigen-specific T cells and/or activated T cells to provide sequence reads from which clonotypes are determined; (d) sequencing recombined nucleic acids encoding a TCR chain or a portion thereof from the non-antigen-specific T cells and/or un-activated T cells to provide sequence reads from which clonotypes are determined; and (e) determining antigen-specific T cells in the tissue sample as T cells whose clonotype frequencies increase in the subset of sorted antigen-specific and/or activated T cells relative to the frequencies of the same clonotypes in the subset of sorted non-antigen-specific and/or un-activated T cells.

In some embodiments, the present disclosure provides methods of determining antigen-specific T cell receptors from a sample containing T cells comprising the following steps: (a) sequencing recombined nucleic acids encoding one or more TCR chain(s), or a portion thereof, from a first portion of the sample to generate a first multiplicity (number greater than 2) of sequence reads obtained from un-stimulated T cells; (b) partitioning a second portion of the sample into a plurality (number equal or greater than 2) of reaction mixtures and exposing each reaction mixture of the plurality of reaction mixtures to antigens; (c) for each reaction mixture in the plurality of reaction mixtures, separating T cells that interact with one or more antigens in the reaction mixture to obtain a subset of antigen-specific T cells, wherein each of the subsets of antigen-specific T cells corresponds to one reaction mixture in the plurality of reaction mixtures; (d) for each of the subsets of antigen-specific T cells separated in step (c), sequencing recombined nucleic acids encoding one or more TCR chain(s), or a portion thereof, to generate sequence reads obtained from each of the subsets of antigen-specific T cells; (e) for each reaction mixture in the plurality of reaction mixtures, identifying a plurality of antigen-specific TCR chains, or portion thereof, by comparing the sequence reads obtained from each of the subsets of antigen-specific T cells in step (d) to the sequence reads obtained from unstimulated T cells in step (a), wherein the frequency of the sequence reads for the WT-1 antigen-specific TCR chains, or portion thereof, is increased in the sequence reads obtained from the subsets of antigen-specific T cells compared to the frequency of sequence reads for the antigen-specific TCR chains, or portion thereof, in the sequence reads obtained from unstimulated T cells; and (f) identifying one or more TCR chains, or portion thereof, specific for one of the antigens from the one or more TCR chains, or a portion thereof, identified in step (e), wherein the frequency of the sequence reads for the one or more TCR chains, or portion thereof, specific for the antigen is increased in the sequence reads obtained from each of the subsets of antigen-specific T cells in which the antigen was present in the corresponding reaction mixture.

In some embodiments, the present disclosure provides a recombinant T cell receptor (TCR) that binds Wilms' tumor antigen-1 (WT1), comprising an alpha chain and a beta chain, wherein the beta chain comprises a CDR3 sequence comprising or consisting of an amino acid sequence set forth in SEQ ID NOs: 22 or 30. In some embodiments, the alpha chain comprises a CDR3 sequence comprising or consisting of an amino acid sequence set forth in SEQ ID NOs: 19 or 27. In some embodiments, the beta chain comprises a CDR2 sequence comprising or consisting of an amino acid sequence set forth in SEQ ID NOs: 21 or 29. In some embodiments, the alpha chain comprises a CDR2 sequence comprising or consisting of an amino acid set forth in SEQ ID NOs: 18 or 26. In some embodiments, the beta chain comprises a CDR1 sequence comprising or consisting of an amino acid sequence set forth in SEQ ID NOs: 20 or 28. In some embodiments, the alpha chain comprises a CDR1 sequence comprising or consisting of an amino acid sequence set forth in SEQ ID NOs: 17 or 25.

In some embodiments, the present disclosure provides a recombinant TCR comprising an alpha chain CDR1 comprising or consisting of an amino acid sequence according to SEQ ID NO: 17; an alpha chain CDR2 comprising or consisting of an amino acid sequence according to SEQ ID NO: 18; an alpha chain CDR3 comprising or consisting of an amino acid sequence according to SEQ ID NO: 19; a beta chain CDR1 comprising or consisting of an amino acid sequence according to SEQ ID NO: 20; a beta chain CDR2 comprising or consisting of an amino acid sequence according to SEQ ID NO: 21; and a beta chain CDR3 comprising or consisting of an amino acid sequence according to SEQ ID NO: 22.

In some embodiments, the present disclosure provides a recombinant TCR comprising an alpha chain CDR1 comprising or consisting of an amino acid sequence according to SEQ ID NO: 25; an alpha chain CDR2 comprising or consisting of an amino acid sequence according to SEQ ID NO: 26; an alpha chain CDR3 comprising or consisting of an amino acid sequence according to SEQ ID NO: 27; a beta chain CDR1 comprising or consisting of an amino acid sequence according to SEQ ID NO:28; a beta chain CDR2 comprising or consisting of an amino acid sequence according to SEQ ID NO: 29; and a beta chain CDR3 comprising or consisting of an amino acid sequence according to SEQ ID NO: 30.

In some embodiments, the present disclosure provides a recombinant TCR that binds WT1, comprising an alpha chain and a beta chain, wherein the amino acid sequence of the alpha chain TCR comprises an amino acid sequence having at least 95%, at least 96%, at least 97%, at least 98%, or at least 99% identity to a sequence set forth in SEQ ID NOs: 23 or 31 and the beta chain comprises an amino acid sequence having at least 95%, at least 96%, at least 97%, at least 98%, or at least 99% identity to a sequence set forth in SEQ ID NOs: 24 or 32. In some embodiments, the amino acid sequence of the alpha chain TCR comprises an amino acid sequence having at least 95%, at least 96%, at least 97%, at least 98%, or at least 99% identity to a sequence set forth in SEQ ID NO: 23 and the beta chain comprises an amino acid sequence having at least 95%, at least 96%, at least 97%, at least 98%, or at least 99% identity to a sequence set forth in SEQ ID NO: 24. In some embodiments, the amino acid sequence of the alpha chain TCR comprises an amino acid sequence having at least 95%, at least 96%, at least 97%, at least 98%, or at least 99% identity to a sequence set forth in SEQ ID NO: 31 and the beta chain comprises an amino acid sequence having at least 95%, at least 96%, at least 97%, at least 98%, or at least 99% identity to a sequence set forth in SEQ ID NO:32. In some embodiments, the amino acid sequence of the alpha chain TCR comprises or consists of an amino acid sequence set forth in SEQ ID NO: 23 and the beta chain comprises or consists of an amino acid sequence set forth in SEQ ID NO: 24. In some embodiments, the amino acid sequence of the alpha chain TCR comprises or consists of an amino acid sequence set forth in SEQ ID NO: 31 and the beta chain comprises or consists of an amino acid sequence set forth in SEQ ID NO:32.

In some embodiments, the present disclosure provides a recombinant TCR comprising an alpha chain and a beta chain, wherein the beta chain comprises a CDR3 sequence comprising an amino acid sequence having at least 90%, at least 95%, at least 96%, at least 97%, at least 98%, or at least 99% sequence identity to an amino acid sequence set forth in SEQ ID NOs: 6, 14, 22, 30, 38, or 46. In some embodiments, the present disclosure provides a recombinant TCR that binds WT1, comprising an alpha chain and a beta chain, wherein the alpha chain comprises a CDR3 sequence comprising an amino acid sequence having at least 90%, at least 95%, at least 96%, at least 97%, at least 98%, or at least 99% sequence identity to an amino acid sequence set forth in SEQ ID NOs: 3, 11, 19, 27, 35, or 43. In some embodiments, the beta chain comprises a CDR2 sequence comprising an amino acid sequence having at least 90%, at least 95%, at least 96%, at least 97%, at least 98%, or at least 99% sequence identity to an amino acid sequence set forth in SEQ ID NOs: 5, 13, 21, 29, 37, or 45. In some embodiments, the alpha chain comprises a CDR2 sequence comprising an amino acid sequence having at least 90%, at least 95%, at least 96%, at least 97%, at least 98%, or at least 99% sequence identity to an amino acid sequence set forth in SEQ ID NOs: 2, 10, 18, 26, 34, or 42. In some embodiments, the beta chain comprises a CDR1 sequence comprising an amino acid sequence having at least 90%, at least 95%, at least 96%, at least 97%, at least 98%, or at least 99% sequence identity to an amino acid sequence set forth in SEQ ID NOs: 4, 12, 20, 28, 36, or 44. In some embodiments, the alpha chain comprises a CDR1 sequence comprising an amino acid sequence having at least 90%, at least 95%, at least 96%, at least 97%, at least 98%, or at least 99% sequence identity to an amino acid sequence set forth in SEQ ID NOs: 1, 9, 17, 25, 33, or 41.

In some embodiments, the present disclosure provides a recombinant TCR, wherein the TCR comprises a) an alpha chain CDR3 comprising or consisting of an amino acid sequence according to SEQ ID NO: 3 and a beta chain CDR3 comprising or consisting of an amino acid sequence according to SEQ ID NO: 6; or b) an alpha chain CDR3 comprising or consisting of an amino acid sequence according to SEQ ID NO: 11 and a beta chain CDR3 comprising or consisting of an amino acid sequence according to SEQ ID NO: 14; or c) an alpha chain CDR3 comprising or consisting of an amino acid sequence according to SEQ ID NO: 19 and a beta chain CDR3 comprising or consisting of an amino acid sequence according to SEQ ID NO: 22; or d) an alpha chain CDR3 comprising or consisting of an amino acid sequence according to SEQ ID NO: 27 and a beta chain CDR3 comprising or consisting of an amino acid sequence according to SEQ ID NO: 30; or e) an alpha chain CDR3 comprising or consisting of an amino acid sequence according to SEQ ID NO: 35 and a beta chain CDR3 comprising or consisting of an amino acid sequence according to SEQ ID NO: 38; or f) an alpha chain CDR3 comprising or consisting of an amino acid sequence according to SEQ ID NO: 43 and a beta chain CDR3 comprising or consisting of an amino acid sequence according to SEQ ID NO: 46.

In some embodiments, the present disclosure provides a recombinant TCR comprising an alpha chain CDR1 comprising or consisting of an amino acid sequence according to SEQ ID NO: 1; an alpha chain CDR2 comprising or consisting of an amino acid sequence according to SEQ ID NO: 2; an alpha chain CDR3 comprising or consisting of an amino acid sequence according to SEQ ID NO: 3; a beta chain CDR1 comprising or consisting of an amino acid sequence according to SEQ ID NO: 4; a beta chain CDR2 comprising or consisting of an amino acid sequence according to SEQ ID NO: 5; and a beta chain CDR3 comprising or consisting of an amino acid sequence according to SEQ ID NO: 6.

In some embodiments, the present disclosure provides a recombinant TCR comprising an alpha chain CDR1 comprising or consisting of an amino acid sequence according to SEQ ID NO: 9; an alpha chain CDR2 comprising or consisting of an amino acid sequence according to SEQ ID NO: 10; an alpha chain CDR3 comprising or consisting of an amino acid sequence according to SEQ ID NO: 11; a beta chain CDR1 comprising or consisting of an amino acid sequence according to SEQ ID NO: 12; a beta chain CDR2 comprising or consisting of an amino acid sequence according to SEQ ID NO: 13; and a beta chain CDR3 comprising or consisting of an amino acid sequence according to SEQ ID NO: 14.

In some embodiments, the present disclosure provides a recombinant TCR comprising an alpha chain CDR1 comprising or consisting of an amino acid sequence according to SEQ ID NO: 17; an alpha chain CDR2 comprising or consisting of an amino acid sequence according to SEQ ID NO: 18; an alpha chain CDR3 comprising or consisting of an amino acid sequence according to SEQ ID NO: 19; a beta chain CDR1 comprising or consisting of an amino acid sequence according to SEQ ID NO: 20; a beta chain CDR2 comprising or consisting of an amino acid sequence according to SEQ ID NO: 21; and a beta chain CDR3 comprising or consisting of an amino acid sequence according to SEQ ID NO: 22.

In some embodiments, the present disclosure provides a recombinant TCR comprising an alpha chain CDR1 comprising or consisting of an amino acid sequence according to SEQ ID NO: 25; an alpha chain CDR2 comprising or consisting of an amino acid sequence according to SEQ ID NO: 26; an alpha chain CDR3 comprising or consisting of an amino acid sequence according to SEQ ID NO: 27; a beta chain CDR1 comprising or consisting of an amino acid sequence according to SEQ ID NO:28; a beta chain CDR2 comprising or consisting of an amino acid sequence according to SEQ ID NO: 29; and a beta chain CDR3 comprising or consisting of an amino acid sequence according to SEQ ID NO: 30.

In some embodiments, the present disclosure provides a recombinant TCR comprising an alpha chain CDR1 comprising or consisting of an amino acid sequence according to SEQ ID NO: 33; an alpha chain CDR2 comprising or consisting of an amino acid sequence according to SEQ ID NO: 34; an alpha chain CDR3 comprising or consisting of an amino acid sequence according to SEQ ID NO: 35; a beta chain CDR1 comprising or consisting of an amino acid sequence according to SEQ ID NO: 36; a beta chain CDR2 comprising or consisting of an amino acid sequence according to SEQ ID NO: 37; and a beta chain CDR3 comprising or consisting of an amino acid sequence according to SEQ ID NO: 38.

In some embodiments, the present disclosure provides a recombinant TCR comprising an alpha chain CDR1 comprising or consisting of an amino acid sequence according to SEQ ID NO: 41; an alpha chain CDR2 comprising or consisting of an amino acid sequence according to SEQ ID NO: 42; an alpha chain CDR3 comprising or consisting of an amino acid sequence according to SEQ ID NO: 43; a beta chain CDR1 comprising or consisting of an amino acid sequence according to SEQ ID NO: 44; a beta chain CDR2 comprising or consisting of an amino acid sequence according to SEQ ID NO: 45; and a beta chain CDR3 comprising or consisting of an amino acid sequence according to SEQ ID NO: 46.

In some embodiments, the present disclosure provides a recombinant TCR comprising an alpha chain and a beta chain, wherein the amino acid sequence of the alpha chain TCR comprises an amino acid sequence having at least 90%, at least 95%, at least 96%, at least 97%, at least 98%, or at least 99% identity to a sequence set forth in SEQ ID NOs: 7, 15, 23, 31, 39, or 47 and the beta chain comprises an amino acid sequence having at least 90%, at least 95%, at least 96%, at least 97%, at least 98%, or at least 99% identity to a sequence set forth in SEQ ID NOs: 8, 16, 24, 32, 40, or 48. In some embodiments, the amino acid sequence of the alpha chain TCR comprises an amino acid sequence having at least 90%, at least 95%, at least 96%, at least 97%, at least 98%, or at least 99% identity to a sequence set forth in SEQ ID NO: 7 and the beta chain comprises an amino acid sequence having at least 90%, at least 95%, at least 96%, at least 97%, at least 98%, or at least 99% identity to a sequence set forth in SEQ ID NO: 8. In some embodiments, the amino acid sequence of the alpha chain TCR comprises an amino acid sequence having at least 90%, at least 95%, at least 96%, at least 97%, at least 98%, or at least 99% identity to a sequence set forth in SEQ ID NO: 15 and the beta chain comprises an amino acid sequence having at least 90%, at least 95%, at least 96%, at least 97%, at least 98%, or at least 99% identity to a sequence set forth in SEQ ID NO: 16. In some embodiments, the amino acid sequence of the alpha chain TCR comprises an amino acid sequence having at least 90%, at least 95%, at least 96%, at least 97%, at least 98%, or at least 99% identity to a sequence set forth in SEQ ID NO: 23 and the beta chain comprises an amino acid sequence having at least 90%, at least 95%, at least 96%, at least 97%, at least 98%, or at least 99% identity to a sequence set forth in SEQ ID NO: 24. In some embodiments, the amino acid sequence of the alpha chain TCR comprises an amino acid sequence having at least 90%, at least 95%, at least 96%, at least 97%, at least 98%, or at least 99% identity to a sequence set forth in SEQ ID NO: 31 and the beta chain comprises an amino acid sequence having at least 90%, at least 95%, at least 96%, at least 97%, at least 98%, or at least 99% identity to a sequence set forth in SEQ ID NO: 32. In some embodiments, the amino acid sequence of the alpha chain TCR comprises an amino acid sequence having at least 90%, at least 95%, at least 96%, at least 97%, at least 98%, or at least 99% identity to a sequence set forth in SEQ ID NO: 39 and the beta chain comprises an amino acid sequence having at least 90%, at least 95%, at least 96%, at least 97%, at least 98%, or at least 99% identity to a sequence set forth in SEQ ID NO: 40. In some embodiments, the amino acid sequence of the alpha chain TCR comprises an amino acid sequence having at least 90%, at least 95%, at least 96%, at least 97%, at least 98%, or at least 99% identity to a sequence set forth in SEQ ID NO: 47 and the beta chain comprises an amino acid sequence having at least 90%, at least 95%, at least 96%, at least 97%, at least 98%, or at least 99% identity to a sequence set forth in SEQ ID NO: 48.

In some embodiments, the present disclosure provides a recombinant TCR comprising an alpha chain and a beta chain, wherein the amino acid sequence of the alpha chain TCR comprises or consists of an amino acid sequence selected from the group consisting of SEQ ID NOs: 7, 15, 23, 31, 39, and 47 and the beta chain comprises or consists of an amino acid sequence selected from the group consisting of SEQ ID NOs: 8, 16, 24, 32, 40, and 48. In some embodiments, the amino acid sequence of the alpha chain TCR comprises or consists of an amino acid sequence set forth in SEQ ID NO: 7 and the beta chain comprises or consists of an amino acid sequence set forth in SEQ ID NO: 8. In some embodiments, the amino acid sequence of the alpha chain TCR comprises or consists of an amino acid sequence set forth in SEQ ID NO: 15 and the beta chain comprises or consists of an amino acid sequence set forth in SEQ ID NO: 16. In some embodiments, the amino acid sequence of the alpha chain TCR comprises or consists of an amino acid sequence set forth in SEQ ID NO: 23 and the beta chain comprises or consists of an amino acid sequence set forth in SEQ ID NO: 24. In some embodiments, the amino acid sequence of the alpha chain TCR comprises or consists of an amino acid sequence set forth in SEQ ID NO: 31 and the beta chain comprises or consists of an amino acid sequence set forth in SEQ ID NO: 32. In some embodiments, the amino acid sequence of the alpha chain TCR comprises or consists of an amino acid sequence set forth in SEQ ID NO: 39 and the beta chain comprises or consists of an amino acid sequence set forth in SEQ ID NO: 40. In some embodiments, the amino acid sequence of the alpha chain TCR comprises or consists of an amino acid sequence set forth in SEQ ID NO: 47 and the beta chain comprises or consists of an amino acid sequence set forth in SEQ ID NO: 48.

In some embodiments, the present disclosure provides a recombinant TCR that is capable of binding to an epitope on the WT1 protein epitope or capable of eliciting a functional T cell response. In some embodiments, the T cell response is measured by CD69 expression or T cell cytolysis. In some embodiments, the epitope comprises a sequence according to SEQ ID NO: 97. In some embodiments, the TCR is capable of binding to a WT1/HLA-A2 complex with an interaction half-life ($t_{1/2}$) of less than 100 seconds, or about 30 seconds to about 1000 seconds. In some embodiments, the TCR binds a WT1/HLA-A2 complex and is capable of activating a functional T cell response and having an $EC_{50}$ less than about 100 nM, less than about 10 nM, less than about 1 nM, less than about 500 pM, less than about 100 pM, or less than about 1 pM.

In some embodiments, the present disclosure provides a recombinant TCR, wherein the TCR is a soluble TCR. In some embodiments, the TCR is coupled to an antibody or fragment thereof. In some embodiments, the antibody or fragment thereof is a monoclonal antibody, scFv, or Fab. In some embodiments, the antibody or fragment thereof is an anti-CD3 scFv or an anti-CD3 Fab.

In some embodiments, the present disclosure provides a method for treating cancer in a subject in need thereof, comprising administering to the subject an effective amount of a composition comprising a recombinant TCR described herein. In some embodiments, the present disclosure provides a recombinant TCR for use in a method of treating cancer in a subject in need thereof. In some embodiments, the cancer is a leukemia.

In some embodiments, the present disclosure provides a recombinant host cell comprising an exogenous TCR, wherein the exogenous TCR comprises an exogenous alpha chain and an exogenous beta chain, wherein the alpha chain and the beta chain each comprise CDR1, CDR2, and CDR3, wherein the alpha chain CDR3 comprises an amino acid sequence having at least 90%, at least 95%, at least 96%, at least 97%, at least 98%, or at least 99% sequence identity to an amino acid sequence selected from the group consisting of SEQ ID NOs: 3, 11, 19, 27, 35, and 43. In some embodiments, the present disclosure provides a recombinant host cell comprising an exogenous TCR, wherein the exogenous TCR comprises an exogenous alpha chain and an exogenous beta chain, wherein the alpha chain and the beta chain each comprise CDR1, CDR2, and CDR3, wherein the beta chain CDR3 comprises an amino acid sequence having at least 90%, at least 95%, at least 96%, at least 97%, at least 98%, or at least 99% sequence identity to an amino acid sequence selected from the group consisting of SEQ ID NOs: 6, 14, 22, 30, 38, and 46. In some embodiments, the alpha chain comprises a CDR2 sequence comprising an amino acid sequence having at least 90%, at least 95%, at least 96%, at least 97%, at least 98%, or at least 99% sequence identity to an amino acid sequence selected from the group consisting of SEQ ID NOs: 2, 10, 18, 26, 34, and 42. In some embodiments, the beta chain comprises a CDR2 sequence comprising an amino acid sequence having at least 90%, at least 95%, at least 96%, at least 97%, at least 98%, or at least 99% sequence identity to an amino acid sequence selected from the group consisting of SEQ ID NOs: 5, 13, 21, 29, 37, and 45. In some embodiments, the alpha chain comprises a CDR1 sequence comprising an amino acid sequence having at least 90%, at least 95%, at least 96%, at least 97%, at least 98%, or at least 99% sequence identity to an amino acid sequence selected from the group consisting of SEQ ID NOs: 1, 9, 17, 25, 33, and 41. In some embodiments, the beta chain comprises a CDR1 sequence comprising an amino acid sequence having at least 90%, at least 95%, at least 96%, at least 97%, at least 98%, or at least 99% sequence identity to an amino acid sequence selected from the group consisting of SEQ ID NOs: 4, 12, 20, 28, 36, and 44.

In some embodiments, the present disclosure provides a recombinant host cell comprising an exogenous TCR, wherein the exogenous TCR comprises a) an alpha chain CDR3 comprising or consisting of an amino acid sequence according to SEQ ID NO: 3 and a beta chain CDR3 comprising or consisting of an amino acid sequence according to SEQ ID NO: 6; or b) an alpha chain CDR3 comprising or consisting of an amino acid sequence according to SEQ ID NO: 11 and a beta chain CDR3 comprising or consisting of an amino acid sequence according to SEQ ID NO: 14; or c) an alpha chain CDR3 comprising or consisting of an amino acid sequence according to SEQ ID NO: 19 and a beta chain CDR3 comprising or consisting of an amino acid sequence according to SEQ ID NO: 22; or d) an alpha chain CDR3 comprising or consisting of an amino acid sequence according to SEQ ID NO: 27 and a beta chain CDR3 comprising or consisting of an amino acid sequence according to SEQ ID NO: 30; or e) an alpha chain CDR3 comprising or consisting of an amino acid sequence according to SEQ ID NO: 35 and a beta chain CDR3 comprising or consisting of an amino acid sequence according to SEQ ID NO: 38; or f) an alpha chain CDR3 comprising or consisting of an amino acid sequence according to SEQ ID NO: 43 and a beta chain CDR3 comprising or consisting of an amino acid sequence according to SEQ ID NO: 46.

In some embodiments, the present disclosure provides a recombinant host cell comprising an exogenous TCR, wherein the exogenous TCR comprises an alpha chain CDR1 comprising or consisting of an amino acid sequence according to SEQ ID NO: 1; an alpha chain CDR2 comprising or consisting of an amino acid sequence according to SEQ ID NO: 2; an alpha chain CDR3 comprising or consisting of an amino acid sequence according to SEQ ID NO: 3; a beta chain CDR1 comprising or consisting of an amino acid sequence according to SEQ ID NO: 4; a beta chain CDR2 comprising or consisting of an amino acid sequence according to SEQ ID NO: 5; and a beta chain CDR3 comprising or consisting of an amino acid sequence according to SEQ ID NO: 6.

In some embodiments, the present disclosure provides a recombinant host cell comprising an exogenous TCR, wherein the exogenous TCR comprises an alpha chain CDR1 comprising or consisting of an amino acid sequence according to SEQ ID NO: 9; an alpha chain CDR2 comprising or consisting of an amino acid sequence according to SEQ ID NO: 10; an alpha chain CDR3 comprising or consisting of an amino acid sequence according to SEQ ID NO: 11; a beta chain CDR1 comprising or consisting of an amino acid sequence according to SEQ ID NO: 12; a beta chain CDR2 comprising or consisting of an amino acid sequence according to SEQ ID NO: 13; and a beta chain CDR3 comprising or consisting of an amino acid sequence according to SEQ ID NO: 14.

In some embodiments, the present disclosure provides a recombinant host cell comprising an exogenous TCR, wherein the exogenous TCR comprises an alpha chain CDR1 comprising or consisting of an amino acid sequence according to SEQ ID NO: 17; an alpha chain CDR2 comprising or consisting of an amino acid sequence according to SEQ ID NO: 18; an alpha chain CDR3 comprising or consisting of an amino acid sequence according to SEQ ID NO: 19; a beta chain CDR1 comprising or consisting of an amino acid sequence according to SEQ ID NO: 20; a beta chain CDR2 comprising or consisting of an amino acid sequence according to SEQ ID NO: 21; and a beta chain CDR3 comprising or consisting of an amino acid sequence according to SEQ ID NO: 22.

In some embodiments, the present disclosure provides a recombinant host cell comprising an exogenous TCR, wherein the exogenous TCR comprises an alpha chain CDR1 comprising or consisting of an amino acid sequence according to SEQ ID NO: 25; an alpha chain CDR2 comprising or consisting of an amino acid sequence according to SEQ ID NO: 26; an alpha chain CDR3 comprising or consisting of an amino acid sequence according to SEQ ID NO: 27; a beta chain CDR1 comprising or consisting of an amino acid sequence according to SEQ ID NO: 28; a beta chain CDR2 comprising or consisting of an amino acid sequence according to SEQ ID NO: 29; and a beta chain CDR3 comprising or consisting of an amino acid sequence according to SEQ ID NO: 30.

In some embodiments, the present disclosure provides a recombinant host cell comprising an exogenous TCR, wherein the exogenous TCR comprises an alpha chain CDR1 comprising or consisting of an amino acid sequence according to SEQ ID NO: 33; an alpha chain CDR2 comprising or consisting of an amino acid sequence according to SEQ ID NO: 34; an alpha chain CDR3 comprising or consisting of an amino acid sequence according to SEQ ID NO: 35; a beta chain CDR1 comprising or consisting of an amino acid sequence according to SEQ ID NO: 36; a beta chain CDR2 comprising or consisting of an amino acid sequence according to SEQ ID NO: 37; and a beta chain CDR3 comprising or consisting of an amino acid sequence according to SEQ ID NO: 38.

In some embodiments, the present disclosure provides a recombinant host cell comprising an exogenous TCR, wherein the exogenous TCR comprises an alpha chain CDR1 comprising or consisting of an amino acid sequence according to SEQ ID NO: 41; an alpha chain CDR2 comprising or consisting of an amino acid sequence according to SEQ ID NO: 42; an alpha chain CDR3 comprising or consisting of an amino acid sequence according to SEQ ID NO: 43; a beta chain CDR1 comprising or consisting of an amino acid sequence according to SEQ ID NO: 44; a beta chain CDR2 comprising or consisting of an amino acid sequence according to SEQ ID NO: 45; and a beta chain CDR3 comprising or consisting of an amino acid sequence according to SEQ ID NO: 46.

In some embodiments, the present disclosure provides a recombinant host cell comprising an exogenous TCR, wherein the amino acid sequence of the TCR alpha chain comprises an amino acid sequence selected from the group consisting of SEQ ID NOs: 7, 15, 23, 31, 39, and 47 and the TCR beta chain comprises an amino acid sequence selected from the group consisting of SEQ ID NOs: 8, 16, 24, 32, 40, and 48. In some embodiments, the amino acid sequence of the alpha chain TCR comprises an amino acid sequence having at least 90%, at least 95%, at least 96%, at least 97%, at least 98%, or at least 99% identity to SEQ ID NO: 7 and the beta chain comprises an amino acid sequence having at least 90%, at least 95%, at least 96%, at least 97%, at least 98%, or at least 99% identity to SEQ ID NO: 8. In some embodiments, the amino acid sequence of the alpha chain TCR comprises an amino acid sequence having at least 90%, at least 95%, at least 96%, at least 97%, at least 98%, or at least 99% identity to SEQ ID NO: 15 and the beta chain comprises an amino acid sequence having at least 90%, at least 95%, at least 96%, at least 97%, at least 98%, or at least 99% identity to SEQ ID NO: 16. In some embodiments, the amino acid sequence of the alpha chain TCR comprises an amino acid sequence having at least 90%, at least 95%, at least 96%, at least 97%, at least 98%, or at least 99% identity to SEQ ID NO: 23 and the beta chain comprises an amino acid sequence having at least 90%, at least 95%, at least 96%, at least 97%, at least 98%, or at least 99% identity to SEQ ID NO: 24.3

In some embodiments, the amino acid sequence of the alpha chain TCR comprises an amino acid sequence having at least 90%, at least 95%, at least 96%, at least 97%, at least 98%, or at least 99% identity to SEQ ID NO: 31 and the beta chain comprises an amino acid sequence having at least 90%, at least 95%, at least 96%, at least 97%, at least 98%, or at least 99% identity to SEQ ID NO: 32. In some embodiments, the amino acid sequence of the alpha chain TCR comprises an amino acid sequence having at least 90%, at least 95%, at least 96%, at least 97%, at least 98%, or at least 99% identity to SEQ ID NO: 39 and the beta chain comprises an amino acid sequence having at least 90%, at least 95%, at least 96%, at least 97%, at least 98%, or at least 99% identity to SEQ ID NO: 40. In some embodiments, the amino acid sequence of the alpha chain TCR comprises an amino acid sequence having at least 90%, at least 95%, at least 96%, at least 97%, at least 98%, or at least 99% identity to SEQ ID NO: 47 and the beta chain comprises an amino acid sequence having at least 90%, at least 95%, at least 96%, at least 97%, at least 98%, or at least 99% identity to SEQ ID NO: 48.

In some embodiments, the present disclosure provides a recombinant host cell comprising an exogenous TCR wherein the amino acid sequence of the alpha chain TCR comprises or consists of an amino acid sequence set forth in SEQ ID NO: 7 and the beta chain comprises or consists of an amino acid sequence set forth in SEQ ID NO: 8. In some embodiments, the present disclosure provides a recombinant host cell comprising an exogenous TCR wherein the amino acid sequence of the alpha chain TCR comprises or consists of an amino acid sequence set forth in SEQ ID NO: 15 and the beta chain comprises or consists of an amino acid sequence set forth in SEQ ID NO: 16. In some embodiments, the present disclosure provides a recombinant host cell comprising an exogenous TCR wherein the amino acid sequence of the alpha chain TCR comprises or consists of an amino acid sequence set forth in SEQ ID NO: 23 and the beta chain comprises or consists of an amino acid sequence set forth in SEQ ID NO: 24. In some embodiments, the present disclosure provides a recombinant host cell comprising an exogenous TCR wherein the amino acid sequence of the alpha chain TCR comprises or consists of an amino acid sequence set forth in SEQ ID NO: 31 and the beta chain comprises or consists of an amino acid sequence set forth in SEQ ID NO: 32. In some embodiments, the present disclosure provides a recombinant host cell comprising an exogenous TCR wherein the amino acid sequence of the alpha chain TCR comprises or consists of an amino acid sequence set forth in SEQ ID NO: 39 and the beta chain comprises or consists of an amino acid sequence set forth in SEQ ID NO: 40. In some embodiments, the present disclosure provides a recombinant host cell comprising an exogenous TCR wherein the amino acid sequence of the alpha chain TCR comprises or consists of an amino acid sequence set forth in SEQ ID NO: 47 and the beta chain comprises or consists of an amino acid sequence set forth in SEQ ID NO: 48.

In some embodiments, the present disclosure provides a recombinant host cell comprising an exogenous TCR wherein the host cell is a hematopoietic progenitor cell. In some embodiments, the host cell is an immune cell. In some embodiments, the immune cell is a T cell, NK cell, or NK T cell. In some embodiments, the T cell is a naïve T cell, an effector T cell, a central memory T cell, an effector memory T cell, a CD4+ T cell, a CD8+ T cell, an alpha/beta T cell, a gamma/delta T cell, or any combination thereof. In some embodiments, the T cell is a CD8+ T cell.

In some embodiments, the present disclosure provides a host cell comprising an exogenous TCR, wherein the exogenous TCR comprises one or more modifications to reduce the frequency of mis-pairing between exogenous TCR alpha and beta chains with endogenous TCR alpha and beta chains in the T cell. In some embodiments, the one or more modifications are selected from the group consisting of one or more cysteine mutations, one or more knob-and-hole mutations, dimerization peptides fused to the exogenous TCR alpha and/or beta chains, or one or more linker molecules linking the exogenous TCR alpha and beta chains. In some embodiments, the one or more cysteine mutations is present in the constant region of the exogenous TCR.

In some embodiments, the present disclosure provides a host cell comprising an exogenous TCR, wherein the cell is further engineered to express an exogenous immune activating molecule. In some embodiments, the immune activating molecule is a cytokine or a ligand. In some embodiments, the immune activating molecule is selected from the group consisting of IL-12, TNFα, IFNγ, IL2, IL-7, IL-15, IL-18, CD40L, and IL-21.

In some embodiments, the present disclosure provides a method for treating cancer in a subject in need thereof, comprising administering to the subject a recombinant host cell described herein. In some embodiments, the present disclosure provides use of a recombinant host cell described herein in a method for treating cancer. In some embodiments, the cancer is a leukemia.

In some embodiments, the present disclosure provides a method for treating cancer in a subject in need thereof, comprising the steps of: a) isolating T cells from peripheral blood mononuclear cells (PBMC) obtained from the subject;

b) transducing or transfecting the T cells with a nucleic acid comprising a sequence selected from the group consisting of SEQ ID NOs: 55, 56, 63, 64, 71, 72, 79, 80, 87, 88, 95, and/or 96; and c) administering the transduced or transfected T cells to the subject. In some embodiments, the present disclosure provides a method for treating cancer in a subject in need thereof, comprising the steps of: a) obtaining T cells from a donor source; b) transducing or transfecting the T cells with a nucleic acid comprising a sequence selected from the group consisting of SEQ ID NOs: 55, 56, 63, 64, 71, 72, 79, 80, 87, 88, 95, and/or 96; and c) administering the transduced or transfected T cells to the subject. In some embodiments, the T cells are transduced or transfected a nucleic acid sequence comprising or consisting of a) SEQ ID NOs: 55 and 56; or b) SEQ ID NOs: 63 and 64; or c) SEQ ID NOs: 71 and 72; or d) SEQ ID NOs: 79 and 80; or e) SEQ ID NOs: 87 and 88; or f) SEQ ID NOs: 95 and 96.

In some embodiments, the nucleic acid sequence is comprised in a vector. In some embodiments, the T cells are further transduced or transfected with a nucleic acid encoding an immune activating molecule. In some embodiments, the immune activating molecule is a ligand or a cytokine. In some embodiments, the immune activating molecule is selected from the group consisting of IL-12, TNFα, IFNγ, IL2, IL-7, IL-15, IL-18, CD40L, and IL-21. In some embodiments, the method further comprises expanding the transduced or transfected T cells prior to administration to the subject.

In some embodiments, the present disclosure provides a method of producing a T cell comprising exogenous alpha and beta TCR chains, the method comprising transducing or transfecting an isolated T cell with one or more polynucleotides, wherein the polynucleotides comprises a sequence selected from the group consisting of SEQ ID NOs: 55, 56, 63, 64, 71, 72, 79, 80, 87, 88, 95, and/or 96; and incubating the cell under conditions suitable for expression of the exogenous alpha and beta TCR chains by the cell. In some embodiments, the isolated T cell is transduced or transfected with polynucleotides comprising or consisting of a). SEQ ID NOs: 55 and 56; or b). SEQ ID NOs: 63 and 64; or c). SEQ ID NOs: 71 and 72 or d). SEQ ID NOs: 79 and 80 or e). SEQ ID NOs: 87 and 88 or f). SEQ ID NOs: 95 and 96. In some embodiments, the method further comprises transducing or transfecting the isolated T cell with a nucleic acid encoding an immune activating molecule. In some embodiments, the immune activating molecule is a ligand or a cytokine. In some embodiments, the immune activating molecule is selected from the group consisting of IL-12, TNFα, IFNγ, IL2, IL-7, IL-15, IL-18, CD40L, and IL-21.

In some embodiments, the present disclosure provides a pharmaceutical composition comprising a recombinant TCR described herein. In some embodiments, the present disclosure provides a pharmaceutical composition comprising a combination of TCRs comprising amino acid sequences selected from the group consisting of SEQ ID NOs: 1-48. In some embodiments, the present disclosure provides a vector capable of expressing a nucleic acid molecule encoding a TCR alpha chain having an amino acid sequence selected from the group consisting of SEQ ID NOs: 7, 15, 23, 31, 39, or 47. In some embodiments, the present disclosure provides a vector capable of expressing a nucleic acid molecule encoding a TCR beta chain having an amino acid sequence selected from the group consisting of SEQ ID NOs: 8, 16, 24, 32, 40, or 48. In some embodiments, the present disclosure provides a cell comprising a vector described herein.

In some embodiments, the present disclosure provides a cell comprising a first vector capable of expressing a nucleic acid molecule encoding a TCR alpha chain comprising an amino acid sequence having at least 90%, 95%, 96%, 97%, 98%, or 99% sequence identity to an amino acid sequence selected from the group consisting of SEQ ID NOs: 7, 15, 23, 31, 39, and 47 and a second vector capable of expressing a nucleic acid molecule encoding a TCR beta chain comprising an amino acid sequence having at least 90%, 95%, 96%, 97%, 98%, or 99% sequence identity to an amino acid sequence selected from the group consisting of SEQ ID NOs: 8, 16, 24, 32, 40, and 48.

In some embodiments, the first vector is capable of expressing a nucleic acid molecule encoding a TCR alpha chain comprising or consisting of an amino acid sequence according to SEQ ID NO: 7 and the second vector is capable of expressing a nucleic acid molecule encoding a TCR beta chain comprising or consisting of an amino acid sequence according to SEQ ID NO: 8. In some embodiments, the first vector is capable of expressing a nucleic acid molecule encoding a TCR alpha chain comprising or consisting of an amino acid sequence according to SEQ ID NO: 15 and the second vector is capable of expressing a nucleic acid molecule encoding a TCR beta chain comprising or consisting of an amino acid sequence according to SEQ ID NO: 16. In some embodiments, the first vector is capable of expressing a nucleic acid molecule encoding a TCR alpha chain comprising or consisting of an amino acid sequence according to SEQ ID NO: 23 and the second vector is capable of expressing a nucleic acid molecule encoding a TCR beta chain comprising or consisting of an amino acid sequence according to SEQ ID NO: 24. In some embodiments, the first vector is capable of expressing a nucleic acid molecule encoding a TCR alpha chain comprising or consisting of an amino acid sequence according to SEQ ID NO: 31 and the second vector is capable of expressing a nucleic acid molecule encoding a TCR beta chain comprising or consisting of an amino acid sequence according to SEQ ID NO: 32. In some embodiments, the first vector is capable of expressing a nucleic acid molecule encoding a TCR alpha chain comprising or consisting of an amino acid sequence according to SEQ ID NO: 39 and the second vector is capable of expressing a nucleic acid molecule encoding a TCR beta chain comprising or consisting of an amino acid sequence according to SEQ ID NO: 40. In some embodiments, the first vector is capable of expressing a nucleic acid molecule encoding a TCR alpha chain comprising or consisting of an amino acid sequence according to SEQ ID NO: 47 and the second vector is capable of expressing a nucleic acid molecule encoding a TCR beta chain comprising or consisting of an amino acid sequence according to SEQ ID NO: 48.

In some embodiments, the present disclosure provides a cDNA encoding a T cell receptor (TCR) that binds Wilms' tumor antigen-1 (WT1), comprising an alpha chain and a beta chain, wherein the beta chain comprises a CDR3 sequence comprising an amino acid sequence having at least 90%, 95%, 96%, 97%, 98%, or 99% sequence identity to an amino acid sequence set forth in SEQ ID NOs: 6, 14, 22, 30, 38, or 46. In some embodiments, the present disclosure provides a cDNA encoding a TCR that binds WT1, comprising an alpha chain and a beta chain, wherein the alpha chain comprises a CDR3 sequence comprising an amino acid sequence having at least 90%, 95%, 96%, 97%, 98%, or 99% sequence identity to an amino acid sequence set forth in SEQ ID NOs: 3, 11, 19, 27, 35, or 43.

In some embodiments, the present disclosure provides a T cell receptor (TCR) or a portion thereof that binds WT-1, comprising an alpha chain and a beta chain, wherein the beta chain comprises a CDR3 sequence comprising an amino acid sequence having at least 90% sequence identity to an amino acid sequence set forth in SEQ ID NOs: 6, 14, 22, 30, 38, or 46, wherein the antigen specificity of the TCR or portion thereof is determined by a method comprising the steps of: (a) sequencing recombind nucleic acids encoding one or more TCR chain(s), or a portion thereof, from a first portion of a sample comprising T cells to generate a first multiplicity of sequence reads obtained from T cells prior to WT-1 antigen exposure of the sample, wherein the sequencing is high-throughput sequencing; (b) partitioning a second portion of the sample comprising T cells into a plurality of reaction mixtures and exposing each reaction mixture of the plurality of reaction mixtures to WT-1 antigens; (c) for each reaction mixture in the plurality of reaction mixtures, separating T cells that interact with one or more WT-1 antigens in the reaction mixture to obtain a subset of WT-1 antigen-specific T cells, wherein each of the subsets of antigen-specific T cells corresponds to one reaction mixture in the plurality of reaction mixtures; (d) for each of the subsets of WT-1 antigen-specific T cells separated in step (c), sequencing recombined nucleic acids encoding one or more TCR chain(s), or a portion thereof, to generate a multiplicity of sequence reads obtained from each of the subsets of antigen-specific T cells, wherein the sequencing is high-throughput sequencing; (e) for each reaction mixture in the plurality of reaction mixtures, identifying a plurality of antigen-specific TCR chains, or portion thereof, by comparing the multiplicity of sequence reads obtained from each of the subsets of WT-1 antigen-specific T cells in step (d) to the first multiplicity of sequence reads obtained from unstimulated T cells in step (a), wherein the frequency of the sequence reads for the WT-1 antigen-specific TCR chains, or portion thereof, is increased in the multiplicity of sequence reads obtained from the subsets of antigen-specific T cells compared to the frequency of sequence reads for the antigen-specific TCR chains, or portion thereof, in the first multiplicity of sequence reads obtained from unstimulated T cells; and (f) identifying one or more TCR chains, or portion thereof, specific for the WT-1 antigen from the one or more TCR chains, or a portion thereof, identified in step (e), wherein the frequency of the sequence reads for the one or more TCR chains, or portion thereof, specific for the antigen is increased in the multiplicity of sequence reads obtained from each of the subsets of antigen-specific T cells in which the antigen was present in the corresponding reaction mixture.

In some embodiments, the present disclosure provides a T cell receptor (TCR) or a portion thereof that binds WT-1, comprising an alpha chain and a beta chain, wherein the beta chain comprises a CDR3 sequence comprising an amino acid sequence having at least 90% sequence identity to an amino acid sequence set forth in SEQ ID NOs: 6, 14, 22, 30, 38, or 46, wherein the antigen specificity of the TCR or portion thereof is determined by a method comprising the steps of: dividing a tissue sample into a first subset and a second subset; sequencing recombined nucleic acids encoding a TCR or a portion thereof from the first subset to provide sequence reads from which clonotypes are determined; exposing the second subset to WT-1 antigen; separating T cells from the second subset that interact with the antigen to obtain an enriched T cell sample; sequencing recombined nucleic acids encoding a TCR or a portion thereof from the enriched T cell sample to provide sequence reads from which clonotypes are determined; and identifying WT-1 antigen-specific T cells in the tissue sample as T cells whose clonotype frequencies increase in the enriched T cell sample relative to the frequencies of the same clonotype in the first subset.

In some embodiments, the present disclosure provides a T cell receptor (TCR) or a portion thereof that binds WT-1, comprising an alpha chain and a beta chain, wherein the alpha chain comprises a CDR3 sequence comprising an amino acid sequence having at least 90% sequence identity to an amino acid sequence set forth in SEQ ID NOs: 3, 11, 19, 27, 35, or 43, wherein the antigen specificity of the TCR or portion thereof is determined by a method comprising the steps of: dividing a tissue sample into a first subset and a second subset; sequencing recombined nucleic acids encoding a TCR or a portion thereof from the first subset to provide sequence reads from which clonotypes are determined; exposing the second subset to WT-1 antigen; separating T cells from the second subset that interact with the antigen to obtain an enriched T cell sample; sequencing recombined nucleic acids encoding a TCR or a portion In some embodiments, the present disclosure provides a T cell receptor (TCR) or a portion thereof that binds WT-1, comprising an alpha chain and a beta chain, wherein the alpha chain comprises a CDR3 sequence comprising an amino acid sequence having at least 90% sequence identity to an amino acid sequence set forth in SEQ ID NOs: 3, 11, 19, 27, 35, or 43, wherein the antigen specificity of the TCR or portion thereof is determined by a method comprising the steps of: (a) sequencing recombined nucleic acids encoding one or more TCR chain(s), or a portion thereof, from a first portion of a sample comprising T cells to generate a first multiplicity of sequence reads obtained from T cells prior to WT-1 antigen exposure of the sample, wherein the sequencing is high-throughput sequencing; (b) partitioning a second portion of the sample comprising T cells into a plurality of reaction mixtures and exposing each reaction mixture of the plurality of reaction mixtures to WT-1 antigens; (c) for each reaction mixture in the plurality of reaction mixtures, separating T cells that interact with one or more WT-1 antigens in the reaction mixture to obtain a subset of WT-1 antigen-specific T cells, wherein each of the subsets of antigen-thereof from the enriched T cell sample to provide sequence reads from which clonotypes are determined; and identifying WT-1 antigen-specific T cells in the tissue sample as T cells whose clonotype frequencies increase in the enriched T cell sample relative to the frequencies of the same clonotype in the first subset.

In some embodiments, the beta chain comprises a CDR2 sequence comprising an amino acid sequence having at least 90% sequence identity to an amino acid sequence set forth in SEQ ID NOs: 5, 13, 21, 29, 37, or 45. In some embodiments, the alpha chain comprises a CDR2 sequence comprising an amino acid sequence having at least 90% sequence identity to an amino acid sequence set forth in SEQ ID NOs: 2, 10, 18, 26, 34, or 42. In some embodiments, the beta chain comprises a CDR1 sequence comprising an amino acid sequence having at least 90% sequence identity to an amino acid sequence set forth in SEQ ID NO: 4, 12, 20, 28, 36, or 44. In some embodiments, the alpha chain comprises a CDR1 sequence comprising an amino acid sequence having at least 90% sequence identity to an amino acid sequence set forth in SEQ ID NO: 1, 9, 17, 25, 33, or 41. In some embodiments, the TCR is capable of binding to an epitope on the WT1 protein epitope or capable of eliciting a functional T cell response.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE FIGURES

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIG. 1A and FIG. 1B show the avidity and half-life of WT1 tetramers with either the gene expression constructs for either eJH30_WT1C_5 (FIG. 1A) or eJH30_WT1C_8 (FIG. 1B) were electroporated into TCR-deficient cells. WT1-expressing T cells were then stained with WT1/HLA-A2-PE tetramers. Tetramer dissociation over time was plotted as the natural logarithm of tetramer fluorescence intensity (minus background) over time. The slope of this line provided the negative of the dissociation rate (–kd), and (ln(2))/kd represents the half-life ($t_{1/2}$) of WT1/HLA-A2 tetramer's interaction with TCR on the cells.

FIG. 9 shows IFNγ secretion from eJH52_13 expressing T cells in the presence of endogenous WT1 expression only, exogenous WT1 peptide, or WT1-epitope-containing ivtRNA.

FIG. 10A), eJH52_13 (52_13; FIG. 10B), eJH64_6 (64_6; FIG. 10C), and eJH64_9 (64_9; FIG. 10D). TCRs were expressed in a TCR deficient cell line, and incubated with cells that had been pulsed with the indicated concentration (nM) of WT1 peptide (SEQ ID NO: 97). Mean fluorescence intensity (MFI) of CD69 on CD3+ cells was assessed by FACS after a 2 hour incubation to assess the relative potency of the TCRs.

FIG. 17A shows clonotype frequencies from CMV pp65$_{495}$ pentamer+ versus pentamer–CD8+ T cells from a characterized CMV responder. The 8 dots (enclosed in dashed ellipse 600) indicate clonotypes greater than 10-fold enriched and exceeding a 20-cell equivalent minimum frequency threshold in the sorted (pentamer+) population. FIG. 17B shows that all 8 clonotypes identified in FIG. 17A are enriched in (unsorted) PBMCs from the same individual. The dots enclosed by the dashed ellipse (602) indicate clonotypes identified in FIG. 17A.

FIG. 18A-FIG. 18C show data for identification of CMV pp65$_{495}$-specific T cell clonotypes from sorted responding cells following peptide incubation. Clonotype frequencies from sorted responding CD37+ cells following CMV pp65$_{495}$ peptide incubation versus either sorted non-responding CD137– cells (FIG. 18A) or unsorted PBMCs (FIG. 18B). The 9 data points enclosed by dashed ellipse (700) in panel A indicate clonotypes greater than 10-fold enriched and exceeding a 20-cell equivalent minimum frequency threshold in the sorted (CD137+) population. Data points enclosed in dashed ellipse (702) in panel B indicate those clonotypes identified in panel A. Clonotypes identified in panel A are not enriched in sorted CD137+ cells versus CD137– T cells (FIG. 18C arrows indicating data points corresponding to those enclosed by ellipses in FIG. 18A and FIG. 18B) following incubation without peptide.

In FIG. 19A, the plot shows clonotype frequencies of the 8 clonotypes (enclosed by dashed ellipse 800) identified in the pentamer analyses in the clonotype profiles of CD137+ responding cells following CMV pp65$_{495}$ peptide incubation versus sorted non-responding CD137– cells. In FIG. 19B, the plot shows clonotype frequencies of the 9 clonotypes (enclosed by dashed ellipse 802) identified in the CD137 assay analyses in the clonotype profiles of sorted CMV pp65$_{495}$ pentamer+ cells versus pentamer– cells. 8/9 of these clonotypes are overlapping with those identified in FIG. 19A.

In FIG. 20A, clonotype frequencies from sorted proliferating CD8+ T cells following CMV pp65$_{495}$ peptide incubation at day 6 versus fresh unsorted PBMCs. The 16 data points (enclosed by dashed ellipse 900) indicate clonotypes greater than 10-fold enriched and exceeding 1/10,000 minimum frequency threshold in the sorted proliferating cells. FIG. 20B shows data of clonotype frequencies from sorted proliferating CD8+ T cells following incubation without peptide at day 6 versus fresh unsorted PBMCs. Clonotypes (represented by data points enclosed by dashed ellipses (902) are those identified in FIG. 20A. FIG. 20C shows data of clonotype frequencies from CMV pp65$_{495}$ pentamer+ versus pentamer– CD8+ T cells. Dashed ellipses (904) and arrow (906) indicate the 16 clonotypes identified in the proliferation assay whose results are represented in FIG. 20A with those clonotypes identified in the CMV pp65$_{495}$ pentamer+ versus pentamer– CD8+ T cell comparison. FIG. 20D shows data of clonotype frequencies from CMV pp65$_{495}$ pentamer+ versus pentamer– CDK+ cells. Data points enclosed by dashed ellipses (908) and designated by arrows (910) indicate the 25 clonotypes identified in a variant of the proliferation assay described above with those clonotypes identified in the CMV pp65$_{495}$ pentamer+ versus pentamer– CD8-4 T cell comparison. In this assay a pool of 138 overlapping peptides from pp65 was used instead of the single pp65$_{495}$ peptide.

FIG. 21A illustrates concepts of clonotypes in sequence space and distances between closely related clonotypes. FIG. 21B is a flow chart illustrating one embodiment of a method for distinguishing genuinely different clonotypes from clonotypes that differ solely by sequencing errors (which should be coalesced). FIG. 21C illustrates the form of a numerical function used in one embodiment for determining whether or not to coalesce related clonotypes. FIG. 21D and FIG. 21E illustrate the use of sequence trees in a method of coalescing sequence reads.

DETAILED DESCRIPTION

Figure 2:
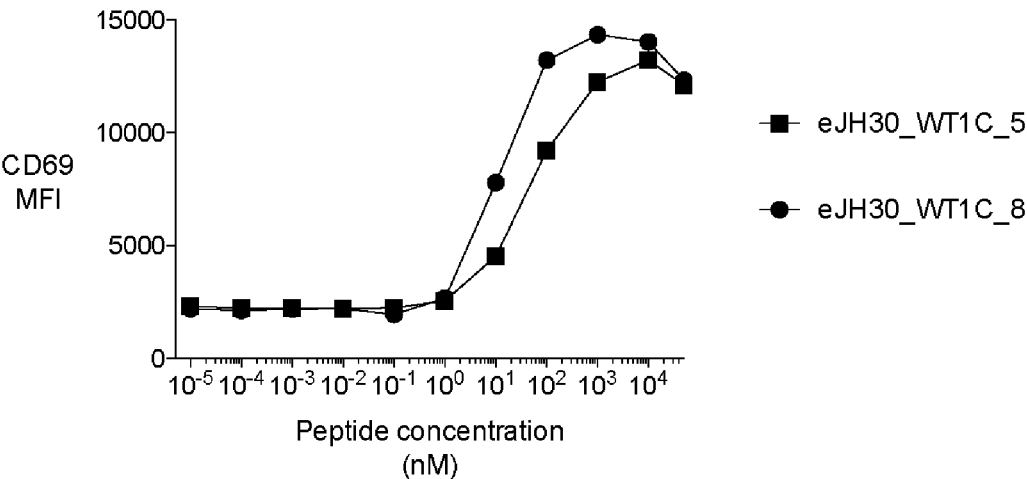
FIG. 2 shows the functional avidity of the TCRs provided herein. TCRs were expressed in a TCR deficient cell line, and incubated with cells that had been pulsed with the indicated concentration (nM) of WT1 peptide (SEQ ID NO: 97). Mean fluorescence intensity (MFI) of CD69 on CD3+ cells was assessed by FACS after a 4 hour incubation to assess the relative potency of the TCRs.

The practice of the present invention may employ, unless otherwise indicated, conventional techniques and descriptions of molecular biology, bioinformatics, cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals.

I. Definitions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W. H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6th edition (Saunders, 2007).

"Activation" or "immune activation" or "activated", especially in reference to T-cells, means a phase of an adaptive immune response that follows the antigen recognition phase (during which antigen-specific lymphocytes bind to antigens) and is characterized by proliferation of lymphocytes and their differentiation into effector cells, e.g. Abbas et al, Cellular and Molecular Immunology, Fourth Edition, (W. B. Saunders Company, 2000). Activation of T cells may be associated with secretion of certain cytokines that are detectable using conventional assays, such as an ELISPOT assay, and may be associated with the expression of characteristic cell surface markers, such as CD25, CD134, CD69, CD137, CD154, or the like, e.g. Gratama et al, Cytometry A, 73A: 971-974 (2008).

"Aligning" means a method of comparing a test sequence, such as a sequence read, to one or more reference sequences to determine which reference sequence or which portion of a reference sequence is closest based on some sequence distance measure. An exemplary method of aligning nucleotide sequences is the Smith Waterman algorithm. Distance measures may include Hamming distance, Levenshtein distance, or the like. Distance measures may include a component related to the quality values of nucleotides of the sequences being compared.

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonotype" means a recombined nucleotide sequence of a lymphocyte which encodes an immune receptor or a portion thereof. More particularly, clonotype means a recombined nucleotide sequence of a T cell or B cell which encodes a T cell receptor (TCR) or B cell receptor (BCR), or a portion thereof. In various embodiments, clonotypes may encode all or a portion of a VDJ rearrangement of IgH, a DJ rearrangement of IgH, a VJ rearrangement of IgK, a VJ rearrangement of IgL, a VDJ rearrangement of TCR beta, a DJ rearrangement of TCR beta, a VJ rearrangement of TCR alpha, a VJ rearrangement of TCR gamma, a VDJ rearrangement of TCR delta, a VD rearrangement of TCR delta, a Kde-V rearrangement, or the like. Clonotypes may also encode translocation breakpoint regions involving immune receptor genes, such as Bcl1-IgH or Bcl1-IgH. In one aspect, clonotypes have sequences that are sufficiently long to represent or reflect the diversity of the immune molecules that they are derived from; consequently, clonotypes may vary widely in length. In some embodiments, clonotypes have lengths in the range of from 25 to 400 nucleotides; in other embodiments, clonotypes have lengths in the range of from 25 to 200 nucleotides.

"Clonotype profile" means a listing of distinct clonotypes and their relative abundances that are derived from a population of lymphocytes. Typically, the population of lymphocytes are obtained from a tissue sample. The term "clonotype profile" is related to, but more general than, the immunology concept of immune "repertoire" as described in references, such as the following: Arstila et al, Science, 286: 958-961 (1999); Yassai et al, Immunogenetics, 61: 493-502 (2009); Kedzierska et al, Mol. Immunol., 45(3): 607-618 (2008); and the like. The term "clonotype profile" includes a wide variety of lists and abundances of rearranged immune receptor-encoding nucleic acids, which may be derived from selected subsets of lymphocytes (e.g. tissue-infiltrating lymphocytes, immunophenotypic subsets, or the like), or which may encode portions of immune receptors that have reduced diversity as compared to full immune receptors. In some embodiments, clonotype profiles may comprise at least $10^3$ distinct clonotypes; in other embodiments, clonotype profiles may comprise at least $10^4$ distinct clonotypes; in other embodiments, clonotype profiles may comprise at least $10^5$ distinct clonotypes; in other embodiments, clonotype profiles may comprise at least $10^6$ distinct clonotypes. In such embodiments, such clonotype profiles may further comprise abundances or relative frequencies of each of the distinct clonotypes.

In one aspect, a clonotype profile is a set of distinct recombined nucleotide sequences (with their abundances) that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, nucleic acid segments defining clonotypes are selected so that their diversity (i.e. the number of distinct nucleic acid sequences in the set) is large enough so that substantially every T cell or B cell or clone thereof in an individual carries a unique nucleic acid sequence of such repertoire. That is, preferably each different clone of a sample has different clonotype. In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a clonotype profile comprising human TCR beta chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In another embodiment, a clonotype profile comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$.

In a particular embodiment, a clonotype profile of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher. In another particular embodiment, a clonotype profile of the invention comprises a set of nucleotide sequences that encodes substantially all segments of the V(D)J region of a TCR beta chain. In another embodiment, a clonotype profile of the invention comprises a set of nucleotide sequences having lengths in the range of from 25-200 nucleotides and including segments of the V, D, and J regions of a TCR beta chain. In another embodiment, a clonotype profile of the invention comprises a set of nucleotide sequences having lengths in the range of from 25-200 nucleotides and including segments of the V, D, and J regions of an IgH chain. In another embodiment, a clonotype profile of the invention comprises a number of distinct nucleotide sequences that is substantially equivalent to the number of lymphocytes expressing a distinct IgH chain. In another embodiment, a clonotype profile of the invention comprises a number of distinct nucleotide sequences that is substantially equivalent to the number of lymphocytes expressing a distinct TCR beta chain. In still another embodiment, "substantially equivalent" means that with ninety-nine percent probability a clonotype profile will include a nucleotide sequence encoding an IgH or TCR beta or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCR beta or portion thereof carried or expressed by every lymphocyte present at a frequency of 0.0001 percent or greater. In some embodiments, clonotype profiles are derived from samples comprising from $10^3$ to $10^7$ lymphocytes. Such numbers of lymphocytes may be obtained from peripheral blood samples of from 1-10 mL.

"Coalescing" means treating two candidate clonotypes with sequence differences as the same by determining that such differences are due to experimental or measurement error and not due to genuine biological differences. In one aspect, a sequence of a higher frequency candidate clonotype is compared to that of a lower frequency candidate clonotype and if predetermined criteria are satisfied then the number of lower frequency candidate clonotypes is added to that of the higher frequency candidate clonotype and the lower frequency candidate clonotype is thereafter disregarded. That is, the read counts associated with the lower frequency candidate clonotype are added to those of the higher frequency candidate clonotype.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Data structure" means an organization of information, usually in a computer or memory device, for better algorithm efficiency. Exemplary data structures include queues, stacks, linked lists, heaps, hash tables, arrays, trees, and the like. Data structures may have substructures that correspond to units of information or to subsets of related information. For example, arrays have rows and columns of entries; trees have nodes, branches, subtrees, and leaves; or the like. In one aspect, a data structure used herein is a sequence tree, an array or a hash table.

As used herein, the term "exogenous" refers to a molecule, nucleic acid, protein, or structure that is introduced into the cell by genetic or biochemical means. By contrast, an "endogenous" molecule, nucleic acid, protein, or structure is one that is present in the particular cell and/or in the particular cell at its developmental stage. An exogenous molecule, nucleic acid, protein, or structure can be the same type as an endogenous molecule, nucleic acid, protein, or structure found within the cell, or may be a type of molecule, nucleic acid, protein, or structure that is not normally found in the cell.

The term "exogenous TCR," as used herein, refers to a recombinant TCR expressed in a cell via introduction of exogenous coding sequences for a TCR. Thus, the cell comprising an exogenous TCR is capable of expressing a TCR that is not natively expressed in that cell.

The term "isolated," as used herein, refers to a biological component such as a nucleic acid, peptide, protein, or cell that has been substantially separated, produced apart from, or purified away from other biological components of the organism in which the component naturally occurs. Nucleic acids, peptides, proteins, and cells that have been isolated thus include nucleic acids, peptides proteins, and cells that are purified by standard purification methods, or that are prepared by expression, for example expression in a host cell, or that are chemically synthesized. In some embodiments, the isolated cell is an autologous cell, meaning that it may is derived from the subject that will receive the resultant transduced or transformed cell. For example, in some embodiments, the isolated cells are derived from the PBMC and/or hematopoietic stem cells of the subject being treated.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 μm to about 0.1 μm. Microfluidics devices typically have volume capacities in the range of from 1 μL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003).

"Percent homologous," "percent identical," or like terms used in reference to the comparison of a reference sequence and another sequence ("comparison sequence") mean that in an optimal alignment between the two sequences, the comparison sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms, such as that described by Needleman and Wunsch, J. Mol. Biol., 48: 443-453 (1970) ("GAP" program of Wisconsin Sequence Analysis Package, Genetics Computer Group, Madison, Wis.), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package, Genetics Computer Group, Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL.

"Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference.

"Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("tagman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference.

"Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. Typically, the number of target sequences in a multiplex PCR is in the range of from 2 to 50, or from 2 to 40, or from 2 to 30.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: beta-actin, GAPDH, beta$_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17:

9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polymerase cycling assembly" or "PCA" reaction (also referred to herein as "linked PCR") means a PCR that comprises at least one pair of outer primers and at least one pair of inner primers. An inner primer has a 3' portion that is complementary to a target nucleic acid (or its complement) and a 5' portion that is complementary to the 5' portion of another inner primer corresponding to a different target nucleic acid.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Quality score" means a measure of the probability that a base assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Sequence read" means a sequence of nucleotides determined from a sequence or stream of data generated by a sequencing technique, which determination is made, for example, by means of base-calling software associated with the technique, e.g. base-calling software from a commercial provider of a DNA sequencing platform. A sequence read usually includes quality scores for each nucleotide in the sequence. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension. Such initial data is converted into a sequence read.

"Sequence tag" (or "tag") or "barcode" means an oligonucleotide that is attached, usually via a covalent bond, to another molecule or molecular complex and that is used to identify and/or track the other molecule in a reaction or a series of reactions. Sequence tags may vary widely in size and compositions; the following references, which are incorporated herein by reference, provide guidance for selecting sets of sequence tags appropriate for particular embodiments: Brenner, U.S. Pat. No. 5,635,400; Brenner and Macevicz, U.S. Pat. No. 7,537,897; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of sequence tags can vary widely, and the selection of particular lengths and/or compositions depends on several factors including, without limitation, how tags are used to generate a readout, e.g. via a hybridization reaction or via an enzymatic reaction, such as amplification and sequencing; whether they are labeled, e.g. with a fluorescent dye or the like; the number of distinguishable sequence tags required to unambiguously identify a set of molecules of interest, and the like, and how different must tags of a set be in order to ensure reliable identification, e.g. freedom from cross hybridization, misidentification from sequencing errors, or the like. In some embodiments, sequence tags may each have a length within a range of from 6 to 36 nucleotides, or from 4 to 30 nucleotides, or from 8 to 40 nucleotides, or from 6 to 50 nucleotides, respectively; provided, however, that the term "sequence tag" may also be used in reference to a sequence tag of the foregoing lengths sandwiched between a pair of primers that may be used to amplify or otherwise manipulate the sequence tag, for example, in order to identify it by DNA sequencing. In one aspect, sets of sequence tags are used wherein each sequence tag of a set has a unique nucleotide sequence that differs from that of every other tag of the same set by a plurality of bases; in some embodiments, such plurality is at least three bases; in another aspect, sets of sequence tags are used wherein the sequence of each tag of a set differs front that of every other tag of the same set by at least four bases.

"Sequence tree" means a tree data structure for representing nucleotide sequences. In one aspect, a tree data structure of the invention is a rooted directed tree comprising nodes and edges that do not include cycles, or cyclical pathways. Edges from nodes of tree data structures of the invention are usually ordered. Nodes and/or edges are structures that may contain, or be associated with, a value. Each node in a tree has zero or more child nodes, which by convention are shown below it in the tree. A node that has a child is called the child's parent node. A node has at most one parent. Nodes that do not have any children are called leaf nodes. The topmost node in a tree is called the root node. Being the topmost node, the root node will not have parents. It is the node at which operations on the tree commonly begin (although some algorithms begin with the leaf nodes and work up ending at the root). All other nodes can be reached from it by following edges or links.

The term "subject" is herein defined as vertebrate, particularly mammal, more particularly human. For purposes of research, the subject may particularly be at least one animal model, e.g., a mouse, rat and the like.

The term "therapeutically effective amount," as used herein, refers to an amount that elicits an immune-mediated therapeutic effect in the subject. A therapeutic effect may include treatment of symptoms of a disease or disorder, or treatment of the underlying condition, and/or prophylaxis against development or worsening of a disease or disorder. In some embodiments, a "therapeutic vaccine" or "method of vaccination" and the like refers to a composition or method for eliciting an immune response against a pathogen or a component of a pathogen, such as to produce protective immunity (i.e., immunity that prevents or reduces severity of the disease associated with the pathogen).

II. Identification of T-Cell Receptor Chains

In some embodiments, the present disclosure provides methods for matching pairs of immune receptor chains from populations of their encoding nucleic acids that have been sequenced. In some embodiments, the methods described herein provide methods for the identification of immune receptor chains that are specific for a particular antigen and methods of matching those antigen-specific immune receptor chains to form a complete immune receptor molecule (e.g., a complete TCR molecule, also referred to herein as a "reconstituted TCR").

A. Antigens

An antigen may be any compound or composition capable of eliciting a cell-mediated immune response (that is, an adaptive immune response), particularly in a mammal, such as a human. In some embodiments, an antigen may be any compound that can be recognized by a T cell in the context of the MHC molecule. More particularly, antigens include, but is not limited to, cells, tissue extracts, tissue or cell lysates, proteins, individually or as a mixture, a plurality of proteins, peptides, mixtures of peptides, lipids, carbohydrates, sugars, and the like. An antigen can be characteristic of a disease, such as an infectious disease, an autoimmune disease, or a cancer. The antigen can be, for example, a viral antigen, a bacterial antigen, a cancer antigen, etc. In some embodiments, an antigen is a cancer antigen or a viral antigen. By "cancer antigen" is meant any molecule (e.g., protein, peptide, lipid, carbohydrate, etc.) solely or predominantly expressed or over-expressed by a tumor cell or cancer cell, such that the antigen is associated with the tumor or cancer.

A cancer antigen may be a cancer antigen of only one type of cancer or tumor, such that the cancer antigen is associated with or characteristic of only one type of cancer or tumor. Alternatively, a cancer antigen may be a cancer antigen (e.g., may be characteristic) of more than one type of cancer or tumor. For example, a cancer antigen may be expressed by both breast and prostate cancer cells and not expressed at all by normal, non-tumor, or non-cancer cells, or expressed only minimally. A cancer antigen may a melanoma cancer antigen, a breast cancer antigen or a molecule such as Wilms' tumor (WT)-1 which is expressed in a variety of cancers, including chronic myelocytic leukemia, multiple myeloma, acute lymphoblastic leukemia (ALL), acute myeloid leukemia (AML), myelodysplastic syndrome, mesothelioma, ovarian cancer, breast cancer, prostate cancer, gastrointestinal cancers, lung cancer, colon cancer, thyroid cancer, head and neck cancer, glioblastoma, and sarcoma. Other exemplary cancer antigens include those of the group consisting of gp100, MART-1, NY-ESO-1, a member of the MAGE family of proteins, e.g., MAGE-A1, mesothelin, Tyrosinase, TRP-1, TRP-2, PMSA, Her-2, and p53.

An antigen may be a viral antigen. In some embodiments, "viral antigen" means those antigens encoded by a part of a viral genome which can be detected by a specific immunological response. Viral antigens include, for example, a viral coat protein, an influenza viral antigen, an HIV antigen, a Hepatitis B antigen, or a Hepatitis C antigen.

An antigen can be naturally, artificially, or synthetically produced. Thus, an antigen can be a synthetic, isolated, and/or purified protein, polypeptide, or peptide. Methods of making or obtaining such antigens are known in the art. For example, suitable methods of de novo synthesizing polypeptides and proteins (e.g., antigenic polypeptides and proteins) are described in Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwoood et al., Oxford University Press, Oxford, United Kingdom, 2000; and U.S. Pat. No. 5,449,752. Also, polypeptides and proteins (e.g., antigenic polypeptides and proteins) can be produced using nucleic acids which encode the polypeptide or protein using standard methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. The nucleotide sequences of many antigens are known in the art and are available from the GenBank database of the National Center for Biotechnology Information (NCBI) website. Further, an antigen can be isolated and/or purified from a source, such as a plant, a bacterium, an insect, a mammal, e.g., a rat, a human, etc. Methods of isolation and purification are well-known in the art.

An antigen can be a free antigen, e.g., unbound antigenic peptide (e.g., a free peptide), or can be a bound antigen, e.g., an MHC-peptide tetramer or an antigenic peptide presented by a carrier cell which was pulsed with the peptide.

In some embodiments, peripheral blood mononuclear cells (PBMCs) (for example, which may be obtained from blood, for example, as a leukapheresis product) from a subject may be cultured directly in the presence of antigen, to load antigen presenting cells (APCs) among the PBMCs with the antigen and to activate/stimulate antigen-specific T cells present in the PBMC. In this regard, PBMC may be collected from an individual, contacted with an antigen of interest, such as a tumor antigen, or a viral lysate, etc. In this manner, the APCs present in the PBMCs are loaded with the antigen, which is then presented to the T cells present in the sample. In some embodiments, antigen-specific T cells may be activated with peptide-MHC tetramers, see for example Altman, et al., Science 1998 Jun. 19; 280(5371):1821. In some embodiments, a protein antigen may be exposed to T cells indirectly by generating a set of peptides for binding to MHC molecules, where the sequences of the peptides are based on the amino acid sequence of the protein, e.g. Stickler et al, Toxicol. Sci., 77(2): 280-289 (2004). In some such embodiments, peptides are overlapping peptides covering the protein. In some embodiments, peptides each have a size of from 10 to 20 amino acids.

T cells can be obtained from a number of sources, including peripheral blood mononuclear cells, bone marrow, thymus, tissue biopsy, tumor, lymph node tissue, gut associated lymphoid tissue, mucosa associated lymphoid tissue, spleen tissue, or any other lymphoid tissue, and tumors. T cells can be obtained from T cell lines and from autologous or allogeneic sources. T cells may be obtained from a single individual or a population of individuals, for example, a population of individual who all suffer from the same disease, such as, a cancer or an infectious disease.

In some embodiments, cells from the circulating blood of an individual are obtained by apheresis or leukapheresis.

The apheresis product typically contains lymphocytes, including T cells, monocytes, granulocytes, B cells, other nucleated white blood cells, red blood cells, and platelets. In one embodiment, the cells collected by apheresis or leukapheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, Baxter) according to the manufacturer's instructions. After washing, the cells may be re-suspended in a variety of biocompatible buffers, such as, for example, Ca++/Mg++ free PBS. Alternatively, the undesirable components of the apheresis sample may be removed and the cells directly re-suspended in culture media.

In other embodiments, T cells are isolated from peripheral blood lymphocytes by lysing the red blood cells and by centrifugation through a PERCOLL™ gradient. A specific subpopulation of T cells, such as CD28+, CD4+, CD8+, CD45RA+, and CD45RO+ T cells, can be further isolated by positive or negative selection techniques. For example, CD3+, CD28+ T cells can be positively selected using CD3/CD28 conjugated magnetic beads (e.g., DYNA-BEADS® M-450 CD3/CD28 T Cell Expander). In some embodiments, enrichment of a T cell population by negative selection can be accomplished with a combination of antibodies directed to surface markers unique to the negatively selected cells. One such method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Another method for preparing T cells for stimulation is to freeze the cells after the washing step, which does not require the monocyte-removal step. Wishing not to be bound by theory, the freeze and subsequent thaw step provides a more uniform product by removing granulocytes and, to some extent, monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 10 per minute and stored in the vapor phase of a liquid nitrogen storage tank.

B. Samples

Samples, or tissue samples, of T-cells (T lymphocytes) may include, for example, helper T cells (effector T cells or Th cells), cytotoxic T cells (CTLs), memory T cells, and regulatory T cells, as well as other cell types normally found in a tissue sample. In one aspect, a sample of T cells includes at least 1,000 T cells; but more typically, a sample includes at least 10,000 T cells, and more typically, at least 100,000 T cells. In another aspect, a sample includes a number of T cells in the range of 1000 to 100,000 cells.

Samples used in the methods of the invention can come from a variety of tissues as noted above, including, for example, tumor tissue, blood and blood plasma, lymph fluid, cerebrospinal fluid surrounding the brain and the spinal cord, synovial fluid surrounding bone joints, and the like. In one embodiment, the sample is a blood sample. The blood sample can be about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mL. The sample can be a tumor biopsy. The biopsy can be from, for example, from a tumor of the brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

The sample can be a biopsy, e.g., a skin biopsy. The biopsy can be from, for example, brain, liver, lung, heart, colon, kidney, or bone marrow. Any biopsy technique used by those skilled in the art can be used for isolating a sample from a subject. For example, a biopsy can be an open biopsy, in which general anesthesia is used. The biopsy can be a closed biopsy, in which a smaller cut is made than in an open biopsy. The biopsy can be a core or incisional biopsy, in which part of the tissue is removed. The biopsy can be an excisional biopsy, in which attempts to remove an entire lesion are made. The biopsy can be a fine needle aspiration biopsy, in which a sample of tissue or fluid is removed with a needle.

As discussed more fully below, in some embodiments, a sample of lymphocytes is sufficiently large so that substantially every T cell or B cell with a distinct clonotype is represented therein, thereby forming a repertoire (as the term is used herein). In some embodiments, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of T cells includes at least a half million cells, and in another embodiment such sample includes at least one million cells.

Blood samples are of particular interest and may be obtained using conventional techniques, e.g. Innis et al, editors, PCR Protocols (Academic Press, 1990); or the like. For example, white blood cells may be separated from blood samples using convention techniques, e.g. RosetteSep kit (Stem Cell Technologies, Vancouver, Canada). Blood samples may range in volume from 100 μL to 10 mL; in one aspect, blood sample volumes are in the range of from 200 μL to 2 mL. Optionally, subsets of white blood cells, e.g. lymphocytes, may be further isolated using conventional techniques, e.g. fluorescently activated cell sorting (FACS) (Becton Dickinson, San Jose, Calif.), magnetically activated cell sorting (MACS) (Miltenyi Biotec, Auburn, Calif.), or the like.

Since the identifying recombinations are present in the DNA of each individual's adaptive immunity cells as well as their associated RNA transcripts, either RNA or DNA can be sequenced in the methods of the provided invention. A recombined sequence from a T-cell encoding a T cell receptor molecule, or a portion thereof, is referred to as a clonotype. The DNA or RNA can correspond to sequences from T-cell receptor (TCR) genes. For example, the DNA and RNA can correspond to sequences encoding alpha, beta, gamma, or delta chains of a TCR. In a majority of T-cells, the TCR is a heterodimer consisting of an alpha-chain and beta-chain. The TCR alpha chain is generated by VJ recombination, and the beta chain receptor is generated by V(D)J recombination. For the TCR beta chain, in humans there are 48 V segments, 2 D segments, and 13 J segments. Several bases may be deleted and others added (called N and P nucleotides) at each of the two junctions. In a minority of T-cells, the TCRs consist of gamma and delta chains. The TCR gamma chain is generated by VJ recombination, and the TCR delta chain is generated by V(D)J recombination (Kenneth Murphy, Paul Travers, and Mark Walport, Janeway's Immunology 7th edition, Garland Science, 2007).

C. Amplification of Nucleic Acid Populations

Amplicons of target populations of nucleic acids may be generated by a variety of amplification techniques. In one aspect of the invention, multiplex PCR is used to amplify members of a mixture of nucleic acids, particularly mixtures comprising recombined immune molecules such as T cell receptors, or portions thereof. Guidance for carrying out multiplex PCRs of such immune molecules is found in the following references, which are incorporated by reference U.S. Pat. Nos. 8,236,503; 8,628,927; 5,296,351; 5,837,447; 6,087,096; U.S. Patent Application Publication No. 2006/0234234; European Patent Publication EP 1544308B1; and the like.

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al, Leukemia, 17: 2257-2317 (2003) or van Dongen et al, U.S. Patent Application Publication No. 2006/0234234, which is incorporated by reference. Briefly, an exemplary protocol is as follows: Reaction buffer: ABI Buffer II or ABI Gold Buffer (Life Technologies, San Diego, Calif.); 50 µL final reaction volume; 100 ng sample DNA; 10 pmol of each primer (subject to adjustments to balance amplification as described below); dNTPs at 200 µM final concentration; MgCl$_2$ at 1.5 mM final concentration (subject to optimization depending on target sequences and polymerase); Taq polymerase (1-2 U/tube); cycling conditions: pre-activation 7 min at 95° C.; annealing at 60° C.; cycling times: 30 s denaturation; 30 s annealing; 30 s extension. Polymerases that can be used for amplification in the methods of the invention are commercially available and include, for example, Taq polymerase, AccuPrime polymerase, or Pfu. The choice of polymerase to use can be based on whether fidelity or efficiency is preferred.

Real time PCR, picogreen staining, nanofluidic electrophoresis (e.g. LabChip) or UV absorption measurements can be used in an initial step to judge the functional amount of amplifiable material.

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. As discussed more fully below, amplification bias in PCR may be detected and corrected using conventional techniques so that a set of PCR primers may be selected for a predetermined repertoire that provide unbiased amplification of any sample.

In one embodiment, amplification bias may be avoided by carrying out a two-stage amplification (as described in Faham and Willis, cited above) wherein a small number of amplification cycles are implemented in a first, or primary, stage using primers having tails non-complementary with the target sequences. The tails include primer binding sites that are added to the ends of the sequences of the primary amplicon so that such sites are used in a second stage amplification using only a single forward primer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 100,000 molecules to the secondary amplification would degrade the precision of estimating the relative abundance of the different species in the original sample. The 100 fold dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

D. Generating Sequence Reads for Clonotypes

Any high-throughput technique for sequencing nucleic acids can be used in the method of the invention. Preferably, such technique has a capability of generating in a cost-effective manner a volume of sequence data from which at least 1000 clonotypes can be determined, and preferably, from which at least 10,000 to 1,000,000 clonotypes can be determined. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has been carried out by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR).

In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)).

In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths.

In one aspect, a sequence-based clonotype profile of an individual is obtained using the following steps: (a) obtaining a nucleic acid sample, for example, a sample containing T-cells of the individual; (b) spatially isolating individual molecules derived from such nucleic acid sample, the individual molecules comprising at least one template generated from a nucleic acid in the sample, which template comprises a somatically rearranged region or a portion thereof, each individual molecule being capable of producing at least one sequence read; (c) sequencing said spatially isolated individual molecules to provide sequence reads; and (d) determining abundances of different sequences of the nucleic acid molecules from the nucleic acid sample to generate the clonotype profile. In some embodiments, the step of sequencing includes coalescing at least a plurality of sequence reads to form each clonotype. As described more fully below, such a step of coalescing is a process of combining sequence reads with error rates (for example, from sequencing and/or amplification errors) to produce clonotypes that are correct with a high degree of likelihood, such as with a 99% confidence level.

In one aspect, for each sample from an individual, the sequencing technique used in the methods of the invention generates sequences of least 1000 sequence reads per run; in another aspect, such technique generates sequences of at least 10,000 sequence reads per run; in another aspect, such technique generates sequences of at least 100,000 sequence reads per run; in another aspect, such technique generates sequences of at least 500,000 sequence reads per run; and in another aspect, such technique generates sequences of at least 1,000,000 sequence reads per run. From such sequence reads clonotypes are determined, for example, as described below, or as disclosed in Faham and Willis (described above).

The sequencing techniques used in the methods generate sequence reads having lengths of at least 30 nucleotides. In some embodiments, a step of sequencing generates sequence reads having lengths of at least 50 nucleotides; and in some embodiments, a step of sequencing generates sequence reads having lengths of at least 100 nucleotides.

E. Clonotype Determination from Sequence Data

Constructing clonotypes from sequence read data depends in part on the sequencing method used to generate such data, as the different methods have different expected read lengths and data quality. In one approach, a Solexa sequencer is employed to generate sequence read data for analysis. In one embodiment, a sample is obtained that provides at least $0.5\text{-}1.0 \times 10^6$ lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

In one aspect of the invention, sequences of clonotypes (including but not limited to those derived from TCR alpha, TCR beta, TCR gamma, and/or TCR delta, may be determined by combining information from a plurality of sequence reads sequence reads, for example, along the V(D)J regions of the selected chains. In another aspect, sequences of clonotypes are determined by combining information from a plurality of sequence reads. Such pluralities of sequence reads may include one or more sequence reads along a sense strand (i.e. "forward" sequence reads) and one or more sequence reads along its complementary strand (i.e. "reverse" sequence reads).

Sequence reads of the invention may have a wide variety of lengths, depending in part on the sequencing technique being employed. For example, for some techniques, several trade-offs may arise in its implementation, for example, (i) the number and lengths of sequence reads per template and (ii) the cost and duration of a sequencing operation. In one embodiment, sequence reads are in the range of from 20 to 400 nucleotides; in another embodiment, sequence reads are in a range of from 30 to 200 nucleotides; in still another embodiment, sequence reads are in the range of from 30 to 120 nucleotides. In one embodiment, 2 to 1000 sequence reads are generated for determining the sequence of each clonotype; in another embodiment, 2 to 100 sequence reads are generated for determining the sequence of each clonotype; and in another embodiment, 2 to 10 sequence reads are generated for determining the sequence of each clonotype; and in still another embodiment, at least 10 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read; for example, the starting location and length of a sequence read may be designed to provide the length of an NDN region as well as its nucleotide sequence; thus, sequence reads spanning the entire NDN region are selected. In other aspects, one or more sequence reads that in combination (but not separately) encompass a D and/or NDN region are sufficient.

In another aspect of the invention, sequences of clonotypes are determined in part by aligning sequence reads to one or more V region reference sequences and one or more J region reference sequences, and in part by base determination without alignment to reference sequences, such as in the highly variable NDN region. A variety of alignment algorithms may be applied to the sequence reads and reference sequences. For example, guidance for selecting alignment methods is available in Batzoglou, Briefings in Bioinformatics, 6: 6-22 (2005), which is incorporated by reference. In one aspect, whenever V reads or C reads (as mentioned above) are aligned to V and J region reference sequences, a tree search algorithm may be employed, e.g. as described generally in Gusfield (cited above) and Cormen et al, Introduction to Algorithms, Third Edition (The MIT Press, 2009).

In another aspect, an end of at least one forward read and an end of at least one reverse read overlap in an overlap region (e.g. 308 in FIG. 14A), so that the bases of the reads are in a reverse complementary relationship with one another. Thus, for example, if a forward read in the overlap region is "5'-acgttgc", then a reverse read in a reverse complementary relationship is "5'-gcaacgt" within the same overlap region. In one aspect, bases within such an overlap region are determined, at least in part, from such a reverse complementary relationship. That is, a likelihood of a base call (or a related quality score) in a prospective overlap region is increased if it preserves, or is consistent with, a reverse complementary relationship between the two sequence reads.

Figure 14A:
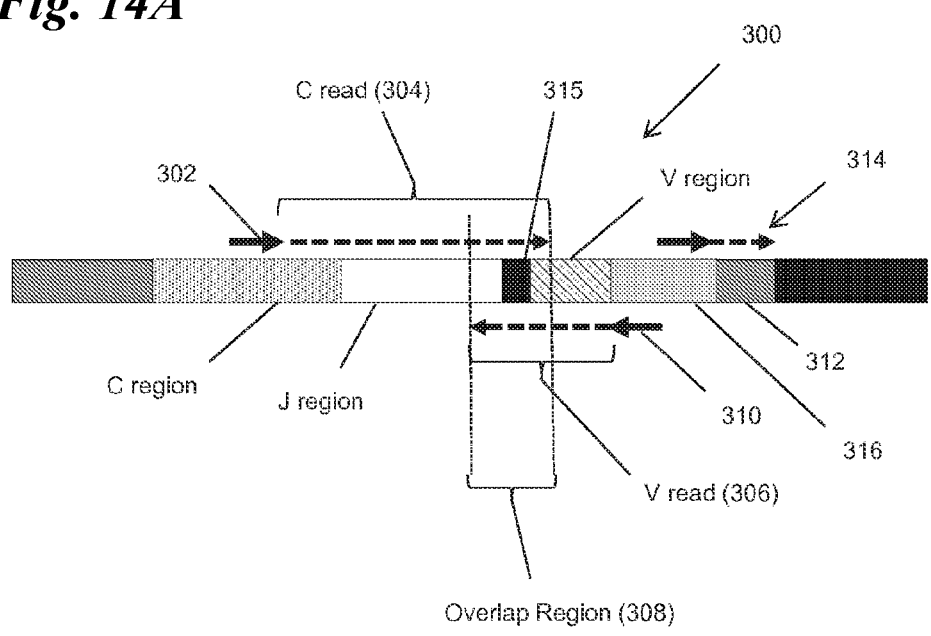
FIG. 14A-FIG. 14B illustrate details of embodiments for determining a nucleotide sequence of the PCR product of FIG. 13C.
Figure 14B:
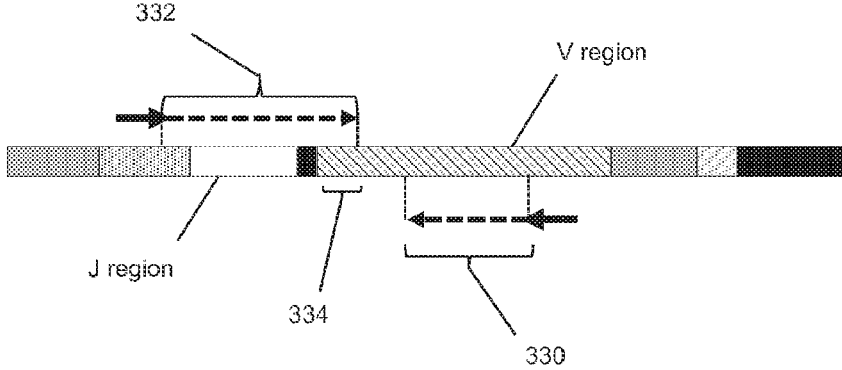

In one aspect, clonotypes of TCR beta and IgH chains (illustrated in FIG. 14A) are determined by at least one sequence read starting in its J region and extending in the direction of its associated V region (referred to herein as a "C read" (304)) and at least one sequence read starting in its V region and extending in the direction of its associated J region (referred to herein as a "V read" (306)). Overlap region (308) may or may not encompass the NDN region (315) as shown in FIG. 14A. Overlap region (308) may be entirely in the J region, entirely in the NDN region, entirely in the V region, or it may encompass a J region-NDN region boundary or a V region-NDN region boundary, or both such boundaries (as illustrated in FIG. 3B). Typically, such sequence reads are generated by extending sequencing primers, e.g. (302) and (310) in FIG. 14A, with a polymerase in a sequencing-by-synthesis reaction, e.g. Metzger, Nature Reviews Genetics, 11: 31-46 (2010); Fuller et al, Nature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the TCR beta or IgH chain and includes a portion of the adjacent V region, e.g. as illustrated in FIGS. 14A and 14B. In one aspect, the overlap of the V read and the C read in the V region is used to align the reads with one another. In other embodiments, such alignment of sequence reads is not necessary, e.g. with TCR beta chains, so that a V read may only be long enough to identify the particular V region of a clonotype. This latter aspect is illustrated in FIG. 14B. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing run time and reagent costs are reduced by minimizing the number of sequencing cycles in an analysis. Optionally, as illustrated in FIG. 14A, amplicon (300) is produced with sample tag (312) to distinguish between clonotypes originating from different biological samples, e.g. different patients. Sample tag (312) may be identified by annealing a primer to primer binding region (316) and extending it (314) to produce a sequence read across tag (312), from which sample tag (312) is decoded.

Reducing a set of reads for a given sample to a set of distinct clonotypes and recording the number of reads for each clonotype would be a trivial computational problem if sequencing technology was error free. However, in the presence of sequencing errors, each genuine clonotype is surrounded by a "cloud" of reads with varying numbers of errors with respect to the its sequence. The "cloud" of sequencing errors drops off in density as the distance increases from the clonotype in sequence space. A variety of algorithms are available for converting sequence reads into clonotypes. In one approach, coalescing of sequence reads (that is, merging candidate clonotypes determined to have one or more sequencing errors) depends on at least three factors: the number of sequences obtained for each of the clonotypes being compared; the number of bases at which they differ; and the sequencing quality score at the positions at which they are discordant. A likelihood ratio may be constructed and assessed that is based on the expected error rates and binomial distribution of errors. For example, two clonotypes, one with 150 reads and the other with 2 reads with one difference between them in an area of poor sequencing quality will likely be coalesced as they are likely to be generated by sequencing error. On the other hand two clonotypes, one with 100 reads and the other with 50 reads with two differences between them are not coalesced as they are considered to be unlikely to be generated by sequencing error.

In one embodiment of the invention, the algorithm described below may be used for determining clonotypes from sequence reads. In one approach, sequence reads are first converted into candidate clonotypes. Such a conversion depends on the sequencing platform employed. For platforms that generate high Q score long sequence reads, the sequence read or a portion thereof may be taken directly as a candidate clonotype. For platforms that generate lower Q score shorter sequence reads, some alignment and assembly steps may be required for converting a set of related sequence reads into a candidate clonotype. For example, for Solexa-based platforms, in some embodiments, candidate clonotypes are generated from collections of paired reads from multiple clusters, e.g. 10 or more, as mentioned above.

The cloud of sequence reads surrounding each candidate clonotype can be modeled using the binomial distribution and a simple model for the probability of a single base error. This latter error model can be inferred from mapping V and J segments or from the clonotype finding algorithm itself, via self-consistency and convergence. A model is constructed for the probability of a given "cloud" sequence Y with read count $C_2$ and E errors (with respect to sequence X) being part of a true clonotype sequence X with perfect read count $C_1$ under the null model that X is the only true clonotype in this region of sequence space. A decision is made whether or not to coalesce sequence Y into the clonotype X according the parameters $C_1$, $C_2$, and E. For any given $C_1$ and E a max value $C_2$ is pre-calculated for deciding to coalesce the sequence Y. The max values for $C_2$ are chosen so that the probability of failing to coalesce Y under the null hypothesis that Y is part of clonotype X is less than some value P after integrating over all possible sequences Y with error E in the neighborhood of sequence X. The value P is controls the behavior of the algorithm and makes the coalescing more or less permissive.

If a sequence Y is not coalesced into clonotype X because its read count is above the threshold $C_2$ for coalescing into clonotype X then it becomes a candidate for seeding separate clonotypes (such as with candidate clonotype 2. An algorithm implementing such principles would also make sure that any other sequences Y2, Y3, etc. which are 'nearer' to this sequence Y (that had been deemed independent of X) are not aggregated into X. This concept of "nearness" includes both error counts with respect to Y and X and the absolute read count of X and Y, i.e. it is modeled in the same fashion as the above model for the cloud of error sequences around clonotype X. In this way 'cloud' sequences can be properly attributed to their correct clonotype if they happen to be 'near' more than one clonotype.

In some embodiments, an algorithm proceeds in a top down fashion by starting with the sequence X with the highest read count. This sequence seeds the first clonotype. Neighboring sequences are either coalesced into this clonotype if their counts are below the pre-calculated thresholds (see above), or left alone if they are above the threshold or "closer" to another sequence that was not coalesced. After searching all neighboring sequences within a maximum error count, the process of coalescing reads into clonotype X is finished. Its reads and all reads that have been coalesced into it are accounted for and removed from the list of reads available for making other clonotypes. The next sequence is then moved on to with the highest read count. Neighboring reads are coalesced into this clonotype as above and this process is continued until there are no more sequences with read counts above a given threshold, e.g. until all sequences with more than 1 count have been used as seeds for clonotypes.

As mentioned above, in another embodiment of the above algorithm, a further test may be added for determining whether to coalesce a candidate sequence Y into an existing clonotype X, which takes into account quality score of the relevant sequence reads. The average quality score(s) are determined for sequence(s) Y (averaged across all reads with sequence Y) were sequences Y and X differ. If the average score is above a predetermined value then it is more likely that the difference indicates a truly different clonotype that should not be coalesced and if the average score is below such predetermined value then it is more likely that sequence Y is caused by sequencing errors and therefore should be coalesced into X. Successful implementation of the above algorithm for coalescing candidate clonotypes is dependent upon having an efficient way of finding all sequences with less than E errors (i.e. less than some sequence distance measure) from some input sequence X. One approach is using a sequence tree. The implementation of such trees has some unusual features in that the nodes of the tree are not restricted to being single letters of the DNA sequences of the candidate clonotypes. The nodes can have arbitrarily long sequences, which allows for a more efficient use of computer memory.

For example, all of the reads of a given sample are placed into the sequence tree. Each leaf nodes holds pointers to its associated reads. A unique sequence of a candidate clonotype is retrieved by traversing backwards in the tree from the leaf to the root node. The first sequence is placed into a simple tree with one root node and one leaf node that contains the full sequence of the read. Sequences are next added one by one. For each added sequence either a new branch is formed at the last point of common sequence between the read and the existing tree or add the read to an existing leaf node if the tree already contains the sequence. Having placed all the reads into the tree it is easy to use the tree for the following purposes: 1) Finding the highest read count: sorting leaf nodes by read count allows one to find the leaf node (i.e. sequence) with the most reads, and successively lower numbers of reads; 2) Finding neighboring leafs: for any sequence all paths through the tree which have less than X errors with respect to this sequence are searchable. A path is started at the root and branch this path into separate paths proceeding along the tree. The current error count of each path as proceeding along the tree is noted. When the error count exceeds the max allowed errors the given path is terminated. In this way large parts of the tree are pruned as early as possible. This is an efficient way of finding all paths (i.e. all leafs) within X errors from any given sequence.

F. TCR Beta Repertoire Analysis

In this approach, TCR beta chains are analyzed and clonotypes are determined. The analysis includes amplification, sequencing, and analyzing the TCR beta sequences. One primer is complementary to a common sequence in C beta1 and C beta2, and there are 34 V primers capable of amplifying all 48 V segments. C beta1 or C beta2 differ from each other at position 10 and 14 from the J/C junction. The primer for C beta1 and C beta2 ends at position 16 bp and has no preference for C beta1 or C beta2. The 34 V primers are modified from an original set of primers disclosed in Van Dongen et al, U.S. Patent Application Publication No. 2006/0234234, which is incorporated herein by reference. The modified primers are disclosed in Faham et al, U.S. Patent Application Publication No. 2010/0151471, which is also incorporated herein by reference.

Figures 13A, 13B, 13C:
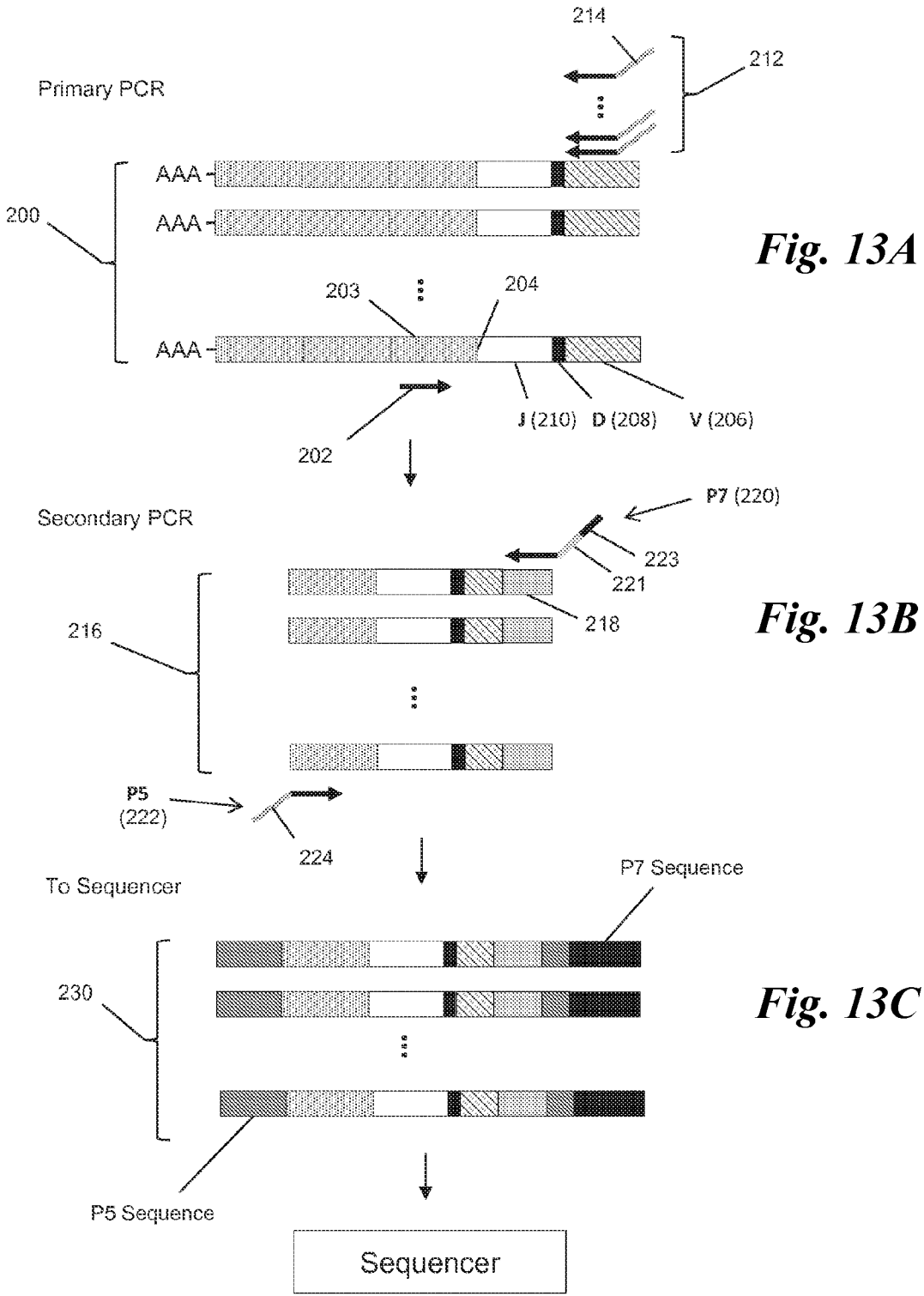
FIG. 13A-FIG. 13C show a two-staged PCR scheme for amplifying TCR beta genes.

The Illumina Genome Analyzer is used to sequence the amplicon produced by the above primers. A two-stage amplification is performed on messenger RNA transcripts (200), as illustrated in FIGS. 13A-13B, the first stage employing the above primers and a second stage to add common primers for bridge amplification and sequencing. As shown in FIG. 13A, a primary PCR is performed using on one side a 20 bp primer (202) whose 3' end is 16 bases from the J/C junction (204) and which is perfectly complementary to C beta1 (203) and the two alleles of C beta2. In the V region (206) of RNA transcripts (200), primer set (212) is provided which contains primer sequences complementary to the different V region sequences (34 in one embodiment). Primers of set (212) also contain a non-complementary tail (214) that produces amplicon (216) having primer binding site (218) specific for P7 primers (220). After a conventional multiplex PCR, amplicon (216) is formed that contains the highly diverse portion of the J(D)V region (206, 208, and 210) of the mRNA transcripts and common primer binding sites (203 and 218) for a secondary amplification to add a sample tag (221) and primers (220 and 222) for cluster formation by bridge PCR. In the secondary PCR, on the same side of the template, a primer (222 in FIG. 13B and referred to herein as "C10-17-P5") is used that has at its 3' end the sequence of the 10 bases closest to the J/C junction, followed by 17 bp with the sequence of positions 15-31 from the JC junction, followed by the P5 sequence (224), which plays a role in cluster formation by bridge PCR in Solexa sequencing. (When the C10-17-P5 primer (222) anneals to the template generated from the first PCR, a 4 bp loop (position 11-14) is created in the template, as the primer hybridizes to the sequence of the 10 bases closest to the J/C junction and bases at positions 15-31 front the J/C junction. The looping of positions 11-14 eliminates differential amplification of templates carrying C beta1 or C beta2. Sequencing is then done with a primer complementary to the sequence of the 10 bases closest to the J/C junction and bases at positions 15-31 from the J/C junction (this primer is called C'). C10-17-P5 primer can be HPLC purified in order to ensure that all the amplified material has intact ends that can be efficiently utilized in the cluster formation.)

In FIG. 13A, the length of the overhang on the V primers (212) is preferably 14 bp. The primary PCR is helped with a shorter overhang (214). Alternatively, for the sake of the secondary PCR, the overhang in the V primer is used in the primary PCR as long as possible because the secondary PCR is priming from this sequence. A minimum size of overhang (214) that supports an efficient secondary PCR was investigated. Two series of V primers (for two different V segments) with overhang sizes from 10 to 30 with 2 bp steps were made. Using the appropriate synthetic sequences, the first PCR was performed with each of the primers in the series and gel electrophoresis was performed to show that all amplified.

As illustrated in FIG. 13A, the primary PCR uses 34 different V primers (212) that anneal to V region (206) of RNA templates (200) and contain a common 14 bp overhang on the 5' tail. The 14 bp is the partial sequence of one of the Illumina sequencing primers (termed the Read 2 primer). The secondary amplification primer (220) on the same side includes P7 sequence, a tag (221), and Read 2 primer sequence (223) (this primer is called Read2_tagX_P7). The P7 sequence is used for cluster formation. Read 2 primer and its complement are used for sequencing the V segment and the tag respectively. A set of 96 of these primers with tags numbered 1 through 96 are created (see below). These primers are HPLC purified in order to ensure that all the amplified material has intact ends that can be efficiently utilized in the cluster formation.

As mentioned above, the second stage primer, C-10-17-P5 (222, FIG. 2B) has interrupted homology to the template generated in the first stage PCR. The efficiency of amplification using this primer has been validated. An alternative primer to C-10-17-P5, termed CsegP5, has perfect homology to the first stage C primer and a 5' tail carrying P5. The efficiency of using C-10-17-P5 and CsegP5 in amplifying first stage PCR templates was compared by performing real time PCR. In several replicates, it was found that PCR using the C-10-17-P5 primer had little or no difference in efficiency compared with PCR using the CsegP5 primer.

Amplicon (230) resulting from the 2-stage amplification illustrated in FIGS. 13A-13C has the structure typically used with the Illumina sequencer as shown in FIG. 13C. Two primers that anneal to the outmost part of the molecule, Illumina primers P5 and P7 are used for solid phase amplification of the molecule (cluster formation). Three sequence reads are done per molecule. The first read of 100 bp is done with the C' primer, which has a melting temperature that is appropriate for the Illumina sequencing process. The second read is 6 bp long only and is solely for the purpose of identifying the sample tag. It is generated using a tag primer provided by the manufacturer (Illumina). The final read is the Read 2 primer, also provided by the manufacturer (Illumina). Using this primer, a 100 bp read in the V segment is generated starting with the 1st PCR V primer sequence.

II. Identifying Paired T-Cell Receptor Chains without Antigen-Specific Selection In one aspect, the invention provides methods for matching pairs of immune receptor chains from populations of their encoding nucleic acids that have been sequenced. In accordance with one embodiment of the invention, nucleic acid populations encoding repertoires of heavy chain variable regions and light chain variable regions are sequenced so that two separate lists of sequences are formed without any correspondence between members of each list. This may be achieved by carrying out separate sequencing operations, or runs, for each chain, or it may be accomplished by carrying out a single sequence run with the nucleic acids tagged according to the identity of the type of chain it encodes. In accordance with another embodiment of the invention, nucleic acid populations encoding repertoires of T cell receptor alpha (TCR alpha) chains and T cell receptor beta (TCR beta) chains are sequenced, so that two separate lists of sequences are formed without any correspondence between members of each list. In accordance with another embodiment of the invention, nucleic acid populations encoding repertoires of T cell receptor gamma (TCR gamma) chains and T cell receptor delta (TCR delta) chains are sequenced, so that two separate lists of sequences are formed without any correspondence between members of each list. As above, this may be achieved by carrying out separate sequencing runs for each chain, or it may be accomplished by carrying out a single sequence run with the nucleic acids tagged according to the identity of the type of chain it encodes (that is, either TCR alpha and TCR beta, or TCR gamma and TCR delta, respectively). In the latter embodiments, two approaches may be followed for matching or pairing TCR alpha and TCR beta (or TCR gamma and TCR delta) chains into chains that are functional, for example, because they originate from the same T cell. In a first approach, the frequencies of each encoding nucleic acid are determined and TCR alpha chains and TCR beta chains whose encoding nucleotide sequences have the same frequencies are paired to form a functional, or reconstituted, TCR. TCR gamma and TCR delta chains may be matched by the same process. In a second approach, which is applicable to matching all three types of immune receptor pairs, a lymphocyte population is repeatedly divided into a plurality of subsets. Such subsets may be obtained by aliquoting a tissue sample into separate reaction vessels or chambers. Separately from each of a portion, or subpopulation, of the subsets, nucleic acids encoding the two different immune receptor chains are extracted and sequenced, so that two separate lists of sequences are formed without any correspondence between members of each list. As described above, this may be achieved by carrying out separate sequencing runs for each chain, or it may be accomplished by carrying out a single sequence run with the nucleic acids tagged according to the identity of the type of chain it encodes. To illustrate by an example, if a sample containing T cells or B cells is aliquoted into 100 sub-samples, so that on average each aliquot contains a subset consisting of about 1/100 of the total number of T cells or B cells in the original sample, then 20 such subsets may be randomly selected as a portion of the total number of subsets. (Such portion could be any number greater than one and less than 100, although as described more fully below, a number in the range of from 10 to 20 is a good trade-off between amount of sequencing required and likelihood of identifying receptor pairs present at a frequency of interest). In one embodiment, a plurality of subsets is in the range of from 20 to 2000 and a portion of subsets thereof is in the range of from 10 to 50. In another embodiment, a portion of subsets is in the range of from 10 to 20. Examples of the above embodiments are illustrated in FIGS. 12A and 12B.

Figure 12A:
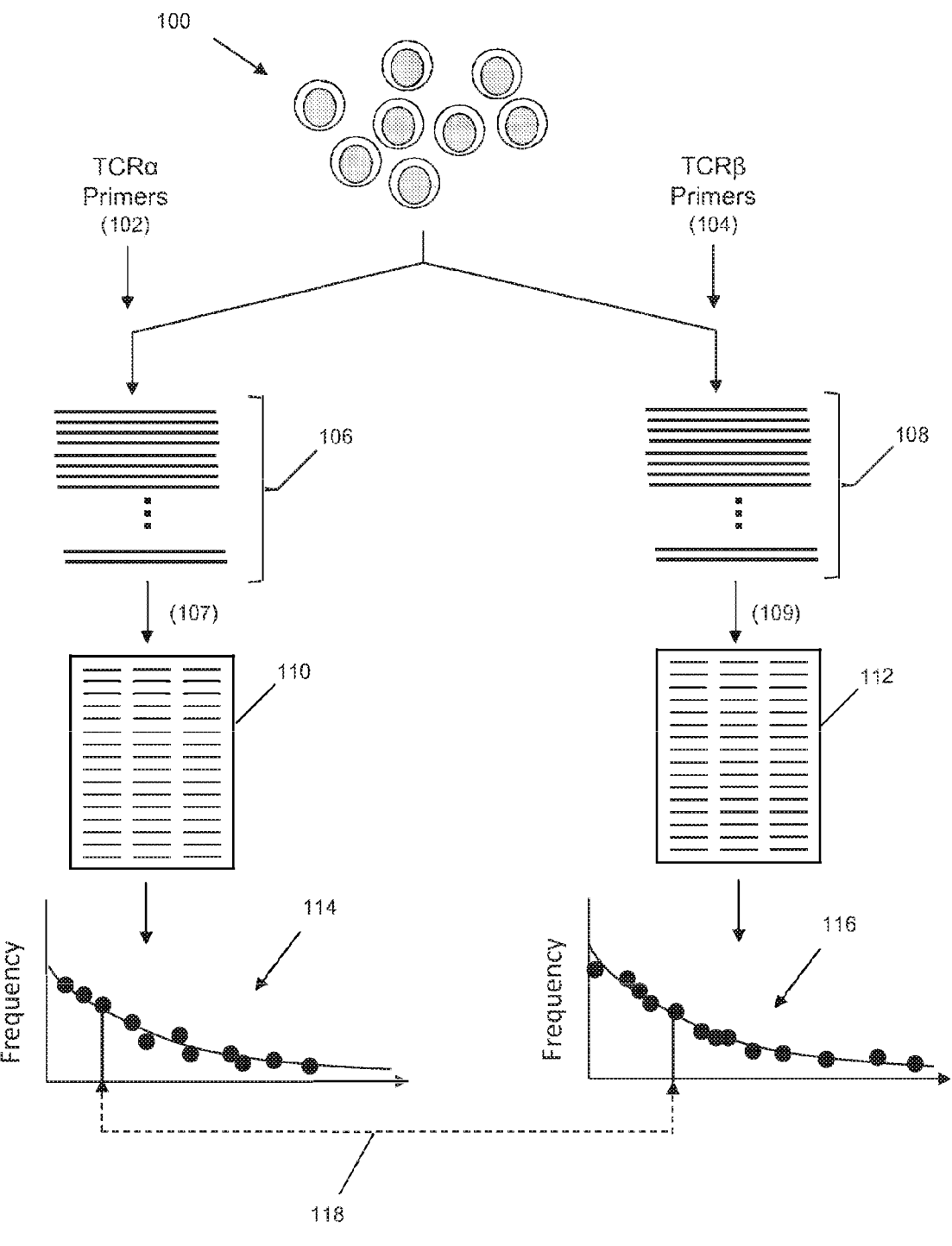
FIG. 12A illustrates diagrammatically steps of one embodiment of the invention for matching TCR alpha and TCR beta chains from separately sequenced molecules.
Figure 12B:
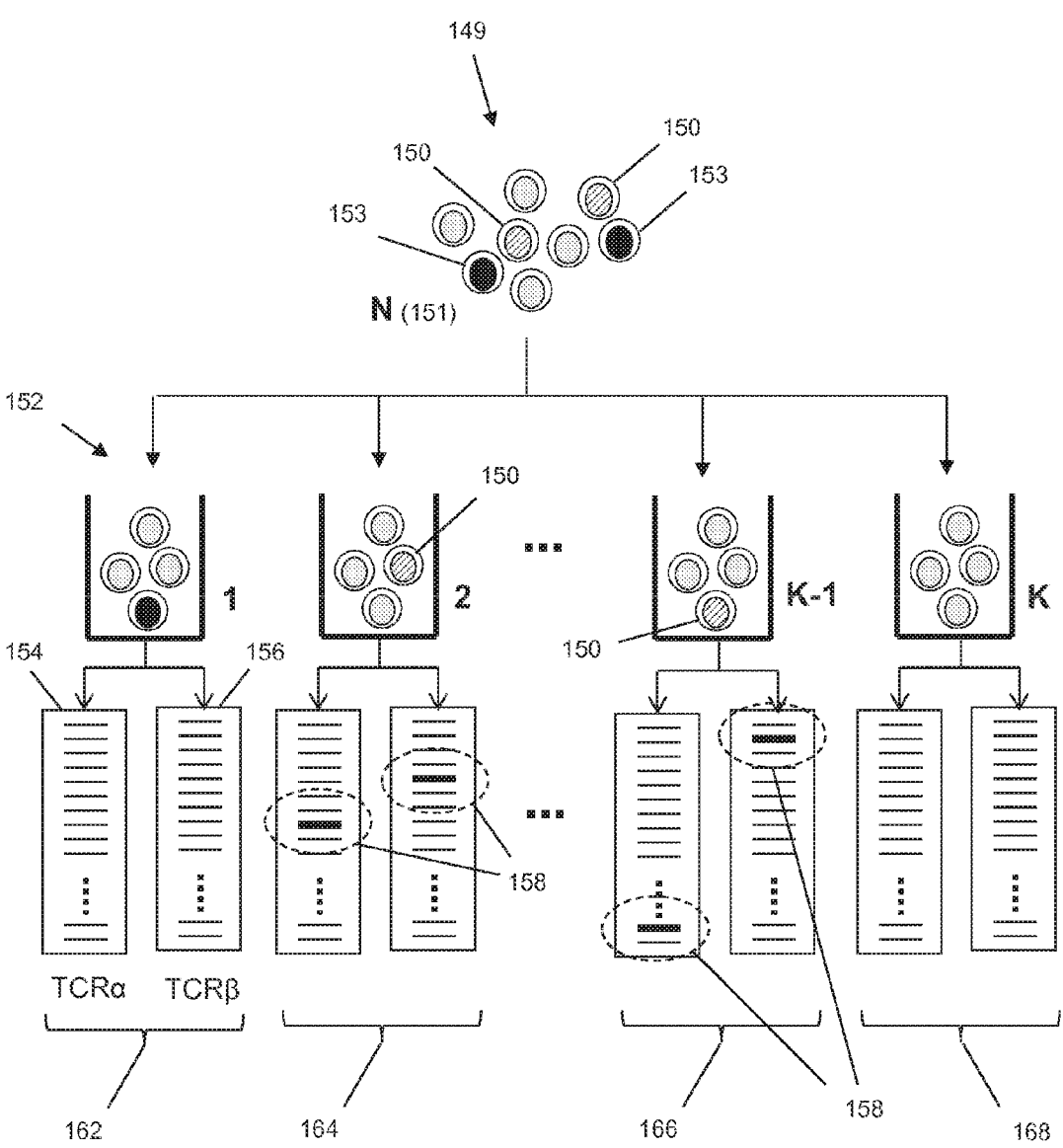
FIG. 12B illustrates diagrammatically steps of another embodiment of the invention for determining either TCR alpha or TCR beta chains that originate from the same T cell or heavy and light chain immunoglobulins that originate from the same B cell.

As illustrated in FIG. 12A, nucleic acid (which may be DNA or RNA) is extracted from a sample containing T cells (100), after which in separate reaction volumes, primers (102) specific for a nucleic acids encoding TCR alpha chains (or a portion thereof) and primers (104) specific for nucleic acids encoding TCR beta chains (or a portion thereof) are combined under conditions that allow the respective nucleic acid populations to be amplified, e.g. by a two-stage polymerase chain reaction (PCR), such as disclosed by Faham and Willis (cited above). Guidance and disclosures for selecting such primers and carrying out such reactions are described extensively in the molecular immunology literature and below (for TCR beta and IgH) and in references such as, Yao et al, Cellular and Molecular Immunology, 4: 215-220 (2007) (for TCR alpha), the latter reference being incorporated herein by reference. In one embodiment, amplicons (106) and (108) produced by a two-stage PCR are ready for sequence analysis using a commercially available next generation sequencer, such as MiSeq Personal Sequencer (Illumina, San Diego, Calif.). After nucleotide sequences have been determined (107) and (109), databases or tables (110 and 112, respectively) are obtained. Like sequences may be counted and frequency versus sequence plots (114 and 116) are constructed. Reconstituted TCRs may be determined by matching (118) TCR alpha chains and TCR beta chains with identical frequencies or with frequencies having the same rank ordering. Clearly, this embodiment of the method works most efficiently when frequencies of different TCR alpha chains and TCR beta chains are not too close together, i.e. are distinct, even taking into account experimental error.

Once a pair of clonotype sequences having equal (or equally ranked) frequencies are identified full length sequences encoding each chain may be reconstructed from the known constant and variable regions using conventional techniques for genetic manipulation and expression, e.g. Walchli et al, PLosOne, 6(11): e27930 (2011); or the like.

Greater accuracy in the determination of receptor chain frequencies may be obtained in a variation of the above embodiment, which may be seen in reference to FIGS. 13A and 13B where RNA encoding TCR beta is amplified in a two-staged PCR. As described more fully below, primer (202) and primer set (212) are used in a first stage amplification to attach common primer binding site (214) to all nucleic acids encoding TCR betas. FIG. 13B illustrates the components of a second stage amplification for generating more material and for attaching primer binding sites P5 (222) and P7 (220) which are used in cluster formation (via bridge PCR) in the Solexa-based sequencing protocol. Primer P7 (220) may also include sample tag (221) for multiplexing up to 96 samples for concurrent sequencing in the same run, e.g. Illumina application note 770-2008-011 (2008). A different type of tag in the same primer may be used to increase the accuracy of the determination of receptor chain frequencies. In this embodiment, primer P7 is modified to include a highly diverse tag set, so that instead of 96 tags, primer P7 is engineered to have 10,000 distinct tags, or more. In other words, primer P7 is a mixture of 10,000 or more distinct oligonucleotides each having an identical template binding region, a distinct tag sequence, and an identical 5' tail portion (e.g., (223) in FIG. 13B). With this arrangement, any subset of nucleic acids encoding the same receptor chain (e.g. less than 100) will receive a different tag with high probability. Such a process of pairing members of a small set of nucleic acids with a much larger set of tags for counting, labeling, sorting purposes is well known and is disclosed in various forms in the following references that are incorporated by reference, U.S. Pat. Nos. 6,172,214; 7,537,897; International PCT Publication No. WO US2005/111242; Brenner et al, Proc. Natl. Acad. Sci., 97: 1665-1670 (2000); Casbon et al, Nucleic Acids Research, 39(12): e81 (2011); Fu et al, Proc. Natl. Acad. Sci., 108: 9026-9031 (2011).

Construction of sets of minimally cross-hybridizing oligonucleotide tag, or tags with other useful properties, is disclosed in the following exemplary references, which are incorporated by reference: Brenner, U.S. Pat. No. 6,172,214; Morris et al, U.S. patent publication 2004/0146901; Mao et al, U.S. patent publication 2005/0260570; and the like. Preferably, the tag set should be at least 100 times (or more) the size of the set of nucleic acids to be labeled if all nucleic acids are to receive a unique tag with high probability. For immune receptor chains, in one embodiment, the number of distinct tags is in the range of from 10,000 to 100,000; in another embodiment, the number of distinct tags is in the range of from 10,000 to 50,000; and in another embodiment, the number of distinct tags is in the range of from 10,000 to 20,000. As disclosed in U.S. Pat. No. 6,172,214, such large mixtures of oligonucleotide tags may be synthesized by combinatorial methods; alternatively, primers containing unique tags may be synthesized individually by non-combinatorial methods, such as disclosed by Cleary et al, Nature Methods, 1: 241-248 (2004); York et al, Nucleic Acids Research, 40(1): e4 (2012); LeProust et al, Nucleic Acids Research, 38(8): 2522-2540 (2010); and the like.

In one aspect, the above embodiment may be carried out by the following steps: (a) obtaining a sample containing T cells; (b) determining nucleotide sequences of TCR alpha chains of T cells from the sample, each TCR alpha chain having a frequency of occurrence in the sample; (c) determining nucleotide sequences of TCR beta chains of T cells from the sample, each TCR beta chain having a frequency of occurrence in the sample; and (d) identifying paired TCR alpha chains and TCR beta chains as those having the same frequency within the sample. Frequencies of the respective TCR alpha chains and TCR beta chains may be determined from the tabulations of encoding nucleic acids, or clonotypes. Alternatively, frequencies of the respective TCR alpha chains and TCR beta chains may be determined from the tabulations of polypeptides encoded by the clonotypes. As mentioned above, clonotype frequencies may be determined by counting clonotypes directly or indirectly by using a tagging scheme as described above.

FIG. 12B illustrates another embodiment for identifying matching receptor subunits which may be applied to either TCRs or BCRs and which may be used even when receptor frequencies among subunit chains are close or indistinguishable, whether because of experimental error or otherwise. Starting with a sample containing lymphocytes (149), which may be either T cells or B cells, subsets are formed by separating or partitioning the sample into a plurality of subsets (152), 1 through K (in the figure). In some embodiments, only a portion of the K subset are analyzed; thus, it is not necessary to actually form all K subsets. One may form subsets of only the portion that are actually analyzed. For example, if the sample has a volume of 100 μL and K=100, but only a portion consisting of 20 subset is to be analyzed, then only twenty 1 μL subsets need be formed. From each subset (152) nucleic acids encoding each different immune receptor chain (TCR alpha and TCR beta being shown under subset 1) are sequenced, thereby forming pairs of lists, for example, (162), (164), (166) and (168) for subsets 1, 2 . . . K−1, K, respectively. Each pair of such lists contains a first list of nucleotide sequences of a first immune receptor chain, e.g. list (154) for TCR alpha of subset 1, and a second list of nucleotide sequences of a second immune receptor chain, e.g. list (156) for TCR beta of subset 1. In one embodiment, the number of subsets, K, is a number in the range of from 5 to 500; in another embodiment, K is a number in the range of from 10 to 100; in another embodiment, K is a number in the range of from 20 to 50. In some embodiments, a portion of subsets analyzed is 10 or fewer subsets; in other embodiments, a portion of subsets analyzed is 20 or fewer subsets; in other embodiments, a portion of subsets analyzed is at least five percent of the subsets; in other embodiments, a portion of subsets analyzed is at least ten percent of the subsets; in other embodiments, a portion of subsets analyzed is at least twenty percent of the subsets.

Each kind of lymphocyte in sample, e.g. lymphocyte (150), is present in the sample at a particular frequency. The distribution of lymphocytes into the subsets is readily approximated by a binomial model; thus, for an arbitrary lymphocyte (for example (150)) having a particular clonotype, (a) its frequency in the sample, (b) the total number of lymphocytes in the sample, and (c) the number of subsets may be related to the expectation of finding at least one of the particular lymphocyte in a predetermined fraction of subsets. This relationship may be expressed as follows: $r=(1-f)^{(N/K)}$, where r is the fraction of subsets containing at least one of the particular lymphocyte, f is the frequency of the particular lymphocyte in the sample, N is the total number of lymphocytes in the sample, and K is the number of subsets. Thus, if one sets r=1/2 and takes N as a constant, then one may select successive values of K so that lymphocytes of different frequencies are present in about half of the subsets. Other values of r could be selected, but r=1/2 provides results with the highest statistical power, thus the value r≈1/2 is preferred. Once such lists are obtained they are examined to identify pairs of first and second nucleotide sequences that either occur in a subset together or are both absent from a subset. By way of example, the members of pair (158) appear in lists (164) of subset 2 and in lists (166) of subset K−1, but neither member of the pair appears in lists (162) or (168) of subsets 1 and K, either alone or together. This of course reflects the presence or absence of the particular lymphocyte that is in subsets 2 and K−1, but is absent from subsets 1 and K, such as lymphocyte (150). Such a pattern confirms that the members of pair (158) go together and correspond to the chains of a functional immune receptor. Other lymphocytes in sample (149) may be present in approximately the same frequency, such as lymphocyte (153). However, the probability that at least one of lymphocyte (153) will occur in exactly the same subsets as lymphocyte (150) is extremely low, especially if r is approximately one half and the portion of the K subsets analyzed is in the range of from 10 to 20, or more.

In one aspect of the invention, matched first and second chains of lymphocytes from a succession of frequency classes may be determined by carrying out the above process repeatedly for different values of K. For example, a 1 mL sample of peripheral blood of a normal individual contains about $1-4.8\times10^6$ lymphocytes of which about 10-15 percent are B cells, about 70-85 percent are T cells and about 10 percent are NK cells; thus, the 1 mL sample may contain from about $7\times10^5$ to about $4\times10^6$ T cells. If the number of T lymphocytes in a 1 mL sample is $N=10^6$, then matching TCR chains of T cells of the following frequencies are matched by identifying those that appear together in fifty percent of the subsets and not at all in the other fifty percent of subsets:

| Frequency | Number of Subsets | Volume (μL) |
|---|---|---|
| .001 | 1443 | 0.7 |
| .0005 | 722 | 1.4 |
| .0001 | 144 | 6.9 |
| .00005 | 72 | 13.9 |

As mentioned above, not all the subsets at a particular frequency need be analyzed. If there are a large number of lymphocytes that have frequencies at or close to a selected frequency, e.g. f=0.001, they may all be resolved by taking a larger and larger portion of the total number of subsets until every pair that appears together in fifty percent of the subsets can be distinguished from every other pair at the same frequency. This is because the probability of two different lymphocytes occurring in exactly the same subsets of the fifty percent becomes infinitesimal as the portion of subsets is increased.

III. Identifying Paired and Unpaired T-Cell Receptor Chains with Antigen-Specific Selection In some embodiments, the invention is directed to identifying antigen-specific T cells by one or a pair of immune receptor chains, such as TCR alpha, or TCR beta, or TCR alpha and TCR beta together; or TCR delta, or TCR gamma, or TCR delta and TCR gamma together. In some embodiments, the nucleotide sequence encoding a single immune receptor chain, such as TCR beta, is used to identify antigen-specific T cells. Sometimes such nucleotide sequences are referred to herein as a "clonotype," although clonotypes also may be ordered pairs of nucleotide sequences specific to a particular T cell, such as the nucleotide sequences encoding the T cell's TCR alpha and TCR beta chains, which may be represented (for example) as $(S_\alpha, S_\beta)$, or like notation, where $S_\alpha$ is a sequence of a segment of TCR alpha and $S_\beta$ is a sequence of a segment of TCR beta, and as a pair they are a clonotype of the cell they originate from.

Figure 12C:
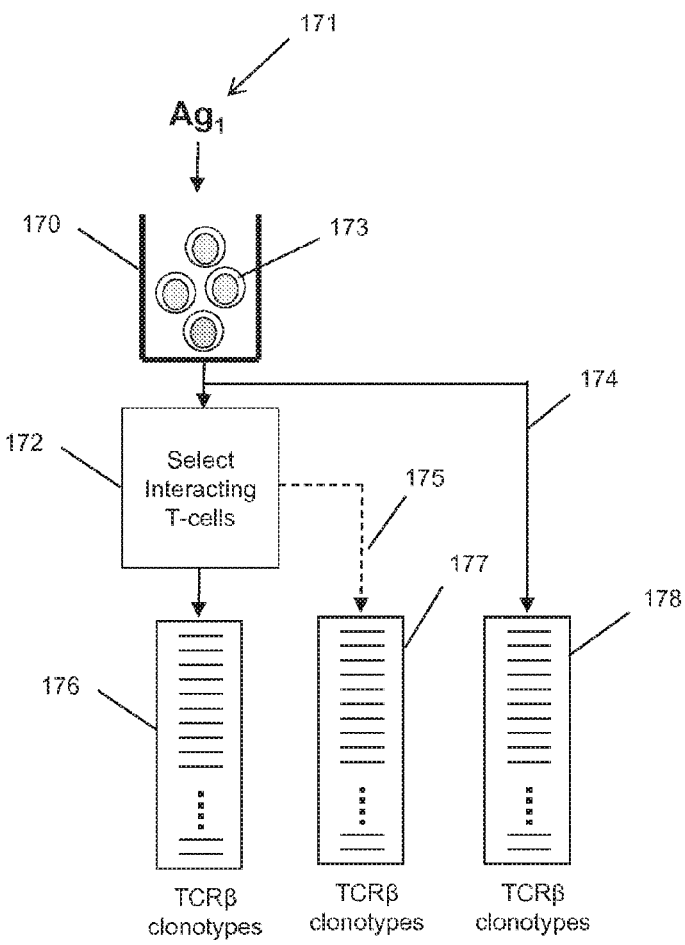
FIG. 12C illustrates diagrammatically an embodiment of the invention for identifying antigen-specific T cells that interact with a single antigen.

Features of some embodiments of the invention are illustrated in FIG. 12C. To a tissue sample (170) comprising T cells (173) is added antigen (171) under interaction conditions so that T cells specific for antigen (171) may interact with antigen (171). Such interaction may be direct or indirect. Direct interactions include binding of antigen (171) to antigen-specific T cells, binding of antigen peptide-multimer conjugates to antigen-specific T cells, and the like. Peptide-multimer conjugates, such as tetramers, are well-known reagents to those of ordinary skill, e.g. Bousso, Microbes Infect. 2(4): 425-429 (2000); Klenerman et al, Nature Reviews Immunol., 2(4): 263-272 (2002); and the like. Indirect interactions include presentation of antigen or anti-gen peptides to antigen-specific T cells by antigen presenting cells, such as, dendritic cells, artificial APCs, and the like. In some interactions, antigen-specific T cells may become activated T cells that may proliferate and/or develop or express activation markers both of which provide means for selecting and/or enriching antigen-specific T cells using conventional techniques. Antigen (171) may comprise a wide variety of compounds or compositions as discussed more fully below. Proteins and peptides derived from one or more proteins are of special interest, particularly when the proteins are associated with cancers or infectious diseases, such as bacterial or virus infections. Antigen (171) may be combined with, exposed to, or added to, tissue sample (170) in a variety of ways known in the art, e.g. Berzofsky et al, J. Clin. Investigation, 113: 1515-1525 (2004). After com-bining antigen (171) with tissue sample (170) in a reaction mixture, antigen-specific T cells (173) and non-antigen-specific T cells alike are exposed to antigen (171) with which they interact either directly or indirectly.

In some embodiments, antigen-specific T cells (173) are activated, possibly after a period of incubation with antigen (171). A period of incubation may vary widely. In some embodiments, incubation may be for an interval of from a few minutes (for example, 10 minutes) to an hour or more; in other embodiments, incubation may be for an interval of a few hours (for example, 2 hours) to 8 or more hours. In other embodiments, antigen-specific T cells (173) interact with antigen by binding to or forming complexes with antigen or antigen reagents, such as antigen peptide-multi-mer conjugates, such that activation may not take place. A step of exposing may include the step of incubating a tissue sample with an antigen. For example, in the case of a protein antigen and a tissue sample that comprises PBMCs, a step of exposing may include combining the tissue sample with peptides derived from the protein antigen such that dendritic cells in the tissue sample present the peptides to antigen-specific T cells in the tissue sample which, in turn, interact with the antigen-presenting dendritic cells and are activated. After exposing T cells (173) to antigen so that antigen-specific T cells interact with antigen, antigen-specific T cells may be selected (172) and/or enriched based on some feature resulting from the interaction, such as antigen pep-tide-multimer binding, activation markers induced, prolif-eration of the T cells, or the like. As mentioned above, the step of selecting (172) antigen-specific T cells may be alternatively a step of enriching antigen-specific T cells from the reaction mixture, and/or a step of separating antigen-specific T cells from the reaction mixture, and/or a step of isolating antigen-specific T cells from the reaction mixture. After antigen-specific T cells are enriched, separated, and/or isolated (172) their clonotypes are determined by sequenc-ing a predetermined segment of a recombined nucleic acid that encodes a portion of an immune receptor, such as TCR beta and/or TCR alpha.

A predetermined segment chosen may vary widely; in some embodiments, it encompasses all or a portion of a V(D)J region, so that clonotypes based thereon have maxi-mal diversity for unique identification of cell clones. Deter-mination of clonotypes is described more fully below, but briefly, recombined nucleic acids encoding one or more selected immune receptors (such as TCR beta as shown in FIG. 12C) are sequenced (for example, by spatially isolating molecules thereof, amplifying such molecules, and carrying out sequencing steps by a high-throughput sequencing chemistry, such as available with commercial next-genera-tion DNA sequencers). As a result of these sequencing steps, sequence reads (176) are produced which are used to deter-mine clonotypes and clonotype frequencies of antigen-specific T cells. Clonotypes and clonotype frequencies are also determined either for T cells of the tissue sample (174) from sequence reads (178) or for non-antigen-specific T cells (175) from sequence reads (177). Non-antigen-specific T cells may be obtained from a two-way sorting procedure (for example, using FACS or MACS) based on T cells labeled according to an interaction, such as, an interaction of antigen-specific T cells with fluorescently labeled antigen peptide multimers. These data may then be analyzed to identify clonotypes associated with antigen-specific T cells, for example, as described in the Example below and FIGS. 17-20. Briefly, in some embodiments, antigen-specific T cells may be associated with clonotype frequencies that increase in the selected population of T cells relative to frequencies of the same clonotype in populations of non-antigen specific T cells or in the population of T cells in tissue sample (170).

Exemplary steps for implementing this embodiment of the invention (i.e., for determining clonotypes associated with antigen-specific T cells in a tissue sample) may include the following: (a) exposing the T cells of the sample to an antigen so that T cells specific for the antigen interact with the antigen; (b) sequencing recombined nucleic acids encod-ing a T-cell receptor chain or a portion thereof from a sample of T cells from the tissue sample to provide sequence reads from which clonotypes are determined; (c) isolating antigen-specific T cells from the tissue sample based on their interaction with the antigen; (d) sequencing recombined nucleic acids encoding a T-cell receptor chain or a portion thereof from a sample of the isolated antigen-specific T cells to provide sequence reads from which clonotypes are deter-mined; and (e) determining antigen-specific T cells in the tissue sample as T cells whose clonotype frequencies increase in the sample of isolated T cells relative to the frequencies of the same clonotypes in a sample of T cells in the tissue sample.

In some embodiments, a step of exposing may be carried out by reacting under interaction conditions an antigen with a tissue sample; in still other embodiments, a step of exposing may be carried out by reaction under activation conditions an antigen with a tissue sample. As mentioned above the step of exposing for this and other embodiments may vary widely, and its implementation may depend on the nature of the tissue sample and the nature of the antigen, as well as other factors. For example, if a tissue sample includes antigen-presenting cells, such as dendritic cells, then exposing may include either addition of an antigen, such as a protein, directly to the tissue sample, or it may include producing antigenic material from an antigen of interest followed by addition of the antigenic material. More efficient T cell activation to a protein antigen, for example, may be accomplished by exposing a tissue sample to a set of overlapping peptides derived from the protein antigen of interest, using conventional techniques. Alternatively, arti-ficial antigen-presenting compositions may be used in the exposing step or its equivalent, e.g. Oelke et al, Nature Medicine, 9(5): 619-624 (2003).

The step of exposing T cells in a tissue sample may include exposing such T cells to whole cells containing antigen, to gene-modified cells expressing antigen, to whole protein, to peptides derived from a protein antigen, to viral vectors expressing an antigen, to antigen-modified, or loaded, dendritic cells. In some embodiments, a tissue sample is a blood sample; in other embodiments, a tissue sample is a sample of peripheral blood mononuclear cells (PBMCs) derived from peripheral blood using conventional techniques. In some embodiments the step of exposing may be carried out by reacting under activation conditions a tissue sample comprising T cells with an antigen, where various activation conditions are described above. In view of the wide variety of tissue samples and antigens, the step of exposing may be alternatively carried out by a step of reacting under activation conditions a tissue sample comprising T cells with an antigen.

Further exemplary steps for implementing the above method may comprise: (a) reacting under activation conditions a tissue sample comprising T cells to an antigen; (b) sorting from the tissue sample activated T cells and un-activated T cells; (b) sequencing recombined nucleic acids encoding a T-cell receptor chain or a portion thereof from a sample of T cells from the activated T cells to provide sequence reads from which clonotypes are determined; (c) sequencing recombined nucleic acids encoding a T-cell receptor chain or a portion thereof from a sample of T cells from the un-activated T cells to provide sequence reads from which clonotypes are determined; and (d) determining anti-gen-specific T cells in the tissue sample as T cells whose clonotype frequencies increase in the sample of activated T cells relative to the frequencies of the same clonotypes in the tissue sample or in a sample of un-activated T cells. Like-wise, exemplary steps for implementing the above method may comprise: (a) reacting under interaction conditions a tissue sample comprising T cells with an antigen; (b) sorting T cells of the tissue sample into a first subset of T cells that form complexes with the antigen or antigen reagents thereof and into a second subset of T cells that do not form complexes with the antigen or antigen reagents thereof, (b) sequencing recombined nucleic acids encoding a T-cell receptor chain or a portion thereof from a sample of the first subset to provide sequence reads from which clonotypes are determined; (c) sequencing recombined nucleic acids encod-ing a T-cell receptor chain or a portion thereof from a sample of T cells from the tissue sample or the second subset to provide sequence reads from which clonotypes are deter-mined; and (d) determining antigen-specific T cells in the tissue sample as T cells whose clonotype frequencies increase in the sample of T cells of the first subset relative to the frequencies of the same clonotypes in the tissue sample or in a sample of T cells from the second subset. As used herein, the term "antigen reagents" means reagents derived from an antigen designed to bind to, or form complexes with, T cells whose TCRs are specific for the antigen. Exemplary antigen reagents include, but are not limited to, multimers conjugated with peptides derived from an antigen.

In some embodiments, the above method of determining antigen-specific T cells in a tissue sample may be carried out by steps comprising: (a) reacting under activation conditions in a reaction mixture a tissue sample comprising T cells to an antigen or antigen reagents thereof; (b) sequencing recombined nucleic acids encoding a T-cell receptor chain or a portion thereof from a sample of T cells from the reaction mixture prior to addition of the antigen to the reaction mixture to provide sequence reads from which clonotypes are determined; (c) incubating the reaction mixture after addition of the antigen or antigen reagent thereof for a predetermined interval; (d) sequencing recombined nucleic acids encoding a T-cell receptor chain or a portion thereof from a sample of T cells from the incubated reaction mixture to provide sequence reads from which clonotypes are deter-mined; (d) determining antigen-specific T cells in the tissue sample as T cells whose clonotype frequencies increase in the incubated reaction mixture relative to the frequencies of the same clonotypes in the reaction mixture prior to the addition of antigen. In some embodiments, a predetermined interval for incubation is usually greater than eight hours; in other embodiments, a predetermined interval may be greater than 24 hours; in further embodiments, a predetermined interval may be within a range of from 8 hours to 72 hours.

In some embodiments, step of isolating antigen-specific T cells may be substituted with either a step of separating a sample of antigen-specific T cells from the tissue sample after exposure to an antigen of interest or a step of recov-ering antigen-specific T cells from the tissue sample after exposure to an antigen of interest. In some embodiments, such step of isolating may be carried out by sorting antigen-interacting and/or activated T cells from a tissue sample; likewise, in some embodiments, non-antigen-specific T cells and/or un-activated T cells may be sorted from a tissue sample. Such steps of the various embodiments may be carried out by a variety of methods including, but not limited to, (i) peptide-MHC multimer staining reagents (such as, tetramers, pentamers, or the like), followed by sorting, panning, or otherwise capturing complexes between such reagents and antigen-specific T cells, (ii) sorting or panning or capturing based on activation markers, such as CD137, CD154, or others (described more fully below), or (iii) proliferation (and therefore, for example, an increase in frequency) of antigen-specific T cells over antigen-non-specific T cells. Thus, in some embodiments, said step of isolating may comprise a step isolating activated T cells; or a step of separating activated T cells from the tissue sample. In some of such embodiments, T cell activation markers, as noted above, may be used to sort, pan or otherwise capture activated T cells, using conventional techniques. Generally, a step is taken for obtaining a sample of T cells from a pool of T cells derived from the tissue sample, which pool is enriched in antigen-specific T cells and/or activated T cells. In some embodiments, T cells with an activation marker may be sorted or isolated using a binding compound, such as an antibody, which specifically binds to the activation marker and which can be directly or indirectly labeled in accordance with conventional methods, e.g. FACS, magnetic bead-based separation, or like techniques.

In another application of the above embodiment, T cell immunogenicity may be measured in the following steps: (a) reacting under activation conditions a tissue sample com-prising T cells with an antigen or an antigen reagent thereof, (b) sequencing recombined nucleic acids encoding a T-cell receptor chain or a portion thereof from a sample of T cells from the tissue sample exposed to antigen or antigen reagents thereof to provide sequence reads from which clonotypes are determined; (c) isolating activated T cells from the tissue sample; (d) sequencing recombined nucleic acids encoding a T-cell receptor chain or a portion thereof from a sample of the activated T cells isolated from the tissue sample to provide sequence reads from which clono-types are determined; and (e) quantifying immunogenicity of the antigen as a function of increases in frequencies of clonotypes in the sample of isolated T cells exposed to antigen with respect to frequencies of the same clonotypes in the tissue sample prior to said step of isolating. Exemplary functions of increases in frequencies of clonotypes include an average of increases among the isolated antigen-specific T cells; another exemplary function of increases includes an average distance of data points of clonotypes registering increases in frequency from the diagonal in plots such as those of FIG. 17, 18 or 19. Still another measure of T cell immunogenicity includes any of several similarity measures of a clonotype profile of T cells of the exposed tissue sample prior to isolating and a clonotype profile of T cells of a sample of T cells isolated (or separated) from the tissue sample, such as described in Faham et al, International Patent Publication No. WO 2013/036459, which is incorporated herein by reference. In this embodiment, antigens of particular interest are therapeutic proteins, such as therapeutic antibodies.

In one aspect, a similarity measure for use with these embodiments of the invention is a monotonically varying function that maps (or is capable of mapping by a simple transformation) at least two sets of clonotype frequency measurements (e.g. two sequence-based clonotype profiles) to the unit interval [0,1]. Simple transformations include, but are not limited to, any linear transformation of dependent variables, logarithmic transformations, such as $y_{ij}=\ln(n_{ij}+1)$ (where $n_{ij}$ is the number of clonotype i in sample j), or the like. A value of zero means no similarity between clonotype profiles and a value of one means two clonotype profiles are statistically identical.

Exemplary similarity measures that may be implemented in these embodiments are described in Legendre and Legendre, Numerical Ecology (Elsevier, 1998); Magurran, Measurement of Biological Diversity (Wiley-Blackwell, 2003); Wolda, Occologia (Berl), 50: 296-302 (1981); and like references, which are incorporated by reference. Such similarity measures include, but are not limited to, Czekanowski's index, Dice's coefficient, Horn's information theory index, Canberra metric, Morisita's index, Kaczynski's similarity index, Sorensen's index, Jacquard's index, Bray-Curtis index, and the like. In one aspect, similarity measures are similarity metrics; or in other words, the similarity measures employed have properties of a distance measure, such as, (i) the value of the measure is always non-negative, (ii) the measure is zero if and only if the clonotype profile measurements are identical, (iii) the value of the measure is invariant with respect to the ordering of the clonotype profile measurements (sometimes expressed as d(x,y)=d(y,x)), (iv) the triangle inequality holds with respect to three different clonotype profile measurements. In another aspect, similarity measures may be correlation coefficients (subject to a simple transformation, e.g. taking its absolute value, squaring its value, or the like, so that its value is restricted to the unit interval). Exemplary correlation coefficients include, but are not limited to, Pearson product-moment correlation coefficient and rank correlations, such as Spearman's rank correlation coefficient, Kendall's tau rank correlation coefficient, and the like. In one embodiment a Morisita-Horn index ($C_{12}$) (including Morisita-Horn index with a logarithmic transformation), as disclosed in Wolda (cited above), is employed with the embodiments.

Figure 12D:
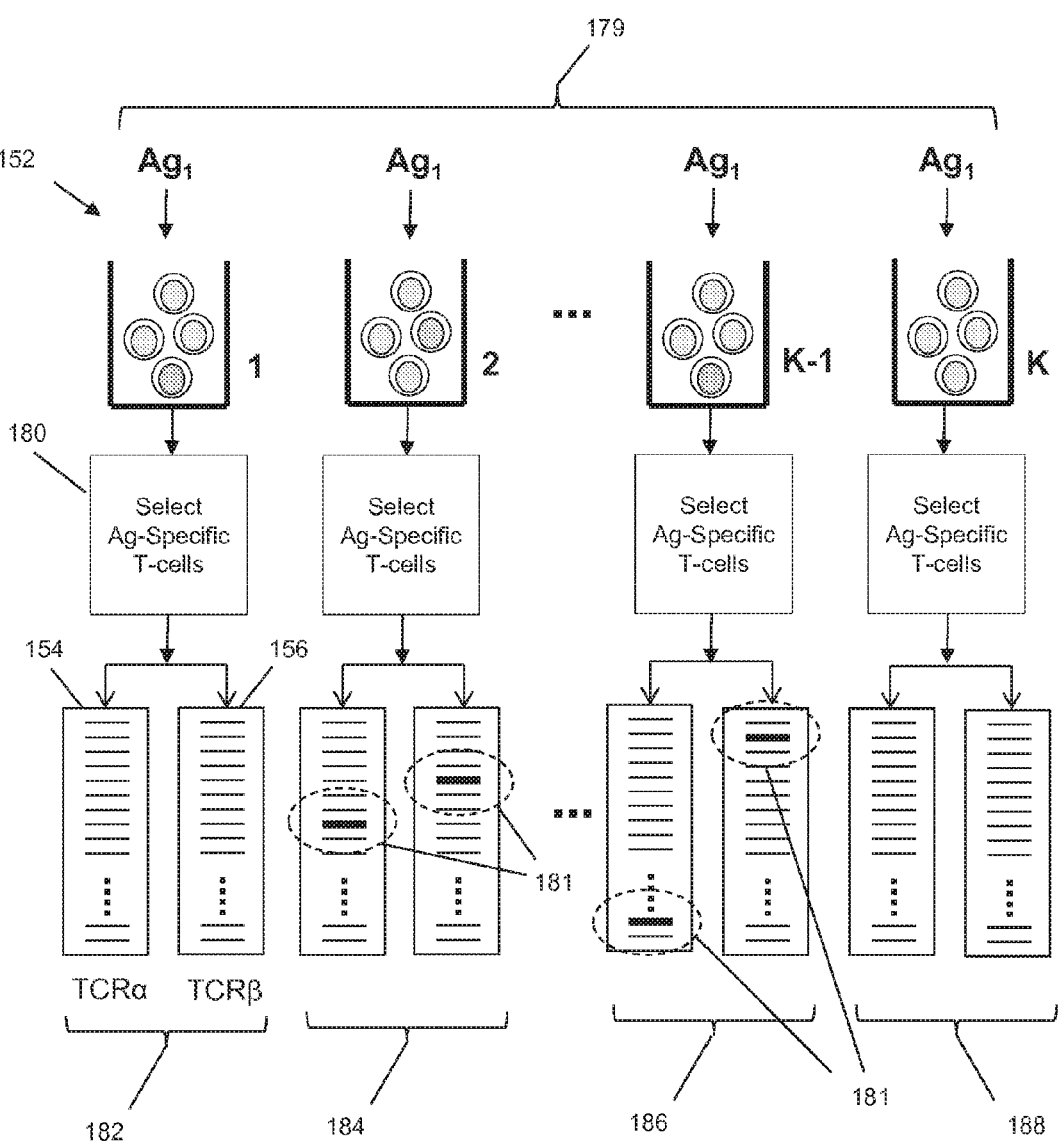
FIG. 12D illustrates diagrammatically an embodiment of the invention for identifying antigen-specific T cells that interact with a plurality of antigens.

Another embodiment for identifying pairs of immune receptor chains of antigen-specific T cells is illustrated in FIG. 12D, where T cell containing reaction mixtures are exposed to a single antigen. Similarly to the embodiment of FIG. 12B, a tissue sample is partitioned into subsets (152) from 1 to K and a portion of the subsets may be selected for analysis. Ranges in the values of K and the portion selected may be the same as for the embodiment of FIG. 12B. In one embodiment, as above, the partitions may be aliquots of the tissue sample, in which approximately equal amounts of tissue sample are provided to each subset, for example, by distributing equal amounts of tissue sample to each of K reaction mixtures, which may be contained by vessels or reactors, such as wells in a multi-well plate. Tissue samples may also be distributed to a plurality of K separate chambers of a microfluidics device in connection with this and/or the embodiments described above. T cells of each subset are exposed to antigen (179) after which reaction mixtures in the K vessels are incubated for a time (for example, a predetermined interval) sufficient for T cells to respond to, or interact with, the antigen, either directly or in a processed form (for example, as an antigen reagent). Such response may include forming a stable complex with antigen or a processed form thereof, or may include the development and/or expression of activation markers by T cells, or may include proliferation by T cells specific for the antigen. Antigen-interacting or antigen-responding T cells are then selected (180) and isolated (for example, sorted) from each of the K chambers, after which recombined nucleic acids encoding predetermined portions of one or both TCR chains are sequenced to provide sequence reads from which clonotypes and clonotype profiles (for example, 154 and 156) are formed. As above with the embodiment of FIG. 12B, once such profiles are obtained they are examined to identify pairs of first and second nucleotide sequences that either occur in a subset together or are both absent from a subset. By way of example, the members of pair (181) appear in lists (184) of subset 2 and in lists (186) of subset K–1, but neither member of the pair appears in lists (182) or (188) of subsets 1 and K, either alone or together. As above, this reflects the presence or absence of a particular lymphocyte, which in this illustration is in subsets 2 and K–1, but is absent from subsets 1 and K. Such a pattern confirms that the members of pair (181) go together and correspond to the chains of a functional immune receptor that is specific for antigen, $Ag_1$ (179).

In some embodiments, the above method of determining receptors of antigen-specific T cells in a tissue sample may comprise the following steps: (a) partitioning a tissue sample containing T cells into a plurality of subsets; (b) exposing the T cells of each of a portion of subsets to an antigen so that T cells specific for the antigen are activated; (c) isolating the activated T cells of each subset of the portion; (d) sequencing recombined nucleic acids encoding T-cell receptor a chains in each subset of the portion to provide sequence reads from which a chain clonotypes are determined; (e) sequencing recombined nucleic acids encoding T-cell receptor beta chains in each subset of the portion to provide sequence reads from which beta chain clonotypes are determined; and (f) identifying as antigen-specific T cell receptors with those pairs of alpha chain clonotypes and beta chain clonotypes that for every subset of the portion (i) either both the a chain clonotype and beta chain clonotype are present in a subset or neither are present in a subset, and (ii) both the a chain clonotype and beta chain clonotype are present in at least one subset of the portion and the a chain clonotype and beta chain clonotype are not present in at least one subset of the portion.

Alternatively, in some embodiments, the above method of determining receptors of antigen-specific T cells in a tissue sample may comprise the following steps: (a) forming a plurality of subsets from a tissue sample containing T cells; (b) reacting under activation conditions the T cells of each subset to an antigen; (c) isolating the antigen-specific T cells of each subset; (d) sequencing recombined nucleic acids encoding T-cell receptor a chains in each subset to provide sequence reads from which a chain clonotypes are determined; (e) sequencing recombined nucleic acids encoding T-cell receptor beta chains in each subset to provide sequence reads from which beta chain clonotypes are determined; (d) identifying as antigen-specific T cell receptors with those pairs of a chain clonotypes and beta chain clonotypes that for every subset (i) either both the alpha chain clonotype and beta chain clonotype are present in a subset or neither are present in a subset, and (ii) both the a chain clonotype and beta chain clonotype are present in at least one subset and the a chain clonotype and beta chain clonotype are not present in at least one subset. In some of these latter embodiments, the plurality of subsets formed may correspond to a portion of the plurality into which a tissue sample is partitioned in the former embodiments. In some embodiments, the step of forming a plurality of subsets may comprise aliquoting portions of a tissue sample into separate reaction vessels. In some embodiments, such portions are equal portions.

Figure 16A:
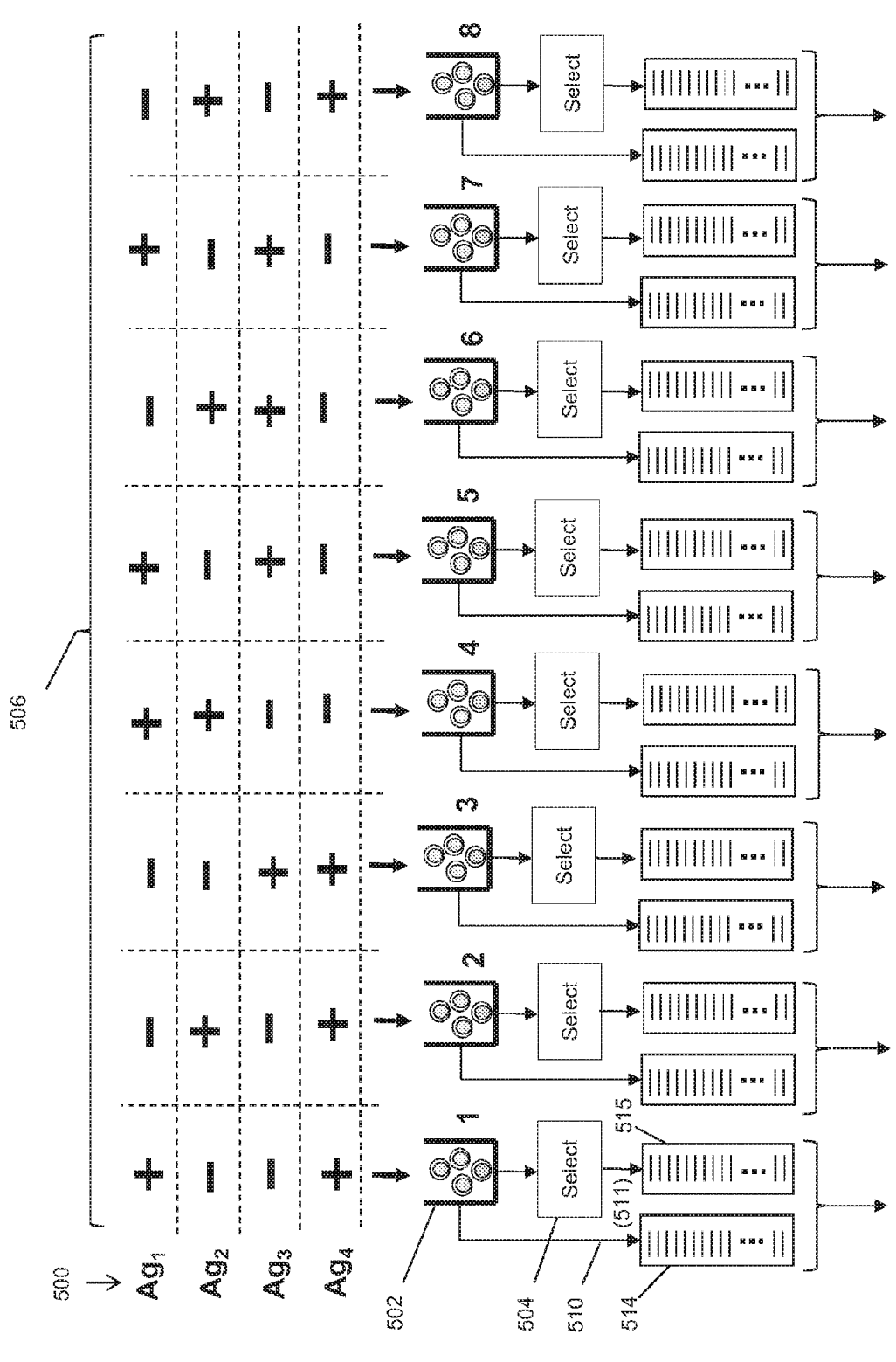
FIG. 16A-FIG. 16B illustrate an embodiment of the invention for determining T-cells and TCRs specific for a plurality of antigens.
Figure 16B:
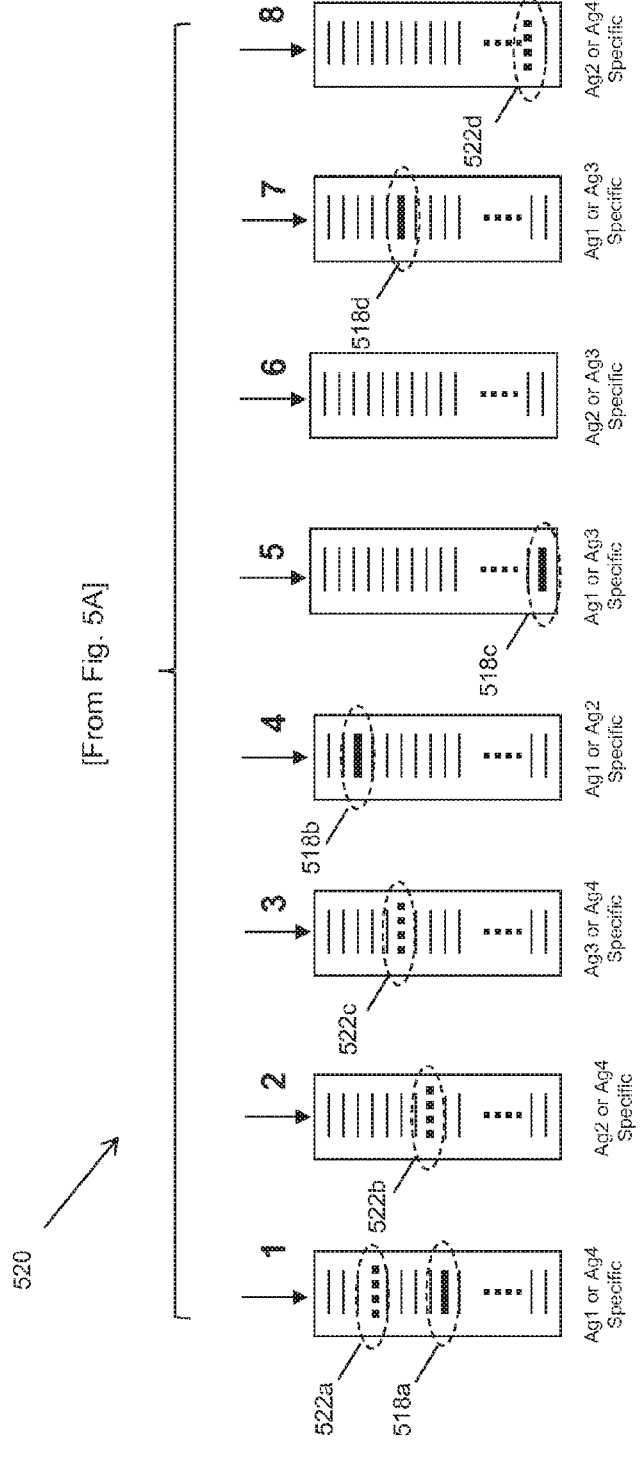

Another embodiment for identifying clonotypes of antigen-specific T cells is illustrated in FIGS. 16A-16B, where a plurality of antigens (500) is exposed to T cells in a plurality of different reaction mixtures. In one aspect, this embodiment permits the identification of antigen-specific T cells from scarce tissue samples, such as from a cancer patient whose tissue sample will be used to identify clonotypes for immune monitoring (e.g. minimal residual disease (MRD) analysis), to produce a patient-specific immunotherapeutic reagent using cancer antigen-specific T cells, or the like. Subsets (or reaction mixtures) (502) from 1 to K (shown in FIGS. 16A-16B as 1-8) are formed from a tissue sample.

The number of different antigens employed may vary widely and in some embodiments the number depends on the nature of the antigens. For protein antigens, in some embodiments, a plurality (a number equal to or greater than 2) of protein antigens may be employed; in further embodiments, a plurality of protein antigens may be in the range of from 2 to 100 protein antigens; in other embodiments, a plurality may be in the range of from 2 to 50 protein antigens; in other embodiments, a plurality may be in the range of from 2 to 10 protein antigens; in still other embodiments, a plurality may be in the range of from 2 to 1000 protein antigens. In some embodiments, a plurality of protein antigens may be in the range of from 10 to 50 protein antigens; in other embodiments, a plurality may be in the range of from 10 to 100 protein antigens; in other embodiments, a plurality may be in the range of from 10 to 1000 protein antigens; in still other embodiments, a plurality may be in the range of from 10 to 500 protein antigens; in still other embodiments, a plurality may be in the range of from 500 to 1000 protein antigens.

As illustrated in FIGS. 16A and 16B, each antigen of plurality (500) is exposed to (or presented to) T cells of a subplurality of reaction mixtures (502) less than the total plurality of K reaction mixtures (in this illustration, subpluralities are each 4). Selections of the subsets of reaction mixtures into which antigens are placed are predetermined for each antigen. In some embodiments, each antigen is applied or exposed to a unique subplurality of subsets. That is, the selection of subsets making up a subplurality corresponding to a particular antigen is unique to that antigen. The size of the subpluralities may be the same or different for each antigen; but in some embodiments, the size of the subpluralities (i.e. the number of subsets in each) are the same for each antigen (which is equal to 4 in FIGS.

16A-16B). In some embodiments, subpluralities of subsets correspond to a different combination of subsets out of the plurality (in this case 8), as mentioned above. Thus, for some embodiments, the number of possible subsets is the same as the number of different combinations of R subsets selected from the total number of subsets, K. (For example, for R=4 and K=8, the number of different combinations is K!/(R! (K−R)!).

A selection of different combinations (or subpluralities) for antigens (500) is indicated by matrix (506) of +'s and −'s which indicate which antigen is exposed to T cells of which subsets. As mentioned above, the selection of subsets into which an antigen is applied (or exposed) is predetermined; thus, for example, antigen $Ag_1$ is applied to subplurality of subsets 1, 4, 5 and 7. A subplurality of subsets which are exposed to antigen may vary between 2 and K−1; however, in some embodiments, the size of the subplurality is an integer equal to or closest to K/2. As above, after exposure to antigen and optional incubation, antigen-specific T cells are selected (504) (e.g. based on interaction with an antigen in the reaction mixture) and clonotype profiles are generated for recombined nucleic acids encoding a selected TCR chain or a portion thereof (as illustrated for subset 1), which permits its corresponding T cell to be identified and/or isolated. Prior to exposure, a sample of T cells may be taken from the tissue sample subsets (for example, 510). Recombined nucleic acids encoding clonotypes of the same TCR segment are sequenced both in sample (510) and in sample (511) to produce sequence reads (514) and (515) from which clonotypes and clonotype frequencies are determined. Frequencies of clonotypes that increase in the selected pools of T cells (illustrated as lists (520) in FIG. 16B) correspond to T cells specific for antigens (for example, Ag1 or Ag4 in reaction mixture 1).

An antigen-specific clonotype may be identified by observing a clonotype that increases in frequency in every reaction mixture of a given antigen. For example, in FIGS. 16A-16B, the same clonotype (518a, 518b, 518c and 518d) is observed to have increased in frequency within reaction mixtures 1, 4, 5 and 7 which corresponds to the unique subplurality of subsets into which antigen 1 was added, but not to have increased in the other reaction mixtures where antigen 1 was absent; therefore, clonotype (518) identifies a T cell with a TCR specific for antigen 1. Likewise, the same clonotype (522a, 522b, 522c and 522d) is observed to have increased in frequency within reaction mixtures 1, 2, 3 and 8, which corresponds to the unique subplurality of subsets into which antigen 4 was added, but not to have increased in frequency in the other reaction mixtures where antigen 4 was absent; therefore, clonotype (522) identifies a T cell with a TCR specific for antigen 4. Since each antigen is exposed to T cells in a unique subplurality of reaction mixtures (or subsets), whenever the same clonotype is observed in each reaction mixture of the unique subplurality, then the clonotype corresponds to a TCR specific for the antigen corresponding to the subplurality.

In one aspect, the above embodiments of the invention for determining clonotypes of antigen-specific T cells in a tissue sample may be carried out with the following steps: (a) forming a plurality of subsets from a tissue sample containing T cells; (b) exposing under interaction conditions T cells in a subplurality of subsets to one or more antigens so that T cells specific for any of the one or more antigens are capable of interacting therewith, and wherein each different antigen is exposed to T cells in a different subplurality; (c) enriching the antigen-interacting T cells of each subset of a subplurality; (d) sequencing recombined nucleic acids encoding a T-cell receptor chain or a portion thereof from said enriched T cells in each subset of the subplurality to provide sequence reads from which clonotypes are determined; (e) sequencing recombined nucleic acids encoding T-cell receptor chain or a portion thereof from said T cells in each subset of the subplurality prior to said step of enriching or from non-enriched T cells in each subset of the subplurality to provide sequence reads from which clonotypes are determined; and (f) identifying a clonotype of a T cell specific for an antigen of the one or more antigens as a clonotype whose frequency increases in each subset of a subplurality corresponding to the antigen and does not increase in subsets outside of such subplurality. That is, in some embodiments, such clonotypes are identified by observing the clonotypes in all reaction mixtures that increase in frequency (520 in FIG. 16B) and identifying clonotypes that appear in each of the subsets of the subplurality corresponding to a given antigen and that is absent in all of the other subsets. In other words, a clonotype of a T cell specific for an antigen increases in frequency only in the subsets or reaction mixtures to which the antigen was added and not in the others. In some embodiments, a clonotype of an antigen-specific T cell may be identified whenever the frequency such clonotype increases in substantially every subset of a subplurality corresponding to the antigen and does not increase in substantially every other subset (every subset not part of the subplurality).

Figure 15:
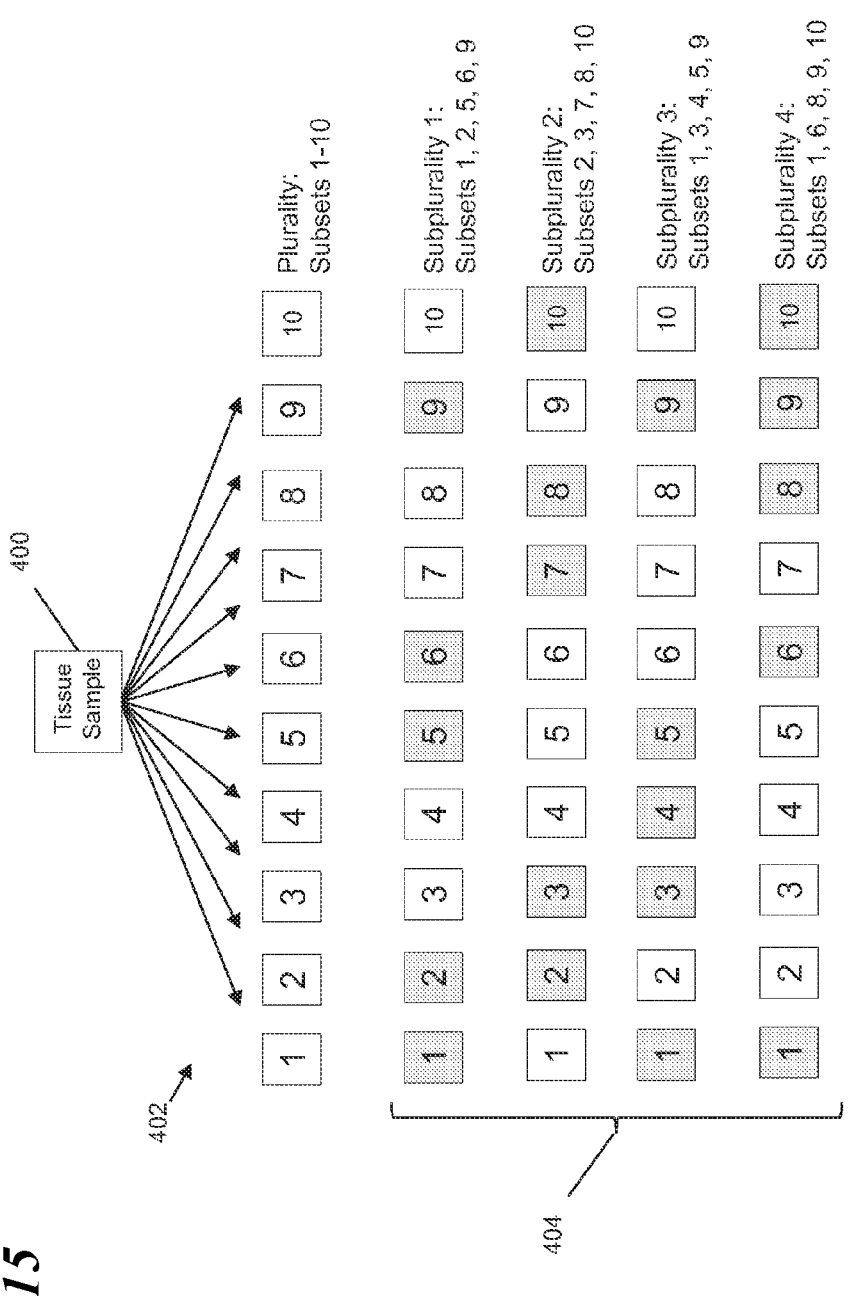
FIG. 15 illustrates an example of a tissue sample divided or aliquoted into a plurality of subsets 1 through 10 and examples of different subpluralities of subsets of the plurality.

For clarity, FIG. 15 illustrates the process of selecting subpluralities of a plurality of subset in accordance with some embodiments of the invention. Tissue sample (400) is separated into a plurality of subsets (402), for example, 10 as shown in FIG. 15. Tissue sample (400) may also be aliquoted into a plurality of subsets, or a plurality of subsets may be formed from it, which may or may not use the entire amount of tissue sample (400). A subplurality of plurality (402) is a selection of from two to nine subsets of plurality (402). In some embodiments, several subpluralities are selected that each have the same number of subsets, such as illustrated in FIG. 15, where each subplurality consists of five subsets. In some embodiments of the invention, a different antigen is exposed to T cells in subsets of a different subplurality. Thus, for example, subplurality 1 may be exposed to antigen 1, subplurality 2 exposed to antigen 2, and so forth. Consequently, in FIG. 15, subset 1 is exposed to antigen 1, antigen 3 and antigen 4; likewise, subset 2 is exposed to antigen 1 and antigen 2; and so forth.

Figure 12E:
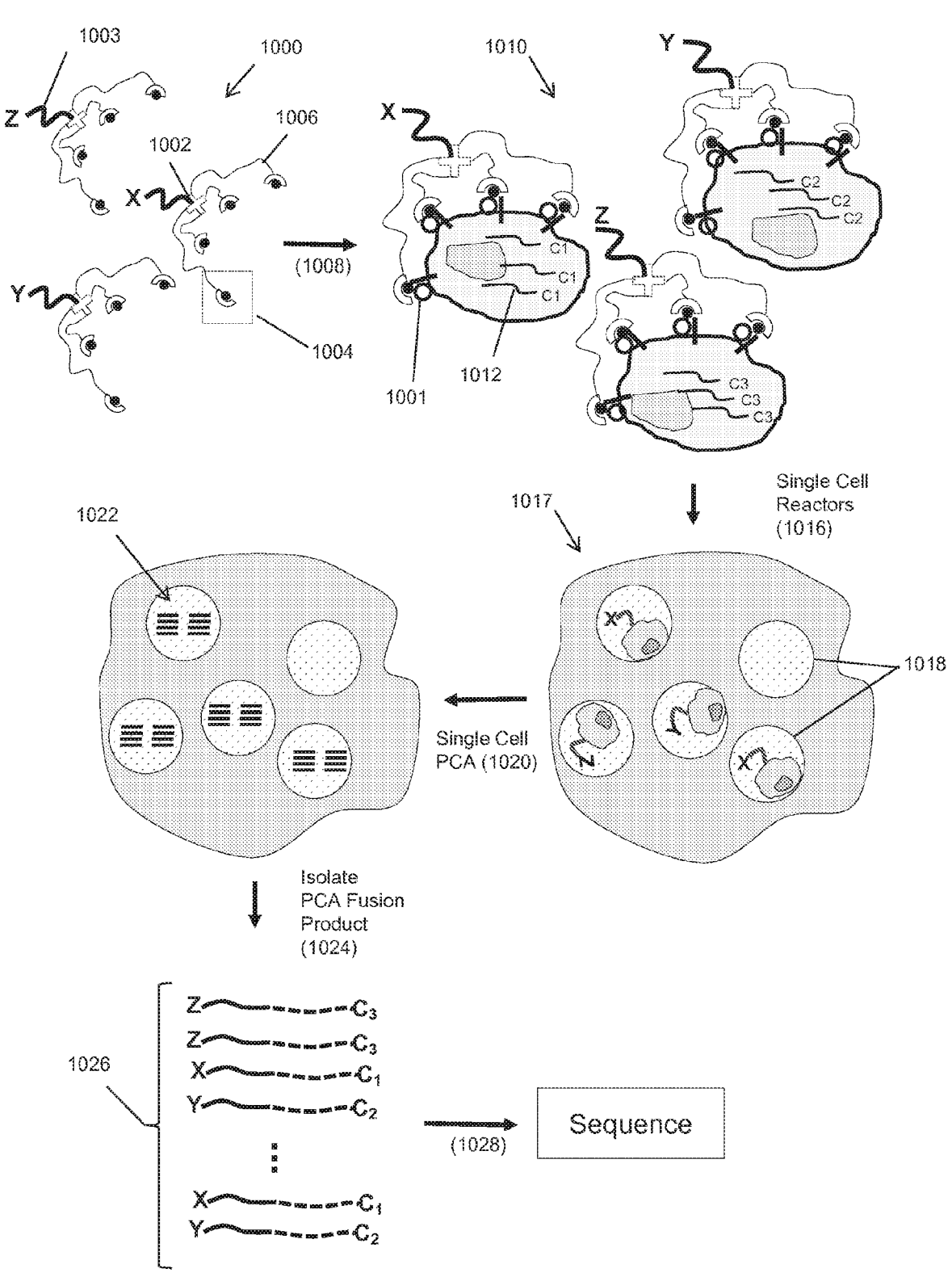
FIG. 12E illustrates steps of an embodiment of the invention for physical identification of antigen-specific T cells using single cell methodology.

IV. Identification of Antigen-Specific T Cell Clonotypes Using Single Cell Techniques In some embodiments, antigen-specific T cell clonotypes may be identified using single cell techniques, such as disclosed in Faham and Willis, U.S. Pat. Nos. 8,236,503 and 8,507,205, which are incorporated herein by reference. In one aspect, the step of selecting T cells that interact with antigen is carried out by disposing T cells exposed to antigen(s) into reactors so that a substantial fraction of reactors contain a single T cell and a single labeled antigen reagent, usually bound to a TCR of the T cell. An objective of these embodiments of the invention is to carry out a polymerase cycling assembly (PCA) reaction (also sometimes referred to as a "linking PCR") on individual cells in the reactors to link their recombined nucleic acid sequences (e.g., encoding a portion of a TCR) to a sequence tag that is associated with, or labels, an antigen reagent present in the reactor with the single T cell. The products of such linking are referred to herein as "fusion products." After their generation, fusion products can be sequenced to identify both the clonotype of the TCR and the sequence tag which, in turn, identifies the antigen reagent. FIG. 12E gives an overview on one embodiment of the invention. Lymphoid cells (1010) (shown combined with antigen reagents (1000)) each have a distinct identifying nucleic acid (1012), which in the figure are exemplified (without any intention of being limiting) as messenger RNAs (mRNAs) (1012), which in the three cells illustrated in the figure are labeled "$C_1$", "$C_2$", and "$C_3$", to indicate that they are three different recombined nucleic acids unique to each cell, respectively. These recombined nucleic acids encode TCRs (for example, 1001) expressed on the surface of the respective T cells. As mentioned above, T cells (1010) are shown combined with antigen reagents (1000), which may be conventional multimers, such as tetramers, which are labeled with sequence tags (for example, 1003) that identify the MHC and peptide portions of the antigen reagent (for example, as shown enclosed in dashed box 1004). Antigen reagent (1000) is exemplified with a conventional structure comprising a framework component (1002), such as a streptavidin molecule; MHC linking moieties (such as, biotinylated peptides (for example, 1006)); and MHC-peptide complexes (1004).

Antigen reagent (1000) may also include sequence tag labels (such as, 1003), which may be produced as taught by Kwong et al, U.S. Pat. No. 8,394,590, which is incorporated herein by reference. The MHC and peptide portion determines the specificity of the reagent for a TCR and vice versa. Antigen reagents (1000) are produced so that substantially every different antigen reagent (e.g. every different multimer) has a different sequence tag. In some embodiments, sequence tags and MHC-peptide portions are selected so that with the knowledge of a tag's sequence, the identity of the MHC-peptide portion can be uniquely determined. That is, for example, there is a one-to-one correspondence between a sequence tag and an MHC-peptide complex, so that (for example), a sequence tag "X" indicates the presence of recombined nucleic acid "$C_1$", a sequence tag "Y" indicates the presence of recombined nucleic acid "$C_2$", and a sequence tag "Z" indicates the presence of recombined nucleic acid "$C_3$". Antigen reagents (1000) are combined (1008) with T cells (1010) in a reaction mixture and are incubated under antigen-interaction conditions which permit the formation of T cell-reagent complexes whenever a TCR is specific for an antigen reagent. After such incubation, cells are disposed (1016) in single cell reactors, which may vary widely and may include, but not be limited to, plates with arrays of nanoliter-volume wells, microfluidic devices, and the like, as described more fully below. In some embodiments, single cell reactors are aqueous micelles in an emulsion, such as illustrated (1017) in FIG. 12E, where a substantial fraction of micelles in the emulsion contain a single T cell together with a single antigen reagent. In one aspect, single-cell emulsion (126) is generated using a microfluidic emulsion generator, such as disclosed by Zeng et al, Anal. Chem., 82: 3183-3190 (2010), or the like.

Reactors (1018) contain a PCA reaction mixture that, for example, may comprise a nucleic acid polymerase, outer primers and linking primers (described more fully below), nucleoside triphosphates, a buffer solution, and the like. In some embodiments, a PCA reaction mixture may also include one or more cell lysing reagents, to give the foregoing reagents access to intracellular recombined nucleic acids, such as mRNAs. For each reactor (1018) containing a cell, PCA reaction (1020) generates fusion products (1022) that may comprise one or more pairs of sequences, such that one member of the pair is a sequence tag and the other member is a predetermined recombined nucleic acid. In other embodiments, fusion products may comprise triplets of sequences, or higher order concatenations, for example, as taught by Faham and Willis, U.S. Pat. No. 8,507,205. In some embodiments of the method of the invention, a single kind of fusion product may be generated for each cell (or per reactor) or a plurality of different kinds of fusion products may be generated for each cell (or per reactor). Such plurality may be at least 2, or it may be in the range of from 2 to 500, or from 2 to 200, or from 2 to 100, or from 2 to 20. In one embodiment, such plurality may be in the range of from 2 to 10. In some embodiments, such plurality is two.

After completion of PCA reaction (1020), emulsion (1017) is broken and fusion products (1026) are isolated (1024). Fusion products (1026) are represented in FIG. 12E as conjugates of sequence tags (X, Y or Z) and recombined nucleic acids (e.g. clonotypes) ($C_1$, $C_2$ and $C_3$). A variety of conventional methods may be used to isolate fusion products (1026) from the reaction mixture, including, but not limited to, column chromatography, ethanol precipitation, affinity purification after use of biotinylated primers, gel electrophoresis, and the like. As part of PCA reaction (1020) or after isolation (1024), additional sequences may be added to fusion products (1026) as necessary for sequencing (1028). Sequencing may be carried out using a conventional high-throughput instrument, e.g. Genome Analyzer IIx (Illumina, Inc., San Diego), or the like.

Polymerase cycling assembly (PCA) reactions permit a plurality of nucleic acid fragments to be fused together to form a single fusion product in one or more cycles of fragment annealing and polymerase extension, e.g. Xiong et al, FEBS Micro biol. Rev., 32: 522-540 (2008). PCA reactions come in many formats. In one format of interest, PCA follows a plurality of polymerase chain reactions (PCRs) taking place in a common reaction volume, wherein each component PCR includes at least one linking primer that permits strands from the resulting amplicon to anneal to strands from another amplicon in the reaction and to be extended to form a fusion product or a precursor of a fusion product. PCA in its various formats (and under various alternative names) is a well-known method for fragment assembly and gene synthesis, several forms of which are disclosed in the following references: Yon et al, Nucleic Acids Research, 17: 4895 (1989); Chen et al, J. Am. Chem. Soc., 116: 8799-8800 (1994); Stemmer et al, Gene, 164: 49-53 (1995); Hoover et al, Nucleic Acids Research, 30: e43 (2002); Xiong et al, Biotechnology Advances, 26: 121-134 (2008); Xiong et al, FEBS Microbiol. Rev., 32: 522-540 (2008); and the like.

Figure 12F:
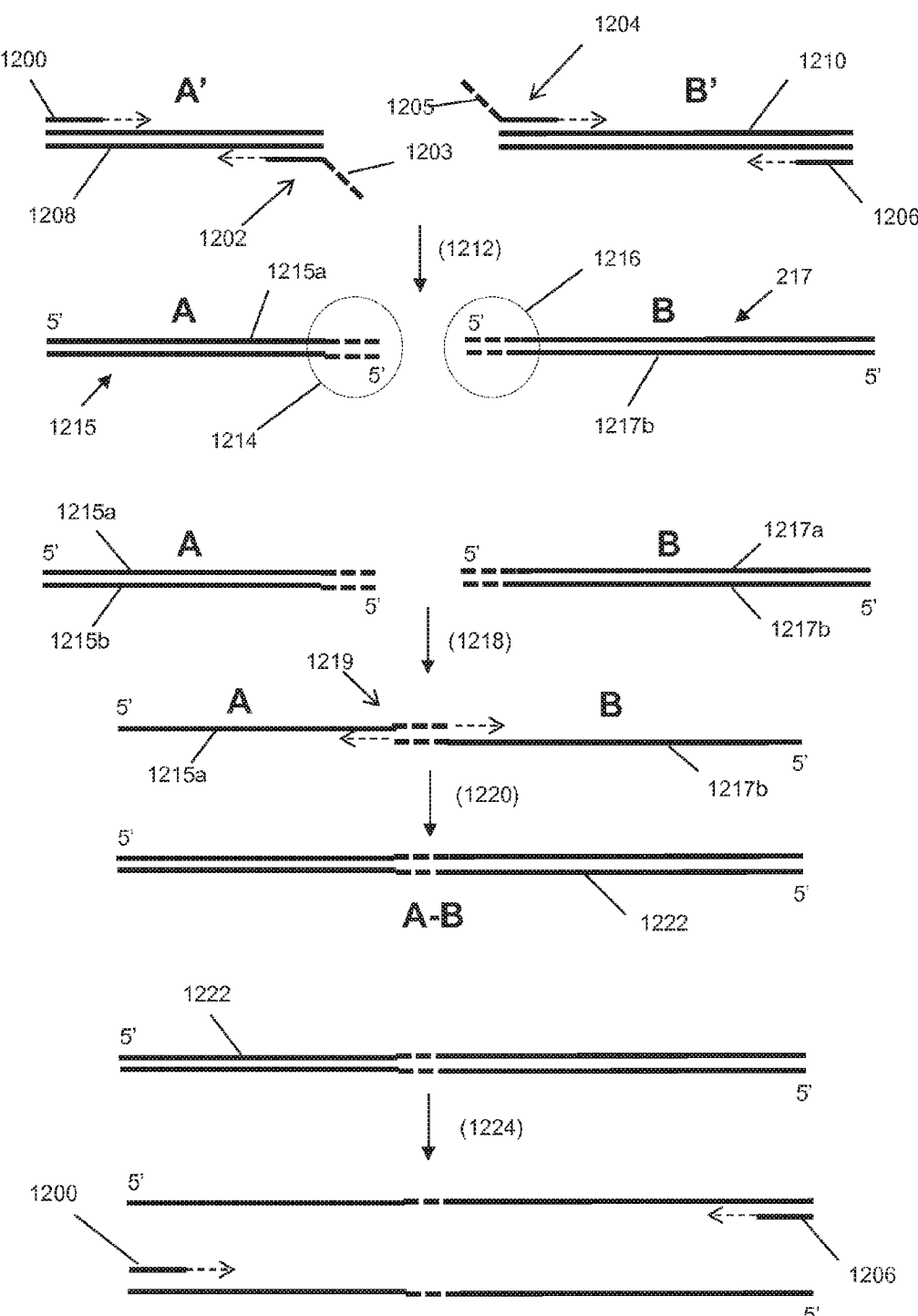
FIG. 12F illustrates a PCA scheme for linking target sequences where pairs of internal primers have complementary.

An exemplary (but not limiting) PCA format useful in the present embodiments is described in FIG. 12F, which illustrates a PCA scheme for joining two separate fragments A' (1208) and B' (1210) into a single fusion product (1222). Fragment A' (1208) is amplified with primers (1200) and (1202) and fragment B' (1210) is amplified with primers (1206) and (1204) in the same PCR mixture. Primers (1200) and (1206) are "outer" primers of the PCA reaction and primers (1202) and (1204) are the "inner" primers of the PCA reaction. Inner primers (1202) and (1204) each have a tail (1203 and 1205, respectively) that are not complementary to A' or B' (or adjacent sequences if A' and B' are segments imbedded in a longer sequence). Tails (1203) and (1205) are complementary to one another. Generally, such inner primer tails are selected for selective hybridization to its corresponding inner primer (and not elsewhere); but otherwise such tails may vary widely in length and sequence. In one aspect, such tails have a length in the range of from 8 to 30 nucleotides; or a length in the range of from 14 to 24 nucleotides. As the PCRs progress (1212), product fragments A (1215) and B (1217) are produced that incorporate tails (1203) and (1205) into end regions (1214) and (1216), respectively. During the PCRs product fragments A (1215) and B (1217) will denature and some of the "upper" strands (1215*a*) of A anneal (1218) to lower strands (1217*b*) of B and the 3' ends are extended (1219) to form (1220) fusion product A-B (1222). Fusion product A-B (1222) may be further amplified by an excess of outer primers (1200) and (1206). In some embodiments, the region of fusion product (1222) formed from tails (1203) and (1205) may include one or more primer binding sites for use in later analysis, such as high-throughput sequencing. Typically, in PCA reactions the concentrations of outer primers are greater than the concentrations of inner primers so that amplification of the fusion product continues after initial formation. For example, in one embodiment for fusing two target nucleic acids outer primer concentration may be from about 10 to 100 times that of the inner primers, e.g. 1 µM for outer primers and 0.01 µM for inner primers. Otherwise, a PCA reaction may comprise the components of a PCR.

Single Cell Analysis

As mentioned above, in some embodiments of the invention, cells from a population are disposed in reactors each containing a single cell. This may be accomplished by a variety of large-scale single-cell reactor platforms known in the art, e.g. U.S. Patent Application Publication Nos. 2010/0255471, 2010/0285975, 2010/0021984, 2010/0173394, and 2009/0181859; and International Patent Publication No. WO 2009/145925; Novak et al, Angew. Chem. Int. Ed., 50: 390-395 (2011); Chen et al, Biomed Microdevices, 11: 1223-1231 (2009); and the like, which are incorporated herein by reference.

In one aspect, cells are disposed in wells of a microwell array where reactions, such as PCA reactions, take place; in another aspect, cells are disposed in micelles of a water-in-oil emulsion, where micelles serve as reactors. Micelle reactors generated by microfluidics devices, e.g. Mathies et al (cited above) or Edd et al (cited above), are of particular interest because uniform-sized micelles may be generated with lower shear and stress on cells than in bulk emulsification processes. Compositions and techniques for emulsifications, including carrying out amplification reactions, such as PCRs, in micelles is found in the following references, which are incorporated by reference: Becher, "Emulsions: Theory and Practice," (Oxford University Press, 2001); Griffiths and Tawfik, U.S. Pat. Nos. 6,489,103; 7,842,457; 8,012,690; 8,048,627; Tawfik and Griffiths, Nature Biotechnology, 16: 652-656 (1998); Nakano et al, J. Biotechnology, 102: 117-124 (2003); Dressman et al, Proc. Natl. Acad. Sci., 100: 8817-8822 (2003); Diehl et al, Nature Methods, 3: 551-559 (2006); Williams et al, Nature Methods, 3: 545-550 (2006); Zeng et al, Analytical Chemistry, 82(8): 3183-3190 (2010); Micellula DNA Emulsion & Purification Kit instructions (EUR_x, Gdansk, Poland, 2011); and the like.

In one embodiment, the mixture of homogeneous sequence tags (e.g. beads) and reaction mixture is added dropwise into a spinning mixture of biocompatible oil (e.g., light mineral oil, Sigma) and allowed to emulsify. In another embodiment, the homogeneous sequence tags and reaction mixture are added dropwise into a cross-flow of biocompatible oil. The oil used may be supplemented with one or more biocompatible emulsion stabilizers. These emulsion stabilizers may include Atlox 4912, Span 80, and other recognized and commercially available suitable stabilizers. In some embodiments, the emulsion is heat stable to allow thermal cycling, e.g., to at least 94° C., at least 95° C., or at least 96° C. Preferably, the droplets formed range in size from about 5 microns to about 500 microns, more preferably from about 10 microns to about 350 microns, even more preferably from about 50 to 250 microns, and most preferably from about 100 microns to about 200 microns. Advantageously, cross-flow fluid mixing allows for control of the droplet formation, and uniformity of droplet size.

In some embodiments, micelles are produced having a uniform distribution of volumes so that reagents available in such reactors result in similarly amplified target nucleic acids and sequence tags. That is, widely varying reactor volumes, e.g. micelle volumes, may lead to amplification failures and/or widely varying degrees of amplification. Such failures and variation would preclude or increase the difficulty of making quantitative comparisons of target nucleic acids in individual cells of a population, e.g. differences in gene expression. In one aspect, micelles are produced that have a distribution of volumes with a coefficient of variation (CV) of thirty percent or less. In some embodiments, micelles have a distribution of volumes with a CV of twenty percent of less.

Cells of a tissue sample and antigen reagent may be suspended in a reaction mixture prior to disposition into reactors. In one aspect, a reaction mixture is a PCA reaction mixture and is substantially the same as a PCR reaction mixture with at least one pair of inner (or linking) primers and at least one pair of outer primers. In some embodiments, a step of lysing cells may be accomplished by heating cells to a temperature of 95° C. or above in the presence of a nonionic detergent, e.g. 0.1% Triton X-100 or Tween-20, for a period prior to carrying out an amplification reaction. In one embodiment, such period of elevated temperature may be from 10-20 minutes. Alternatively, a step of lysing cells may be accomplished by one or more cycles of heating and cooling, e.g. 96° C. for 15 min followed by 10° C. for 10 min, in the presence of a nonionic detergent, e.g. 0.1% Triton X-100 or Tween-20. Guidance for carrying out a lysing step is disclosed in Brown et al, J. R. Soc. Interface 5: S131-S138 (2008).

Clearly many microfluidics device configurations may be employed to generate micelles containing single cells, e.g. Zagoni et al, Chapter 2, Methods of Cell Biology, 102: 25-48 (2011); Bronzes, Chapter 10, Methods of Cell Biology, 102: 105-139 (2011); Wiklund et al, Chapter 14, Methods of Cell Biology, 102: 177-196 (2011); Le Gac et al, Chapter 7, Methods of Molecular Biology, 853: 65-82 (2012); and the like.

In some embodiments, this aspect of the invention for determining antigen-specific T cells may be implemented with the following steps: (a) exposing under interaction conditions a tissue sample containing T cells to antigen reagents labeled with sequence tags; (b) disposing in multiple reactors single T cells specifically bound to at least one antigen reagent, each reactor containing a polymerase cycling assembly (PCA) reaction mixture comprising a pair of outer primers and one or more pairs of linking primers, at least one pair of such outer and linking primers being specific for a recombined nucleic acid encoding a segment of a TCR chain of the T cell and one or more pairs of such outer and linking primers being specific for a sequence tag attached to the antigen reagent; (c) performing a PCA reaction in the reactors to form fusion products comprising said recombined nucleic acids and said sequence tag; (d) spatially isolating individual molecules of fusion products from the reactors; (e) sequencing the spatially isolated fusion products from the reactors to generate sequence reads from which pairs of clonotypes and sequence tags are determined; and (f) identifying antigen-specificity of T cells by their clonotype and sequence tag pairs. In some embodiments, the reactors are aqueous micelles of a water-in-oil emulsion. In some embodiments, aqueous micelles are generated by a microfluidics device. In some embodiments, the reactors are nanoliter wells in a planar substrate. In some embodiments, a further step of lysing the single T cells in the reactors is carried out prior to performing the PCA reaction.

V. Antigen-Specific TCRs

In some embodiments, the present disclosure provides antigen-specific TCRs (e.g., antigen-specific TCR alpha and/or TCR beta chains). In some embodiments, such TCRs are specific for an epitope on the oncoprotein WT1. WT1 is a multifunctional zinc finger transcription factor that was originally identified as a tumor suppressor gene associated with Wilms' tumor, a nephroblastoma. However, WT1 is complex and more recently has been appreciated as an oncogene. Aberrant or overexpressed WT1 has been shown in a variety of cancers including Wilms' tumors, chronic myelocytic leukemia, multiple myeloma, acute lymphoblastic leukemia (ALL), acute myeloid leukemia (AML), myelodysplastic syndrome, mesothelioma, ovarian cancer, breast cancer, prostate cancer, gastrointestinal cancers, lung cancer, colon cancer, thyroid cancer, head and neck cancer, glioblastoma, and sarcoma, among others. In particular, clinical and experimental data indicate that WT1 is a potentially useful target for treatment of leukemias.

The WT1 epitope may be any WT1 antigen. In particular embodiments, the WT1 antigen is a WT1 peptide comprising, consisting essentially of, or consisting of SEQ ID NO: 97. Thus, in one aspect, the present disclosure provides TCRs that bind to an epitope of the WT protein. The TCRs provided herein, in some embodiments, recognize WT1 epitopes that are HLA-A2 restricted. In humans, approximately 50% of the population expresses the MHC class I molecule HLA-A2. HLA-A*02 alleles include HLA-A*0201, *0202, *0203, *0206, and *0207. The TCRs provided herein bind strongly to the WT1 antigen (SEQ ID NO: 97) when loaded by HLA-A*0201. In some embodiments, the TCRs of the invention bind to the WT1 protein antigen when loaded by other HLAs, for example, HLA-A*0203 and HLA-A*0206.

The TCRs provided may bind with different strengths to the WT1 antigen. In some embodiments, the TCRs bind strongly to the WT1 antigen and exhibit potent activity. In some embodiments, the TCRs bind strongly to the WT1 antigen but do not exhibit potent activity. In some embodiments, the TCRs do not bind strongly to the WT1 protein or bind with lower or moderate on/off kinetics, but exhibit highly potent activity. For example, in some embodiments, the TCRs provided herein exhibit high functional avidity and/or high cytolytic activity but do not exhibit long $t_{1/2}$ or slow off rate kinetics.

In some embodiments, the TCRs of the invention bind a WT1/HLA-A2 complex and elicit functional T cell activity. As referred to herein, the $EC_{50}$ refers to the effective concentration of antigen that is loaded onto antigen-presenting cells to elicit a half maximal response of antigen specific activation or cytolysis. In some embodiments, the TCRs of the invention have an $EC_{50}$ for activation of less than about 1 μM, less than about 500 nM, less than about 100 nM, less than about 75 nM, less than about 50 nM, less than about 25 nM, less than about 20 nM, less than about 15 nM, less than about 10 nM, less than about 5 nM, less than about 1 nM, less than about 500 pM, less than about 100 pM, or less than about 1 pM. In some embodiments, the TCRs of the invention have an $EC_{50}$ for cytolysis of less than about 1 μM, less than about 500 nM, less than about 100 nM, less than about 75 nM, less than about 50 nM, less than about 25 nM, less than about 20 nM, less than about 15 nM, less than about 10 nM, less than about 5 nM, less than about 1 nM, less than about 500 pM, less than about 100 pM, or less than about 1 pM. In some embodiments, the $EC_{50}$ for the TCRs provided herein is the concentration of the antigen loaded onto antigen presenting cells (such as T2 cells) that induces 50% of the maximum response.

In some embodiments, the present disclosure provides recombinant TCRs which specifically bind to an epitope of the WT1 protein and have high functional avidity. In some embodiments, the epitope comprises an amino acid sequence set forth in SEQ ID NO: 97. In some embodiments, the high functional avidity is measured by T cell activation and/or T cell-mediated cytolysis. In some embodiments, the high functional avidity is measured by the $EC_{50}$ for T cell activation and/or T cell-mediated cytolysis. Thus, in some embodiments, the present disclosure provides TCRs that specifically bind to an epitope of the WT1 protein and have an $EC_{50}$ for activation and/or cytolysis of less than about 1 μM, less than about 500 nM, less than about 100 nM, less than about 75 nM, less than about 50 nM, less than about 25 nM, less than about 20 nM, less than about 15 nM, less than about 10 nM, less than about 5 nM, less than about 1 nM, less than about 500 pM, less than about 100 pM, or less than about 1 pM.

TCRs may be provided as individual chains, portions thereof, or as complete molecules comprising an alpha and a beta chain. In some embodiments, each of the TCR alpha and beta chains comprise three complementarity determining regions (CDRs), CDR1, CDR2, and CDR3. These regions determine the specificity of the TCR. The CDR1 and CDR2 regions are each found in the variable domain (V). The more diverse CDR3 region of a T cell includes a portion of V, the diverse (D) heavy chains and joint (J) chains and is therefore critical in imparting both diversity of the TCR repertoire as a whole and the antigen specificity of each T cell within the repertoire. CDRs of the alpha and beta chains are generally defined using the nomenclature system used in the Immunogenetics (IMGT) database, but may also be longer or shorter than in the IMGT database system. For example, in some embodiments, the beta chain CDR3 may include the amino acid sequence for the beta chain CDR3 provided herein and additional amino acids C-terminal and/ or N-terminal to the terminal amino acids of the CDR sequence provided. CDRs may also be defined by other nomenclature systems known in the art, such as, for example, the Garcia system (Garcia et al. (1999), Ann. Rev. Immunol 17, 369, incorporated herein by reference in its entirety).

TCRs may be defined by amino acid sequence and/or nucleic acid sequence. In some embodiments, the nucleic acid and amino acid sequences encompassed in the present disclosure have at least 75%, at least 80%, at least 85%, at least 90%, at least 91%, at least 92%, at least 93%, at least 94%, at least 95%, at least 96%, at least 97%, at least 98%, or at least 99% sequence identity to the particular sequences disclosed herein. In some embodiments, amino acid sequences have one or more substitution, deletion, or insertion. In some embodiments, amino acid sequences have two or more, three or more, four or more, or five or more substitutions, deletions, or insertions. In some embodiments, the amino acid substitutions are conservative amino acid substitutions. "Conservative amino acid substitutions" is understood by the skilled artisan to mean that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides, which are to recognize their cognate antigen in the context of an MHC. The ordinarily skilled artisan can readily and routinely screen variant amino acids and/or the nucleic acids encoding them to determine if these variations substantially lessen or destroy the ligand binding capacity by methods known in the art.

In some embodiments, the TCR (e.g., a WT1-specific TCR) comprises an alpha chain CDR1 having an amino acid sequence with at least 85%, at least 90%, at least 95%, at least 96%, at least 97%, at least 98%, or at least 99% sequence identity to an amino acid sequence selected from the group consisting of SEQ ID NOs: 1, 9, 17, 25, 33, and 41. In further embodiments, the TCR alpha chain CDR1 comprises or consists of an amino acid sequence selected from the group consisting of SEQ ID NOs: 1, 9, 17, 25, 33, and 41. In some embodiments, the TCR comprises an alpha chain CDR2 having an amino acid sequence with at least 85%, at least 90%, at least 95%, at least 96%, at least 97% at least 98%, or at least 99% sequence identity to an amino acid sequence selected from the group consisting of SEQ ID NOs: 2, 10, 18, 26, 34, and 42. In further embodiments, the TCR alpha chain CDR2 comprises or consists of an amino acid sequence selected from the group consisting of SEQ ID NOs: 2, 10, 18, 26, 34, and 42. In some embodiments, the TCR comprises an alpha chain CDR3 having an amino acid sequence with at least 85%, at least 90%, at least 95%, at least 96%, at least 97%, at least 98%, or at least 99% sequence identity to an amino acid sequence selected from the group consisting of SEQ ID NOs: 3, 11, 19, 27, 35, and 43. In further embodiments, the TCR alpha chain CDR3 comprises or consists of an amino acid sequence selected from the group consisting of SEQ ID NO: 3, 11, 19, 27, 35, and 43.

In some embodiments, the TCR (e.g., a WT1-specific TCR) comprises a beta chain CDR1 having an amino acid sequence with at least 85%, at least 90%, at least 95%, at least 96%, at least 97%, at least 98%, or at least 99% sequence identity to an amino acid sequence selected from the group consisting of SEQ ID NO: 4, 12, 20, 28, 36, and 44. In further embodiments, the TCR beta chain CDR1 comprises or consists of an amino acid sequence selected from the group consisting of SEQ ID NO: 4, 12, 20, 28, 36, and 44. In some embodiments, the TCR comprises beta chain CDR2 having an amino acid sequence with at least 85%, at least 90%, at least 95%, at least 96%, at least 97%, at least 98%, or at least 99% sequence identity to an amino acid sequence selected from the group consisting of SEQ ID NO: 5, 13, 21, 29, 37, and 45. In further embodiments, the TCR beta chain CDR2 comprises or consists of an amino acid sequence selected from the group consisting of SEQ ID NO: 5, 13, 21, 29, 37, and 45. In some embodiments, the TCR comprises beta chain CDR3 having an amino acid sequence with at least 85%, at least 90%, at least 95%, at least 96%, at least 97%, at least 98%, or at least 99% sequence identity to an amino acid sequence selected from the group consisting of SEQ ID NO: 6, 14, 22, 30, 38, and 46. In further embodiments, the TCR beta chain CDR3 comprises or consists of an amino acid sequence selected from the group consisting of SEQ ID NO: 6, 14, 22, 30, 38, and 46.

In some embodiments, the TCR (e.g., a WT1-specific TCR) comprises an alpha chain amino acid sequence with at least 75%, at least 80%, at least 85%, at least 90%, at least 95%, at least 96%, at least 97%, at least 98%, or at least 99% sequence identity to an amino acid sequence selected from the group consisting of SEQ ID NO: 7, 15, 23, 31, 39, and 47. In some embodiments, the alpha chain TCR comprises or consists of an amino acid sequence selected from the group consisting of SEQ ID NO: 7, 15, 23, 31, 39, and 47. In some embodiments, the beta chain TCR comprises an amino acid sequence with at least 75%, at least 80%, at least 85%, at least 90%, at least 95%, at least 96%, at least 97%, at least 98%, or at least 99% sequence identity to an amino acid sequence selected from the group consisting of SEQ ID NO: 8, 16, 24, 32, 40, and 48. In some embodiments, the beta chain TCR comprises or consists of an amino acid sequence selected from the group consisting of SEQ ID NO: 8, 16, 24, 32, 40, and 48.

In some embodiments, the TCR (e.g., a WT1-specific TCR) comprises, as a complete molecule, paired alpha and beta chains, wherein the alpha chain comprises an amino acid sequence with at least 75%, at least 80%, at least 85%, at least 90%, at least 95%, at least 96%, at least 97%, at least 98%, at least 99%, or 100% sequence identity to SEQ ID NO: 7 and the beta chain comprises an amino acid sequence with at least 75%, at least 80%, at least 85%, at least 90%, at least 95%, at least 96%, at least 97%, at least 98%, at least 99%, or 100% sequence identity to SEQ ID NO: 8. In some embodiments, the TCR (e.g., a WT1-specific TCR) comprises, as a complete molecule, paired alpha and beta chains, wherein the alpha chain comprises or consists of an amino acid sequence of SEQ ID NO: 7 and the beta chain comprises or consists of an amino acid sequence of SEQ ID NO: 8.

In some embodiments, the TCR (e.g., a WT1-specific TCR) comprises, as a complete molecule, paired alpha and beta chains, wherein the alpha chain comprises an amino acid sequence with at least 75%, at least 80%, at least 85%, at least 90%, at least 95%, at least 96%, at least 97%, at least 98%, at least 99%, or 100% sequence identity to SEQ ID NO: 15 and the beta chain comprises an amino acid sequence with at least 75%, at least 80%, at least 85%, at least 90%, at least 95%, at least 96%, at least 97%, at least 98%, at least 99%, or 100% sequence identity to SEQ ID NO: 16. In some embodiments, the TCR (e.g., a WT1-specific TCR) comprises, as a complete molecule, paired alpha and beta chains, wherein the alpha chain comprises or consists of an amino acid sequence of SEQ ID NO: 15 and the beta chain comprises or consists of an amino acid sequence of SEQ ID NO: 16.

In some embodiments, the TCR (e.g., a WT1-specific TCR) comprises, as a complete molecule, paired alpha and beta chains, wherein the alpha chain comprises an amino acid sequence with at least 75%, at least 80%, at least 85%, at least 90%, at least 95%, at least 96%, at least 97%, at least 98%, at least 99%, or 100% sequence identity to SEQ ID NO: 23 and the beta chain comprises an amino acid sequence with at least 75%, at least 80%, at least 85%, at least 90%, at least 95%, at least 96%, at least 97%, at least 98%, at least 99%, or 100% sequence identity to SEQ ID NO: 24. In some embodiments, the TCR (e.g., a WT1-specific TCR) comprises, as a complete molecule, paired alpha and beta chains, wherein the alpha chain comprises or consists of an amino acid sequence of SEQ ID NO: 23 and the beta chain comprises or consists of an amino acid sequence of SEQ ID NO: 24.

In some embodiments, the TCR (e.g., a WT1-specific TCR) comprises, as a complete molecule, paired alpha and beta chains, wherein the alpha chain comprises an amino acid sequence with at least 75%, at least 80%, at least 85%, at least 90%, at least 95%, at least 96%, at least 97%, at least 98%, at least 99%, or 100% sequence identity to SEQ ID NO: 31 and the beta chain comprises an amino acid sequence with at least 75%, at least 80%, at least 85%, at least 90%, at least 95%, at least 96%, at least 97%, at least 98%, at least 99%, or 100% sequence identity to SEQ ID NO: 32. In some embodiments, the TCR (e.g., a WT1-specific TCR) comprises, as a complete molecule, paired alpha and beta chains, wherein the alpha chain comprises or consists of an amino acid sequence of SEQ ID NO: 31 and the beta chain comprises or consists of an amino acid sequence of SEQ ID NO: 32.

In some embodiments, the TCR (e.g., a WT1-specific TCR) comprises, as a complete molecule, paired alpha and beta chains, wherein the alpha chain comprises an amino acid sequence with at least 75%, at least 80%, at least 85%, at least 90%, at least 95%, at least 96%, at least 97%, at least 98%, at least 99%, or 100% sequence identity to SEQ ID NO: 39 and the beta chain comprises an amino acid sequence with at least 75%, at least 80%, at least 85%, at least 90%, at least 95%, at least 96%, at least 97%, at least 98%, at least 99%, or 100% sequence identity to SEQ ID NO: 40. In some embodiments, the TCR (e.g., a WT1-specific TCR) comprises, as a complete molecule, paired alpha and beta chains, wherein the alpha chain comprises or consists of an amino acid sequence of SEQ ID NO: 39 and the beta chain comprises or consists of an amino acid sequence of SEQ ID NO: 40.

In some embodiments, the TCR (e.g., a WT1-specific TCR) comprises, as a complete molecule, paired alpha and beta chains, wherein the alpha chain comprises an amino acid sequence with at least 75%, at least 80%, at least 85%, at least 90%, at least 95%, at least 96%, at least 97%, at least 98%, at least 99%, or 100% sequence identity to SEQ ID NO: 47 and the beta chain comprises an amino acid sequence with at least 75%, at least 80%, at least 85%, at least 90%, at least 95%, at least 96%, at least 97%, at least 98%, at least 99%, or 100% sequence identity to SEQ ID NO: 48. In some embodiments, the TCR (e.g., a WT1-specific TCR) comprises, as a complete molecule, paired alpha and beta chains, wherein the alpha chain comprises or consists of an amino acid sequence of SEQ ID NO: 47 and the beta chain comprises or consists of an amino acid sequence of SEQ ID NO: 48.

With reference to the tables of sequences provided herein, TCRs according to the invention may also be referred to as eJH30_WT1C_5 (used interchangeably herein with the terms "eJH30_5" and "30_5"). eJH30_WT1C_5 comprises an alpha chain TCR amino acid sequence set forth in SEQ ID NO: 7 and a beta chain TCR amino acid sequence set forth in SEQ ID NO: 8. In some embodiments, a TCR provided herein is referred to as eJH30_WT1C_8 (used interchangeably herein with the terms "eJH30_8" and "30_8"). eJH30_WT1C_8 comprises an alpha chain TCR amino acid sequence set forth in SEQ ID NO: 15 and a beta chain TCR amino acid sequence set forth in SEQ ID NO: 16.

In some embodiments, a TCR provided herein is referred to as eJH52_WT1C_13 (used interchangeably herein with the terms "eJH52_13" and "52_13"). eJH52_WT1C_13 comprises an alpha chain TCR amino acid sequence set forth in SEQ ID NO: 23 and a beta chain TCR amino acid sequence set forth in SEQ ID NO: 24. In some embodiments, a TCR provided herein is referred to as eJH64_WT1C_9 (used interchangeably herein with the terms "eJH64_9" and "64_9"). eJH64_WT1C_9 comprises an alpha chain TCR amino acid sequence set forth in SEQ ID NO: 31 and a beta chain TCR amino acid sequence set forth in SEQ ID NO: 32. In some embodiments, a TCR provided herein is referred to as eJH64_WT1C_6 (used interchangeably herein with the terms "eJH64_6" and "64_6"). eJH64_WT1C_6 comprises an alpha chain TCR amino acid sequence set forth in SEQ ID NO: 39 and a beta chain TCR amino acid sequence set forth in SEQ ID NO: 40. In some embodiments, a TCR provided herein is referred to as eJH30_WT1C_7 (used interchangeably herein with the terms "eJH30_7" and "30_7"). eJH30_WT1C_7 comprises an alpha chain TCR amino acid sequence set forth in SEQ ID NO: 47 and a beta chain TCR amino acid sequence set forth in SEQ ID NO: 48.

Advantageously, a TCR as provided herein exhibits high functional avidity and/or high cytolytic activity in vitro. In other embodiments, the TCR provided herein exhibits moderate functional avidity and/or moderate cytolytic activity in vitro. In some embodiments, higher functional avidity and in vitro activity corresponds with higher in vivo potency. In other embodiments, desirable in vivo potency is associated with a particular range of functional avidity and cytolytic activity in vitro, such as, for example, moderate avidity and cytolytic in vitro activity. In some embodiments, the TCRs provided herein exhibit the ability to recognize an endogenous WT1 peptide that is presented on the surface of a cell in the context of endogenously expressed MHC molecules. In some embodiments, the TCRs provided herein recognize the endogenous WT1 peptides with a greater affinity and/or avidity than previously described TCRs recognizing WT1 peptides.

TCR avidity for a particular antigen determines the value of the TCR for therapeutic approaches. For example, in cancer patients, treatment by adoptive immunotherapy of cells expressing TCRs with high avidity for a cancer antigen can be an effective treatment. TCR avidity is a combination of the affinity that it has for the presented antigen, which is determined by the on-rate and off-rate the TCR/peptide-MHC interaction, and the density at which it is displayed on the surface of the T cell. Flow cytometry-based technologies exist that allow the discrimination of T cells that express high affinity and high avidity TCRs due to fast on-rates or slow off-rates in combination with its surface display density. These technologies can be used in conjunction with the described technology to identify high affinity TCRs based on these parameters.

In some embodiments, the WT1 TCRs provided herein exhibit a tetramer half-life of about 30 seconds to about 100 seconds. In some embodiments, the WT1 TCRs provided herein exhibit a tetramer half-life of about 100 seconds to about 300 seconds. In some embodiments, the WT1 TCRs provided herein exhibit a tetramer half-life of less than about 100 seconds or about 100 to about 300 seconds. In some embodiments, the WT1 TCRs provided herein exhibit a tetramer half-life of about 300 seconds to about 1200 seconds. In further embodiments, the TCRs exhibit a tetramer half-life of about 600 seconds to about 900 seconds. In some embodiments, the TCRs exhibit a tetramer half-life of at least about 30, at least about 50, at least about 100, 300, at least about 400, at least about 500, at least about 600, at least about 700, at least about 800, at least about 900, at least about 1000, or more seconds. In some embodiments, the TCRs exhibit a tetramer half-life of about 600, about 625, about 650, about 700, about 750, about 800, about 850, about 900 or about 950 seconds.

In some embodiments, the present disclosure describes nucleic acids encoding the TCRs or portions thereof (e.g., nucleic acids encoding a WT1-specific TCR, or portions thereof). The nucleic acids, in some embodiments, comprise a nucleic acid sequence having at least 75%, at least 80%, at least 85%, at least 90%, at least 95%, at least 96%, at least 97%, at least 98%, at least 99%, or 100% sequence identity to a sequence selected from the group consisting of SEQ ID NOs: 49-96. In some embodiments, the nucleic acids encoding the TCRs described herein are provided as cDNA molecules. In some embodiments, the nucleic acids encoding the TCRs described herein are provided as in vitro transcribed RNA (ivtRNA) molecules. In some embodiments, the present disclosure provides vectors comprising the nucleic acids provided herein. In some embodiments, a vector comprising a nucleic acid encoding a TCR provided herein is used to transduce or transfect a cell, such that the cell will exogenously express the TCR encoded by the nucleic acid. Transducing or transfecting the cells with nucleic acids provided herein may be achieved with any method known in the art.

In some embodiments, the present disclosure provides a nucleic acid sequence encoding a TCR alpha chain comprising a nucleic acid sequence selected from the group consisting of SEQ ID NOs: 55, 63, 71, 79, 87, and 95 or a sequence having at least 90%, at least 95%, or at least 99% sequence identity to a sequence selected from the group consisting of SEQ ID NOs: 55, 63, 71, 79, 87, and 95. In some embodiments, the present disclosure provides nucleic acid sequence encoding a TCR beta chain comprising a nucleic acid sequence selected from the group consisting of SEQ ID NO: 56, 64, 72, 80, 88, and 96, or a sequence having at least 90%, at least 95%, or at least 99% sequence identity to a sequence selected from the group consisting of SEQ ID NOs: 56, 64, 72, 80, 88, and 96.

In some embodiments, the present disclosure provides a first nucleic acid sequence encoding a TCR alpha chain and a second nucleic acid sequence encoding a TCR beta chain, wherein the first nucleic acid sequence is at least 90%, at least 95%, at least 96%, at least 97%, at least 98%, or at least 99% identical to SEQ ID NO: 55 and wherein the second nucleic acid sequence is at least 90%, at least 95%, at least 96%, at least 97%, at least 98%, or at least 99% identical to SEQ ID NO: 56. In some embodiments, the first nucleic acid sequence comprises or consists of SEQ ID NO: 55 and the second nucleic acid sequence comprises or consists of SEQ ID NO: 56. In some embodiments, the first nucleic acid sequence is at least 90%, at least 95%, at least 96%, at least 97%, at least 98%, or at least 99% identical to SEQ ID NO: 63 and the second nucleic acid sequence is at least 90%, at least 95%, at least 96%, at least 97%, at least 98%, or at least 99% identical to SEQ ID NO: 64. In some embodiments, the first nucleic acid sequence comprises or consists of SEQ ID NO: 63 and the second nucleic acid sequence comprises or consists of SEQ ID NO: 64.

In some embodiments, the present disclosure provides a first nucleic acid sequence encoding a TCR alpha chain and a second nucleic acid sequence encoding a TCR beta chain, wherein the first nucleic acid sequence is at least 90%, at least 95%, at least 96%, at least 97%, at least 98%, or at least 99% identical to SEQ ID NO: 71 and wherein the second nucleic acid sequence is at least 90%, at least 95%, at least 96%, at least 97%, at least 98%, or at least 99% identical to SEQ ID NO: 72. In some embodiments, the first nucleic acid sequence comprises or consists of SEQ ID NO: 71 and the second nucleic acid sequence comprises or consists of SEQ ID NO: 72. In some embodiments, the first nucleic acid sequence is at least 90%, at least 95%, at least 96%, at least 97%, at least 98%, or at least 99% identical to SEQ ID NO: 79 and the second nucleic acid sequence is at least 90%, at least 95%, at least 96%, at least 97%, at least 98%, or at least 99% identical to SEQ ID NO: 80. In some embodiments, the first nucleic acid sequence comprises or consists of SEQ ID NO: 79 and the second nucleic acid sequence comprises or consists of SEQ ID NO: 80.

In some embodiments, the present disclosure provides a first nucleic acid sequence encoding a TCR alpha chain and a second nucleic acid sequence encoding a TCR beta chain, wherein the first nucleic acid sequence is at least 90%, at least 95%, at least 96%, at least 97%, at least 98%, or at least 99% identical to SEQ ID NO: 87 and wherein the second nucleic acid sequence is at least 90%, at least 95%, at least 96%, at least 97%, at least 98%, or at least 99% identical to SEQ ID NO: 88. In some embodiments, the first nucleic acid sequence comprises or consists of SEQ ID NO: 87 and the second nucleic acid sequence comprises or consists of SEQ ID NO: 88. In some embodiments, the first nucleic acid sequence is at least 90%, at least 95%, at least 96%, at least 97%, at least 98%, or at least 99% identical to SEQ ID NO: 95 and the second nucleic acid sequence is at least 90%, at least 95%, at least 96%, at least 97%, at least 98%, or at least 99% identical to SEQ ID NO: 96. In some embodiments, the first nucleic acid sequence comprises or consists of SEQ ID NO: 95 and the second nucleic acid sequence comprises or consists of SEQ ID NO: 96.

The present disclose further encompasses TCRs with enhanced or preferential pairing of chains. A limitation in the use of T cell therapies using cells expressing exogenous TCRs has been the mispairing of TCR chains. For example, mispairing of an exogenous TCR α chain with an endogenous TCR β chain, or vice versa, can reduce the efficacy of the T cell therapy, and/or may result in the generation of autoimmune responses in patients. For example, the mixed exogenous/endogenous TCR pairings may trigger graft-versus-host disease (GVHD) or other self-reactive responses. Thus, in some embodiments, the present disclosure encompasses host cells, compositions and methods for enhancing or ensuring the preferential pairing of exogenous TCR chains and/or preventing pairing of exogenous chains with endogenous chains. Strategies for reducing mispairing are known in the art and include strategies wherein the endogenous TCR is not disrupted and strategies wherein the presence or expression or activity of the endogenous TCR is disrupted.

For example, TCRs in some embodiments, the preferential pairing of exogenous TCR chains is achieved by adding one or more disulfide bonds to the constant regions of the exogenous TCR chains via introduction of one or more cysteine residues. Exemplary cysteine substitutions to form disulfide bonds are provided, for example, in U.S. Patent Application Publication Nos. 2010-0047220 (U.S. Pat. No. 8,361,794) and 2014-0112925, and PCT Publication No. WO 2016/70814, each of which is incorporated herein by reference in its entirety. Preferably, the cysteine residue substitution is selected from: Tyr10 to Cys, Ser15 to Cys, Thr45 to Cys, Thr48 to Cys, R53 to Cys, and P89 to Cys of the alpha chain; and/or Ser17 to Cys, Ala19 to Cys, Glu20 to Cys, Ser54 to Cys, Ser57 to Cys, Asp59 to Cys, Ser77 to Cys, and Ser78 to Cys of the beta chain. In some embodiments, the cysteine residue substitution is at one or more of the following pairs of locations: Thr48 of the alpha chain and Ser57 of the beta chain; Thr45 of the alpha chain and Ser77 of the beta chain; Tyr10 of the alpha chain and Ser17 of the beta chain; Thr45 of the alpha chain and Asp59 of the beta chain; or Ser15 of the alpha chain and Glu15 of the beta chain.

In some embodiments, the preferential pairing of exogenous TCR chains is achieved by introducing non-human amino acid residues into the constant region or by using a non-human amino acid constant region. Thus, in some embodiments, the present disclosure provides TCRs comprising human variable regions and non-human constant regions. Non-human constant regions may be constant regions from any mammal such as mice, rats, or non-human primates. Non-human primates include, for example, gorillas, monkeys (e.g., rhesus monkeys, macaque monkeys), apes, chimpanzees, baboons, and orangutans. In some embodiments, the present disclosure provides TCRs wherein murine amino acid residues have been introduced into the constant region, such that the TCRs are fully or partially murinized.

In some embodiments, the preferential pairing of exogenous TCR chains is achieved by introducing mutations in the constant regions of the alpha and/or beta chains that provide steric associations that elicit preferential pairing. For example, the TCR chains may have knob-and-hole mutations. Exemplary knob-and-hole mutations are known in the art and include, for example, mutations and mutation strategies disclosed in US Patent Application Publication No. 2006-0166314, incorporated herein by reference in its entirety. In some embodiments, the knob-and-hole mutation is generated by making one or more amino acid mutation that results in a sterically projecting group on one chain and a sterically recessed group on the other chain. Thus, in some embodiments, the steric interactions of the two chains with the mutations result in preferential pairing of the exogenous TCR alpha and beta chains.

In some embodiments, the preferential pairing of exogenous TCR chains is achieved by use of a physical linkage between the exogenous alpha and beta chains. For example, the exogenously expressed chains can be linked via one or more linkers, such as a flexible peptide linker or paired linkers. In some embodiments, the exogenous TCR chains are paired via dimerization peptides fused to the exogenous TCR alpha and/or beta chains.

In some embodiments, the present disclosure provides single chain TCRs, wherein the TCR alpha and beta chains of the single chain TCR are comprised in a single polypeptide chain. Use of single chain TCRs also prevents mispairing of endogenous with exogenous TCR chains. In some embodiments, the single chain TCR comprises the variable alpha and beta chains linked or conjugated to one another to form a single chain. In some embodiments, the single chain TCR comprises an alpha chain variable region fused to the N terminus of an alpha chain extracellular constant domain sequence, and a beta chain variable region fused to the N terminus of a beta chain extracellular constant and transmembrane sequence, and a linker linking the alpha and beta chains. In other embodiments, the single chain TCR comprises a beta chain variable region fused to the N terminus of the beta chain extracellular constant domain sequence, and an alpha chain variable region fused to the N-terminus of a beta chain extracellular constant and transmembrane sequence, and a linker linking the alpha and beta chains.

VI. Uses of TCRs

The TCRs described herein and/or TCRs identified by the methods described herein have a variety of uses including, but not limited to, as binding compounds for immunotherapy, as components of transfected T cells for adoptive immunotherapy, as antigen sources in vaccines, and as indicators of immune status. For example, an individual complete TCR molecule (e.g., comprising matched alpha and beta chains specific for the same antigen) or a population of complete TCR molecules (e.g., two or more complete TCR molecules that are specific for the same antigen or for different antigens) can be provided in a soluble format may be used as high affinity binding compounds linked to T cell capturing agents for unique anti-cancer therapeutics, e.g. as taught by Jakobsen et al, U.S. Pat. Nos. 7,329,731 and 7,666,604; which are incorporated herein by reference. In some embodiments, the soluble TCR comprises an alpha and a beta chain, wherein the transmembrane sequence in one or both chains has been deleted. In some embodiments, the soluble TCR is a single chain soluble TCR. A soluble single chain TCR, in some embodiments, comprises the variable alpha and variable beta chains fused or covalently linked together through a linker peptide.

In some embodiments, the present disclosure provides a therapeutic vaccine for the treatment of cancer comprising a TCR provided herein. In some embodiments, the vaccine comprise a nucleic acid encoding an alpha chain TCR and/or a beta chain TCR provided herein. In some embodiments, the vaccines described herein are administered with an adjuvant. Common adjuvants known in the art and suitable for use according to the present disclosure include, but are not limited to, alum (e.g., aluminum hydroxide, aluminum phosphate), emulsion-based formulations including mineral oil, oligonucleotides (e.g., CpG DNA), bacterial cell wall components (e.g., LPS), squalene, Freund's complete adjuvant, and Freund's incomplete adjuvant.

In some embodiments, nucleic acid sequences encoding matched TCR alpha and beta chains may be used to construct vectors which may, in turn, be introduced to autologous T cells for use in adoptive immunotherapy of a patient. In some embodiments, samples from which TCRs are analyzed may be taken before and after a patient has been immunized with a cancer antigen, so that elevated TCR chains specific for the cancer antigen are readily matched and selected (e.g., by the methods described herein). References disclosing such applications include Turcotte et al, Adv. Surg., 45: 341-360 (2011); Morgan et al, Science, 314: 126-129 (2006); Walchli et al, PlosOne, 6: e27930 (2011); Robins et al, U.S. Patent Application Publication No. 2010/0034834; and the like.

A population of matched or reconstituted TCRs from a sample comprises a unique profile of an individual's immune system, which contains much more information than profiles of single-sequence clonotypes. That is, a population of matched TCR chains or matched heavy and light chain immunoglobulins comprises a clonotype profile where the clonotypes are pairs of nucleotide sequences that encode pairs of TCR chains expressed in the same T cell or pairs of heavy and light chain immunoglobulins expressed in the same B cell. In both cases, such pairs may be related directly to T cell function, for example, by interaction with sets of MHC tetramer-peptide complexes, e.g. Palmowski et al, Immunol. Rev., 188: 155-163 (2002); Hadrup et al, Nature Methods, 6: 520-526 (2009), or to B cell function, for example, by ELISAs, e.g. Reddy et al, Nature Biotechnology, 28(9): 965-969 (2010).

In one embodiment, clonotype profiles of matched immune receptor chains comprise at least 100 clonotype pairs, wherein each clonotype of the pair comprises a sequence of from 30 to 300 nucleotides. In another embodiment, clonotype profiles of matched immune receptor chains comprise at least 500 clonotype pairs, wherein each clonotype of the pair comprises a sequence of from 30 to 300 nucleotides. In another embodiment, clonotype profiles of matched immune receptor chains comprise at least 1000 clonotype pairs, wherein each clonotype of the pair comprises a sequence of from 30 to 300 nucleotides. In still another embodiment, such clonotype profiles of matched immune receptor chains comprise pairs of TCR alpha and TCR beta clonotypes. In another embodiment, such clonotype profiles of matched immune receptor chains comprise pairs of TCR gamma and TCR delta clonotypes.

The vectors may comprise a nucleic acid encoding an alpha chain TCR provided herein, a beta chain TCR provided herein, or both an alpha and a beta chain TCR provided herein. In some embodiments, the vectors may comprise nucleic acids encoding more than one alpha chain TCR provided herein, more than one beta chain TCR provided herein or more than one alpha chain TCR and more than one beta chain TCR provided herein. In some embodiments, the vectors provided herein are capable of delivering polynucleotides to a host cell. A vector may be a viral vector, a bacterial vector, a plasmid, a cosmid, a phage particle, an RNA molecule, or a DNA molecule. In some embodiments, the vector is an expression vector that has the ability to express the nucleic acids provided herein. In further embodiments, the expression vector may comprise a nucleic acid that is operably linked to one or more control sequences capable of effecting the expression of the nucleic acid molecule in a host cell. Control sequences include transcriptional promoters, operator sequences, sequences encoding mRNA ribosome binding sites, and other sequences involved in transcription and translation. In some embodiments, the vector provided herein is a viral vector, such as, for example, a retrovirus or an adenovirus. In some embodiments, the vector is a lentiviral vector, parvoviral vector, or other retroviral vector. In some embodiments, the present disclosure provides a host cell comprising the vector provided herein. In some embodiments, the host cell comprises one or more vectors. For example, in some embodiments, the host cell comprises a vector comprising a nucleic acid encoding an alpha chain TCR provided herein and a vector comprising a nucleic acid encoding a beta chain TCR provided herein.

For certain approaches to their use, one or more of the TCRs provided herein are exogenously expressed in a cell. Thus, in some embodiments, the present disclosure provides cells express one or more exogenous TCRs (e.g., an exogenous TCR specific for WT1 as provided herein). The cell may be a stem cell, a hematopoietic progenitor cell, a peripheral blood mononuclear cell (PBMC), and/or an immune cell. The immune cell may be an antigen presenting cell, dendritic cell, macrophage, Natural Killer (NK) cell, NK T cell, B cell, T cell, or any combination thereof. In some embodiments, the cell is a T cell or an NK cell. The T cell may be a naïve T cell, an effector T cell, a central memory T cell, an effector memory T cell, a CD4+ T cell, a CD8+ T cell, an alpha/beta T cell, a gamma/delta T cell, a regulatory T cell, or any combination thereof. In some embodiments, the T cell is a T cell that is capable of cytolytic activity (CTL). T cells may be obtained from many sources including PBMC, bone marrow, thymus, tissue biopsy, tumor, lymph node tissue, gut associated lymphoid tissue, mucosa associated lymphoid tissue, spleen tissue, or any other lymphoid tissue. Sources of T cells, or other cells with cytolytic activity, may be autologous or allogenic, and may be from a single individual or from a population of individuals.

In some embodiments, the T cell is isolated from a subject. In some embodiments, the T cell is isolated from a sample collected from a subject. In some embodiments, the present disclosure provides methods for isolating T cells from a sample or subject and engineering the T cells to exogenously express one or more TCR provided herein. In one aspect, the isolated T cell is a CD4+ T cell or a CD8+ T cell. In a particular embodiment, the T cell is a CD8+ T cell that natively expresses at least one endogenous TCR. In some embodiments, the CD8+ T cells have been engineered to decrease or eliminate endogenous TCR expression.

In some embodiments, the T cell is a PD-1 knockout T cell. More specifically, in some embodiments, the T cell has been engineered to lack expression of programmed death ligand 1 (PD-1), which is an inhibitory signaling protein expressed on T cells. Knockdown of PD-1 expression in the T cell may be achieved by any method for gene silencing or gene editing disclosed herein or any method known in the art, such as gene deletion, gene disruption, genome editing (via, for example, ZFN, TALEN, or CRISPR/Cas nuclease systems), miRNA, siRNA, shRNA, or antisense approaches.

In some embodiments, the present disclosure encompasses recombinant host cells, compositions and methods wherein endogenous TCR chain expression is reduced or eliminated. For example, expression of the endogenous TCRs may be inhibited or blocked by gene deletion, gene disruption, genome editing, miRNA, siRNA, shRNA, or antisense approaches. Gene modification may be achieved using an engineered nuclease, such as a zinc finger nuclease (ZFN), TALE-nuclease (TALEN) system, or CRISPR/Cas nuclease. For example, zinc fingered proteins or TALEs may be fused to nuclease domains to generate ZFNs and TAL-ENs, which recognize their intended nucleic acid target through their engineered binding domains and cause the DNA to be cut near the ZFP or TALE via the nuclease activity. In particular embodiments, ZFN are used to selectively disrupt endogenous TCR alpha and beta chain expression. Methods for selectively disrupting endogenous TCR alpha and beta chain expression using ZFN technologies are known in the art, for example, see U.S. Publication No. 2011-0158957, which is incorporated herein by reference in its entirety.

In some embodiments, the cell comprising an exogenous TCR does not natively or endogenously express any TCR. In other embodiments, the cell comprising an exogenous TCR expresses a native or endogenous TCR only at low levels, for example, levels that would not be sufficient to induce an immune response. In still other embodiments, the cell comprising an exogenous TCR expresses a native or endogenous TCR at levels similar to those present in a wild type, non-engineered T cell.

In some embodiments, the TCRs and/or host cells and/or engineered T cells provided herein are further engineered to express one or more immune modulating molecule. The immune modulating molecule may be an immune activating molecule. Thus, in some embodiments, the present disclosure provides compositions and methods comprising WT1-specific TCRs and/or cells exogenously expressing the WT1-specific TCRs, wherein the TCRs and/or cells express an immune activating molecule to enhance the immune response. The immune activating molecule may be a cytokine, a ligand or receptor, a chemokine, a chemokine receptor, a costimulatory molecule, or an antigen binding domain. For example, the molecule may be IL-12, TNFα, IFNγ, IL2, IL-7, IL-15, IL-2, IL-18, CD40L, or other immune activating cytokines known in the art. In some embodiments, the immune activating molecule may be selected from CD40, CD28, OX40, 4-1BBL, and ligands thereof. In some embodiments, the immune activating molecule is CD40L, or 4-1BBL.

Methods for exogenously expressing immune activating molecules are known in the art, for example, in U.S. Patent Publication No. 2016-0045551 and PCT Publication No. WO 2016/069283, which are incorporated herein by reference in their entireties. For example, cells known as chimeric antigen receptor T ("CAR-T") cells are T cells that exogenously express an antigen binding protein (e.g., an scFv); "armored CAR-T cells" are CAR-T cells that further express an immune activating molecule. In some embodiments, the TCRs provided herein are "armored TCRs," meaning that the TCRs are expressed in a cell along with an immune activating molecule. In some embodiments, the expression of the immune activating molecule may be exogenously expressed in the cell by way of introduction to the cell of an additional nucleic acid, other than the nucleic acid or nucleic acids encoding the TCR, for example, by way of a vector that is separate and distinct from a vector comprising the TCR nucleic acid sequences. In other embodiments, the immune activating molecule may be expressed on the same vector as the alpha and/or beta chain TCR.

In some embodiments, the present disclosure provides a cell comprising each of the TCR alpha and beta chain pairs provided herein. In some embodiments, the present disclosure provides a cell comprising more than one exogenous TCR pair, wherein each exogenous TCR pair comprises a different mutation or strategy for ensuring or enhancing preferential TCR pairing. For example, in some embodiments, the present disclosure provides a cell comprising an exogenous TCR alpha and beta chain pair having complementary cysteine residue substitutions in the constant region to provide a disulfide bond; an exogenous TCR alpha and beta chain pair having all or part of the constant regions of TCR alpha and beta chains that are non-human constant regions (e.g., murine or non-human primate constant regions); an exogenous TCR alpha and beta chain pair having complementary knob and hole mutations; an exogenous TCR alpha and beta chain pair wherein the alpha and beta chains are physically linked together; an exogenous single chain TCR; and/or any combination thereof. In some embodiments, two sets of paired exogenous TCR alpha and beta chains have different complimentary cysteine residue substitutions in the constant region. In some embodiments, the expression of the endogenous TCR chains has been reduced or eliminated by the genome editing, gene deletion, gene disruption, miRNA, siRNA, shRNA, or antisense approaches described herein, or by other means of knocking down endogenous TCR expression known in the art.

In one aspect, the present disclosure provides microparticles or nanoparticles that comprise TCRs on the microparticle or nanoparticle surface. In some embodiments, the TCR is present on the surface of the microparticle or nanoparticle via linkage, such as by covalent linkage. In one embodiment, the nanoparticle is a non-biodegradable nanoparticle. In one embodiment, the nanoparticle is a polystyrene particle. In one embodiment, the nanoparticle is a biodegradable particle. In one embodiment, the nanoparticle is a PLGA nanoparticle or a citric acid nanoparticle. In one embodiment, the nanoparticle is a mesoporous silica nanoparticle-supported liposome, where the nanoparticle is encapsulated inside a liposome, with the TCR anchored to the liposome surface via chemical linking to a modified phospholipid. In some embodiments, the mesoporous silica nanoparticle contains a cell toxic agent.

The present disclosure also provides for bispecific or multi-specific molecules comprising a TCR provided herein. In further embodiments, the TCR is coupled to an antibody or fragment thereof. In further embodiments, the TCR is coupled to more than one antibody or fragment thereof. The antibody or fragment thereof may be, for example, a polyclonal antibody, a monoclonal antibody, a Fab, scFv, or alternative antigen binding scaffold. The antibody or fragment thereof may be specific for a tumor antigen and/or a T cell molecule such as CD3. In some embodiments, the bispecific or multi-specific molecules comprise a soluble TCR provided herein linked to one or more antibody or fragment thereof, wherein the TCR targets the antibody or fragment thereof to immune cells to deliver a signal thereto. In some embodiments, the signal is an immune activating signal. For example, in some embodiments, a TCR provided herein is linked to a CD3 specific Fab or scFv. The TCR-Fab or TCR-scFv, in some embodiments, directs the lysis of tumor cells, thereby treating a cancer. In some embodiments, the TCR may be covalently linked through a peptide linker to the one or more antibody or fragment thereof. In some embodiments, the TCR, bispecific molecule, or multi-specific molecule provided herein further comprises a drug or therapeutic agent, and the molecule targets the drug or therapeutic agent to the cancer. For example, the TCRs provided herein may be used to deliver a toxin or chemotherapeutic agent to the cancer.

In some embodiments, the present disclosure provides for pharmaceutical compositions comprising one or more recombinant TCRs described herein. In some embodiments, the pharmaceutical compositions further comprise a pharmaceutically acceptable carrier, diluent or excipient. As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, and/or emulsifier which has been approved by the United States Food and Drug Administration as being acceptable for use in humans and/or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

VII. Kits and Vectors

Kits for detecting and/or treatment of WT1-expressing cancer are also useful and so are provided. In some embodiments, the kit comprises at least one vector comprising at least one of the nucleic acids provided herein. In some embodiments, the kit comprises a nucleic acid comprising at least one of SEQ ID NOs: 49-96, or a vector comprising a nucleic acid sequence according to at least one of SEQ ID NOs: 49-96. In some embodiments, the kit comprises a combination of one or more of SEQ ID NOs: 49-96. For example, in some embodiments, the kits provided by the present disclosure comprise at least 2, at least 3, at least 4, at least 5, at least 6, at least 12, at least 18, at least 24, at least 30, or at least 36 nucleic acid sequences selected from SEQ ID NOs: 49-96.

For example, in some embodiments, the kit comprises at least one nucleic acid sequence selected from SEQ ID NOs: 49-54, or a vector comprising at least one nucleic acid sequence selected from SEQ ID NOs: 49-54. In some embodiments, the kit comprises at least 2, at least 3, at least 4, at least 5, or 6 nucleic acid sequences (or a vector comprising the nucleic acid sequences) selected from SEQ ID NOs: 49-54. In some embodiments, the kit comprises at least one nucleic acid sequence selected from SEQ ID NOs: 57-62, or a vector comprising at least one nucleic acid sequence selected from SEQ ID NOs: 57-62. In some embodiments, the kit comprises at least 2, at least 3, at least 4, at least 5, or 6 nucleic acid sequences (or a vector comprising the nucleic acid sequences) selected from SEQ ID NOs: 57-62. In some embodiments, the kit comprises at least one nucleic acid sequence selected from SEQ ID NOs: 65-70, or a vector comprising at least one nucleic acid sequence selected from SEQ ID NOs: 65-70. In some embodiments, the kit comprises at least 2, at least 3, at least 4, at least 5, or 6 nucleic acid sequences (or a vector comprising the nucleic acid sequences) selected from SEQ ID NOs: 65-70.

In some embodiments, the kit comprises at least one nucleic acid sequence selected from SEQ ID NOs: 73-78, or a vector comprising at least one nucleic acid sequence selected from SEQ ID NOs: 73-78. In some embodiments, the kit comprises at least 2, at least 3, at least 4, at least 5, or 6 nucleic acid sequences (or a vector comprising the nucleic acid sequences) selected from SEQ ID NOs: 73-78. In some embodiments, the kit comprises at least one nucleic acid sequence selected from SEQ ID NOs: 81-86, or a vector comprising at least one nucleic acid sequence selected from SEQ ID NOs: 81-86. In some embodiments, the kit comprises at least 2, at least 3, at least 4, at least 5, or 6 nucleic acid sequences (or a vector comprising the nucleic acid sequences) selected from SEQ ID NOs: 81-86. In some embodiments, the kit comprises at least one nucleic acid sequence selected from SEQ ID NOs: 89-94, or a vector comprising at least one nucleic acid sequence selected from SEQ ID NOs: 89-94. In some embodiments, the kit comprises at least 2, at least 3, at least 4, at least 5, or 6 nucleic acid sequences (or a vector comprising the nucleic acid sequences) selected from SEQ ID NOs: 89-94.

In some embodiments, the kit comprises a first vector comprising a first nucleic acid sequence encoding a TCR alpha chain and a second vector comprising a second nucleic acid sequence encoding a TCR beta chain, wherein the first nucleic acid sequence comprises at least 95%, 96%, 97%, 98%, or 99% sequence identity to a nucleic acid sequence selected from the group consisting of SEQ ID NOs: 55, 63, 71, 79, 87, and 95, and the second nucleic acid sequence comprises at least 95%, 96%, 97%, 98%, or 99% sequence identity to a nucleic acid sequence selected from the group consisting of SEQ ID NO: 56, 64, 72, 80, 88, and 96.

In some embodiments, the first nucleic acid sequence comprises at least 95%, 96%, 97%, 98%, or 99% sequence identity to SEQ ID NO: 55 and the second nucleic acid sequence comprises at least 95%, 96%, 97%, 98%, or 99% sequence identity to SEQ ID NO: 56. In some embodiments, the first nucleic acid sequence comprises or consists of SEQ ID NO: 55 and the second nucleic acid sequence comprises or consists of SEQ ID NO: 56. In some embodiments, the first nucleic acid sequence comprises at least 95%, 96%, 97%, 98%, or 99% sequence identity to SEQ ID NO: 63 and the second nucleic acid sequence comprises at least 95%, 96%, 97%, 98%, or 99% sequence identity to SEQ ID NO: 64. In some embodiments, the first nucleic acid sequence comprises or consists of SEQ ID NO: 63 and the second nucleic acid sequence comprises or consists of SEQ ID NO: 64. In some embodiments, the first nucleic acid sequence comprises at least 95%, 96%, 97%, 98%, or 99% sequence identity to SEQ ID NO: 71 and the second nucleic acid sequence comprises at least 95%, 96%, 97%, 98%, or 99% sequence identity to SEQ ID NO: 72. In some embodiments, the first nucleic acid sequence comprises or consists of SEQ ID NO: 71 and the second nucleic acid sequence comprises or consists of SEQ ID NO: 72.

In some embodiments, the first nucleic acid sequence comprises at least 95%, 96%, 97%, 98%, or 99% sequence identity to SEQ ID NO: 78 and the second nucleic acid sequence comprises at least 95%, 96%, 97%, 98%, or 99% sequence identity to SEQ ID NO: 79. In some embodiments, the first nucleic acid sequence comprises or consists of SEQ ID NO: 78 and the second nucleic acid sequence comprises or consists of SEQ ID NO: 79. In some embodiments, the first nucleic acid sequence comprises at least 95%, 96%, 97%, 98%, or 99% sequence identity to SEQ ID NO: 87 and the second nucleic acid sequence comprises at least 95%, 96%, 97%, 98%, or 99% sequence identity to SEQ ID NO: 88. In some embodiments, the first nucleic acid sequence comprises or consists of SEQ ID NO: 87 and the second nucleic acid sequence comprises or consists of SEQ ID NO: 88. In some embodiments, the first nucleic acid sequence comprises at least 95%, 96%, 97%, 98%, or 99% sequence identity to SEQ ID NO: 95 and the second nucleic acid sequence comprises at least 95%, 96%, 97%, 98%, or 99% sequence identity to SEQ ID NO: 96. In some embodiments, the first nucleic acid sequence comprises or consists of SEQ ID NO: 95 and the second nucleic acid sequence comprises or consists of SEQ ID NO: 96.

In some embodiments, the kit further comprises at least one cell. In some embodiments, the kit comprises a cell expressing one or more exogenous TCR alpha and/or beta chains according to any one of SEQ ID NOs: 7, 8, 15, 16, 23, 24, 31, 32, 39, 40, 47, or 48. In some embodiments, the kit comprises two different cells, wherein each cell expresses a different TCR alpha and beta chain pair. For example, in some embodiments, the kit comprises a cell expressing an exogenous TCR alpha chain and an exogenous TCR beta chain according to SEQ ID NOs: 7 and 8, respectively; another cell expressing an exogenous TCR alpha chain and an exogenous TCR beta chain according to SEQ ID NOs: 15 and 16, respectively; another cell expressing an exogenous TCR alpha chain and an exogenous TCR beta chain according to SEQ ID NOs: 23 and 24, respectively; another cell expressing an exogenous TCR alpha chain and an exogenous TCR beta chain according to SEQ ID NOs: 31 and 32, respectively; another cell expressing an exogenous TCR alpha chain and an exogenous TCR beta chain according to SEQ ID NOs: 39 and 40, respectively; and/or another cell expressing an exogenous TCR alpha chain and an exogenous TCR beta chain according to SEQ ID NOs: 47 and 48, respectively.

VIII. Therapy

The present disclosure provides methods for treating WT1-expressing cancer, wherein the methods comprise administering to a subject a cell comprising one or more of the TCRs provided herein. In some embodiments, the method comprises obtaining cells (e.g., immune cells as provided herein) from the subject to be treated or from a cell donor source; introducing one or more nucleic acid encoding one or more of the TCRs provided herein into the cells such that the cells exogenously express the TCRs provided herein; optionally further expanding the cells; and transferring the cells to the subject. Thus, in some embodiments, the methods provided herein are autologous cell transfer methods, and in other embodiments the methods provided herein are allogenic cell transfer methods. In some embodiments, the cells transferred to the subject comprise more than one TCR provided herein. For example, in some embodiments, the cells transferred to the subject are present in a population of cells wherein each cell comprises 1, 2, 3, 4, 5, or 6 different exogenous TCRs. In other embodiments, the cells transferred to the subject are present in a population of cells made up of 1, 2, 3, 4, 5, or 6 subpopulations of cells, wherein each subpopulation of cells comprises 1, 2, 3, 4, 5, or 6 different exogenous TCRs.

Cells comprising TCRs reactive against the WT1 oncoprotein epitope are suitable for use in adoptive transfer methods to provide treatment to a subject in need of treatment for WT1-expressing cancer. The approach to such cell therapy generally comprises adoptively transferring to a subject in need thereof isolated cells expressing one or more of the TCRs provided herein under conditions permissive for expression of the TCR in the subject, as will be known to those of skill in the art. Thus, the present disclosure provides methods for treating WT1-expressing cancer, comprising adoptively transferring to a subject in need thereof isolated cells recombinantly expressing one or more of the TCRs provided herein.

In that respect, the present disclosure provides methods for adoptive transfer of cells comprising the TCRs provided herein. Cells may be isolated from a subject using any method known in the art. For example, cells may be isolated using an isolation kit, Ficoll-Paque density gradient centrifugation, flow cytometer cell sorting, and the like. In some embodiments, isolated cells may be autologous (i.e., derived from the subject that will receive the resultant transduced or transformed cells). For example, the isolated cells may be obtained from PBMCs and/or hematopoietic stem cells of the subject. In other embodiments, isolated cells may be allogenic. In some embodiments, the isolated cell may be an immune cell. The immune cell may be an antigen presenting cell, dendritic cell, macrophage, Natural Killer (NK) cell, NK T cell, B cell, T cell, or any combination thereof. In certain embodiments, the cell is a T cell or an NK cell. The T cell may be a naïve T cell, an effector T cell, a central memory T cell, an effector memory T cell, a CD4+ T cell, a CD8+ T cell, an alpha/beta T cell, a gamma/delta T cell, a regulatory T cell, or any combination thereof. In some embodiments, the isolated cell may be a T cell, such as a CD4+ T cell or a CD8+ T cell. In particular embodiments, the isolated T cell is a CD8+ T cell. CD8+ T cells are also known as cytolytic T cells (CTLs). In some embodiments, the isolated T cells are expanded in vitro after separation from the subject. During expansion, the isolated T cells may be incubated with accessory cells (e.g., PBMC, dendritic cells, B cells, or monocytes) to support expansion of the T cells in vitro prior to transfer to a subject. In some embodiments, unexpanded isolated T cells are transferred, and such T cells may expand and become activated in vivo.

For monitoring of therapy, the TCRs provided herein are associated with a therapeutic agent or detectable moiety. A detectable moiety may be covalently linked to one or both of the alpha and/or beta chains of the TCR. The detectable moiety may be a label suitable for diagnostic purposes. For example, a detectable moiety may be an enzyme, a dye, an MRI-detectable reagent, a radionucleotide, or any suitable moiety known to those skilled in the art. Such labelled TCRs are useful in a method for detecting a peptide-MHC complex (e.g., SEQ ID NO: 97-HLA-A*0201), for example for use in detection of antigen presenting cells carrying the complex for which the high affinity TCRs provided herein are specific.

In some embodiments, the present disclosure provides methods for treating WT1-expressing cancer, wherein the methods comprise administering to a subject a cell comprising one or more of the TCRs provided herein. In some embodiments, the method comprises obtaining cells (e.g., immune cells as provided herein) from the subject to be treated or from a cell donor source; introducing one or more nucleic acid encoding one or more of the TCRs provided herein into the cells such that the cells exogenously express the TCRs provided herein; optionally further expanding the cells; and transferring the cells to the subject. Thus, in some embodiments, the methods provided herein are autologous cell transfer methods, and in other embodiments the methods provided herein are allogenic cell transfer methods. In some embodiments, the cells transferred to the subject comprise more than one TCR provided herein. For example, in some embodiments, the cells transferred to the subject are present in a population of cells wherein each cell comprises 1, 2, 3, 4, 5, or 6 different exogenous TCRs. In other embodiments, the cells transferred to the subject are present in a population of cells made up of 1, 2, 3, 4, 5, or 6 subpopulations of cells, wherein each subpopulation of cells comprises 1, 2, 3, 4, 5, or 6 different exogenous TCRs.

In some embodiments, the treatment methods provided herein comprise administering to a subject about $10^5$, about $10^6$, about $10^7$, about $10^8$, about $10^9$, or about $10^{10}$ cells exogenously expressing the TCRs provided herein. In some embodiments, the treatment methods provided herein comprise administering to a subject about $10^5$ to about $10^{10}$ cells exogenously expressing the TCRs provided herein, or about $10^6$ to about $10^9$ cells exogenously expressing the TCRs provided herein, or about $10^7$ to about $10^8$ cells exogenously expressing the TCRs provided herein. In some embodiments, the methods provided herein comprise administering to the subject about $10^5$ cells/kg body weight, about $10^6$ cells/kg body weight, about $10^7$ cells/kg body weight, about $10^8$ cells/kg body weight, about $10^9$ cells/kg body weight, or about $10^{10}$ cells/kg body weight. In some embodiments, the methods provided herein comprise administering to the subject about $10^5$ cells/kg body weight to about $10^{10}$ cells/kg body weight, or about $10^6$ cells/kg body weight to $10^9$ cells/kg body weight, or about $10^7$ cells/kg body weight to about $10^8$ cells/kg body weight. In some embodiments, the methods comprise administering the cells to the subject in a single dose or in multiple doses. Administration of the cells to the subject may be performed parenterally, for example by intravenous infusion.

In some embodiments, cells expressing one or more of the TCRs provided herein are administered to a subject prior to, concurrently with, or subsequent to an additional therapeutic treatment for cancer. For example, in some embodiments, cells expressing one or more of the TCRs provided herein are administered to a subject prior to, concurrently with, or subsequent to a chemotherapeutic agent and/or a biological cancer therapy. Chemotherapeutic agents may include, but are not limited to, cyclophosphamide, doxorubicin, hydroxydaunomycin, vincristine, taxanes (e.g., paclitaxel), and others known in the art. Anti-viral agents may include, but are not limited to, nucleoside reverse transcriptase inhibitors, non-nucleoside reverse transcriptase inhibitors, protease inhibitors, viral fusion inhibitors, and interferons such as IFNα.

In particular, for use in animal models, the sequence of the TCR α and β chains may be selected based on species. In some embodiments, transgenic animals expressing human MHC molecules may also be useful in evaluating specific aspects of the present invention.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

EXAMPLES

Example 1

In this example steps common to some embodiments, such as the embodiment of FIG. 12C, are described for particular applications, including but not limited to, exposing a tissue sample comprising T cells to antigen, activating T cell in a tissue sample by antigen, obtaining recombined nucleic acids from T cells of a tissue sample, isolating (or recovering, or sorting, or separating) activated T cells, sequencing recombined nucleic acids, forming clonotypes, and determining clonotypes of antigen-specific T cells.

Tissue Samples:

Characterized PBMCs were purchased from Cellular Technology Limited. Cells were thawed, washed and either lysed with RLT plus buffer (Qiagen) for nucleic acid purification or cultured overnight in the presence of peptides (see below) to identify antigen-specific T cells.

Antigen-Specific T Cell Assays, Flow Cytometry and Cell Sorting:

Antigen-specific cells were identified using a variety of assays: pentamer binding, cell surface marker upregulation (CD137, CD107) following short-term peptide incubation, and proliferation following relatively long-term peptide incubation. Pentamer-specific T cells were identified by incubating PBMCs with HCMV pp65$_{495-504}$ Pentamer (Pro-Immune) according to manufacturer's instructions. The procedures for obtaining viable antigen-specific T cells based on acquisition of the cell surface markers CD137/107 (for CD8 antigen-specific T cells) following brief in vitro incubation with peptides are well-known, e.g. Chattopadhyay et al, Nature Medicine, 11: 1113-1117 (2005); Meier et al, Cytometry A, 73: 1035-1042 (2008); Wolfl et al, Blood, 110: 201-210 (2007); Wolfi et al, Cytometry A, 73: 1043-1049 (2008); and the like.

Briefly, complete media containing 15% Fetal Bovine Serum (FBS), non-essential amino acids, glutamine and antibiotics was used for peptide incubations. Thawed PBMCs were washed and suspended at ~400,000 cells/well (96-well i-bottom plates) in complete media. Unconjugated antibodies directed against CD28 and CD49d were then added to the wells containing the suspended cells. Peptides derived from CMV pp65 (HCMVA (pp65) (JPT Peptide Technologies) were added directly to the cell/antibody mixture, according to manufacturer's instructions. A single peptide derived from CMV pp65 (sequence NLVPMVATV (SEQ ID NO: 98); herein referred to as "pp65$_{495}$") was used at 2 µg/mL. pp65 "PepMix" and CEF+ peptide pools (JPT Peptide Technologies) were added directly to the cell/antibody mixture, according to manufacturer's instructions. Following addition of peptides, cells were incubated at 37° C. for ~8 hours. Negative control incubations were prepared as outlined above without addition of peptides.

At the end of the incubation, cells were harvested from the culture and stained with antibodies for analysis and sorting by flow cytometry. For each CD8 antigen-specific assay (CD137 and CD107), fluorescently conjugated antibodies to the following cell surface markers were used for flow cytometry: CD8, CD3 and either CD137 or CD107a and CD107b. Cells were then washed and suspended in PBS containing FBS (2%) and 4',6-diamidino-2-phenylindole (DAPI) for exclusion of non-viable cells. Carboxyfluorescein diacetate, succinimidyl ester (CFSE)-labeled PBMCs were incubated as outlined above for 6 days in the presence of peptide and antibodies directed against CD28 and CD49d. Antigen-specific CD8+ T cells were identified and sorted based on CFSE dilution at day 6. Cells were acquired and sorted using a FACSAria (BD Biosciences) instrument. Sorted antigen-specific (CD3$^+$CD8$^+$CMVpentamer$^+$, CD3$^+$CD8$^+$CD137$^+$, CD3$^+$CD8$^+$CD107a/b$^+$, or CD8$^+$CFSE$^{low}$) and non-antigen-specific (CD3$^+$CD8$^+$CD137$^-$, CD3$^+$CD8$^+$CD107a/b$^-$) cells were pelleted and lysed in RLT Plus buffer for nucleic acid isolation. Analysis of flow cytometry data files was performed using FlowJo (Ashland, Oreg.).

RNA and cDNA Preparation:

RNA (and DNA) was isolated using AllPrep DNA/RNA mini and/or micro kits, according to manufacturer's instructions (Qiagen). RNA was reverse transcribed to cDNA using Vilo kits (Life Technologies).

TCR Beta Amplification and Sequencing.

cDNA was amplified using locus specific primer sets for TCR beta. This amplification reaction reproducibly amplified all possible RNA transcripts found in the sample containing the rearranged TCR beta locus regardless of which variable (V) segment and which common constant (C) region allele each rearranged molecule possessed, while appending the necessary sequences for cluster formation and sample indexing.

First stage primers were designed so as to allow for the amplification of all known alleles of the germline sequences, as described above and in the following; Faham et al, Blood, 120: 5173-5180 (2012). At the 5' ends of the V segment primers, universal sequences complementary to second stage PCR primers were appended. Primers were optimized such that each possible V and C segment was amplified at a similar rate so as to minimally skew the repertoire frequency distribution during the amplification process. Specificity of the primers was, in contrast, not optimized as the primer sequences could be mapped and removed from the eventual sequence read. Thus, a given sequence may have been amplified by multiple primers.

In the second stage PCR, primers on the C side annealed to the C segment with a 5' tail that contained the sequence primer and the P5 sequence used for cluster formation in the Illumina Genome Analyzer sequencer. Primers on the V side annealed to the V segment with a 5' tail that contained the sequence primer and the P7 sequence used for cluster formation. For each sample, one pair of primers is used in the second stage. On the C side, it is always the same primer. On the V side, it is one of a set of primers which differs by a 6 base index. Specifically, the primers on the V side of the amplification constituted one of a set of primers, each of which had a 3' region that annealed to the overhang sequence appended in the first reaction but which further contained one of multiple 6 base pair indices that allowed for sample multiplexing on the sequencer. Each of these primers further contained a 5' tail with the P7 sequence used for cluster formation in the Illumina Genome Analyzer sequencer.

First stage PCR was carried out using a high-fidelity polymerase (AccuPrime, Life Technologies) for 16 cycles. A second stage PCR was carried out for 22 cycles on 1/100 of the amplification products from the first stage PCR. Each sample contained a unique identifying tag. Samples were pooled and purified using the QlAquick PCR purification kit (Qiagen). Cluster formation and sequencing in both directions was carried out per the manufacturer protocol (Illumina, Inc., La Jolla, Calif.). Specifically, three sequencing reactions were performed. First 115 bp were sequenced from the C side sufficient to sequence through the junctional sequence from C to V. At this point, the synthesized strand was denatured and washed off. A second sequencing primer was annealed that allowed the sample index to be sequenced for 6 cycles to identify the sample. At this point the reverse complement strand was generated per the Illumina protocol. A final sequencing read of 95 bp was obtained from the V-to-C direction providing ample sequence to map the V segment accurately. The sequencing data was then analyzed to determine the clonotype sequences, as described above.

Clonotype Determination:

A clonotype was defined when at least 2 identical sequence reads were obtained. Briefly, after exclusion of low quality reads, sequence data were then analyzed to determine the clonotype sequences including mapping to germline V and J consensus sequences. First, the sample index sequences were used to identify which of the sequences originate from which of the pooled samples. Sequences whose index were not a perfect match to one of the indices used in a specific run were excluded. Next the forward read was used to map the J segment. Since all the sequences started from the same position of the J segments, all the J segments started at a predefined sequencing position. The first 25 bp of the J segments were used to map the J segment. Any read with more than 5 high quality mismatches to the known J segments was excluded from further analysis.

After J segment identification, V segments were mapped. The reverse read was used for this purpose. First, the V primer was mapped and excluded. Thereafter, the next 70 bases of the reverse read were mapped to the known V segments. Reads that did not map to J and V segments were excluded. The next step in mapping involved identifying the frame that related the forward and reverse reads and this allowed a continuous sequence from J to V to be constructed. This was done using the last 15 bases of the forward read which were reliably within the V segment regardless of NDN length. While these bases could be of relatively lower sequence quality as they were at the terminal end of a long read, they could be used to map within a single identified V segment in order to identify the position at which the two reads could be joined. Finally, the known V and J sequences to which the reads map were used to identify the point in the forward read at which the sequences at the junctions diverged from these mapped segments.

Following clonotype determination, relative frequencies of the clonotypes were analyzed in the unsorted, antigen-specific and non-antigen-specific populations. Clonotype frequency comparisons between two samples are shown in several figures. Clonotypes that are present in sample A but not in sample B (where frequencies in sample A and B are being compared) are represented to have the frequency of a clonotype with a single read in sample B. Therefore the frequency of the missing clonotype in a sample depends on the sequencing depth of a particular sample. In these cases where a clonotype is missing in a sample, because the frequency of a single read is assigned to these clonotypes, the observed frequency is overestimated. Thus, in the vast majority of these cases, the real clonotype frequency is likely to be overestimated. Clonotypes absent in both samples appear where the axes intersect. Clonotypes present in one sample but not the other however lie along either the x- or y-axis.

Clonotypes from the antigen-specific T cell analyses were selected based on three criteria. First, selected clonotypes had a frequency in sorted antigen-specific populations that was increased by at least 10-fold over the frequency in non-antigen-specific or unsorted cell populations (e.g. FIGS. 17A and 17B). Second, these clonotypes were also present at lower frequencies in sorted, non-antigen specific cells compared to unsorted cells if greater than 1/100,000 in order to avoid sub-sampling error (Poisson noise) associated with very low frequency clonotypes in sorted samples. Third, because of the limited number of input antigen-specific cells after sorting (generally <30,000 cells), a greater than 20-cell equivalent threshold was applied based on the relatively low input number of cells in these samples. This minimum threshold enabled exclusion of clonotypes that appeared enriched in sorted antigen-specific samples but were due only to the presence of one or a few cells in the sample. For example, consider a sorted population of 10,000 pentamer$^+$ cells out of a sample with a million T cells. If a single cell with a frequency of 1 per million in the unsorted sample is incidentally sorted in the pentamer$^+$ sample, its frequency in the sorted sample will be 1/10,000 and would appear to be 100 fold enriched in the pentamer$^+$ sample compared to the unsorted sample. To ameliorate this problem, a clonotype was required to represent 20 cells in the sorted pentamer$^+$ sample. Specifically, the $\log_{10}$ frequency threshold required in the pentamer$^+$ sample was calculated as $\log_{10}(1/(n/20))$, where n is the number of input sorted cells for that sample as determined by flow cytometry (For example, in FIG. 18A, 16,281 is number of input sorted cells and the calculated threshold frequency is $10^{-2.9}$). Those sequences meeting the three criteria outlined above were classified as antigen-specific T cell clonotypes.

Results

The combination of sorting and sequencing was used to identify antigen-specific clonotypes in an individual with a known positive response to a cytomegalovirus (CMV) antigen. First, TCR beta sequencing was paired with a multimer-based immune assay to validate this method for identification of antigen-specific CD8 TCR beta clonotypes. A peptide derived from CMV pp65(495-404) (pp65$_{495}$ peptide) is an HLA-A*0201-restricted immunodominant epitope that induces responses in CMV-positive individuals. To directly identify T cells specific to this antigen, a commercially available pentamer reagent containing pp65$_{495}$ peptide bound to an MHC molecule was used. In principle, all of the T cells carrying the sequences that bind the pentamer should be detected irrespective of their functional potential. pp65$_{495}$-specific CD8 T cells were identified by sequencing the TCR beta repertoire of cells that were sorted based on pentamer binding (pentamer$^+$).

Frozen PBMCs were obtained from an individual with a characterized response to pp65$_{495}$ by ELISPOT assay. Two populations were sorted from this individual: CD8 pentamer$^+$ and pentamer$^-$ T cells. Nucleic acids encoding TCR beta clonotypes were sequenced in these two populations along with the unsorted PBMC sample, so that the relative frequencies of the clonotypes in each population could be determined. Three criteria were used to identify pp65$_{495}$-specific TCR beta clonotypes: 1) Clonotypes that are enriched (i.e. have substantially higher frequency) in the pentamer$^+$ population compared to the pentamer$^-$ population; 2) Clonotypes that are enriched in the pentamer$^+$ population compared to the unsorted sample; and 3) Clonotypes that are de-enriched (i.e. have lower frequency) in the pentamer$^-$ population compared to the unsorted sample.

Figure 17B:
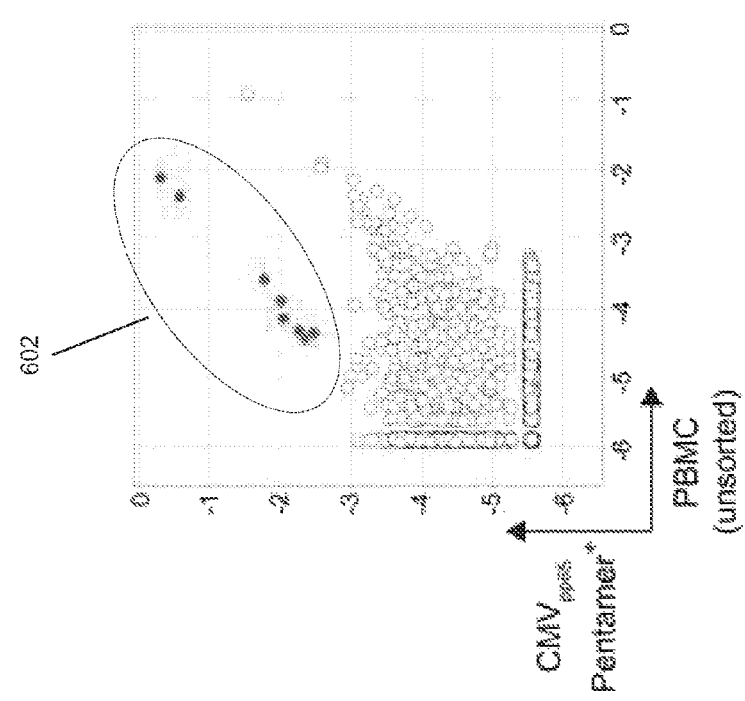
FIG. 17A-FIG. 17B show data for identification of CMV pp65$_{495}$-specific T cell clonotypes from sorted pentamer+ T cells.
Figure 17A:
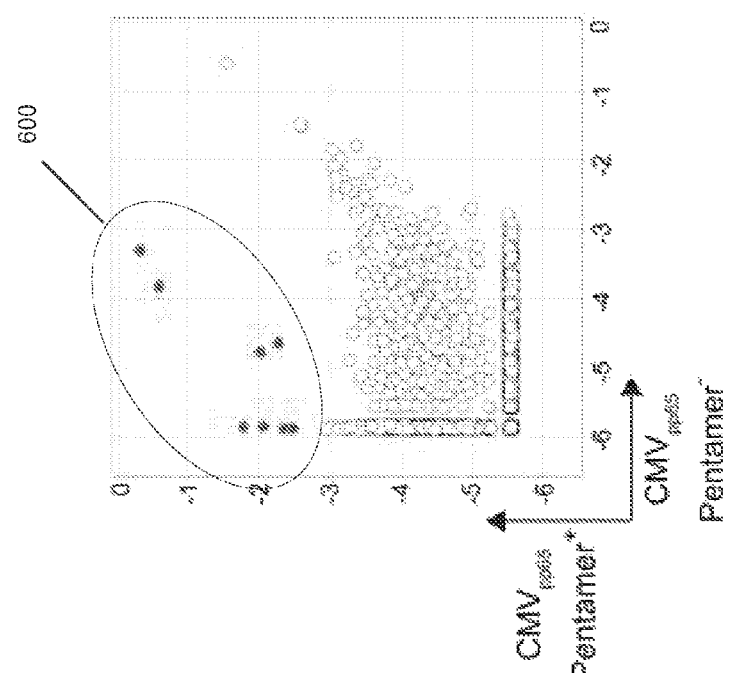
Figure 19B:
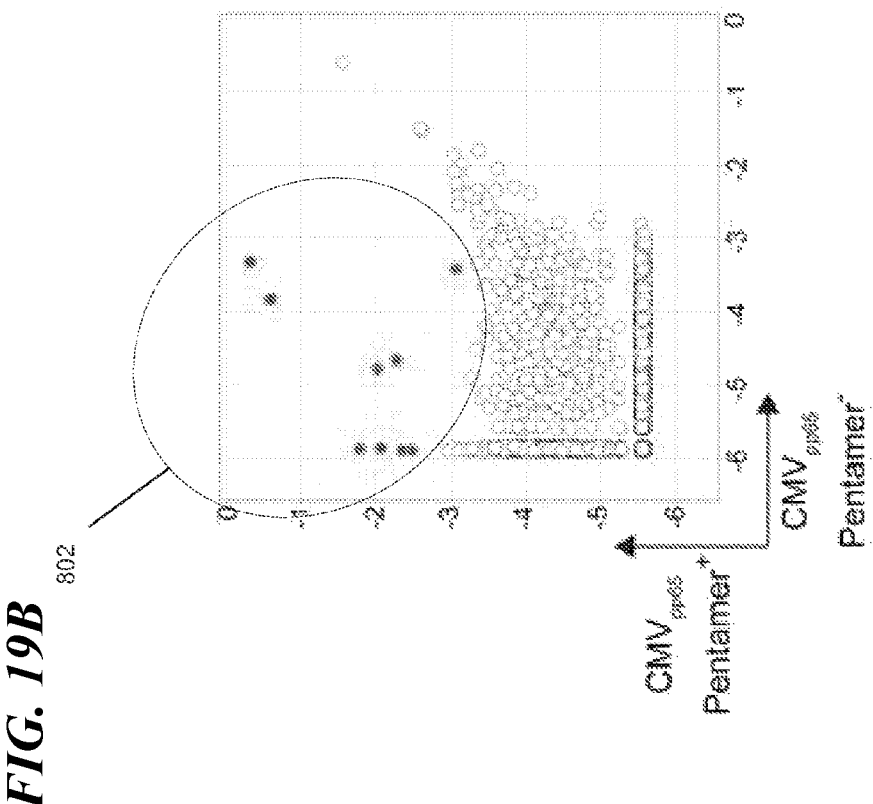
FIG. 19A-FIG. 19B illustrate the overlap between clonotypes identified in pentamer-based and CD137-based assays.
Figure 19A:
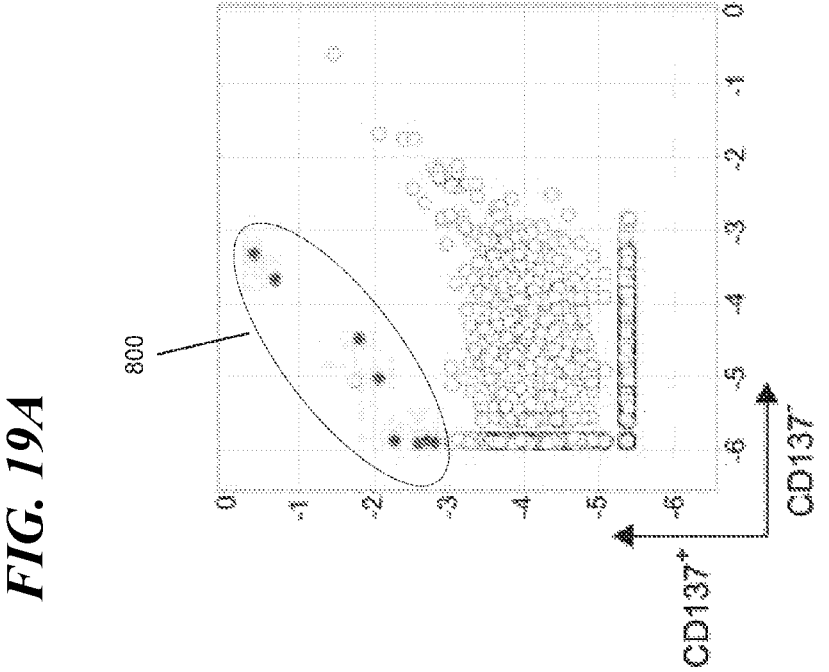

Eight clonotypes were identified that are substantially enriched (~1,000 fold) in the pentamer$^+$ compared to the pentamer$^-$ population (FIG. 17A). The frequencies of these clonotypes were compared in the pentamer$^+$ and the unsorted populations (FIG. 17B). The highest of these clonotypes had a frequency of 0.81% in the unsorted sample, which is consistent with the expected elevated response to pp65$_{495}$ in this individual. However, several of the other clonotypes were present at a level below $10^{-4}$. The 8 clonotypes are enriched in the pentamer$^+$ population by a factor of ~100 fold compared to their frequency in unsorted PBMC.

PBMCs from the same individual were used to assess whether immune assays that rely on indirect or functional changes in the T cells following antigen stimulation are effective for identification of pp65$_{495}$-specific CD8 TCR beta clonotypes. PBMCs were stimulated with pp65$_{495}$ followed by flow cytometry 18 hours after the stimulation to capture cells based on expression of the activation marker CD137. The TCR beta repertoire was amplified and sequenced from sorted CD137⁺ and CD137⁻ cells. The criteria for identification of pp65₄₉₅-specific TCR beta clonotypes with this assay was similar to that used in the pentamer assay. Specifically, pp65₄₉₅-specific TCR beta clonotypes were expected to be present at much higher frequencies in the CD137⁺ population compared to the CD137⁻ population.

Nine clonotypes were identified that are substantially enriched (~1,000 fold) in the CD137⁺ population compared to the CD137⁻ population (FIG. 18A). The frequency of these clonotypes in the unsorted sample ranged from as high as 0.81% to as low as 0.004% (FIG. 18B). These clonotypes were enriched in the CD137⁺ population compared to the unsorted PBMC sample by ~100 fold. To ensure that these cells were activated due to stimulation with the peptide, a control experiment was performed with no peptide. None of the 9 clonotypes that were enriched with the peptide in the CD137⁺ population enriched following incubation without peptide in CD137⁺ cells (FIG. 18C).

Specific clonotypes identified by the pentamer and CD137 assays were compared and found to substantially overlap. All 8 clonotypes that were identified with the pentamer assay were also identified by CD137 assay (FIG. 19A), although an additional clonotype was identified by the CD137 assay that was not identified in the pentamer assay.

A third functional assay for identification of antigen-specific clonotypes was conducted by combining capture of proliferating cells following incubation with pp65₄₉₅ peptide and repertoire sequencing. Cells were labeled with CFSE and incubated with either pp65₄₉₅ or no peptide for 6 days. Proliferating CD8 cells were then sorted based on dilution of CFSE. pp65₄₉₅-specific clonotypes were identified based on their relative frequency in the CFSE$^{low}$ population compared to that of fresh unsorted PBMCs.

Figure 20A:
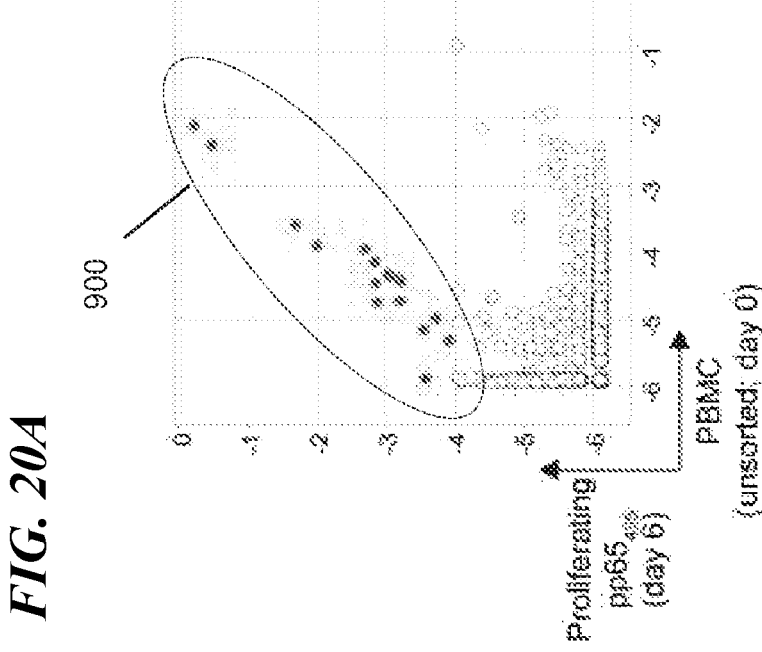
FIG. 20A-FIG. 20D shows data for identification of low-frequency CMV pp65$_{495}$-specific T cell clonotypes following peptide incubation and proliferation.
Figure 20B:
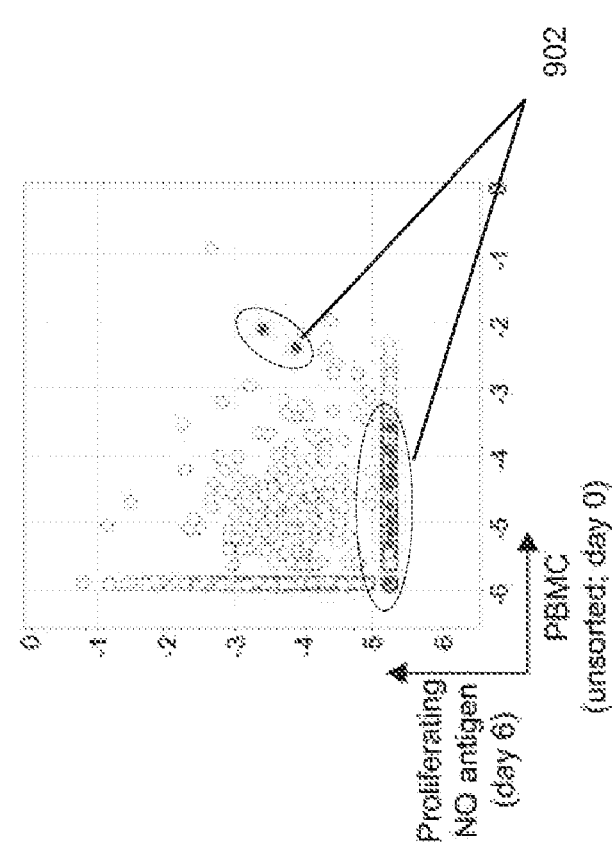
Figure 20D:
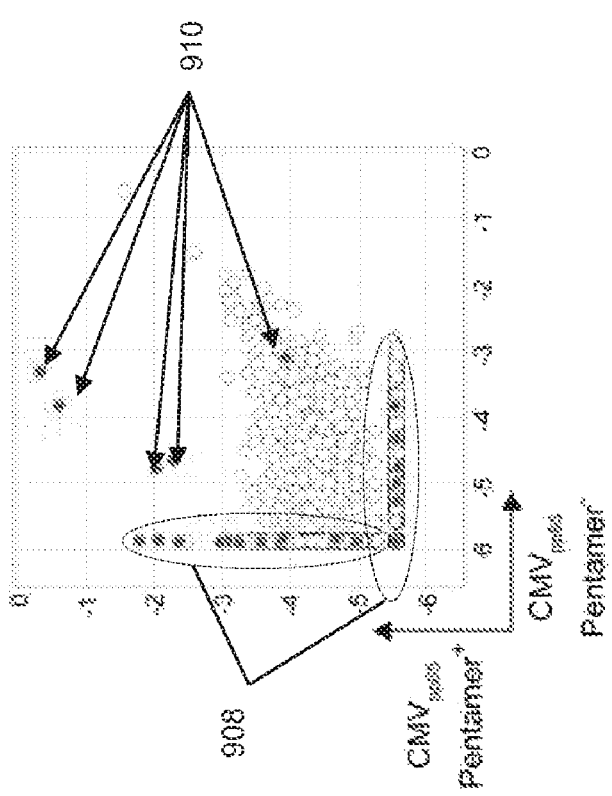
Figure 20C:
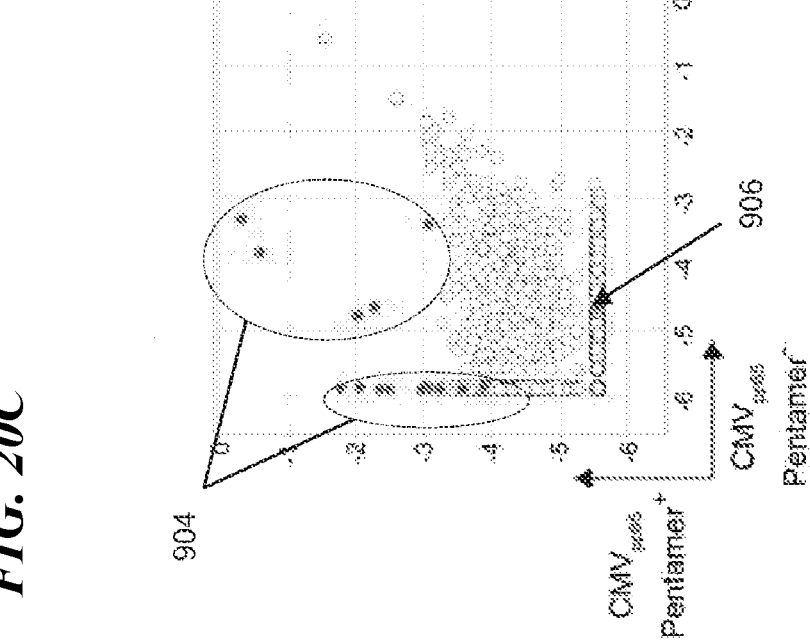
Figure 21A:
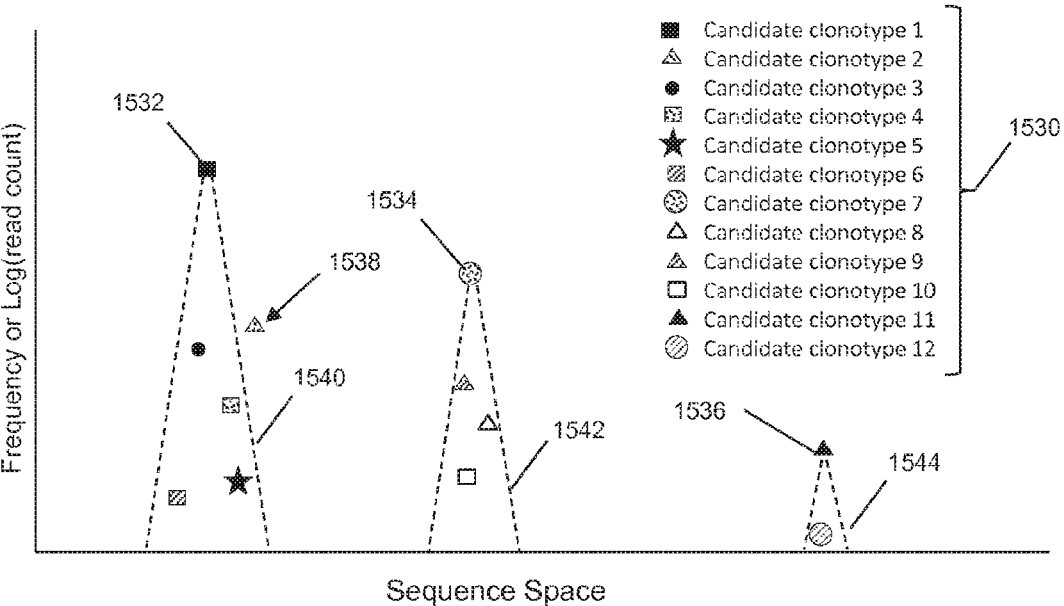
FIG. 21A-FIG. 21E illustrate embodiments of coalescing sequence reads.
Figure 21B:
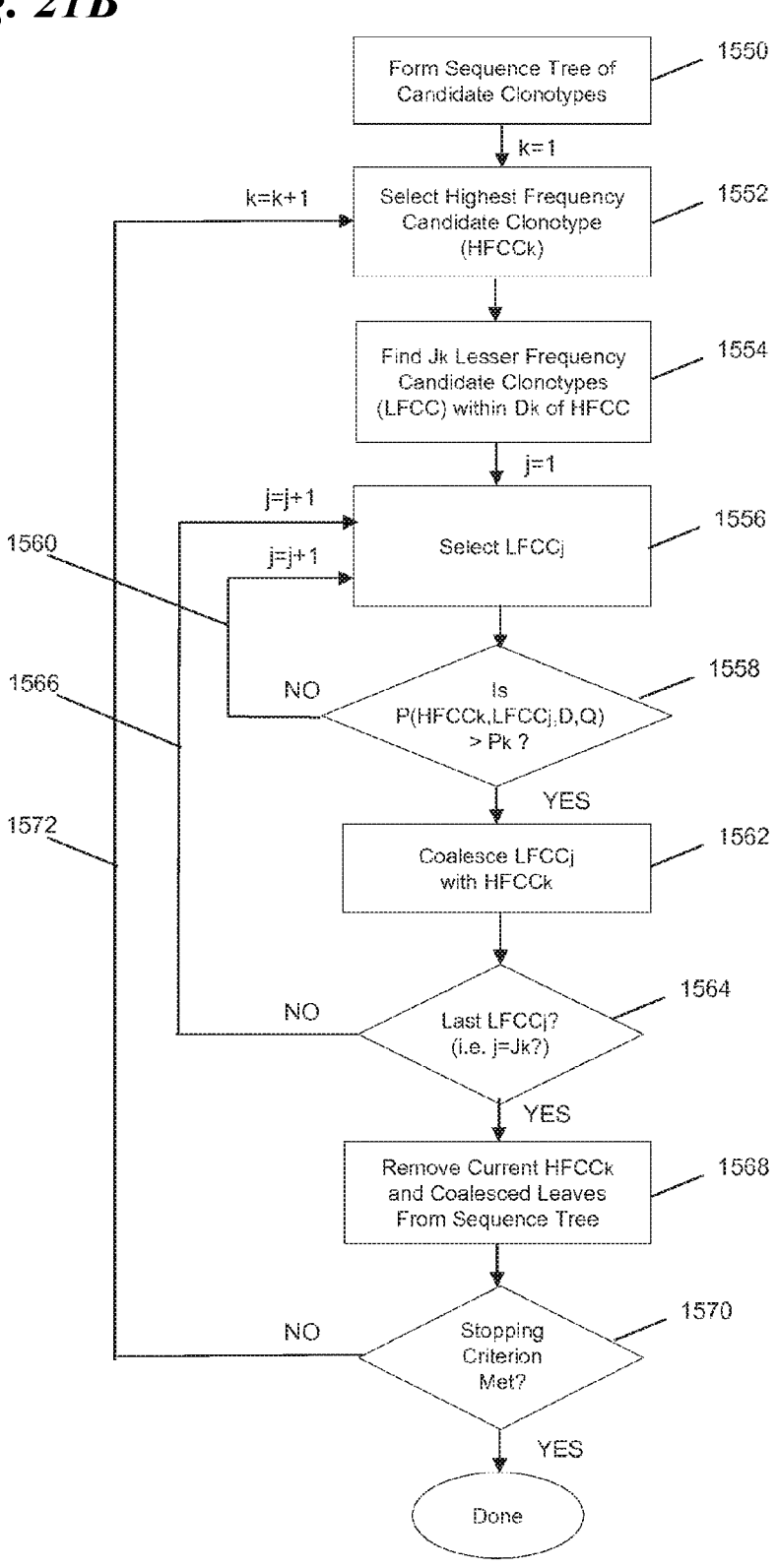
Figure 21C:
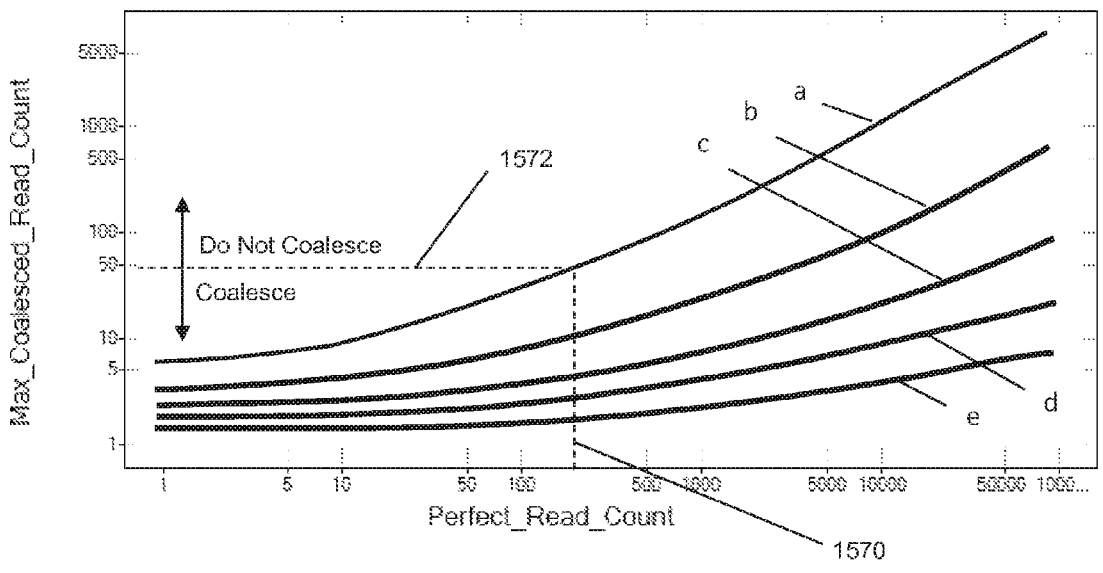
Figure 21D:
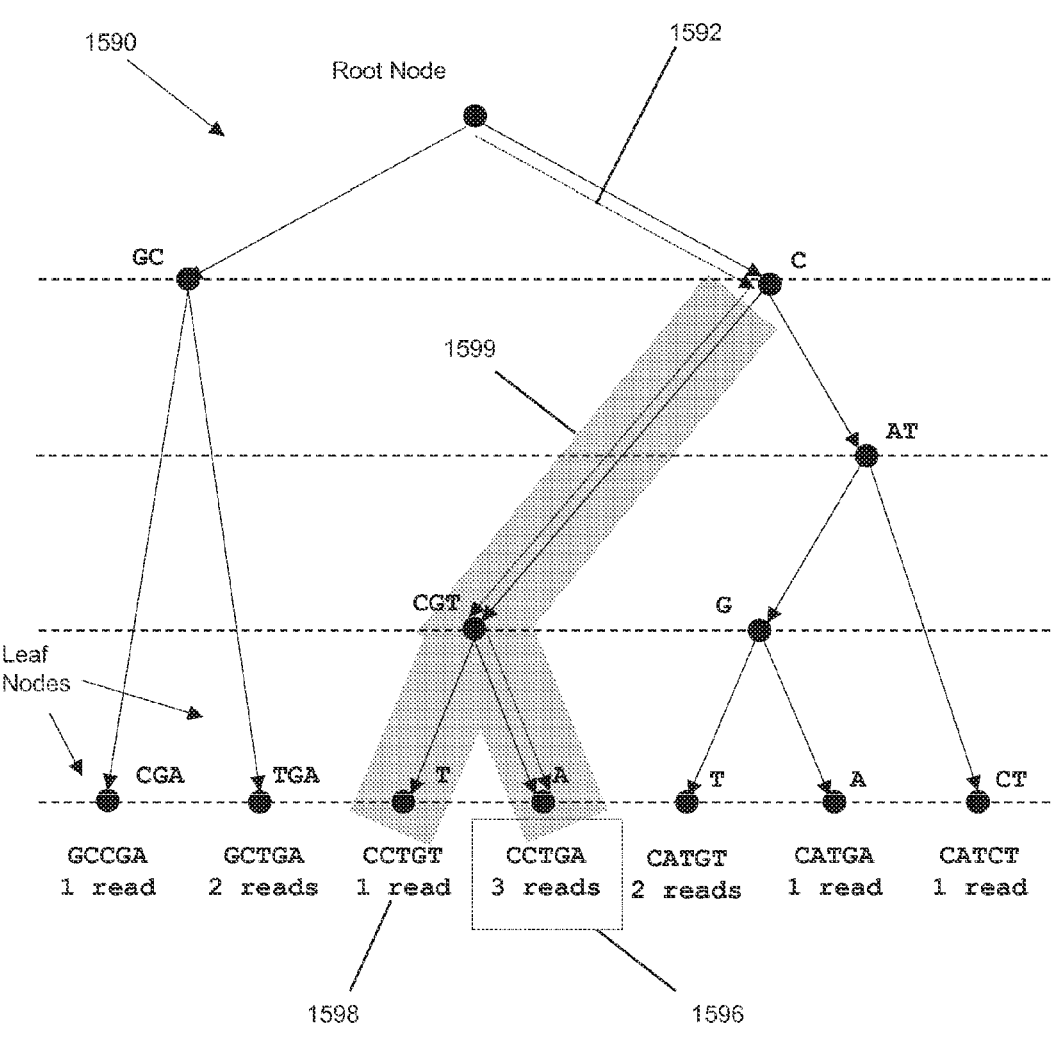
Figure 21E:
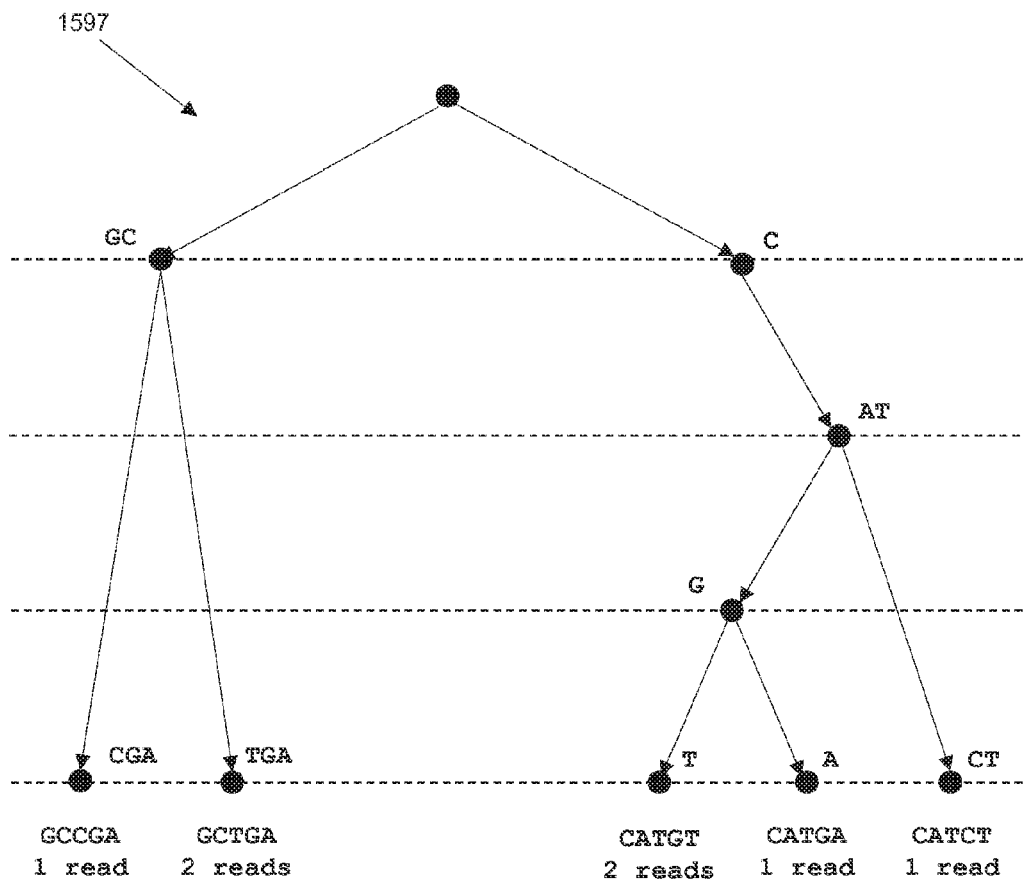

Sixteen clonotypes were identified that were substantially increased in the CFSE$^{low}$ population, and the frequency of some of the identified clonotypes was below 10⁻⁵ (FIG. 20A). An identical proliferation assay was used that lacked the peptide as a control. None of the 16 clonotypes identified by the proliferation assay were enriched in the CFSE$_{low}$ population when no peptide was used (FIG. 20B).

One advantage to using indirect immune monitoring assays compared to pentamer reagents is the ability to assess responses to more than one peptide antigen at the same time. A pool of 138 peptides spanning the entire pp65 protein (herein referred to as pp65pool) was used to stimulate PBMCs in the proliferation assay to identify pp65pool-specific T cells. Repertoire analysis of proliferating cells following pp65pool incubation enabled identification of 25 clonotypes. Of these 25 clonotypes identified using the pp65pool, 12 of these were also deemed antigen-specific with the single pp65₄₉₅ peptide, demonstrating the repeatability of the approach.

Seven of eight clonotypes identified by the pentamer assay were identified in the pp65pool proliferation assay, demonstrating that the use of peptide pool does not substantially decrease sensitivity. In addition the proliferation assay with the pp65pool enabled identification of additional clonotypes that are presumably specific to other peptides within the pool. Most of the additional clonotypes identified with the pp65pool were not enriched in the pentamer⁺ population (FIG. 20D) consistent with them being not specific to the pp65₄₉₅ peptide.

Example 2: Generation of TCRs Against WT1

Bulk naïve T cells were isolated from normal healthy donor peripheral blood mononuclear cells (PBMC) and expanded with anti-CD3/CD28 with IL-2 for 11 days. Cells were incubated with a WT1-derived peptide, (YMLDLQ-PETT; SEQ ID NO: 97, WT1-pep). Antigen-specific T cells were sorted based on expression of CD3, CD8, and CD107 and/or CD137. Nucleic acids were prepared from both positive (CD107⁺ and/or CD137⁺, i.e., antigen-specific) and negative (CD107⁻ and/or CD137⁻) T cells. The TCRα and TCRβ repertoires were amplified and sequenced using next generation sequencing.

Methods for immune repertoire profiling are described in U.S. Pat. No. 8,236,503, PCT International Publication Nos. WO 2010/151416 and WO 2011/106738, U.S. Patent Application Publication Nos. 2014/0256567 and 2012/0058902, which are each incorporated by reference in their entireties. In some embodiments, methods and compositions for controlling amplification bias in a single multiplex PCR are used as described in U.S. Pat. No. 9,150,905, which is incorporated by reference in its entirety.

Nucleotide sequences for the exemplary TCRα and TCRβ chains are provided below in Tables 1 and 2.

TABLE 1

| | | | CDR sequences of WT1 TCRs | |
| --- | --- | --- | --- | --- |
| Name | TCR Chain | CDR | Amino Acid Sequence | SEQ ID NO: |
| eJH30_5 | TCRα | CDR1 | DSASNY | 1 |
| | | CDR2 | IRSNVGE | 2 |
| | | CDR3 | CAAGGRDDKIIF | 3 |
| | TCRβ | CDR1 | SNHLY | 4 |
| | | CDR2 | FYNNEI | 5 |
| | | CDR3 | CASSERLGTMAYN SPLHF | 6 |
| eJH30_8 | TCRα | CDR1 | SIFNT | 9 |
| | | CDR2 | LYKAGEL | 10 |
| | | CDR3 | CAGRGSQGNLIF | 11 |
| | TCRβ | CDR1 | LGHDT | 12 |
| | | CDR2 | YNNKEL | 13 |
| | | CDR3 | CASSHWQETQYF | 14 |
| eJH52_13 | TCRα | CDR1 | TSENNYY | 17 |
| | | CDR2 | QEAYKQQN | 18 |
| | | CDR3 | CAFMGYYGGSQG NLIF | 19 |
| | TCRβ | CDR1 | SGHNS | 20 |
| | | CDR2 | FNNNVP | 21 |
| | | CDR3 | CASSSLQYEQYF | 22 |
| eJH64_9 | TCRα | CDR1 | NSASQS | 25 |
| | | CDR2 | VYSSGN | 26 |
| | | CDR3 | CVVKSLDNNNDMRF | 27 |
| | TCRβ | CDR1 | KGHDR | 28 |
| | | CDR2 | SFDVKD | 29 |
| | | CDR3 | CATSDWTGRNEQFF | 30 |
| eJH64_6 | TCRα | CDR1 | VSGNPY | 33 |
| | | CDR2 | YITGDNLV | 34 |
| | | CDR3 | CAVRDMRYGGAT NKLIF | 35 |
| | TCRβ | CDR1 | LGHNA | 36 |
| | | CDR2 | YSLEER | 37 |
| | | CDR3 | CASSQDGLAGAAS FNNEQFF | 38 |
| eJH30_7 | TCRα | CDR1 | SSNFYA | 41 |
| | | CDR2 | MTLNGDE | 42 |
| | | CDR3 | CAFMRATGANNLFF | 43 |
| | TCRβ | CDR1 | SGHVS | 44 |
| | | CDR2 | FNYEAQ | 45 |
| | | CDR3 | CASSFGGVSYEQYF | 46 |

TABLE 2

| | | | SEQ |
|---|---|---|---|
| Name | Region | Amino Acid Sequence | ID: |

Full TCRα and TCRβ chain sequences of WT1 TCRs

| Name | Region | Amino Acid Sequence | SEQ ID: |
|---|---|---|---|
| eJH30_5 | TCRα | MTSIRAVFIFLWLQLDLVNGENVEQHPSTLSVQEGDSAVIKCTYSDSA SNYFPWYKQELGKGPQLIIDIRSNVGEKKDQRIAVTLNKTAKHFSLHI TETQPEDSAVYFCAAGGRDDKIIFGKGTRLHILPNIQNPDPAVYQLRD SKSSDKSVCLFTDFDSQTNVSQSKDSDVYITDKCVLDMRSMDFKSNSA VAWSNKSDFACANAFNNSIIPEDTFFPSPESSCDVKLVEKSFETDTNL NFQNLSVIGFRILLLKVAGFNLLMTLRLWSS | 7 |
| | TCRβ | MDTWLVCWAIFSLLKAGLTEPEVTQTPSHQVTQMGQEVILRCVPISNH LYFYWYRQILGQKVEFLVSFYNNEISEKSEIFDDQFSVERPDGSNFTL KIRSTKLEDSAMYFCASSERLGTMAYNSPLHFGNGTRLTVTEDLNKVF PPEVAVFEPSEAEISHTQKATLVCLATGFFPDHVELSWWVNGKEVHSG VCTDPQPLKEQPALNDSRYCLSSRLRVSATFWQNPRNHFRCVQFYGL SENDEWTQDRAKPVTQIVSAEAWGRADCGFTSVSYQQGVLSATILYEI LLGKATLYAVLVSALVLMAMVKRKDF | 8 |
| eJH30_8 | TCRα | MLLEHLLIILWMQLTWVSGQQLNQSPQSMFIQEGEDVSMNCTSSSIFN TWLWYKQEPGEGPVLLIALYKAGELTSNGRLTAQFGITRKDSFLNISA SIPSDVGIYFCAGRGSQGNLIFGKGTKLSVKPNIQNPDPAVYQLRDSK SSDKSVCLFTDFDSQTNVSQSKDSDVYITDKCVLDMRSMDFKSNSAVA WSNKSDFACANAFNNSIIPEDTFFPSPESSCDVKLVEKSFETDTNLNF QNLSVIGFRILLLKVAGFNLLMTLRLWSS | 15 |
| | TCRβ | MGCRLLCCVVFCLLQAGPLDTAVSQTPKYLVTQMGNDKSIKCEQNLGH DTMYWYKQDSKKFLKIMFSYNNKELIINETVPNRFSPKSPDKAHLNLH INSLELGDSAVYFCASSHWQETQYFGPGTRLLVLEDLKNVFPPEVAVF EPSEAEISHTQKATLVCLATGFYPDHVELSWWVNGKEVHSGVCTDPQP LKEQPALNDSRYCLSSRLRVSATFWQNPRNHFRCVQFYGLSENDEWT QDRAKPVTQIVSAEAWGRADCGFTSESYQQGVLSATILYEILLGKATL YAVLVSALVLMAMVKRKDSRG | 16 |
| eJH52_13 | TCRα | MTRVSLLWAVVVSTCLESGMAQTVTQSQPEMSVQEAETVTLSCTYDTS ENNYYLFWYKQPPSRQMILVIRQEAYKQQNATENRFSVNFQKAAKSFS LKISDSQLGDTAMYFCAFMGYYGGSQGNLIFGKGTKLSVKPNIQNPDP AVYQLRDSKSSDKSVCLFTDFDSQTNVSQSKDSDVYITDKCVLDMRSM DFKSNSAVAWSNKSDFACANAFNNSIIPEDTFFPSPESSCDVKLVEKS FETDTNLNFQNLSVIGFRILLLKVAGFNLLMTLRLWSS* | 23 |
| | TCRβ | MDSWTFCCVSLCILVAKHTDAGVIQSPRHEVTEMGQEVTLRCKPISGH NSLFWYRQTMMRGLELLIYFNNNVPIDDSGMPEDRFSAKMPNASFSTL KIQPSEPRDSAVYFCASSSLQYEQYFGPGTRLTVTEDLKNVFPPEVAV FEPSEAEISHTQKATLVCLATGFYPDHVELSWWVNGKEVHSGVCTDPQ PLKEQPALNDSRYCLSSRLRVSATFWQNPRNHFRCVQFYGLSENDEW TQDRAKPVTQIVSAEAWGRADCGFTSESYQQGVLSATILYEILLGKAT LYAVLVSALVLMAMVKRKDSRG | 24 |
| eJH64_9 | TCRα | MISLRVLLVILWLQLSWVWSQRKEVEQDPGPFNVPEGATVAFNCTYSN SASQSFFWYRQDCRKEPKLLMSVYSSGNEDGRFTAQLNRASQYISLLI RDSKLSDSATYLCVVKSLDNNNDMRFGAGTRLTVKPNIQNPDPAVYQL RDSKSSDKSVCLFTDFDSQTNVSQSKDSDVYITDKCVLDMRSMDFKSN SAVAWSNKSDFACANAFNNSIIPEDTFFPSPESSCDVKLVEKSFETDT NLNFQNLSVIGFRILLLKVAGFNLLMTLRLWSS* | 31 |
| | TCRβ | MASLLFFCGAFYLLGTGSMDADVTQTPRNRITKTGKRIMLECSQTKGH DRMYWYRQDPGLGLRLIYYSFDVKDINKGEISDGYSVSRQAQAKFSLS LESAIPNQTALYFCATSDWTGRNEQFFGPGTRLTVLEDLKNVFPPEVA VFEPSEAEISHTQKATLVCLATGFYPDHVELSWWVNGKEVHSGVCTDP QPLKEQPALNDSRYCLSSRLRVSATFWQNPRNHFRCVQFYGLSENDE WTQDRAKPVTQIVSAEAWGRADCGFTSESYQQGVLSATILYEILLGKA TLYAVLVSALVLMAMVKRKDSRG | 32 |
| eJH64_6 | TCRα | MASAPISMLAMLFTLSGLRAQSVAQPEDQVNVAEGNPLTVKCTYSVSG NPYLFWYVQYPNRGLQFLLKYITGDNLVKGSYGFEAEFNKSQTSPHLK KPSALVSDSALYFCAVRDMRYGGATNKLIFGTGTLLAVQPNIQNPDPA VYQLRDSKSSDKSVCLFTDFDSQTNVSQSKDSDVYITDKCVLDMRSMD FKSNSAVAWSNKSDFACANAFNNSIIPEDTFFPSPESSCDVKLVEKSF ETDTNLNFQNLSVIGFRILLLKVAGFNLLMTLRLWSS* | 39 |
| | TCRβ | MGCRLLCCAVLCLLGAGELVPMETGVTQTPRHLVMGMTNKKSLKCEQH LGHNAMYWYKQSAKKPLELMFVYSLEERVENNSVPSRFSPECPNSSHL FLHLHTLQPEDSALYLCASSQDGLAGAASFNNEQFFGPGTRLTVLEDL KNVFPPEVAVFEPSEAEISHTQKATLVCLATGFYPDHVELSWWVNGKE VHSGVCTDPQPLKEQPALNDSRYCLSSRLRVSATFWQNPRNHFRCQVQ FYGLSENDEWTQDRAKPVTQIVSAEAWGRADCGFTSESYQQGVLSATI LYEILLGKATLYAVLVSALVLMAMVKRKDSRG | 40 |
| eJH30_7 | TCRα | MEKNPLAAPLLILWFHLDCVSSILNVEQSPQSLHVQEGDSTNFTCSFP SSNFYALHWYRWETAKSPEALFVMTLNGDEKKKGRISATLNTKEGYSY LYIKGSQPEDSATYLCAFMRATGANNLFFGTGTRLTVIPYIQNPDPAV YQLRDSKSSDKSVCLFTDFDSQTNVSQSKDSDVYITDKCVLDMRSMDF | 47 |

TABLE 2-continued

Full TCRα and TCRβ chain sequences of WT1 TCRs

| Name | Region | Amino Acid Sequence | SEQ ID: |
|------|--------|---------------------|---------|
| | TCRβ | KSNSAVAWSNKSDFACANAFNNSIIPEDTFFPSPESSCDVKLVEKSFE TDTNLNFQNLSVIGFRILLLKVAGFNLLMTLRLWSS* MGTSLLCWVVLGFLGTDHTGAGVSQSPRYKVTKRGQDVALRCDPISGH VSLYWYRQALGQGPEFLTYFNYEAQQDKSGLPNDRFSAERPEGSISTL TIQRTEQRDSAMYRCASSFGGVSYEQYFGPGTRLTVTEDLKNVFPPEV AVFEPSEAEISHTQKATLVCLATGFYPDHVELSWWVNGKEVHSGVCTD PQPLKEQPALNDSRYCLSSRLRVSATFWQNPRNHFRCQVQFYGLSEND EWTQDRAKPVTQIVSAEAWGRADCGFTSESYQQGVLSATILYEILLGK ATLYAVLVSALVLMAMVKRKDSRG | 48 |

*indicates presence of stop codon

Example 3. Target pMHC Off-Rate Kinetics

The WT1 peptide antigen used in this experiment is YMLDLQPETT (SEQ ID NO: 97, WT1-pep). This peptide binds to HLA A*02.01 by netMHC with an affinity of about 176 nM.

Tetramer off rate assay: TCR-deficient Jurkat (JRT3) cells were electroporated with either the eJH30_WT1C_5 (FIG. 1A) or the eJH130_WT1C_8 (FIG. 1B) TCR gene constructs and then stained with WT1-pep/HLA-A2-PE tetramers. Initial tetramer fluorescence intensity was assessed by FACS, after which anti-HLA-A2 blocking antibody (BB7.2) was added to prevent tetramer re-binding to cells, and fluorescence intensity was re-assessed every 15 seconds for 3 minutes. Tetramer dissociation overtime was plotted as the natural logarithm of tetramer fluorescence intensity (minus background) over time. The slope of this line provided the negative of the dissociation rate (−kd), and (ln(2))/kd represents the half-life ($t_{1/2}$) of WT1/HLA-A2 tetramer's interaction with TCR on the cells.

The results of the study are provided in Table 3 and FIGS. 1A and 1B.

TABLE 3

Tetramer −kd, tetramer half-life, and
tetramer initial MFI for WT1 TCRs

| TCR ID | −kd | Tetramer $t_{1/2}$ (s) | Tetramer initial MFI |
|--------|-----|------------------------|----------------------|
| eJH30_WT1C_5 | −0.003315 | 209 | 3216 |
| eJH30_WT1C_8 | −0.003729 | 176 | 4132 |

Example 4. Functional Assessment of Wt1 TCRs

A functional avidity assay was carried out to assess the TCRs' relative potency. TCR-deficient Jurkat cells (JRT3) were electroporated with vectors encoding the indicated TCRs and allowed to rest overnight. TAP-I-deficient T2 cells were pulsed with the indicated concentrations of WT1-pep for 30 minutes, washed, and then mixed with JRT3s expressing the TCRs described herein for 4 hours. Cells were stained for CD3 (as a measure of TCR expression) and CD69, then analyzed by FACS. CD69 MFI of the TCR+ JRT3 cells was plotted against peptide concentration to assess the TCRs' relative potency. The results of these experiments are shown in FIG. 2. The mean $EC_{50}$ (nM) for each peptide is provided in Table 4.

TABLE 4

$EC_{50}$ of functional avidity for WT1 TCRs

| TCR ID | $EC_{50}$ (nM) |
|--------|----------------|
| eJH30_WT1C_5 | 51.85 |
| eJH30_WT1C_8 | 10.88 |

A cytolysis assay was performed to assess the antigen-specific killing capacity of the WT1 TCRs. CD8+ T cells were isolated from PBMCs from healthy donors, then expanded 7 days using anti-CD3/anti-CD28 and IL-2. Expanded T cells were electroporated with RNA encoding the indicated TCRs and allowed to rest 4 hours. TAP-I-deficient T2 target cells (T) were pulsed either with 10 µg/mL WT1-pep or with the vital dye CellTrace-647, then mixed in a 50:50 ratio. CD8+ T cells (effector cells; E) were then added to the target cells at the indicated ratios of CD8+ T cell effector cells to antigen+ T2 target cells, then incubated 16 hours. Cells were then analyzed by FACS, and the remaining percentage of antigen+ T2 cells (relative to the control CellTrace+ T2 cells) was plotted against E:T ratio, as a measure of antigen-specific killing capacity.

Figure 3:
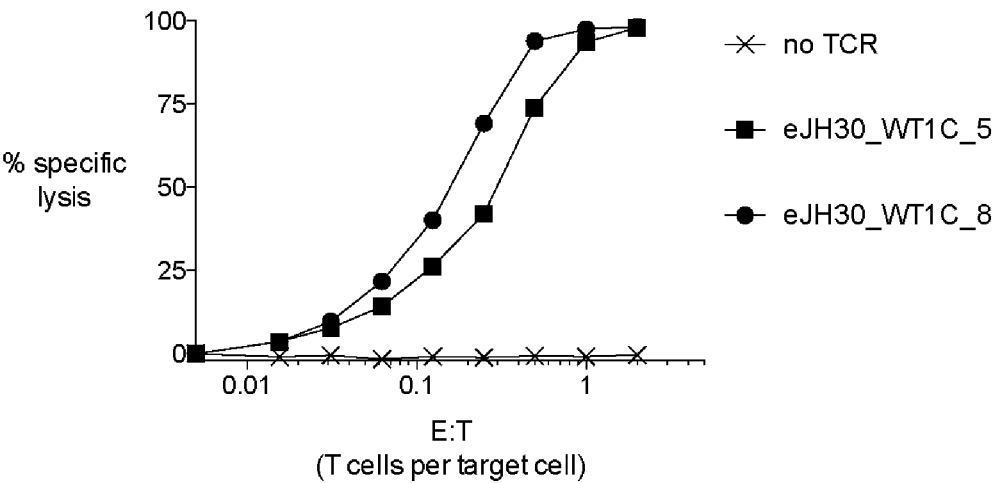
FIG. 3 is a graph showing the antigen-specific killing capacity of cells expressing the TCRs provided herein. The TCRs were expressed in CD8+ T cells expanded from healthy donors. The CD8+ T cells (effector cells; E) were then incubated with a 50:50 mixture of cells that had been pulsed with 10 μg/mL WT1 peptide (SEQ ID NO: 97) and cells pulsed with a dye (target cells; T), at various E:T ratios. The percent of live target cells following the incubation period was assessed by FACS and plotted against the E:T ratio to show the antigen-specific killing capacity of the cells expressing the recombinant TCRs.

An additional cytolysis assay was performed with peptide titration to assess the relative antigen-specific killing potency of each peptide. CD8+ T cells were isolated from PBMCs from healthy donors, then expanded 7 days using anti-CD3/anti-CD28 and IL-2. Expanded T cells were electroporated with RNA encoding the indicated TCRs and allowed to rest 4 hours. TAP-I-deficient T2 target cells were pulsed either with 10 µg/mL of WT1-pep or with the vital dye CellTrace-647, then mixed in a 50:50 ratio. CD8+ T cells (effector cells; E) were then added to the target cells (T) at a ratio of 2:1 E:T (2:1 CD8+ T cells:antigen+ T2 cells) and then incubated 16 hours (FIG. 3).

Figure 4:
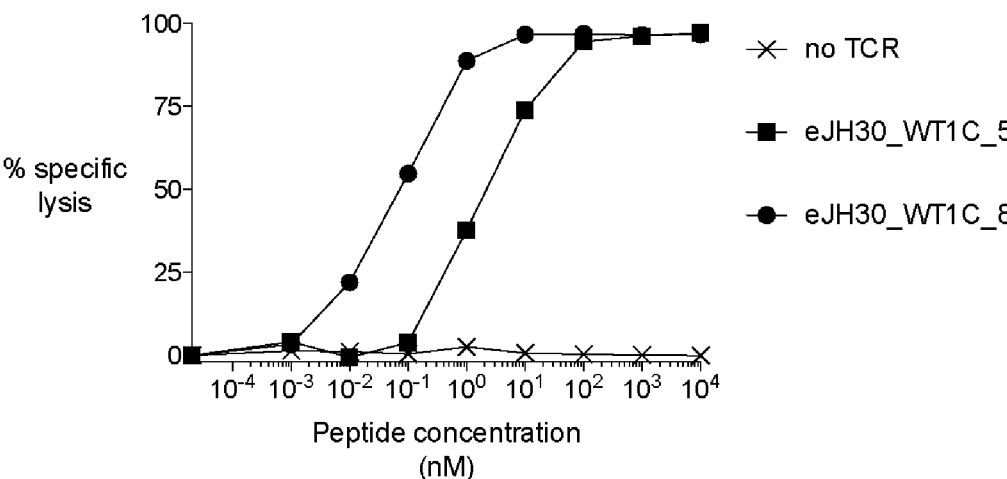
FIG. 4 is a graph showing the antigen-specific killing capacity of cells expressing the TCRs provided herein. The TCRs were expressed in CD8+ T cells expanded from healthy donors. The CD8+ T cells (effector cells; E) were then incubated with a 50:50 mixture of cells that had been pulsed with the indicated amount of the WT1 peptide (SEQ ID NO: 97) and cells pulsed with a dye (target cells; T), at a ratio of 2:1 E:T. The percent of live target cells following the incubation period was assessed by FACS and plotted against peptide concentration to show the antigen-specific killing potency of the two recombinant TCRs.
Figure 5A:
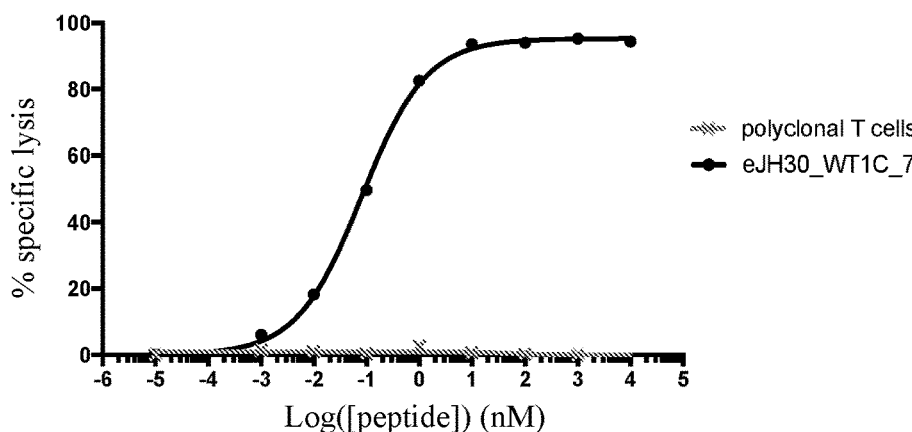
FIG. 5A-FIG. 5F are graphs showing the antigen specific killing capacity of cells expressing eJH30_7 (FIG. 5A), eJH30_5 (FIG. 5B), eJH30_8 (FIG. 5C), eJH52_13 (FIG. 5D), eJH64_6 (FIG. 5E), and eJH64_9 (FIG. 5F). Endogenous, presentation-deficient T2 cells were incubated with the indicated concentrations of WT1 peptide, then incubated 16 hours with polyclonal T cells expressing either no exogenous TCR ('polyclonal T cells'), or expressing the indicated WT1-specific TCR. The remaining viable peptide-loaded T2 cells were enumerated by FACS (in comparison to an internal control population of labeled non-WT1-presenting T2 cells) and expressed as % specific lysis.
Figure 5B:
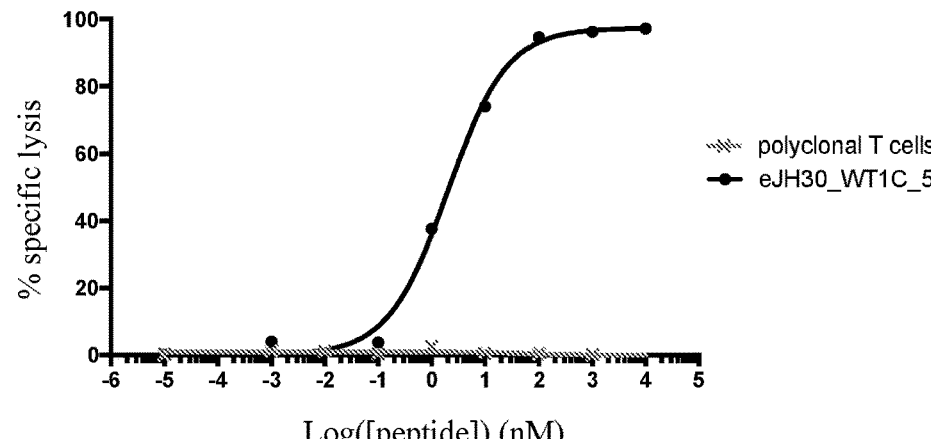
Figure 5C:
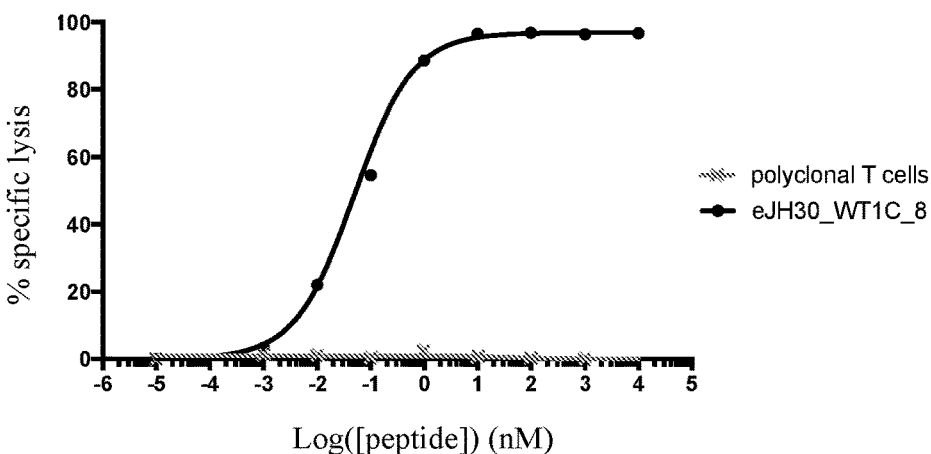
Figure 5D:
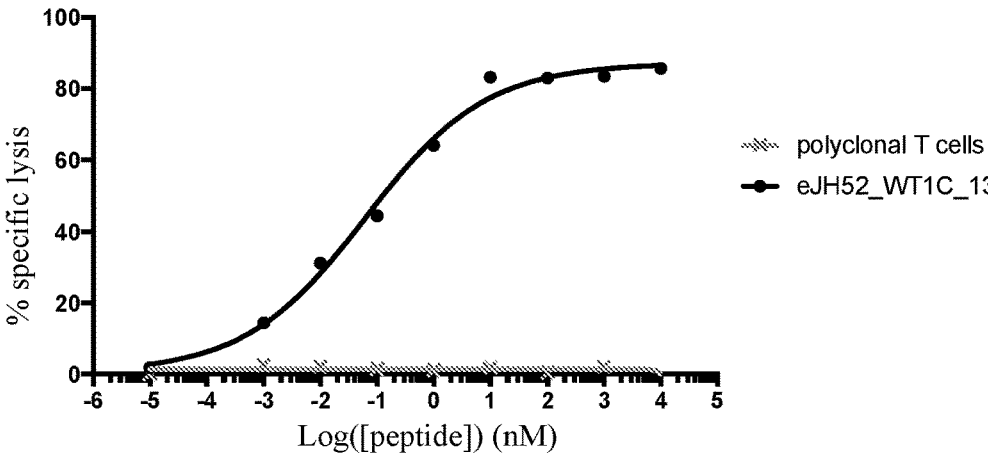
Figure 5E:
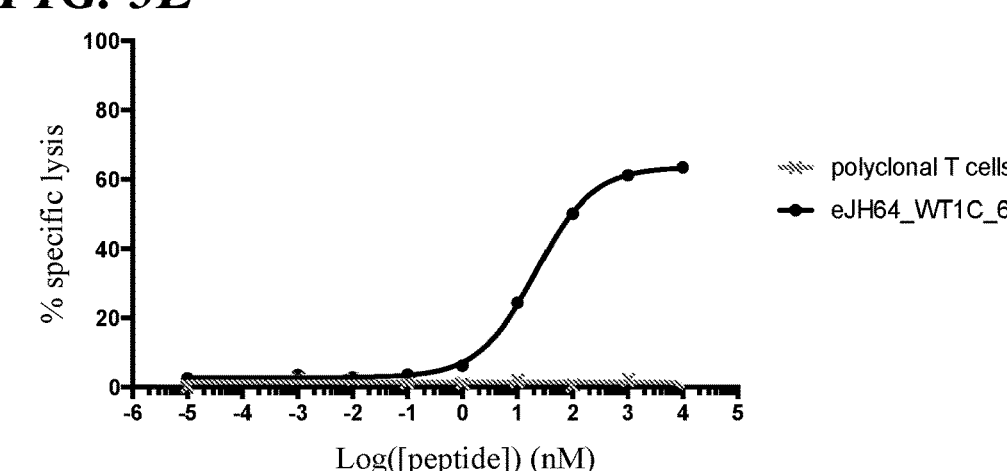
Figure 5F:
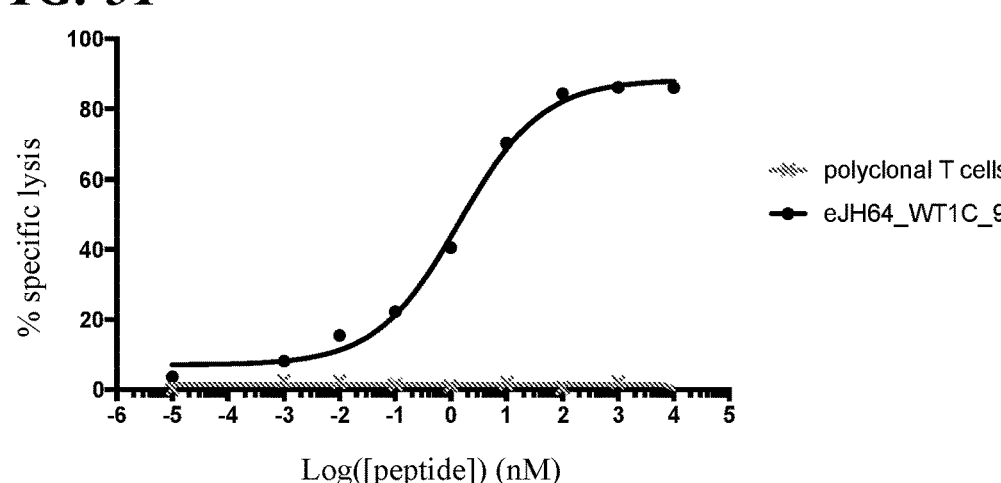
Figure 6A:
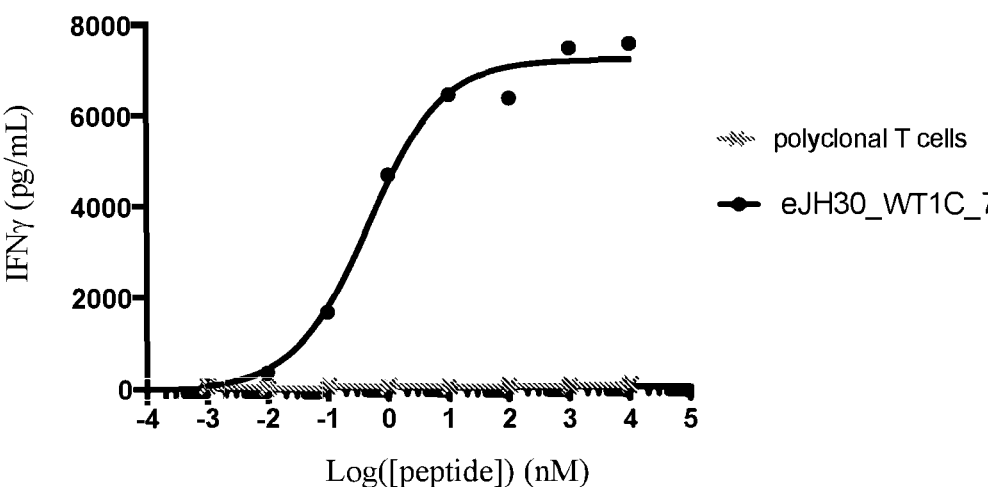
FIG. 6A-FIG. 6F are graphs showing IFNγ secretion by cells expressing eJH30_7 (FIG. 6A), eJH30_5 (FIG. 6B), eJH30_8 (FIG. 6C), eJH52_13 (FIG. 6D), eJH64_6 (FIG. 6E), and eJH64_9 (FIG. 6F). Endogenous, presentation-deficient T2 cells were incubated with the indicated concentrations of WT1 peptide, then incubated 16 hours with polyclonal T cells expressing either no exogenous TCR ('polyclonal T cells'), or expressing the indicated WT1-specific TCR. T cells' IFNγ secretions were assessed after 16 hours.
Figure 6B:
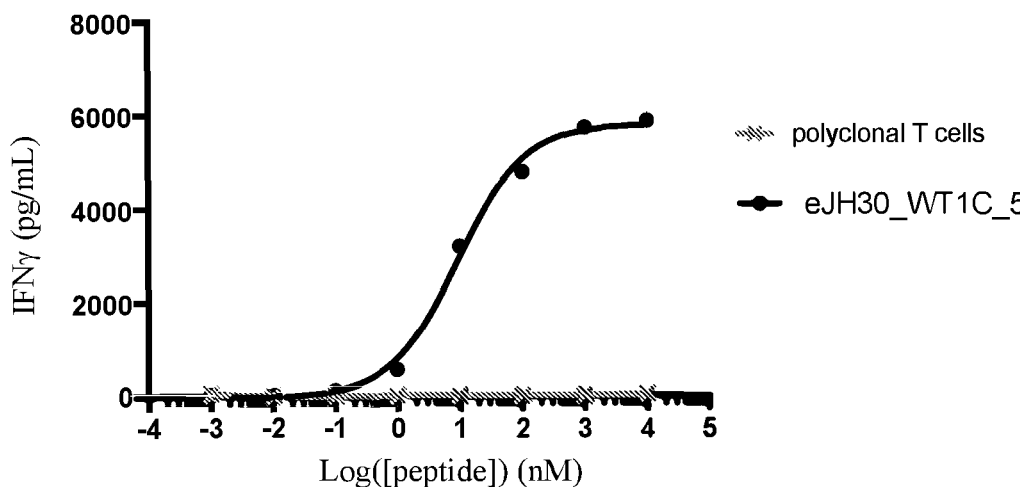
Figure 6C:
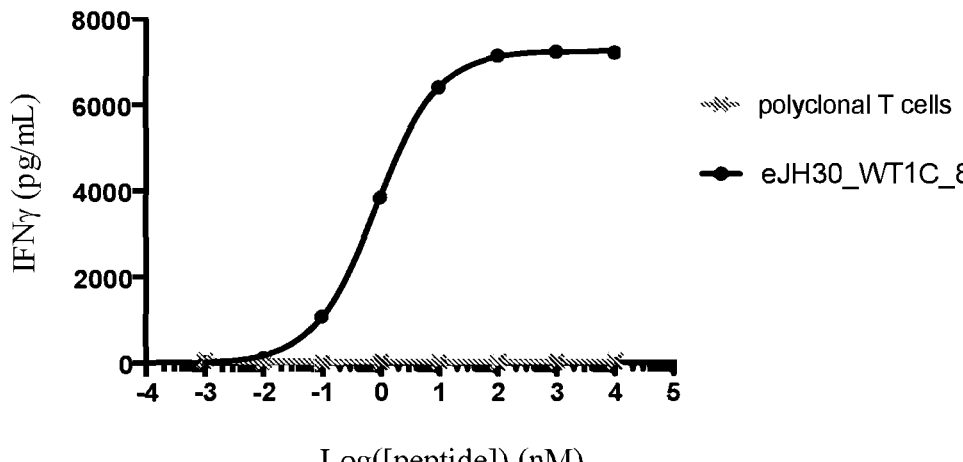
Figure 6D:
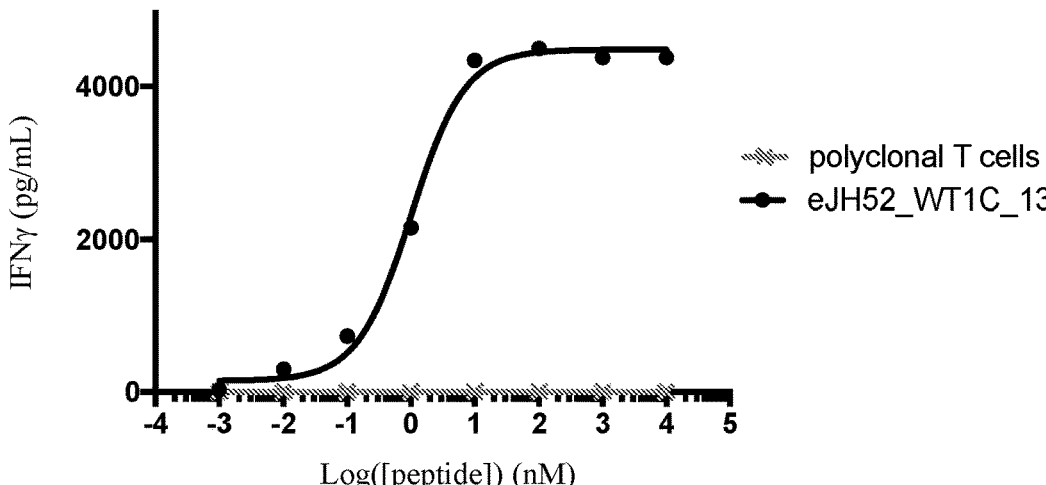
Figure 6E:
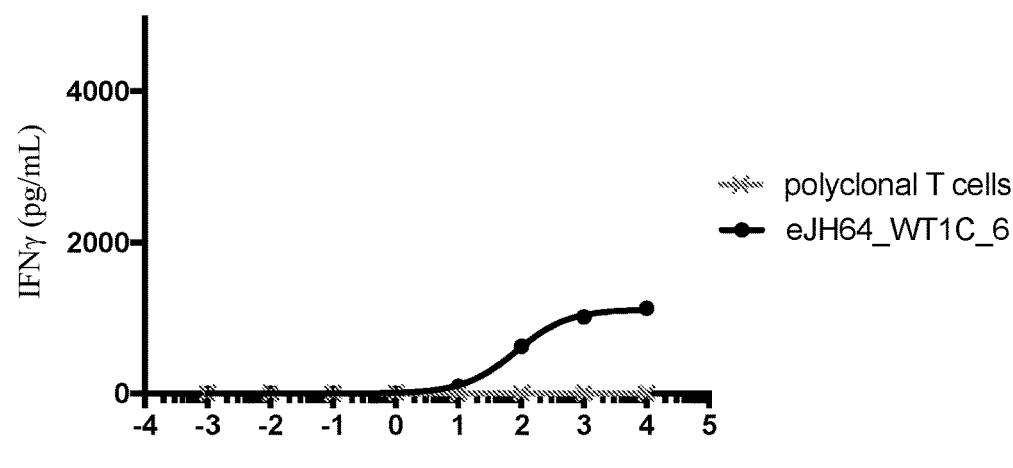
Figure 6F:
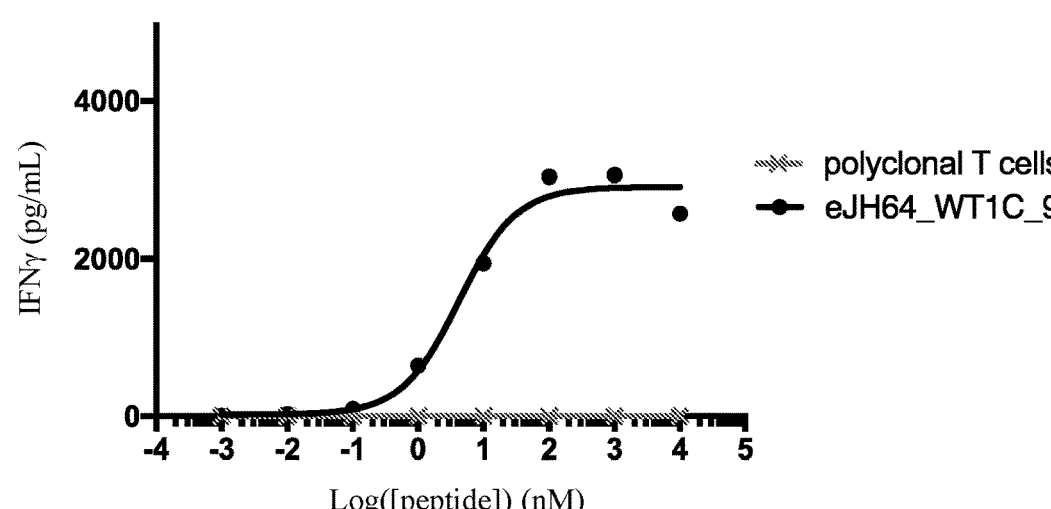

In a separate experiment, TAP-I-deficient T2 target cells were pulsed either with the indicated concentrations of WT1-pep or with the vital dye CellTrace-647, then mixed in a 50:50 ratio. CD8+ T cells (effector cells; E) were then added to the target cells (T) at a ratio of 2:1 CD8+ T cells:antigen+ T2 cells, then incubated 16 hours (FIG. 4). In each experiment, cells were analyzed by FACS, and the remaining percentage of antigen+ T2 cells (relative to the control CellTrace+ T2 cells) was plotted against peptide concentration, as a measure of antigen-specific killing potency.

Example 5. Treatment of Leukemia with Cells Exogenously Expressing TCRs Specific for WT1

A study is conducted to assess the efficacy of the TCRs provided herein in the treatment of patients having leukemia. In some aspects of the study, T cells will be isolated from PMBCs of patients that have been diagnosed with leukemia and are positive for HLA-A*0201, HLA-A*0203, and/or HLA-A*0206, for an autologous transfer of the cells back to the patient after cell modification. In other aspects of the study, the T cells will be donor T cells from a donor source that is positive for HLA-A*0201, HLA-A*0203, and/or HLA-A*0206, for an allogenic cell transfer to the patient after cell modification.

Vectors comprising the TCR alpha and beta chains provided herein will be introduced into the T cells to generate T cells exogenously expressing the WT1-specific TCRs provided herein. The autologous or allogenic cells will be infused into the patients. Patients will receive about $10^5$, $10^6$, $10^7$, $10^8$, or $10^9$ autologous or allogeneic cells per kg body weight.

Patients will be monitored for adverse events, survival and relapse rates, clinical response, and durability of clinical response. Blood tests, CT scans, skin biopsies, and bone marrow biopsies may be conducted to monitor disease progress, tumor size, and immune responses in the patients.

The results of the study will show that the TCRs provided herein provide a safe and effective means of inducing immune responses against WT1 and treating cancer.

Example 6: Functional Assessment of WT1 TCRs

Cytolysis and cytokine expression assays were performed to assess the antigen-specific killing capacities of the following WT1 TCRs: eJH52_13, eJ64_9, eJH64_6, and eJH30_7. The amino acid sequences of each of these TCRs are provided above in Tables 1 and 2.

Endogenous, presentation-deficient T2 cells were incubated with increasing concentrations of WT1 peptide. The cells were then incubated for 16 hours with polyclonal T cells expressing either no exogenous TCR (FIG. 5, polyclonal T cells), or expressing the indicated WT1-specific TCR. For the cytolysis study, following incubation, the remaining viable peptide-loaded T2 cells were enumerated by FACS and expressed as % specific lysis in comparison to an internal control population of labeled non-WT1-presenting T2 cells (FIGS. 5A-5F). As shown, each of the WT1-specific TCRs was able to specifically lyse WT-1 presenting target cells.

For the cytokine expression study, IFNγ secretion was assessed (FIGS. 6A-6F). Endogenous, presentation-deficient T2 cells were incubated with the indicated concentrations of WT1 peptide, then incubated 16 hours with polyclonal T cells expressing either no exogenous TCR (FIG. 6, polyclonal T cells), or expressing the indicated WT1-specific TCR. IFNγ secretion was assessed after 16 hours (FIGS. 6A-6F). As shown, each of the WT1-specific TCRs was able to induce IFNγ production after incubation with WT-1 presenting target cells.

Figure 7:
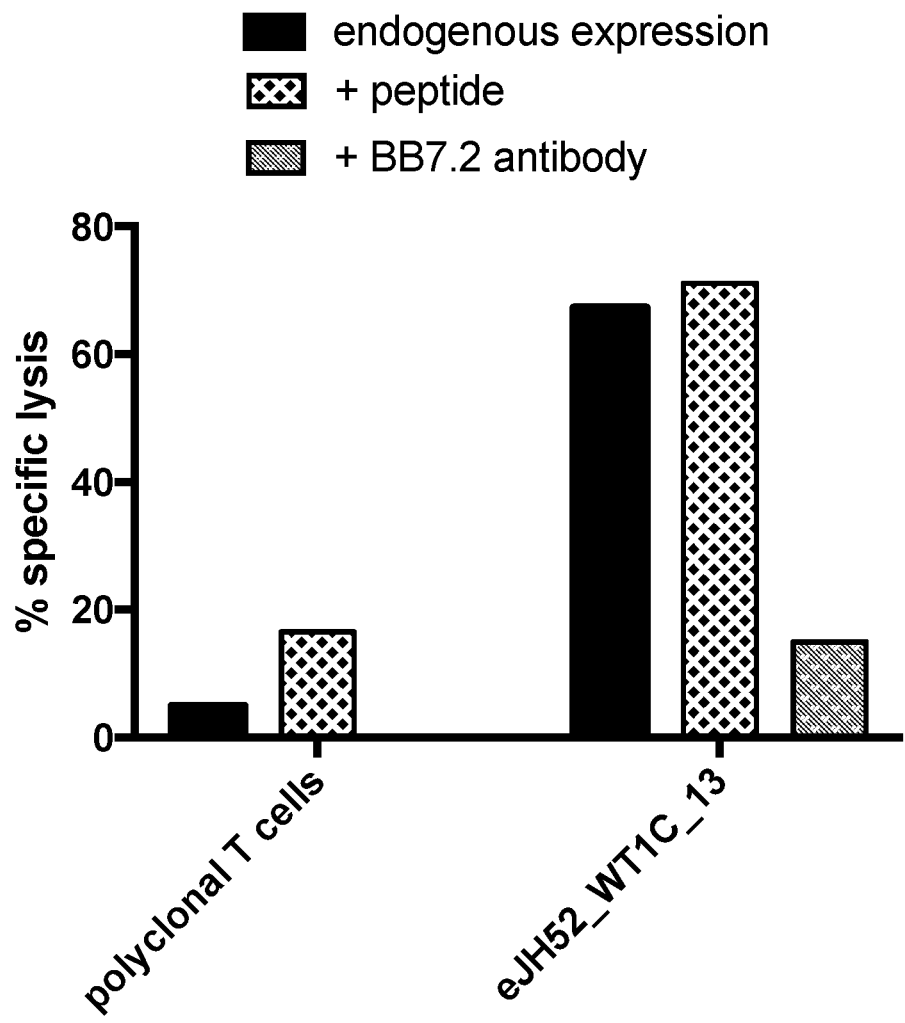
FIG. 7 is a graph showing the capacity of cells expressing eJH52_13 to induce specific lysis of cells expressing endogenous WT1 antigen and/or exogenous WT1 peptide.
Figure 8:
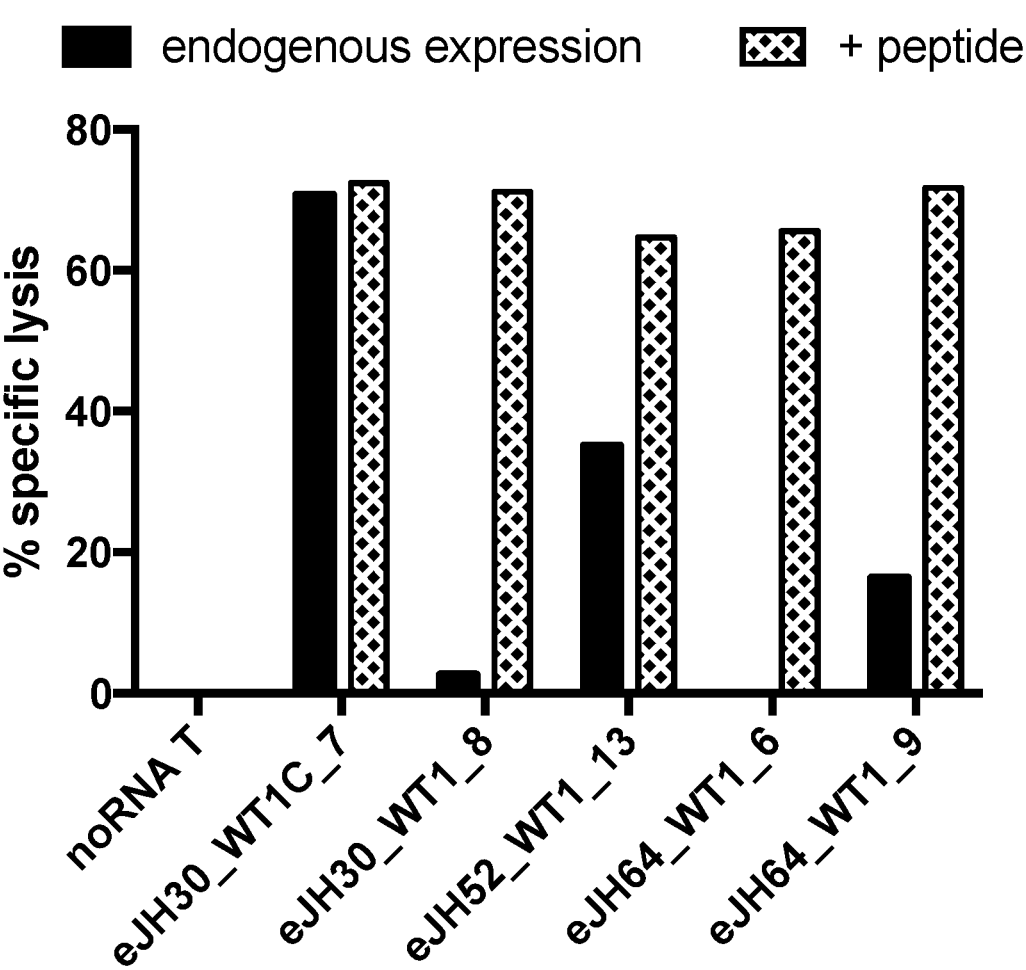
FIG. 8 is a graph showing the capacity of cells expressing the TCR indicated on the x-axis to induce specific lysis of cells expressing endogenous WT1 antigen and/or exogenous WT1 peptide.

Additional cytolysis assays were performed to determine whether the WT1 TCRs are capable of lysing target cells expressing endogenous WT1. FIG. 7 provides the results of a further cytolysis assay for eJH52_13. U266 cells were left un-manipulated (FIG. 7, "endogenous expression") or incubated with WT1 peptide (FIG. 7, "+ peptide"), or incubated with the blocking anti-HLA-A2 antibody BB7.2 (FIG. 7 "+BB7.2 antibody). U266 cells were then incubated for 16 hours with T cells expressing the eJH52_13 TCR. The loss of viable U266 cells was measured by FACS and expressed as % specific lysis in relation to an internal control population of non-WT1-presenting cells. As shown in FIG. 7, T cells expressing eJH52_13 (referred to in the figure as eJH52_WT1C_13) were capable of lysing U266 cells, even when only presenting endogenous levels of WT1. This lysis was MHC-specific as HLA-A2 antibody blockade prevented cell lysis. FIG. 8 provides the results of a similar cytolysis assay for eJH30_7, eJH30_8, eJH52_13, eJH64_6, and eJH64_9. HLA-A2$^+$ K-562 cells were left un-manipulated (FIG. 8 "endogenous expression") or incubated with WT1 peptide (FIG. 8, "+ peptide"). K-562 cells were then incubated 16 hours with T cells expressing the indicated TCRs. The loss of viable K-562 cells was measured by FACS and expressed as % specific lysis in relation to an internal control population of non-WT1-presenting cells. T cells expressing either eJH30_7 (eJH30_WT1C_7), eJH52_13 (eJH52_WT1C_13), or eJH64_9 (eJH64_WT1C_9) were all capable of lysing target cells expressing endogenous levels of WT1.

Similarly, eJH52_13 was capable of eliciting IFNγ expression in response to endogenous WT1. FIG. 9 show the results of the study. HLA-A2$^+$ K-562 cells were left untreated (FIG. 9, "endogenous expression"), incubated with WT1 peptide (FIG. 9 "+ peptide"), or transfected with WT1-epitope-containing in vitro transcribed RNA (ivtRNA) (FIG. 9, "forced overexpression"). Polyclonal or TCR-over-expressing T cells were incubated with the indicated K-562 cells and assayed for IFNγ secretion after 16 hours. eJH52_13-expressing T cells secreted appreciable amounts of IFNγ even when K-562 cells expressed endogenous levels of WT1 (FIG. 9, bottom panel).

Figure 10A:
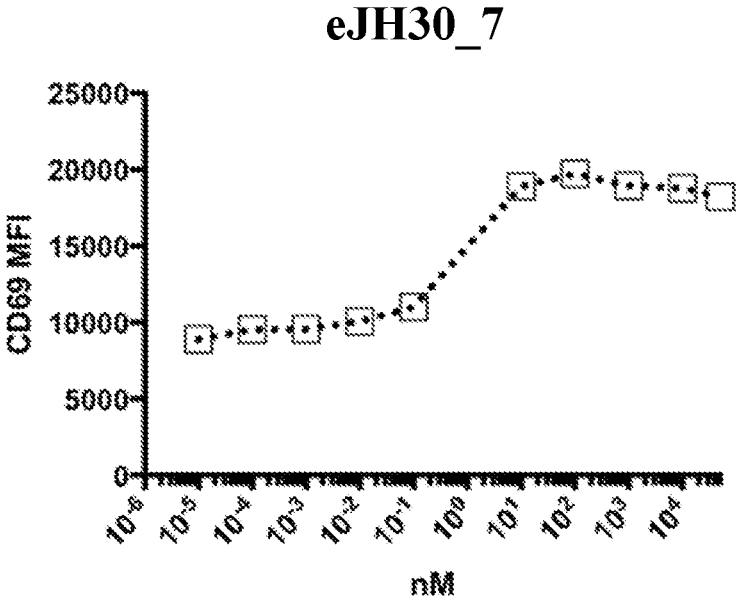
FIGS. 10A-10D show the functional avidity of eJH30_7 (30_7.
Figure 10B:
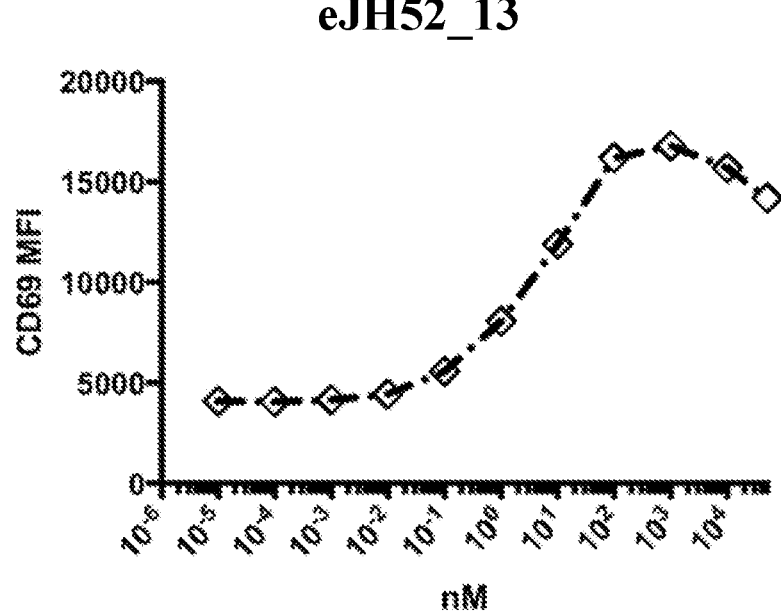
Figure 10C:
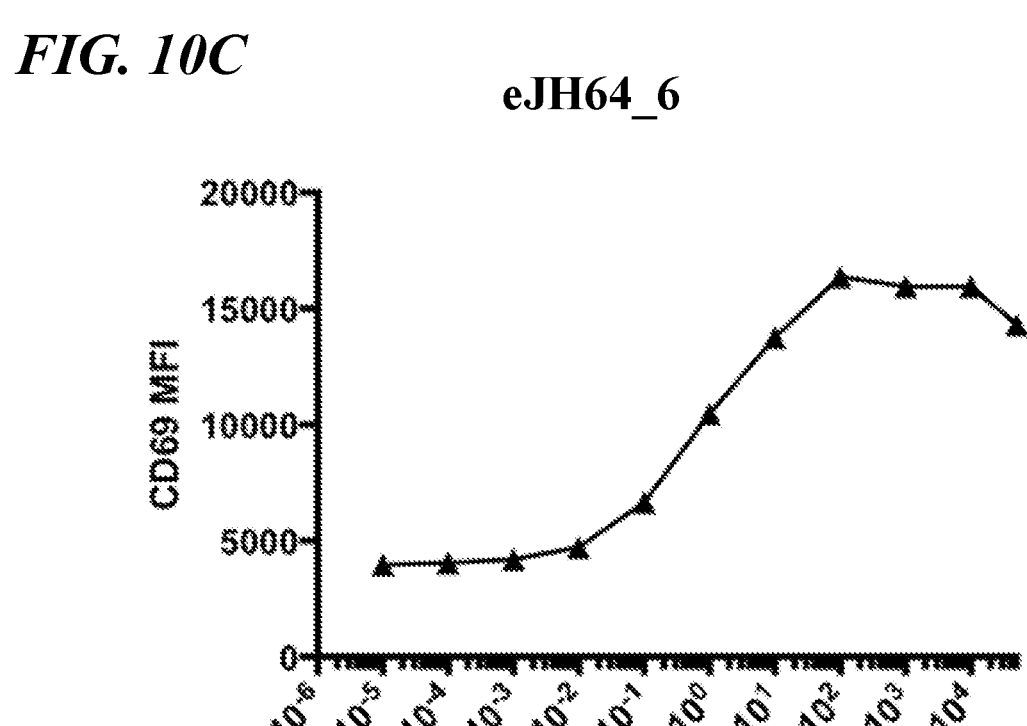
Figure 10D:
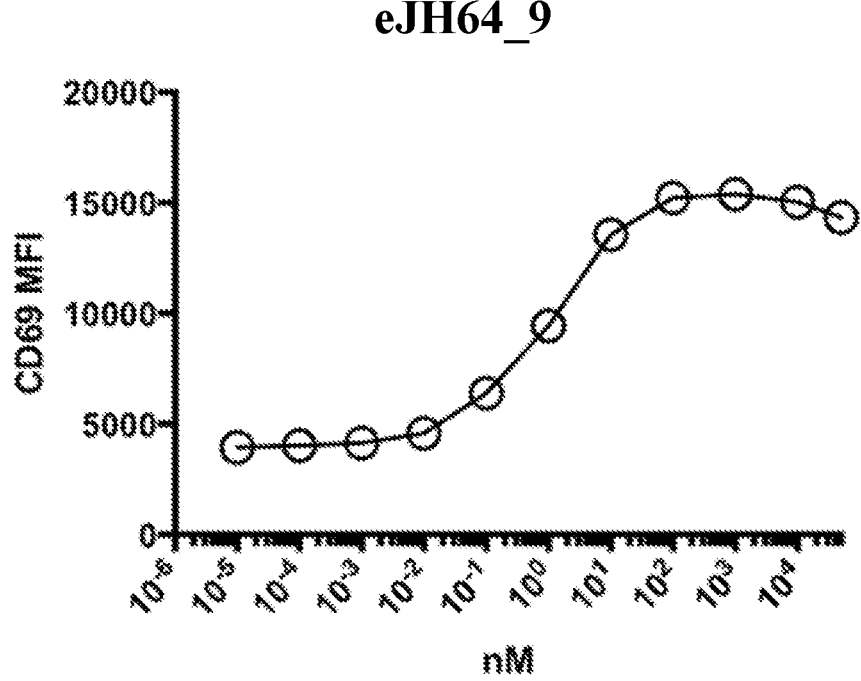
Figure 11:
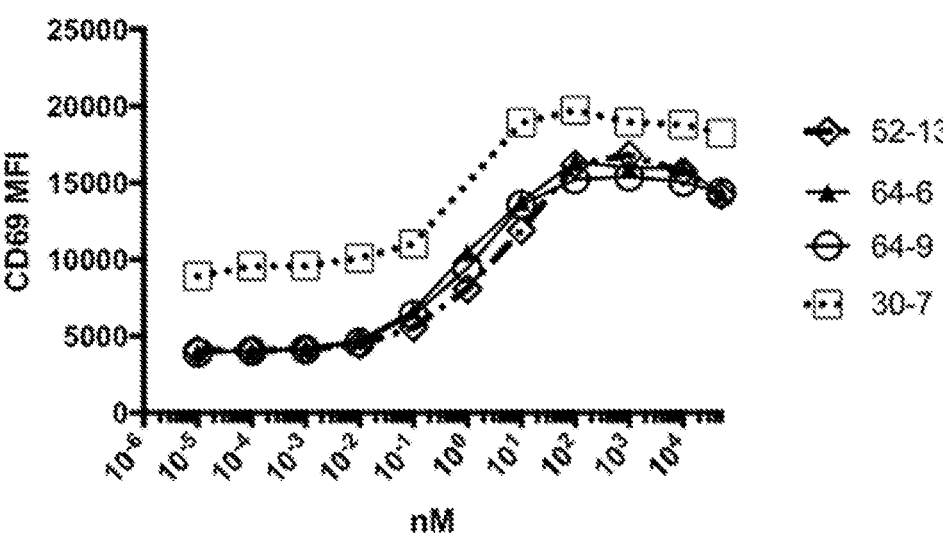
FIG. 11 shows the relative functional avidity of each of eJH30_7, eJH52_13, eJH64_6, and eJH64_9. The results shown in FIGS. 10A-10D are provided in a single graph in FIG. 11.

A functional avidity assay was carried out to assess the potency of WT1 TCRs eJH30_7, eJH52_13, eJH64_6, eJH64_9. The results are provided in FIGS. 10A-10D and FIG. 11, and Table 5. TCR-deficient cells were electroporated with vectors encoding the indicated TCRs and allowed to rest overnight. TAP-I-deficient T2 cells were pulsed with the indicated concentrations of WT1 10 mer peptide (YMLDLQPETT; SEQ ID NO: 97) for 30 minutes, washed, and then mixed with the cells expressing the indicated TCRs for 4 hours. Cells were stained for CD3 (as a measure of TCR expression) and CD69, then analyzed by FACS. CD69 MFI of the TCR$^+$ cells was plotted against peptide concentration to assess the TCRs' relative potency. FIG. 10A provides the potency of eJH30_7. FIG. 10B provides the potency of eJH52_13. FIG. 10C provides the potency of eJH64_6. FIG. 10D provides the potency of eJH64_9. FIG. 11 and Table 5 show the relative potencies of each TCR.

TABLE 5

| $EC_{50}$ of functional avidity for WT1 TCRs | |
|---|---|
| TCR ID | $EC_{50}$ |
| eJH30_7 | 0.3646 |
| eJH52_13 | 2.778 |
| eJH64_6 | 0.7003 |
| eJH64_9 | 0.8948 |

EMBODIMENTS

The following are exemplary enumerated embodiments of the present disclosure.

Embodiment 1. A recombinant T cell receptor (TCR) that binds Wilms' tumor antigen-1 (WT1), comprising an alpha chain and a beta chain, wherein the beta chain comprises a CDR3 sequence comprising an amino acid sequence set forth in SEQ ID NOs: 22 or 30.

Embodiment 2. A recombinant TCR that binds WT1, comprising an alpha chain and a beta chain, wherein the alpha chain comprises a CDR3 sequence set forth in SEQ ID NOs: 19 or 27.

Embodiment 3. The recombinant TCR of Embodiment 1 or 2, wherein the beta chain comprises a CDR2 sequence comprising an amino acid sequence set forth in SEQ ID NOs: 21 or 29.

Embodiment 4. The recombinant TCR of any one of Embodiments 1-3, wherein the alpha chain comprises a CDR2 sequence comprising an amino acid set forth in SEQ ID NOs: 18 or 26.

Embodiment 5. The recombinant TCR of any one of Embodiments 1-4, wherein the beta chain comprises a CDR1 sequence comprising an amino acid sequence set forth in SEQ ID NOs: 20 or 28.

Embodiment 6. The recombinant TCR of any one of Embodiments 1-5, wherein the alpha chain comprises a CDR1 sequence comprising an amino acid sequence set forth in SEQ ID NOs: 17 or 25.

Embodiment 7. The recombinant TCR of Embodiment 1 or 2, wherein the TCR comprises:

an alpha chain CDR1 comprising an amino acid sequence according to SEQ ID NO: 17;

an alpha chain CDR2 comprising an amino acid sequence according to SEQ ID NO: 18;

an alpha chain CDR3 comprising an amino acid sequence according to SEQ ID NO: 19;

a beta chain CDR1 comprising an amino acid sequence according to SEQ ID NO: 20;

a beta chain CDR2 comprising an amino acid sequence according to SEQ ID NO: 21; and a beta chain CDR3 comprising an amino acid sequence according to SEQ ID NO: 22.

Embodiment 8. The recombinant TCR of Embodiment 1 or 2, wherein the TCR comprises:

an alpha chain CDR1 comprising an amino acid sequence according to SEQ ID NO: 25;

an alpha chain CDR2 comprising an amino acid sequence according to SEQ ID NO: 26;

an alpha chain CDR3 comprising an amino acid sequence according to SEQ ID NO: 27;

a beta chain CDR1 comprising an amino acid sequence according to SEQ ID NO:28;

a beta chain CDR2 comprising an amino acid sequence according to SEQ ID NO: 29; and a beta chain CDR3 comprising an amino acid sequence according to SEQ ID NO: 30.

Embodiment 9. The recombinant TCR of any one of Embodiments 1 to 8, wherein the amino acid sequence of the alpha chain TCR comprises an amino acid sequence having at least 95% identity to a sequence set forth in SEQ ID NOs: 23 or 31 and the beta chain comprises an amino acid sequence having at least 95% identity to a sequence set forth in SEQ ID NOs: 24 or 32.

Embodiment 10. The recombinant TCR of Embodiment 9, wherein:

a). the amino acid sequence of the alpha chain TCR comprises an amino acid sequence having at least 95% identity to a sequence set forth in SEQ ID NO: 23 and the beta chain comprises an amino acid sequence having at least 95% identity to a sequence set forth in SEQ ID NO: 24; or b). the amino acid sequence of the alpha chain TCR comprises an amino acid sequence having at least 95% identity to a sequence set forth in SEQ ID NO: 31 and the beta chain comprises an amino acid sequence having at least 95% identity to a sequence set forth in SEQ ID NO:32.

Embodiment 11. The recombinant TCR of Embodiment 9 or 10, wherein:

a). the amino acid sequence of the alpha chain TCR comprises an amino acid sequence set forth in SEQ ID NO: 23 and the beta chain comprises an amino acid sequence set forth in SEQ ID NO: 24; or b). the amino acid sequence of the alpha chain TCR comprises an amino acid sequence set forth in SEQ ID NO: 31 and the beta chain comprises an amino acid sequence set forth in SEQ ID NO:32.

Embodiment 12. The recombinant TCR of any one of Embodiments 1 to 11, wherein the TCR is capable of binding to an epitope on the WT1 protein epitope or capable of eliciting a functional T cell response.

Embodiment 13. The recombinant TCR of Embodiment 12, wherein said T cell response is measured by CD69 expression or T cell cytolysis.

Embodiment 14. The recombinant TCR of Embodiment 12 or 13, wherein the epitope comprises a sequence according to SEQ ID NO: 97.

Embodiment 15. The recombinant TCR of any one of Embodiments 1 to 14, wherein the TCR is capable of binding to a WT1/HLA-A2 complex with an interaction half-life ($t_{1/2}$) of less than 100 seconds, or about 30 seconds to about 1000 seconds.

Embodiment 16. The recombinant TCR of any one of Embodiments 1 to 15, wherein the TCR binds a WT1/HLA-A2 complex and is capable of activating a functional T cell response and having an $EC_{50}$ less than about 100 nM, less than about 10 nM, less than about 1 nM, less than about 500 pM, less than about 100 pM, or less than about 1 pM.

Embodiment 17. The recombinant TCR of any one of Embodiments 1 to 16, wherein the TCR is a soluble TCR.

Embodiment 18. The recombinant TCR of any one of Embodiments 1 to 17, wherein the TCR is coupled to an antibody or fragment thereof.

Embodiment 19. The recombinant TCR of Embodiment 18, wherein the antibody or fragment thereof is an anti-CD3 scFv or an anti-CD3 Fab.

Embodiment 20. A method for treating cancer in a subject in need thereof, comprising administering to the subject an effective amount of a composition comprising the recombinant TCR of any one of Embodiments 1 to 19.

Embodiment 21. The method of Embodiment 20, wherein the cancer is a leukemia.

Embodiment 22. A recombinant host cell comprising an exogenous TCR of any one of Embodiments 1-21.

Embodiment 23. The recombinant host cell of Embodiment 22, wherein the host cell is an immune cell.

Embodiment 24. The recombinant host cell of Embodiment 23, wherein the immune cell is a T cell, NK cell, or NK T cell.

Embodiment 25. The recombinant host cell of Embodiment 24, wherein the T cell is a naïve T cell, an effector T cell, a central memory T cell, an effector memory T cell, a CD4+ T cell, a CD8+ T cell, an alpha/beta T cell, a gamma/delta T cell, or any combination thereof.

Embodiment 26. A method for treating cancer in a subject in need thereof, comprising administering to the subject a recombinant host cell according to any one of Embodiments 22-25.

Embodiment 27. A recombinant T cell receptor (TCR) that binds Wilms' tumor antigen-1 (WT1), comprising an alpha chain and a beta chain, wherein the beta chain comprises a CDR3 sequence comprising an amino acid sequence

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

```
                            SEQUENCE LISTING

Sequence total quantity: 98
SEQ ID NO: 1            moltype = AA  length = 6
FEATURE                Location/Qualifiers
source                 1..6
                       mol_type = protein
                       organism = Homo sapiens
SEQUENCE: 1
DSASNY                                                        6

SEQ ID NO: 2            moltype = AA  length = 7
FEATURE                Location/Qualifiers
source                 1..7
                       mol_type = protein
                       organism = Homo sapiens
SEQUENCE: 2
IRSNVGE                                                       7

SEQ ID NO: 3            moltype = AA  length = 12
FEATURE                Location/Qualifiers
source                 1..12
                       mol_type = protein
                       organism = Homo sapiens
SEQUENCE: 3
CAAGGRDDKI IF                                                 12

SEQ ID NO: 4            moltype = AA  length = 5
FEATURE                Location/Qualifiers
source                 1..5
                       mol_type = protein
                       organism = Homo sapiens
SEQUENCE: 4
SNHLY                                                         5

SEQ ID NO: 5            moltype = AA  length = 6
FEATURE                Location/Qualifiers
source                 1..6
                       mol_type = protein
                       organism = Homo sapiens
SEQUENCE: 5
FYNNEI                                                        6

SEQ ID NO: 6            moltype = AA  length = 18
FEATURE                Location/Qualifiers
source                 1..18
                       mol_type = protein
                       organism = Homo sapiens
SEQUENCE: 6
CASSERLGTM AYNSPLHF                                           18

SEQ ID NO: 7            moltype = AA  length = 271
FEATURE                Location/Qualifiers
source                 1..271
                       mol_type = protein
                       organism = Homo sapiens
SEQUENCE: 7
MTSIRAVFIF LWLQLDLVNG ENVEQHPSTL SVQEGDSAVI KCTYSDSASN YFPWYKQELG  60
KGPQLIIDIR SNVGEKKDQR IAVTLNKTAK HFSLHITETQ PEDSAVYFCA AGGRDDKIIF  120
GKGTRLHILP NIQNPDPAVY QLRDSKSSDK SVCLFTDFDS QTNVSQSKDS DVYITDKCVL  180
DMRSMDFKSN SAVAWSNKSD FACANAFNNS IIPEDTFFPS PESSCDVKLV EKSFETDTNL  240
NFQNLSVIGF RILLLKVAGF NLLMTLRLWS S                            271

SEQ ID NO: 8            moltype = AA  length = 314
FEATURE                Location/Qualifiers
source                 1..314
                       mol_type = protein
                       organism = Homo sapiens
SEQUENCE: 8
MDTWLVCWAI FSLLKAGLTE PEVTQTPSHQ VTQMGQEVIL RCVPISNHLY FYWYRQILGQ  60
```

```
KVEFLVSFYN NEISEKSEIF DDQFSVERPD GSNFTLKIRS TKLEDSAMYF CASSERLGTM  120
AYNSPLHFGN GTRLTVTEDL NKVFPPEVAV FEPSEAEISH TQKATLVCLA TGFFPDHVEL  180
SWWVNGKEVH SGVCTDPQPL KEQPALNDSR YCLSSRLRVS ATFWQNPRNH FRCQVQFYGL  240
SENDEWTQDR AKPVTQIVSA EAWGRADCGF TSVSYQQGVL SATILYEILL GKATLYAVLV  300
SALVLMAMVK RKDF                                                    314
```

```
SEQ ID NO: 9              moltype = AA  length = 5
FEATURE                   Location/Qualifiers
source                    1..5
                          mol_type = protein
                          organism = Homo sapiens
SEQUENCE: 9
SIFNT                                                                5
```

```
SEQ ID NO: 10             moltype = AA  length = 7
FEATURE                   Location/Qualifiers
source                    1..7
                          mol_type = protein
                          organism = Homo sapiens
SEQUENCE: 10
LYKAGEL                                                              7
```

```
SEQ ID NO: 11             moltype = AA  length = 12
FEATURE                   Location/Qualifiers
source                    1..12
                          mol_type = protein
                          organism = Homo sapiens
SEQUENCE: 11
CAGRGSQGNL IF                                                       12
```

```
SEQ ID NO: 12             moltype = AA  length = 5
FEATURE                   Location/Qualifiers
source                    1..5
                          mol_type = protein
                          organism = Homo sapiens
SEQUENCE: 12
LGHDT                                                                5
```

```
SEQ ID NO: 13             moltype = AA  length = 6
FEATURE                   Location/Qualifiers
source                    1..6
                          mol_type = protein
                          organism = Homo sapiens
SEQUENCE: 13
YNNKEL                                                               6
```

```
SEQ ID NO: 14             moltype = AA  length = 12
FEATURE                   Location/Qualifiers
source                    1..12
                          mol_type = protein
                          organism = Homo sapiens
SEQUENCE: 14
CASSHWQETQ YF                                                       12
```

```
SEQ ID NO: 15             moltype = AA  length = 269
FEATURE                   Location/Qualifiers
source                    1..269
                          mol_type = protein
                          organism = Homo sapiens
SEQUENCE: 15
MLLEHLLIIL WMQLTWVSGQ QLNQSPQSMF IQEGEDVSMN CTSSSIFNTW LWYKQEPGEG  60
PVLLIALYKA GELTSNGRLT AQFGITRKDS FLNISASIPS DVGIYFCAGR GSQGNLIFGK  120
GTKLSVKPNI QNPDPAVYQL RDSKSSDKSV CLFTDFDSQT NVSQSKDSDV YITDKCVLDM  180
RSMDFKSNSA VAWSNKSDFA CANAFNNSII PEDTFFPSPE SSCDVKLVEK SFETDTNLNF  240
QNLSVIGFRI LLLKVAGFNL LMTLRLWSS                                    269
```

```
SEQ ID NO: 16             moltype = AA  length = 309
FEATURE                   Location/Qualifiers
source                    1..309
                          mol_type = protein
                          organism = Homo sapiens
SEQUENCE: 16
MGCRLLCCVV FCLLQAGPLD TAVSQTPKYL VTQMGNDKSI KCEQNLGHDT MYWYKQDSKK  60
FLKIMFSYNN KELIINETVP NRFSPKSPDK AHLNLHINSL ELGDSAVYFC ASSHWQETQY  120
FGPGTRLLVL EDLKNVFPPE VAVFEPSEAE ISHTQKATLV CLATGFYPDH VELSWWVNGK  180
EVHSGVCTDP QPLKEQPALN DSRYCLSSRL RVSATFWQNP RNHFRCQVQF YGLSENDEWT  240
QDRAKPVTQI VSAEAWGRAD CGFTSESYQQ GVLSATILYE ILLGKATLYA VLVSALVLMA  300
MVKRKDSRG                                                          309
```

-continued

```
SEQ ID NO: 17             moltype = AA   length = 7
FEATURE                   Location/Qualifiers
source                    1..7
                          mol_type = protein
                          organism = Homo sapiens
SEQUENCE: 17
TSENNYY                                                          7

SEQ ID NO: 18             moltype = AA   length = 8
FEATURE                   Location/Qualifiers
source                    1..8
                          mol_type = protein
                          organism = Homo sapiens
SEQUENCE: 18
QEAYKQQN                                                         8

SEQ ID NO: 19             moltype = AA   length = 16
FEATURE                   Location/Qualifiers
source                    1..16
                          mol_type = protein
                          organism = Homo sapiens
SEQUENCE: 19
CAFMGYYGGS QGNLIF                                                16

SEQ ID NO: 20             moltype = AA   length = 5
FEATURE                   Location/Qualifiers
source                    1..5
                          mol_type = protein
                          organism = Homo sapiens
SEQUENCE: 20
SGHNS                                                            5

SEQ ID NO: 21             moltype = AA   length = 6
FEATURE                   Location/Qualifiers
source                    1..6
                          mol_type = protein
                          organism = Homo sapiens
SEQUENCE: 21
FNNNVP                                                           6

SEQ ID NO: 22             moltype = AA   length = 12
FEATURE                   Location/Qualifiers
source                    1..12
                          mol_type = protein
                          organism = Homo sapiens
SEQUENCE: 22
CASSSLQYEQ YF                                                    12

SEQ ID NO: 23             moltype = AA   length = 278
FEATURE                   Location/Qualifiers
source                    1..278
                          mol_type = protein
                          organism = Homo sapiens
SEQUENCE: 23
MTRVSLLWAV VVSTCLESGM AQTVTQSQPE MSVQEAETVT LSCTYDTSEN NYYLFWYKQP  60
PSRQMILVIR QEAYKQQNAT ENRFSVNFQK AAKSFSLKIS DSQLGDTAMY FCAFMGYYGG  120
SQGNLIFGKG TKLSVKPNIQ NPDPAVYQLR DSKSSDKSVC LFTDFDSQTN VSQSKDSDVY  180
ITDKCVLDMR SMDFKSNSAV AWSNKSDFAC ANAFNNSIIP EDTFFPSPES SCDVKLVEKS  240
FETDTNLNFQ NLSVIGFRIL LLKVAGFNLL MTLRLWSS                         278

SEQ ID NO: 24             moltype = AA   length = 310
FEATURE                   Location/Qualifiers
source                    1..310
                          mol_type = protein
                          organism = Homo sapiens
SEQUENCE: 24
MDSWTFCCVS LCILVAKHTD AGVIQSPRHE VTEMGQEVTL RCKPISGHNS LFWYRQTMMR  60
GLELLIYFNN NVPIDDSGMP EDRFSAKMPN ASFSTLKIQP SEPRDSAVYF CASSSLQYEQ  120
YFGPGTRLTV TEDLKNVFPP EVAVFEPSEA EISHTQKATL VCLATGFYPD HVELSWWVNG  180
KEVHSGVCTD PQPLKEQPAL NDSRYCLSSR LRVSATFWQN PRNHFRCQVQ FYGLSENDEW  240
TQDRAKPVTQ IVSAEAWGRA DCGFTSESYQ QGVLSATILY EILLGKATLY AVLVSALVLM  300
AMVKRKDSRG                                                        310

SEQ ID NO: 25             moltype = AA   length = 6
FEATURE                   Location/Qualifiers
source                    1..6
                          mol_type = protein
                          organism = Homo sapiens
SEQUENCE: 25
```

-continued

```
NSASQS                                                        6

SEQ ID NO: 26          moltype = AA  length = 6
FEATURE                Location/Qualifiers
source                 1..6
                       mol_type = protein
                       organism = Homo sapiens
SEQUENCE: 26
VYSSGN                                                        6

SEQ ID NO: 27          moltype = AA  length = 14
FEATURE                Location/Qualifiers
source                 1..14
                       mol_type = protein
                       organism = Homo sapiens
SEQUENCE: 27
CVVKSLDNNN DMRF                                               14

SEQ ID NO: 28          moltype = AA  length = 5
FEATURE                Location/Qualifiers
source                 1..5
                       mol_type = protein
                       organism = Homo sapiens
SEQUENCE: 28
KGHDR                                                         5

SEQ ID NO: 29          moltype = AA  length = 6
FEATURE                Location/Qualifiers
source                 1..6
                       mol_type = protein
                       organism = Homo sapiens
SEQUENCE: 29
SFDVKD                                                        6

SEQ ID NO: 30          moltype = AA  length = 14
FEATURE                Location/Qualifiers
source                 1..14
                       mol_type = protein
                       organism = Homo sapiens
SEQUENCE: 30
CATSDWTGRN EQFF                                               14

SEQ ID NO: 31          moltype = AA  length = 273
FEATURE                Location/Qualifiers
source                 1..273
                       mol_type = protein
                       organism = Homo sapiens
SEQUENCE: 31
MISLRVLLVI LWLQLSWVWS QRKEVEQDPG PFNVPEGATV AFNCTYSNSA SQSFFWYRQD   60
CRKEPKLLMS VYSSGNEDGR FTAQLNRASQ YISLLIRDSK LSDSATYLCV VKSLDNNNDM  120
RFGAGTRLTV KPNIQNPDPA VYQLRDSKSS DKSVCLFTDF DSQTNVSQSK DSDVYITDKC  180
VLDMRSMDFK SNSAVAWSNK SDFACANAFN NSIIPEDTFF PSPESSCDVK LVEKSFETDT  240
NLNFQNLSVI GFRILLLKVA GFNLLMTLRL WSS                          273

SEQ ID NO: 32          moltype = AA  length = 311
FEATURE                Location/Qualifiers
source                 1..311
                       mol_type = protein
                       organism = Homo sapiens
SEQUENCE: 32
MASLLFFCGA FYLLGTGSMD ADVTQTPRNR ITKTGKRIML ECSQTKGHDR MYWYRQDPGL   60
GLRLIYYSFD VKDINKGEIS DGYSVSRQAQ AKFSLSLESA IPNQTALYFC ATSDWTGRNE  120
QFFGPGTRLT VLEDLKNVFP PEVAVFEPSE AEISHTQKAT LVCLATGFYP DHVELSWWVN  180
GKEVHSGVCT DPQPLKEQPA LNDSRYCLSS RLRVSATFWQ NPRNHFRCQV QFYGLSENDE  240
WTQDRAKPVT QIVSAEAWGR ADCGFTSESY QQGVLSATIL YEILLGKATL YAVLVSALVL  300
MAMVKRKDSR G                                                  311

SEQ ID NO: 33          moltype = AA  length = 6
FEATURE                Location/Qualifiers
source                 1..6
                       mol_type = protein
                       organism = Homo sapiens
SEQUENCE: 33
VSGNPY                                                        6

SEQ ID NO: 34          moltype = AA  length = 8
FEATURE                Location/Qualifiers
source                 1..8
                       mol_type = protein
```

-continued

```
                        organism = Homo sapiens
SEQUENCE: 34
YITGDNLV                                                                                8

SEQ ID NO: 35           moltype = AA  length = 17
FEATURE                 Location/Qualifiers
source                  1..17
                        mol_type = protein
                        organism = Homo sapiens
SEQUENCE: 35
CAVRDMRYGG ATNKLIF                                                                      17

SEQ ID NO: 36           moltype = AA  length = 5
FEATURE                 Location/Qualifiers
source                  1..5
                        mol_type = protein
                        organism = Homo sapiens
SEQUENCE: 36
LGHNA                                                                                   5

SEQ ID NO: 37           moltype = AA  length = 6
FEATURE                 Location/Qualifiers
source                  1..6
                        mol_type = protein
                        organism = Homo sapiens
SEQUENCE: 37
YSLEER                                                                                  6

SEQ ID NO: 38           moltype = AA  length = 20
FEATURE                 Location/Qualifiers
source                  1..20
                        mol_type = protein
                        organism = Homo sapiens
SEQUENCE: 38
CASSQDGLAG AASFNNEQFF                                                                   20

SEQ ID NO: 39           moltype = AA  length = 277
FEATURE                 Location/Qualifiers
source                  1..277
                        mol_type = protein
                        organism = Homo sapiens
SEQUENCE: 39
MASAPISMLA MLFTLSGLRA QSVAQPEDQV NVAEGNPLTV KCTYSVSGNP YLFWYVQYPN                        60
RGLQFLLKYI TGDNLVKGSY GFEAEFNKSQ TSFHLKKPSA LVSDSALYFC AVRDMRYGGA                        120
TNKLIFGTGT LLAVQPNIQN PDPAVYQLRD SKSSDKSVCL FTDFDSQTNV SQSKDSDVYI                        180
TDKCVLDMRS MDFKSNSAVA WSNKSDFACA NAFNNSIIPE DTFFPSPESS CDVKLVEKSF                        240
ETDTNLNFQN LSVIGFRILL LKVAGFNLLM TLRLWSS                                                277

SEQ ID NO: 40           moltype = AA  length = 320
FEATURE                 Location/Qualifiers
source                  1..320
                        mol_type = protein
                        organism = Homo sapiens
SEQUENCE: 40
MGCRLLCCAV LCLLGAGELV PMETGVTQTP RHLVMGMTNK KSLKCEQHLG HNAMYWYKQS                        60
AKKPLELMFV YSLEERVENN SVPSRFSPEC PNSSHLFLHL HTLQPEDSAL YLCASSQDGL                        120
AGAASFNNEQ FFGPGTRLTV LEDLKNVFPP EVAVFEPSEA EISHTQKATL VCLATGFYPD                        180
HVELSWWVNG KEVHSGVCTD PQPLKEQPAL NDSRYCLSSR LRVSATFWQN PRNHFRCQVQ                        240
FYGLSENDEW TQDRAKPVTQ IVSAEAWGRA DCGFTSESYQ QGVLSATILY EILLGKATLY                        300
AVLVSALVLM AMVKRKDSRG                                                                   320

SEQ ID NO: 41           moltype = AA  length = 6
FEATURE                 Location/Qualifiers
source                  1..6
                        mol_type = protein
                        organism = Homo sapiens
SEQUENCE: 41
SSNFYA                                                                                  6

SEQ ID NO: 42           moltype = AA  length = 7
FEATURE                 Location/Qualifiers
source                  1..7
                        mol_type = protein
                        organism = Homo sapiens
SEQUENCE: 42
MTLNGDE                                                                                 7

SEQ ID NO: 43           moltype = AA  length = 14
FEATURE                 Location/Qualifiers
```

-continued

```
source                1..14
                      mol_type = protein
                      organism = Homo sapiens
SEQUENCE: 43
CAFMRATGAN NLFF                                                    14

SEQ ID NO: 44         moltype = AA   length = 5
FEATURE               Location/Qualifiers
source                1..5
                      mol_type = protein
                      organism = Homo sapiens
SEQUENCE: 44
SGHVS                                                             5

SEQ ID NO: 45         moltype = AA   length = 6
FEATURE               Location/Qualifiers
source                1..6
                      mol_type = protein
                      organism = Homo sapiens
SEQUENCE: 45
FNYEAQ                                                            6

SEQ ID NO: 46         moltype = AA   length = 14
FEATURE               Location/Qualifiers
source                1..14
                      mol_type = protein
                      organism = Homo sapiens
SEQUENCE: 46
CASSFGGVSY EQYF                                                   14

SEQ ID NO: 47         moltype = AA   length = 276
FEATURE               Location/Qualifiers
source                1..276
                      mol_type = protein
                      organism = Homo sapiens
SEQUENCE: 47
MEKNPLAAPL LILWFHLDCV SSILNVEQSP QSLHVQEGDS TNFTCSFPSS NFYALHWYRW  60
ETAKSPEALF VMTLNGDEKK KGRISATLNT KEGYSYLYIK GSQPEDSATY LCAFMRATGA  120
NNLFFGTGTR LTVIPYIQNP DPAVYQLRDS KSSDKSVCLF TDFDSQTNVS QSKDSDVYIT  180
DKCVLDMRSM DFKSNSAVAW SNKSDFACAN AFNNSIIPED TFFPSPESSC DVKLVEKSFE  240
TDTNLNFQNL SVIGFRILLL KVAGFNLLMT LRLWSS                          276

SEQ ID NO: 48         moltype = AA   length = 312
FEATURE               Location/Qualifiers
source                1..312
                      mol_type = protein
                      organism = Homo sapiens
SEQUENCE: 48
MGTSLLCWVV LGFLGTDHTG AGVSQSPRYK VTKRGQDVAL RCDPISGHVS LYWYRQALGQ  60
GPEFLTYFNY EAQQDKSGLP NDRFSAERPE GSISTLTIQR TEQRDSAMYR CASSFGGVSY  120
EQYFGPGTRL TVTEDLKNVF PPEVAVFEPS EAEISHTQKA TLVCLATGFY PDHVELSWWV  180
NGKEVHSGVC TDPQPLKEQP ALNDSRYCLS SRLRVSATFW QNPRNHFRCQ VQFYGLSEND  240
EWTQDRAKPV TQIVSAEAWG RADCGFTSES YQQGVLSATI LYEILLGKAT LYAVLVSALV  300
LMAMVKRKDS RG                                                    312

SEQ ID NO: 49         moltype = DNA   length = 18
FEATURE               Location/Qualifiers
source                1..18
                      mol_type = other DNA
                      organism = Homo sapiens
SEQUENCE: 49
gacagcgcct ccaactac                                              18

SEQ ID NO: 50         moltype = DNA   length = 21
FEATURE               Location/Qualifiers
source                1..21
                      mol_type = other DNA
                      organism = Homo sapiens
SEQUENCE: 50
atcagatcca acgtgggcga g                                          21

SEQ ID NO: 51         moltype = DNA   length = 36
FEATURE               Location/Qualifiers
source                1..36
                      mol_type = other DNA
                      organism = Homo sapiens
SEQUENCE: 51
tgtgctgccg gcggaaggga cgacaagatc atcttc                          36
```

-continued

```
SEQ ID NO: 52          moltype = DNA  length = 15
FEATURE                Location/Qualifiers
source                 1..15
                       mol_type = other DNA
                       organism = Homo sapiens
SEQUENCE: 52
agcaaccacc tgtac                                                    15

SEQ ID NO: 53          moltype = DNA  length = 18
FEATURE                Location/Qualifiers
source                 1..18
                       mol_type = other DNA
                       organism = Homo sapiens
SEQUENCE: 53
ttctacaaca acgagatc                                                 18

SEQ ID NO: 54          moltype = DNA  length = 54
FEATURE                Location/Qualifiers
source                 1..54
                       mol_type = other DNA
                       organism = Homo sapiens
SEQUENCE: 54
tgcgccagct ctgagagact gggcaccatg gcctacaaca gccctctgca cttt         54

SEQ ID NO: 55          moltype = DNA  length = 816
FEATURE                Location/Qualifiers
source                 1..816
                       mol_type = other DNA
                       organism = Homo sapiens
SEQUENCE: 55
atgaccagca tcagagccgt gttcatcttc ctgtggctgc agctggacct cgtgaacggc   60
gagaatgtgg aacagcaccc ctccacactg agcgtgcaag agggcgattc tgccgtgatc   120
aagtgcacct acagcgacag cgcctccaac tacttccct ggtacaagca agaactcggc    180
aagggccctc agctgatcat cgacatcaga tccaacgtgg gcgagaagaa ggaccagcgg   240
attgccgtga cactgaacaa gaccgccaag cacttctccc tgcacatcac cgagacacag   300
cctgaggatt ccgccgtgta tttctgtgct gccggcggaa gggacgacaa gatcatcttc   360
ggaaagggca cacgcctgca cattctgccc aacattcaga accccgatcc tgccgtgtac   420
cagctgagag acagcaagag cagcgacaag agcgtgtgtc tgttcaccga cttcgacagc   480
cagaccaacg tgtcccagag caaggacagc gacgtgtaca tcacagataa gtgcgtgctg   540
gacatgcgga gcatggactt caagagcaac agcgccgtgg cctggtccaa caagagcgat   600
ttcgcctgcg ccaacgcctt caacaacagc attatccccg aggacacatt cttcccatca   660
cctgagagca gctgcgacgt gaagctggtg gaaaagagct cgagacaga caccaacctg    720
aacttccaga acctgagcgt gatcggcttc agaatcctgc tgctgaaggt ggccggcttc   780
aatctgctga tgacctgag actgtggtcc tcctga                             816

SEQ ID NO: 56          moltype = DNA  length = 945
FEATURE                Location/Qualifiers
source                 1..945
                       mol_type = other DNA
                       organism = Homo sapiens
SEQUENCE: 56
atggacacct ggctcgtgtg ctgggccatc ttcagcctgc tgaaagccgg actgaccgag   60
cctgaagtga cccagacacc tagccaccaa gtgacacaga tgggccaaga agtgatcctg   120
cgctgcgtgc ccatcagcaa ccacctgtac ttctactggt acagacagat cctgggccag   180
aaagtggaat tcctggtgtc cttctacaac aacgagatca gcgagaagtc cgagatctcc   240
gacgaccagt tcagcgtgga aagacccgac ggcagcaact tcacccctgaa gatcagaagc   300
accaagctcg aggacagcgc catgtacttt tgcgccagct ctgagagact gggcaccatg   360
gcctacaaca gccctctgca ctttggcaac ggcaccagac tgaccgtgac cgaggatctg   420
aacaaggtgt tccctccaga ggtggccgtg ttcgagcctt ctgaggccga gatctctcac   480
acccagaaag ccacactcgt gtgcctggcc accggctttt ttcccgatca gtggaactg    540
tcttggtggg tcaacggcaa agaggtgcac agcggcgtct gtaccgatcc tcagccactg   600
aaagagcagc ccgctctgaa cgacagcaga tactgcctga gcagcagact gagagtgtcc   660
gccaccttct ggcagaaccc cagaaaccac ttcagatgcc aggtgcagtt ctacggcctg   720
agcgagaacg atgagtggac ccaggataga gccaagcctg tgactcagat cgtgtctgcc   780
gaagcctggg gcagagccga ttgtggcttt accagcgtgt cctatcagca gggcgtgctg   840
tctgccacca tcctgtatga gatcctgctg ggcaaagcca ctctgtacgc cgtgctggtg   900
tctgccctgt gctgatggc catggtcaag cggaaggact ctga                    945

SEQ ID NO: 57          moltype = DNA  length = 15
FEATURE                Location/Qualifiers
source                 1..15
                       mol_type = other DNA
                       organism = Homo sapiens
SEQUENCE: 57
agcatcttca acacc                                                    15

SEQ ID NO: 58          moltype = DNA  length = 21
FEATURE                Location/Qualifiers
source                 1..21
```

-continued

```
                              mol_type = other DNA
                              organism = Homo sapiens
SEQUENCE: 58
ctttacaagg ccggggagct g                                       21

SEQ ID NO: 59         moltype = DNA   length = 36
FEATURE               Location/Qualifiers
source                1..36
                      mol_type = other DNA
                      organism = Homo sapiens
SEQUENCE: 59
tgtgccggca gaggcagcca gggcaacctg attttt                       36

SEQ ID NO: 60         moltype = DNA   length = 15
FEATURE               Location/Qualifiers
source                1..15
                      mol_type = other DNA
                      organism = Homo sapiens
SEQUENCE: 60
ctgggccacg acacc                                              15

SEQ ID NO: 61         moltype = DNA   length = 18
FEATURE               Location/Qualifiers
source                1..18
                      mol_type = other DNA
                      organism = Homo sapiens
SEQUENCE: 61
tacaacaaca aagagctg                                           18

SEQ ID NO: 62         moltype = DNA   length = 36
FEATURE               Location/Qualifiers
source                1..36
                      mol_type = other DNA
                      organism = Homo sapiens
SEQUENCE: 62
tgtgccagca gccactggca agagacacag tacttt                       36

SEQ ID NO: 63         moltype = DNA   length = 810
FEATURE               Location/Qualifiers
source                1..810
                      mol_type = other DNA
                      organism = Homo sapiens
SEQUENCE: 63
atgctgctgg aacacctcct gatcatcctg tggatgcagc tgacatgggt gtccggccag   60
cagctgaatc agagccctca gagcatgttc atccaagaag gcgaggacgt ttccatgaac  120
tgtaccagca gcagcatctt caacacctgg ctgtggtata agcaagagcc cggcgaagga  180
cccgtgctgc tgattgctct ttacaaggcc ggggagctga ccagcaacgg cagactgaca  240
gcccagttcg gcattacccg gaaggacagc ttcctgaaca tcagcgccag cattcccagc  300
gacgtgggca tctatttctg tgccggcaga ggcagccagg gcaacctgat ttttggcaag  360
ggcaccaagc tgagcgtgaa gcccaacatt cagaaccccg atcctgccgt gtaccagctg  420
agagacagca agtccagcga caagtccgtg tgcctgttca ccgacttcga cagccagacc  480
aacgtgtccc agagcaagga ctccgacgtg tacatcaccg ataagtgcgt gctggacatg  540
cggagcatgg acttcaagag caactccgcc gtggcctggt ccaacaagag cgatttcgcc  600
tgcgccaacc ccttcaacaa cagcattatc cccgaggaca cattcttccc aagtcctgag  660
agcagctgcg acgtgaagct ggtggaaaag agcttcgaga cagacaccaa cctgaacttc  720
cagaacctgt ccgtgatcgg cttcagaatc ctgctgctga aggtggccgg cttcaacctg  780
ctgatgaccc tgagactgtg gtccagctga                             810

SEQ ID NO: 64         moltype = DNA   length = 930
FEATURE               Location/Qualifiers
source                1..930
                      mol_type = other DNA
                      organism = Homo sapiens
SEQUENCE: 64
atgggctgca gactgctgtg ctgcgttgtg ttctgcctgc tgcaagccgg acctctggat   60
acagccgtgt ctcagacccc taagtacctg gtcacccaga tgggcaacga caagagcatc  120
aagtgcgagc agaacctggg ccacgacacc atgtactggt acaagcagga cagcaagaaa  180
ttcctgaaga tcatgttcag ctacaacaac aaagagctga tcatcaacga cagagtgccc  240
aaccggttca gcccctaagag ccctgataag gcccacctga acctgcacat caacagcctg  300
gaactgggcg acagcgccgt gtactttgt gccagcagcc actggcaaga gacacagtac  360
tttggccctg gcaccaggct gctggtgctg aagatctga agaacgtgtt cccacctgag  420
gtggccgtgt tcgagccttc tgaggccgag atcagccaca cacagaaagc cacactcgtg  480
tgtctggcca ccggcttcta tcccgatcac gtggaactgt cttggtgggt caacggcaaa  540
gaggtgcaca gcggcgtctg taccgatcct cagcctctga aagagcagcc cgctctgaac  600
gacagcagat actgcctgag cagcagactg agagtgtccg ccaccttctg gcagaacccc  660
agaaaccact tcagatgcca ggtgcagttc tacggcctga gcgagaacga tgagtggacc  720
caggatagcc caagcctgt gacacagatc gtgtctgccg aagcctgggg cagagccgat  780
tgtggctttta ccagcgagag ctaccagcag ggcgtgctgt ctgccacaat cctgtacgag  840
atcctgctgg gcaaagccac tctgtacgcc gtgctggtgt ctgccctggt gctgatggcc  900
```

```
atggtcaagc ggaaggactc tagaggctga                                       930

SEQ ID NO: 65              moltype = DNA   length = 21
FEATURE                    Location/Qualifiers
source                     1..21
                           mol_type = other DNA
                           organism = Homo sapiens
SEQUENCE: 65
accagcgaga acaactacta c                                                 21

SEQ ID NO: 66              moltype = DNA   length = 24
FEATURE                    Location/Qualifiers
source                     1..24
                           mol_type = other DNA
                           organism = Homo sapiens
SEQUENCE: 66
caagaggcct ataagcagca gaac                                              24

SEQ ID NO: 67              moltype = DNA   length = 48
FEATURE                    Location/Qualifiers
source                     1..48
                           mol_type = other DNA
                           organism = Homo sapiens
SEQUENCE: 67
tgcgccttta tgggctacta cggcggcagc cagggcaacc tgatcttt                    48

SEQ ID NO: 68              moltype = DNA   length = 15
FEATURE                    Location/Qualifiers
source                     1..15
                           mol_type = other DNA
                           organism = Homo sapiens
SEQUENCE: 68
agcggccaca acagc                                                        15

SEQ ID NO: 69              moltype = DNA   length = 18
FEATURE                    Location/Qualifiers
source                     1..18
                           mol_type = other DNA
                           organism = Homo sapiens
SEQUENCE: 69
ttcaacaaca acgtgccc                                                     18

SEQ ID NO: 70              moltype = DNA   length = 36
FEATURE                    Location/Qualifiers
source                     1..36
                           mol_type = other DNA
                           organism = Homo sapiens
SEQUENCE: 70
tgtgccagca gcagcctgca gtacgagcag tatttt                                 36

SEQ ID NO: 71              moltype = DNA   length = 837
FEATURE                    Location/Qualifiers
source                     1..837
                           mol_type = other DNA
                           organism = Homo sapiens
SEQUENCE: 71
atgaccagag tgtctctgct gtgggccgtc gtggtgtcta catgtctgga atctggcatg       60
gcccagaccg tgacacagtc tcagcctgag atgagcgtgc aagaggccga aacagtgacc      120
ctgacctgca cctacgacac cagcgagaac aactactacc tcttttggta caagcagcct      180
cctagccggc agatgatcct ggtcatcaga caagaggcct ataagcagca gaacgccacc      240
gagaacaggt tcagcgtgaa cttccagaag gccgccaaga gcttcagcct gaaaatcagc      300
gatagccagc tgggcgacac cgccatgtat ttctgcgcct ttatgggcta ctacggcggc      360
agccagggca acctgatctt tggcaagggc accaagctga gcgtgaagcc caacattcag      420
aacccccgatc ctgccgtgta ccagctgaga gacagcaagg cagcgacaa gagcgtgtgt      480
ctgttcaccg acttcgacag ccagaccaac gtgtcccaga gcaaggactc cgacgtgtac      540
atcaccgata agtgcgtgct ggacatgcgg agcatggact tcaagagcaa tagcgccgtg      600
gcctggtcca acaagagcga ttttgcctgc gccaacgcct tcaacaatag catcatcccc      660
gaggacacat tcttcccaag tcctgagagc agctgcgacg tgaagctggt ggaaaagagc      720
ttcgagacag acaccaacct gaatttccag aacctgtccg tgatcggctt cagaatcctg      780
ctgctgaagg tggccggctt caacctgctg atgcacctga ggctgtggtc tagctga         837

SEQ ID NO: 72              moltype = DNA   length = 930
FEATURE                    Location/Qualifiers
source                     1..930
                           mol_type = other DNA
                           organism = Homo sapiens
SEQUENCE: 72
atggacagct ggaccttttg ctgcgtgtcc ctgtgtatcc tggtggccaa acataccgat       60
gccggcgtga tccagtctcc tagacacgaa gtgaccgaga tgggccaaga ggtcacactg      120
```

```
agatgcaagc ccatcagcgg ccacaacagc ctgttctggt acagacagac catgatgaga 180
ggcctggaac tgctgatcta cttcaacaac aacgtgccca tcgacgacag cggcatgccc 240
gaggatagat tcagcgccaa gatgcccaat gccagcttca gcaccctgaa gatccagcct 300
agcgagccta gagacagcgc cgtgtacttt tgtgccagca gcagcctgca gtacgagcag 360
tattttggcc ctggcaccag actgaccgtg accgaggacc tgaagaacgt gttcccacct 420
gaggtggccg tgtttgagcc ttctgaggcc gagatcagcc acacacagaa agccacactc 480
gtgtgcctgg ccaccggctt ttatcccgat cacgtggaac tgtcttggtg ggtcaacggc 540
aaagaggtgc acagcggagt ctgtaccgat cctcagcctc tgaaaagagca gcccgctctg 600
aacgacagca gatactgtct gagcagcaga ctgagagtgt ccgccacctt ctggcagaac 660
cccagaaacc acttcagatg ccaggtgcag ttctacggcc tgagcgagaa tgacgagtgg 720
acccaggata gagccaagcc tgtgacacag attgtgtctg ccgaagcctg gggcagagcc 780
gattgtggct ttacaagcga gagctaccag cagggcgtgc tgagcgccac aatcctgtat 840
gagatcctgc tgggcaaagc cactctgtac gctgtgctgg tgtctgccct ggtgctgatg 900
gccatggtca agagaaagga cagcagaggc 930
```

```
SEQ ID NO: 73               moltype = DNA   length = 18
FEATURE                     Location/Qualifiers
source                      1..18
                            mol_type = other DNA
                            organism = Homo sapiens
SEQUENCE: 73
aacagtgctt ctcagtct                                                      18

SEQ ID NO: 74               moltype = DNA   length = 18
FEATURE                     Location/Qualifiers
source                      1..18
                            mol_type = other DNA
                            organism = Homo sapiens
SEQUENCE: 74
gtatactcca gtggtaat                                                      18

SEQ ID NO: 75               moltype = DNA   length = 42
FEATURE                     Location/Qualifiers
source                      1..42
                            mol_type = other DNA
                            organism = Homo sapiens
SEQUENCE: 75
tgtgtggtga agtccctcga caataacaat gacatgcgct tt                          42

SEQ ID NO: 76               moltype = DNA   length = 15
FEATURE                     Location/Qualifiers
source                      1..15
                            mol_type = other DNA
                            organism = Homo sapiens
SEQUENCE: 76
aagggtcatg ataga                                                         15

SEQ ID NO: 77               moltype = DNA   length = 18
FEATURE                     Location/Qualifiers
source                      1..18
                            mol_type = other DNA
                            organism = Homo sapiens
SEQUENCE: 77
tcctttgatg tcaaagat                                                      18

SEQ ID NO: 78               moltype = DNA   length = 42
FEATURE                     Location/Qualifiers
source                      1..42
                            mol_type = other DNA
                            organism = Homo sapiens
SEQUENCE: 78
tgtgccacca gtgattggac agggcgaaat gagcagttct tc                          42

SEQ ID NO: 79               moltype = DNA   length = 822
FEATURE                     Location/Qualifiers
source                      1..822
                            mol_type = other DNA
                            organism = Homo sapiens
SEQUENCE: 79
atgatctcct tgagagtttt actggtgatc ctgtggcttc agttaagctg ggtttggagc 60
caacggaagg aggtggagca ggatcctgga cccttcaatg ttccagaggg agccactgtc 120
gctttcaact gtacttacag caacagtgct ctctcagtctt tcttctggta cagacaggat 180
tgcaggaaag aacctaagtt gctgatgtcc gtatactcca gtggtaatga agatggaagg 240
tttacagcac agctcaatag agccagccag tatatttccc tgctcatcag agactccaag 300
ctcagtgatt cagccaccta cctctgtgtg gtgaagtccc tcgacaataa caatgacatg 360
cgctttggag cagggaccag actgacagta aaaccaaata tccagaaccc tgaccctgcc 420
gtgtaccagc tgagagactc taaatccagt gacaagtctg tctgcctatt caccgatttt 480
gattctcaaa caaatgtgtc acaaagtaag gattctgatg tgtatatcac agacaaatgc 540
gtgctagaca tgaggtctat ggacttcaag agcaacagtg ctgtggcctg gagcaacaaa 600
```

-continued

```
tctgactttg catgtgcaaa cgccttcaac aacagcatta ttccagaaga caccttcttc    660
cccagcccag aaagttcctg tgatgtcaag ctggtcgaga aaagctttga aacagatacg    720
aacctaaact ttcaaaacct gtcagtgatt gggttccgaa tcctcctcct gaaagtggcc    780
gggtttaatc tgctcatgac gctgcggctg tggtccagct ga                       822

SEQ ID NO: 80              moltype = DNA   length = 933
FEATURE                    Location/Qualifiers
source                     1..933
                           mol_type = other DNA
                           organism = Homo sapiens
SEQUENCE: 80
atggcctccc tgctcttctt ctgtggggcc ttttatctcc tgggaacagg gtccatggat    60
gctgatgtta cccagacccc aaggaatagg atcacaaaga caggaaagag gattatgctg    120
gaatgttctc agactaaggg tcatgataga atgtactggt atcgacaaga cccaggactg    180
ggcctacggt tgatctatta ctcctttgat gtcaaagata taaacaaagg agagatctct    240
gatggataca gtgtctctcg acaggcacag gctaaattct ccctgtccct agagtctgcc    300
atccccaacc agacagctct ttacttctgt gccaccagtg attggacagg gcgaaatgag    360
cagttcttcg ggccagggac acggctcacc gtgctagagg acctgaaaaa cgtgttccca    420
cccgaggtcg ctgtgtttga gccatcagaa gcagagatct cccacaccca aaaggccaca    480
ctggtgtgcc tggccacagg cttctacccc gaccacgtgg agctgagctg gtgggtgaat    540
gggaaggagg tgcacagtgg ggtctgcaca gacccgcagc ccctcaagga gcagcccgcc    600
ctcaatgact ccagatactg cctgagcagc cgcctgagag tctcggccac cttctggcag    660
aaccccgca accacttccg ctgtcaagtc cagttctacg ggctctcgga gaatgacgag      720
tggacccagg atagggccaa acctgtcacc cagatcgtca gcgccgaggc ctggggtaga    780
gcagactgtg gcttcacctc cgagtcttac cagcaagggg tcctgtctgc caccatcctc    840
tatgagatct tgctagggaa ggccaccttg tatgccgtgc tggtcagtgc cctcgtgctg    900
atggccatgg tcaagagaaa ggattccaga ggc                                 933

SEQ ID NO: 81              moltype = DNA   length = 18
FEATURE                    Location/Qualifiers
source                     1..18
                           mol_type = other DNA
                           organism = Homo sapiens
SEQUENCE: 81
gtgtccggca atccctac                                                    18

SEQ ID NO: 82              moltype = DNA   length = 24
FEATURE                    Location/Qualifiers
source                     1..24
                           mol_type = other DNA
                           organism = Homo sapiens
SEQUENCE: 82
tacatcaccg gcgacaacct cgtg                                             24

SEQ ID NO: 83              moltype = DNA   length = 51
FEATURE                    Location/Qualifiers
source                     1..51
                           mol_type = other DNA
                           organism = Homo sapiens
SEQUENCE: 83
tgcgccgtgc gggatatgag atacggcgga gccaccaaca agctgatctt t              51

SEQ ID NO: 84              moltype = DNA   length = 15
FEATURE                    Location/Qualifiers
source                     1..15
                           mol_type = other DNA
                           organism = Homo sapiens
SEQUENCE: 84
ctgggccaca atgcc                                                       15

SEQ ID NO: 85              moltype = DNA   length = 18
FEATURE                    Location/Qualifiers
source                     1..18
                           mol_type = other DNA
                           organism = Homo sapiens
SEQUENCE: 85
tacagcctgg aagagaga                                                    18

SEQ ID NO: 86              moltype = DNA   length = 60
FEATURE                    Location/Qualifiers
source                     1..60
                           mol_type = other DNA
                           organism = Homo sapiens
SEQUENCE: 86
tgtgcctctt ctcaggatgg actggctggc gccgctagct tcaacaacga gcagtttttt    60

SEQ ID NO: 87              moltype = DNA   length = 834
FEATURE                    Location/Qualifiers
source                     1..834
```

```
                          mol_type = other DNA
                          organism = Homo sapiens
SEQUENCE: 87
atggccagcg ctcctatctc catgctggcc atgctgttta ccctgtctgg cctgagagca   60
cagtctgtgg ctcagcccga ggatcaagtg aatgtggccg agggcaatcc cctgaccgtg  120
aagtgtacct acagcgtgtc cggcaatccc tacctgtttt ggtacgtgca gtaccccaac  180
cggggcctgc agttcctgct gaagtacatc accggcgaca acctcgtgaa gggcagctat  240
ggattcgagg ccgagttcaa caagagccag accagcttcc acctgaagaa gcccagcgct  300
ctggtttccg actctgccct gtacttttgc gccgtgcggg atatgagata cggcgggagcc  360
accaacaagc tgatctttgg cactggaaca ctgctggccg tgcagcccaa cattcagaat  420
cctgatcctg ccgtgtacca gctgagagac agcaagagca gcgacaagag cgtgtgtctg  480
ttcaccgact tcgactccca gaccaacgtg tcccagagca aggactccga cgtgtacatc  540
acagataagt gcgtgctgga catgcggagc atggacttca agagcaatag cgccgtggcc  600
tggtccaaca agtccgattt tgcctgcgcc aacgccttca acaatagcat catccccgag  660
gacacattct tcccaagtcc tgagtccagc tgcgacgtga agctggtgga aaagagcttc  720
gagacagaca ccaacctgaa cttccagaac ctgagcgtga tcggcttccg gatcctgctg  780
ctgaaggtgg ccggcttcaa tctgctgatg accctgagac tgtggtccag ctga          834

SEQ ID NO: 88          moltype = DNA   length = 960
FEATURE                Location/Qualifiers
source                 1..960
                       mol_type = other DNA
                       organism = Homo sapiens
SEQUENCE: 88
atgggctgca gactgctgtg ctgtgcagtg ctgtgtctgc ttggagctgg cgagctggtt   60
cctatggaaa ccggcgtgac acagaccct agacaccctg tcatgggcat gacaaacaag   120
aaaagcctga agtgcgagca gcacctgggc cacaatgcca tgtactggta caagcagagc   180
gccaagaaac ccctggaact gatgttcgtg tacagcctgg aagagagagt ggaaaacaac   240
agcgtgccca gcagattcag ccctgagtgc cctaacagca gccacctgtt tctgcatctg   300
cacaccctga gcctgagga tagcgccctg tatctgtgtg cctcttctca ggatggactg    360
gctggcgccg ctagcttcaa caacgagcag tttttggcc ctggcaccag actgaccgtg    420
ctggaagatc tgaagaacgt gttcccacct gaggtggccg tgtttgagcc ttctgaggcc   480
gagatcagcc acacacagaa agccacactc gtgtgcctgg ccaccggctt ttatcccgat   540
cacgtggaac tgtcttggtg ggtcaacggc aaagaggtgc acagcggagt ctgtaccgat   600
cctcagcctc tgaaagagca gcccgctctg aacgacagca gatactgtct gagcagcaga   660
ctgagagtgt ccgccacctt ctggcagaac cccagaaacc acttcagatg ccaggtgcag   720
ttctacggcc tgagcgagaa tgacgagtgg acccaggata gagccaagcc tgtgactcag    780
attgtgtctg ccgaagcctg gggcagagcc gattgtggct ttacaagcga gagctaccag    840
cagggcgtgc tgagcgccac aatcctgtat gagatcctgc tcggcaaggc cacactgtac    900
gctgtgctgg tttctgccct ggtgctgatg gccatggtca agagaaagga cagcagaggc    960

SEQ ID NO: 89          moltype = DNA   length = 18
FEATURE                Location/Qualifiers
source                 1..18
                       mol_type = other DNA
                       organism = Homo sapiens
SEQUENCE: 89
agcagcaact tctacgcc                                                   18

SEQ ID NO: 90          moltype = DNA   length = 21
FEATURE                Location/Qualifiers
source                 1..21
                       mol_type = other DNA
                       organism = Homo sapiens
SEQUENCE: 90
atgaccctga acggcgacga g                                               21

SEQ ID NO: 91          moltype = DNA   length = 42
FEATURE                Location/Qualifiers
source                 1..42
                       mol_type = other DNA
                       organism = Homo sapiens
SEQUENCE: 91
tgcgccttca tgagagccac cggcgccaac aatctgttct tc                       42

SEQ ID NO: 92          moltype = DNA   length = 15
FEATURE                Location/Qualifiers
source                 1..15
                       mol_type = other DNA
                       organism = Homo sapiens
SEQUENCE: 92
tctggccacg tgtcc                                                      15

SEQ ID NO: 93          moltype = DNA   length = 18
FEATURE                Location/Qualifiers
source                 1..18
                       mol_type = other DNA
                       organism = Homo sapiens
SEQUENCE: 93
```

-continued

```
ttcaattacg aggcccag                                                        18

SEQ ID NO: 94              moltype = DNA  length = 42
FEATURE                    Location/Qualifiers
source                     1..42
                           mol_type = other DNA
                           organism = Homo sapiens
SEQUENCE: 94
tgcgccagct cttttggcgg cgtgtcctac gagcagtact tc                             42

SEQ ID NO: 95              moltype = DNA  length = 831
FEATURE                    Location/Qualifiers
source                     1..831
                           mol_type = other DNA
                           organism = Homo sapiens
SEQUENCE: 95
atggaaaaga accctctggc cgctcctctg ctgatcctgt ggtttcacct ggactgcgtg   60
tccagcatcc tgaatgtgga acagagccct cagagcctgc atgtgcaaga gggcgacagc   120
accaacttca cctgtagctt ccccagcagc aacttctacg ccctgcactg gtatagatgg   180
gagacagcca agtctcccga ggcactgttc gtgatgaccc tgaacggcga cgagaagaag   240
aaaggccgga tctccgccac actgaacacc aaagagggct actcctacct gtacatcaag   300
ggcagccagc cagaggatag cgccacatac ctgtgcgcct tcatgagagc caccggcgcc   360
aacaatctgt tcttcggcac cggaaccagg ctgacagtca tcccctacat tcagaacccc   420
gatcctgccg tgtaccagct gagagacagc aagagcagcg acaagtccgt gtgcctgttc   480
accgacttcg acagccagac caacgtgtcc cagagcaagg acagcgacgt gtacatcacc   540
gataagtgcg tgctggacat gcggacgcatg gacttcaaga gcaacagcgc cgtggcctgg   600
tccaacaaga gcgatttcgc ctgcgccaac gccttcaaca acagcattat ccccgaggac   660
acattcttcc caagtcctga gagcagctgc gacgtgaagc tggtggaaaa gagcttcgag   720
acagacacca acctgaactt ccagaacctg agcgtgatcg gcttccggat cctgctgctg   780
aaagtggccg gattcaacct gctgatgaca ctgagactgt ggtccagctg a             831

SEQ ID NO: 96              moltype = DNA  length = 936
FEATURE                    Location/Qualifiers
source                     1..936
                           mol_type = other DNA
                           organism = Homo sapiens
SEQUENCE: 96
atgggcacca gcctgctgtg ttgggttgtg ctgggctttc tgggcaccga tcatacaggt   60
gccggtgtca gccagtctcc tcggtacaaa gtgaccaagc gcggacagca tgtggccctg   120
agatgcgatc ctatctctgg ccacgtgtcc ctgtactggt acagacaggc tctcggacag   180
ggccccgagt tcctgaccta cttcaattac gaggcccagc aggacaagag cggcctgcct   240
aacgatagat tcagcgccga aagacccgag ggcagcatca gcacactgac catccagaga   300
accgagcaga gggacagcgc catgtacaga tgcgccagct cttttggcgg cgtgtcctac   360
gagcagtact tcggccctgg caccagactg accgtgaccg aggatctgaa gaacgtgttc   420
ccacctgagg tggccgtgtt cgagccttct gaggccgaga tcagccacac acagaaagcc   480
acactcgtgt gtctggccac cggcttctat cccgatcacg tggaactgtc ttggtgggtc   540
aacggcaaag aggtgcacag cggcgtctgt accgatcctc agcctctgaa agagcagccc   600
gctctgaacg acagcagata ctgcctgagc agcagactga gagtgtccgc caccttctgg   660
cagaacccca gaaccacttc agatgccag gtgcagttct acggcctgag cgagaacgat   720
gagtggaccc aggatagagc caagcctgtg acacagatcg tgtctgccga gcctgggggc   780
agagccgatt gtggctttac cagcgagagc taccagcagg gcgtgctgtc tgccacaatc   840
ctgtacgaga ttctgctggg caaagccact ctgtacgccg tgctggtgtc tgccctggtg   900
ctgatggcca tggtcaagcg gaaggactct agaggc                               936

SEQ ID NO: 97              moltype = AA  length = 10
FEATURE                    Location/Qualifiers
source                     1..10
                           mol_type = protein
                           organism = Homo sapiens
SEQUENCE: 97
YMLDLQPETT                                                                10

SEQ ID NO: 98              moltype = AA  length = 9
FEATURE                    Location/Qualifiers
source                     1..9
                           mol_type = protein
                           organism = Homo sapiens
SEQUENCE: 98
NLVPMVATV                                                                 9
```

The invention claimed is:

1. One or more nucleic acids encoding a recombinant T cell receptor (TCR) that binds Wilms' tumor antigen-1 (WT1), wherein the recombinant TCR comprises an alpha chain and a beta chain, and wherein the beta chain comprises a CDR3 sequence comprising the amino acid sequence set forth in SEQ ID NO: 6, 14, 22, 30, 38, or 46.

2. The one or more nucleic acids of claim 1, wherein the beta chain comprises a CDR3 sequence comprising the amino acid sequence set forth in SEQ ID NO: 22.

3. The one or more nucleic acids of claim 1, wherein the alpha chain comprises a CDR3 sequence comprising the amino acid sequence set forth in SEQ ID NO: 19.

4. The one or more nucleic acids of claim 2, wherein the alpha chain comprises a CDR3 sequence comprising the amino acid sequence set forth in SEQ ID NO: 19.

5. A recombinant host cell comprising the one or more nucleic acids of claim 1.

6. A recombinant host cell comprising the one or more nucleic acids of claim 2.

7. A recombinant host cell comprising the one or more nucleic acids of claim 3.

8. A recombinant host cell comprising the one or more nucleic acids of claim 4.

\* \* \* \* \*